（12） United States Patent
Guiry et al.

(10) Patent No.: US 11,161,824 B2
(45) Date of Patent: Nov. 2, 2021

(54) HETEROCYCLIC LIPOXIN ANALOGS AND USES THEREOF

(71) Applicant: University College Dublin, National University of Ireland, Dublin, Dublin (IE)

(72) Inventors: Patrick Guiry, Dublin (IE); Catherine Godson, Dublin (IE); Monica De Gaetano, Dublin (IE); Eibhlin Butler, Dublin (IE); Claire Wilson, Dublin (IE); Catherine Tighe, Dublin (IE); Denise Moran, Dublin (IE); Andrea Zanetti, Dublin (IE); Kevin Gahan, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 246 days.

(21) Appl. No.: 16/326,453

(22) PCT Filed: Aug. 18, 2017

(86) PCT No.: PCT/EP2017/070979
§ 371 (c)(1),
(2) Date: Feb. 19, 2019

(87) PCT Pub. No.: WO2018/033642
PCT Pub. Date: Feb. 22, 2018

(65) Prior Publication Data
US 2021/0053927 A1    Feb. 25, 2021

(30) Foreign Application Priority Data
Aug. 19, 2016 (GB) .................................... 1614224

(51) Int. Cl.
*C07D 239/26* (2006.01)
*C07D 215/14* (2006.01)
*C07D 217/02* (2006.01)
*C07D 239/74* (2006.01)
*C07D 241/42* (2006.01)
*C07D 231/12* (2006.01)
*C07D 307/36* (2006.01)
*C07D 307/79* (2006.01)
*C07D 333/06* (2006.01)
*A61K 31/341* (2006.01)
*A61K 31/343* (2006.01)
*A61K 31/381* (2006.01)
*A61K 31/40* (2006.01)
*A61K 31/404* (2006.01)
*A61K 31/47* (2006.01)
*A61K 31/472* (2006.01)
*A61P 11/06* (2006.01)
*A61P 13/12* (2006.01)
*C07D 215/18* (2006.01)
*C07D 217/22* (2006.01)
(Continued)

(52) U.S. Cl.
CPC ......... *C07D 241/42* (2013.01); *C07D 215/14* (2013.01); *C07D 215/18* (2013.01); *C07D 217/22* (2013.01); *C07D 233/68* (2013.01); *C07D 263/32* (2013.01); *C07D 263/34* (2013.01); *C07D 307/80* (2013.01); *C07D 333/56* (2013.01); *C07D 405/06* (2013.01); *C07D 407/06* (2013.01); *C07D 409/06* (2013.01); *C07D 413/06* (2013.01)

(58) Field of Classification Search
CPC .. C07D 239/26; C07D 215/14; C07D 217/02; C07D 239/74; C07D 241/42; C07D 231/12; C07D 307/36; C07D 307/79; C07D 333/06; A61K 31/341; A61K 31/343; A61K 31/381; A61K 31/40; A61K 31/404; A61K 31/47; A61K 31/472
See application file for complete search history.

(56) References Cited

U.S. PATENT DOCUMENTS 8,809,382 B2    8/2014 Powell et al.
2005/0203184 A1    9/2005 Petasis

OTHER PUBLICATIONS

PCT International Search Report and Written Opinion for International Application No. PCT/EP2017/070979, dated Oct. 30, 2017, 12 pages.
(Continued)

Primary Examiner — Bruck Kifle
(74) Attorney, Agent, or Firm — Hoffman Warnick LLC

(57) ABSTRACT

The present invention relates to a compound of formula (I): wherein L is an optionally substituted heterocyclic group excluding unsubstituted monocyclic pyridine groups; wherein a is 0, 1 or 2; wherein $R^1$ is H or with $R^2$ is a bond; wherein $R^2$ is an optionally substituted alkoxy or aryloxy group, or with $R^1$ forms a bond; wherein $R^3$ is an optionally substituted alkyl group; and wherein $R^4$ is $CH_2$, $CMe_2$ or O. Such compounds may be used in the treatment or prophylaxis of a disease or condition in which inhibition of acute inflammation and/or promotion of its resolution and/or suppression of fibrosis.

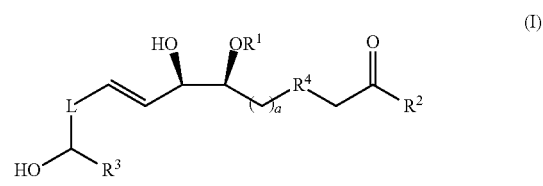

(I)

16 Claims, 19 Drawing Sheets

(51) Int. Cl.
| | |
|---|---|
| *C07D 233/68* | (2006.01) |
| *C07D 263/32* | (2006.01) |
| *C07D 263/34* | (2006.01) |
| *C07D 307/80* | (2006.01) |
| *C07D 333/56* | (2006.01) |
| *C07D 405/06* | (2006.01) |
| *C07D 407/06* | (2006.01) |
| *C07D 409/06* | (2006.01) |
| *C07D 413/06* | (2006.01) |

(56) References Cited

OTHER PUBLICATIONS

Duffy et al., "Synthesis and Biological Evaluation of Pyridine-Containing Lipoxin A4 Analogues," Communications, Wiley-VCH Verlag GmbH & Co. KGaA, Weinheim, ChemMedChem, 2010, 5, 517-522.

Japanese Patent Application No. 2019-530542, Office Action dated Jun. 3, 2021.

Native compound (R) epimer (1R)-9

*(S)* epimer (1S)-9

KG 5-22 (R)

HETEROCYCLIC LIPOXIN ANALOGS AND USES THEREOF

FIELD

The invention relates to compounds comprising synthetic analogues of Lipoxin $A_4$ ($LXA_4$), which display significant biological activity and metabolic stability. These compounds may be useful in the development of a range of therapies, such as anti-inflammatory, anti-fibrotic, anti-atherosclerotic and/or immunomodulatory agents.

BACKGROUND

In 1984, a new class of arachidonic acid metabolites was isolated by Samuelsson and Serhan (1). These molecular agents, named Lipoxin $A_4$ and $B_4$, are produced by transcellular metabolism of eicosanoid derivatives. Lipoxins (herein after referred to as LX) are typically formed by the sequential actions of 15- and 5-, or 5- and 12-lipoxygenases on arachidonic acid, depending on the cellular context (2). These compounds are biologically important with LX being observed in many human diseases, including asthma, glomerulonephritis and rheumatoid arthritis (3-6). Both in vivo and in vitro studies show that lipoxins regulate polymorphonuclear leukocytes (PMN), chemotaxis, adhesion and transmigration (7-10). $LXA_4$ appears to block some leukocyte response to leukotrienes including PNM adhesion mediated by CD11/CD18 expression and endothelial neutrophil adhesion dependent on endothelial P-selection and PNM-mesangial cell adhesion (10,11). The inventors of the present invention have previously demonstrated that LXs are involved in the resolution of inflammation by promoting non-phlogistic phagocytosis of apoptotic PMN by macrophages in vitro and in vivo (12,13). Furthermore the inventors have shown distinct fibrosuppressant activities of LXs in experimental models (13a, 13b). Consistent with a biological role for LXs in the resolution of inflammation is evidence that their production at an inflammatory focus is coincident with the resolution of inflammation (14,15).

LX are rapidly metabolised either by oxidation at C-15 or reduction of the C13-C14 double bond (16). 15-Hydroxy-prostaglandin dehydrogenase (15-PGDH) catalyses the dehydrogenation of the C-15 hydroxyl to afford the corresponding ketone 15-oxo-$LXA_4$. Alternatively, leukotriene $B_4$ 12-hydroxydehydrogenase (PGR/LTB4DH) may catalyse the reduction of the C13-C14 double bond of $LXA_4$ or 15-oxo-$LXA_4$ to give 13,14-dihydro-$LXA_4$ or 13,14-dihydro-15-oxo-$LXA_4$ respectively. LX are also subject to □-oxidation at C20 (17).

SUMMARY OF THE INVENTION

The inventors have recognised that the instability of endogenously generated lipoxins and their difficult/costly synthesis is a significant obstacle to their use as pharmaceutical entities. To overcome these problems the inventors have sought to mimic the core structure of $LXA_4$ by replacing certain functionalities with alternative groups with the aim of improving the metabolic stability of the compounds whilst retaining their potent biological activity, as shown in Scheme 1 below.

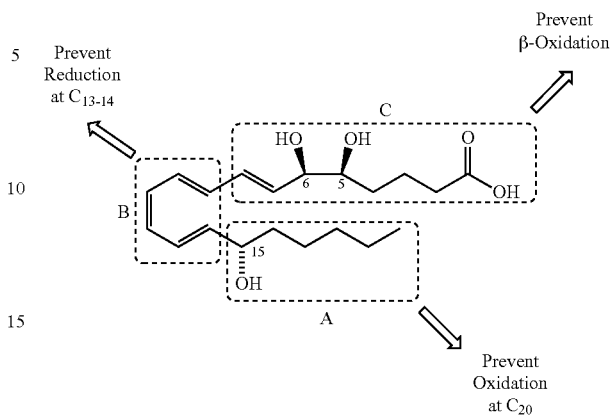

Scheme 1

The strategies include (A) structural modifications of the $C_{15-20}$ chain; (B) replacement of the triene with chemically stable aromatic/heteroaromatic systems: and (C) modifications of the $C_{1-8}$ unit (18).

It is therefore one aim of the present invention, amongst others, to provide a compound, composition, use or method that addresses at least one disadvantage of the prior art, whether identified here or elsewhere, or to provide an alternative to existing compounds, compositions, uses or methods. For instance it may be an aim of the present invention to provide a compound which has an improved metabolic stability compared to lipoxin and has sufficient biological activity to enable the inhibition of acute inflammation and/or the promotion of its resolution and/or the suppression of fibrosis.

It may be a further or an alternative aim of the present invention to provide a compound for use in the treatment or prophylaxis of asthma and/or glomerulonephritis and/or atherosclerosis.

It may be a further or an alternative aim of the present invention to provide a compound for use in the treatment or prophylaxis of the macro and/or microvascular complications associated with metabolic diseases, for example diabetes.

According to aspects of the present invention, there is provided a compound, composition, use or method as set forth in the appended claims. Other features of the invention will be apparent from the dependent claims, and the description which follows.

According to a first aspect of the present invention, there is provided a compound of formula (I):

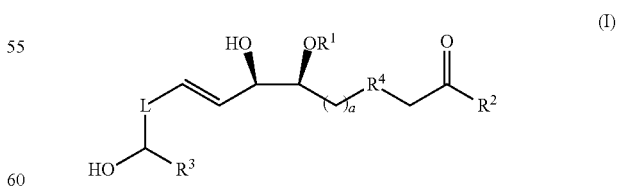

wherein L is an optionally substituted heterocyclic group excluding unsubstituted monocyclic pyridine groups;
wherein a is 0, 1 or 2;
wherein $R^1$ is H or with $R^2$ is a bond;
wherein $R^2$ is OH or an optionally substituted alkoxy or aryloxy group, or with $R^1$ forms a bond;

wherein R³ is an optionally substituted alkyl group; and wherein R⁴ is CH₂, CMe₂ or O.

L is an optionally substituted heterocyclic group which provides a link between the upper and lower chains of the compounds of this first aspect. Therefore L has a bond to each of the upper and lower chains. By "upper chain" we mean the portion:

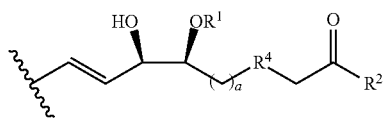

By lower chain we mean the portion:

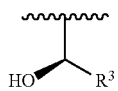

Suitably L bonds to the upper and lower chains through different atoms. Suitably L bonds to the upper and lower chains through carbon atoms. Suitably L bonds to the upper and lower chains through adjacent atoms in the heterocyclic group, therefore having the upper and lower chains arranged in a "1,2 substitution" on the heterocyclic group. L may bond to the upper and lower chains through atoms in the heterocyclic group which are one atom apart, therefore having the upper and lower chains arranged in a "1,3 substitution" on the heterocyclic group. L may bond to the upper and lower chains through atoms in the heterocyclic group which are two atoms apart, therefore having the upper and lower chains arranged in a "1,4 substitution" on the heterocyclic group.

L is an optionally substituted heterocyclic group by which we mean that the heterocyclic group may have any number and combination of substituents on the appropriate atoms to which the upper and lower chains are not bonded.

L is an optionally substituted heterocyclic group excluding optionally substituted monocyclic pyridine groups. Therefore L is not a pyridine ring but may be a heterocyclic group which contains a pyridine ring as part of a larger heterocyclic ring system, for example a quinoline group.

L is an optionally substituted heterocyclic group excluding unsubstituted monocyclic pyridine groups. Therefore L is not an unsubstituted monocyclic pyridine group. Suitably L is an optionally substituted heterocyclic group excluding optionally substituted monocyclic pyridine groups. Therefore, suitably L is not an optionally substituted monocyclic pyridine group.

R¹ may with R² form a bond. Therefore optionally the atoms to which the R¹ and R² groups are attached may be joined by a bond in some embodiments.

The compound according to claim 1, wherein L selected from an optionally substituted pyrimidine, quinoline, isoquinoline, quinazoline, five-membered heterocyclic ring or benzo-fused five membered heterocyclic ring.

In some embodiments, L is selected from an unsubstituted pyrimidine, quinoline, isoquinoline, quinazoline, five-membered heterocyclic ring or benzo-fused five membered heterocyclic ring.

Suitably L is selected from an unsubstituted pyrimidine, quinoline, isoquinoline or quinazoline.

In some embodiments L is selected from the optionally substituted heterocyclic groups:

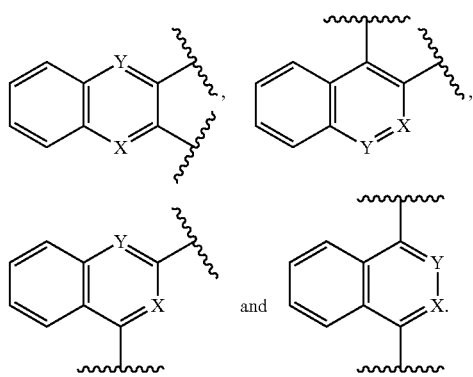

wherein X is selected from C or N,
wherein Y is selected from C or N, and
wherein at least one of X and Y is N.

In this context by optionally substituted we mean that the H atoms attached to the heterocyclic ring atoms may be replaced with a suitable substituent, for example alkyl groups, alkoxy groups or halogens.

The incomplete bonds shown in these structures show where the upper and lower chains are connected to the group L. The arrangement of the incomplete bonds does not specifically define which of the incomplete bonds is the bond to the upper chain and which to the lower chain. Therefore either of the incomplete bonds in these structures can be to the upper chain or the lower chain.

Suitably L is selected from the unsubstituted heterocyclic groups:

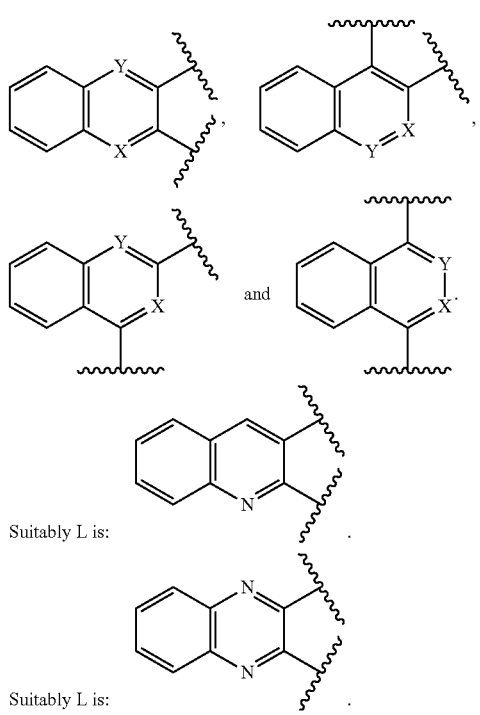

Suitably L is:

Suitably L is:

-continued

Suitably L is: 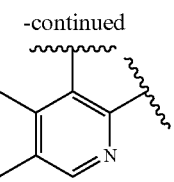

Suitably L is: 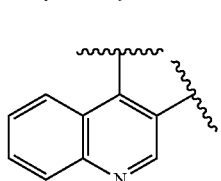

Suitably L is: 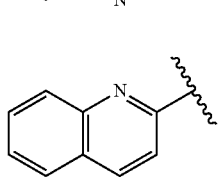

Suitably L is: 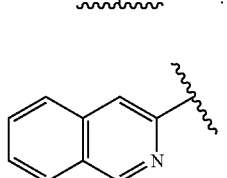

Suitably L is: 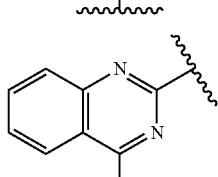

Suitably L is: 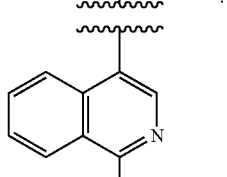

Suitably L is: 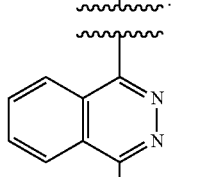

In some embodiments L is the optionally substituted group:

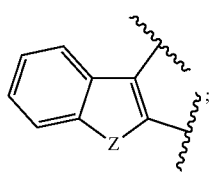

wherein Z is selected from N, O and S.

In some embodiments L is:

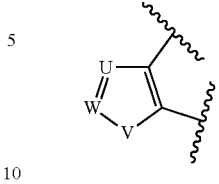

wherein V is selected from $NR^5$, O and S; wherein $R^5$ is H or an optionally substituted alkyl or aryl group;

wherein W is selected from $CR^6$, N, O and S; wherein $R^6$ is H or an optionally substituted alkyl or aryl group; and wherein U is selected from $CR^7$ or N; wherein $R^7$ is H or an optionally substituted alkyl or aryl group.

Suitably L is: 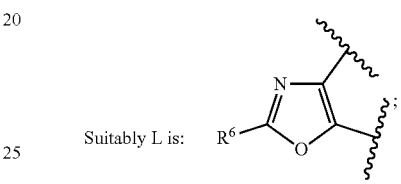

wherein $R^6$ is H or an optionally substituted alkyl or aryl group.

Suitably L is: 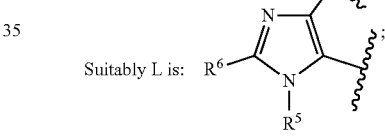

wherein $R^5$ is H or an optionally substituted alkyl or aryl group and wherein $R^6$ is H or an optionally substituted alkyl or aryl group.

Suitably L is: 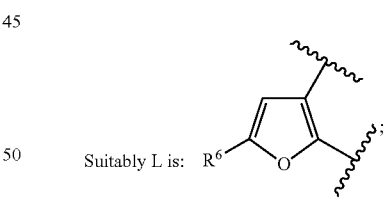

wherein $R^6$ is H or an optionally substituted alkyl or aryl group.

Suitably L is: 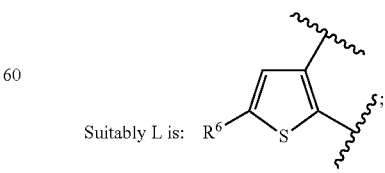

wherein $R^6$ is H or an optionally substituted alkyl or aryl group.

Suitably L is: 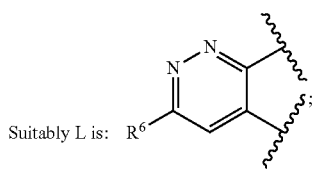

wherein $R^6$ is H or an optionally substituted alkyl or aryl group.

Suitably L is: 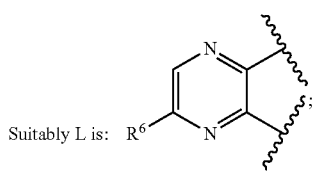

wherein $R^6$ is H or an optionally substituted alkyl or aryl group.

Suitably L is: 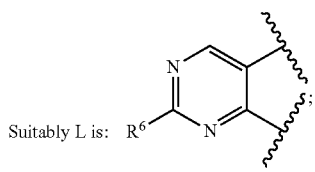

wherein $R^6$ is H or an optionally substituted alkyl or aryl group.

Suitably L is: 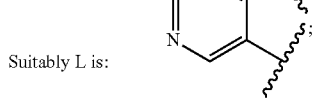

wherein $R^6$ is H or an optionally substituted alkyl or aryl group.

Suitably L is: 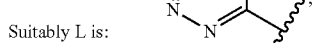

wherein $R^6$ is H or an optionally substituted alkyl or aryl group.

Suitably L is: 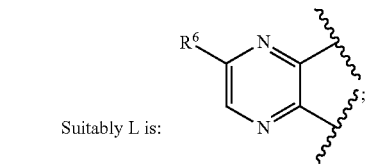

wherein $R^6$ is H or an optionally substituted alkyl or aryl group.

$R^2$ is OH an optionally substituted alkoxy or aryloxy group, or with $R^1$ forms a bond. Suitably $R^2$ is a $C_{1-4}$ alkoxy group. Therefore the compound of this first aspect is suitably an ester with the $R^2$ group and the adjacent carbonyl group provided the ester group. Suitably $R^2$ is $OCH_3$, $OCH_2CH_3$ or $OCH(CH_3)_2$.

$R^1$ may with $R^2$ form a bond. Therefore in some embodiments the compound of this first aspect may have the formula (II):

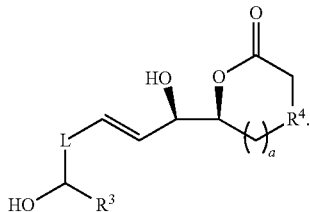

(II)

Suitably, $R^4$ is $CH_2$. Suitably a is 1.

In some embodiments $R^3$ is an optionally substituted $C_{1-9}$ alkyl group. Suitably $R^3$ is an optionally substituted $C_{3-7}$ alkyl group. Suitably $R^3$ is an unsubstituted $C_{1-9}$ alkyl group, suitably an unsubstituted $C_{3-7}$ alkyl group.

In some embodiments $R^3$ comprises an aryloxy group, suitably an optionally substituted phenoxy group.

Suitably $R^3$ has the formula (IIIa):

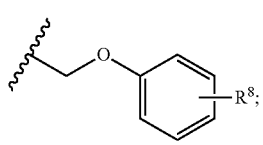

(IIIa)

wherein $R^6$ is selected from H, OH, CN, halogens and optionally substituted alkyl, aryl, alkoxy, amino, sulphide, sulphoxide and sulphonate groups.

Suitably $R^3$ has the formula (III):

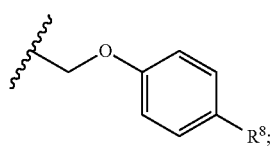

(III)

Suitably $R^6$ is selected from H, F and $CF_3$.

The stereochemistry of the chiral centres on the upper chain of the compound of this first aspect are as shown in formula (I). The stereochemistry of the chiral centre on the lower chain of the compound of this first aspect may be either in the R or S form or be a mixture of the two, for example an approximately equal mixture of the R and S diastereoisomers. Suitably the compound of this first aspect is provided as substantially one diastereoisomer, for example in a diasteromeric excess of at least 90%, suitably at least 95%, suitably at least 99%.

In some embodiments, the compound of this first aspect has the R stereochemistry at the chiral centre in the lower chain. Therefore, suitably the compound of this first aspect has the formula (IV):

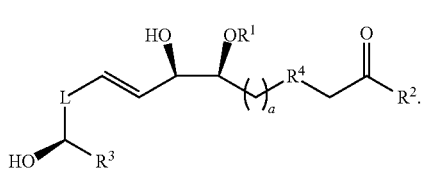

(IV)

In some embodiments, the compound of this first aspect has the S stereochemistry at the chiral centre in the lower chain. Therefore, suitably the compound of this first aspect has the formula (V):

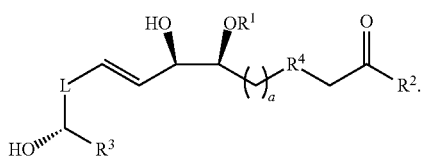

(V)

Suitably the compound of this first aspect has the formula (VIaa):

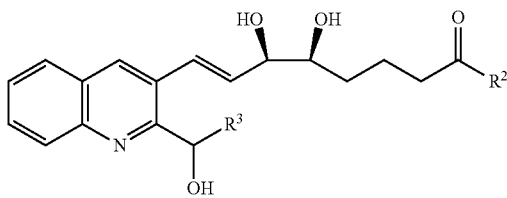

(VIaa)

wherein R² is OH or a C$_{1-4}$ alkoxy group and wherein R³ is an optionally substituted alkyl group.

Suitably the compound of this first aspect has the formula (VIa):

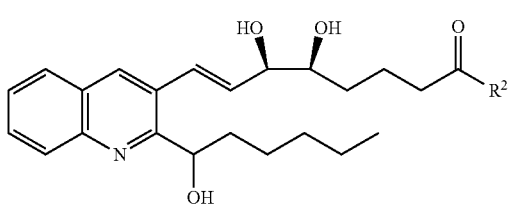

(VIa)

wherein R² is OH or a C$_{1-4}$ alkoxy group.

Suitably the compound of this first aspect has the formula (VIbb):

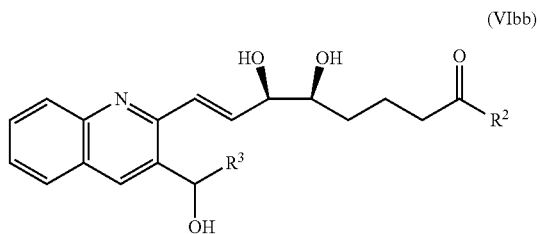

(VIbb)

wherein R² is OH or a C$_{1-4}$ alkoxy group and wherein R³ is an optionally substituted alkyl group.

Suitably the compound of this first aspect has the formula (VIb):

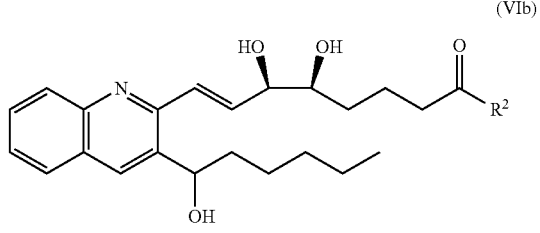

(VIb)

wherein R² is OH or a C$_{1-4}$ alkoxy group.

Suitably the compound of this first aspect has the formula (VIbb2):

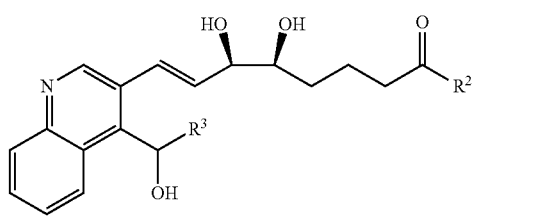

(VIbb2)

wherein R² is OH or a C$_{1-4}$ alkoxy group and wherein R³ is an optionally substituted alkyl group.

Suitably the compound of this first aspect has the formula (VIb2):

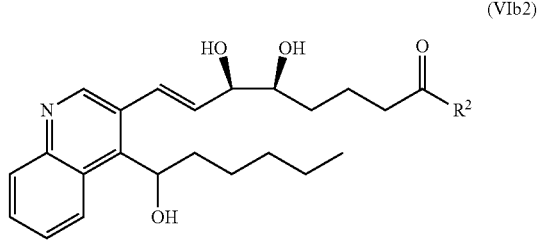

(VIb2)

wherein R² is OH or a C$_{1-4}$ alkoxy group.

Suitably the compound of this first aspect has the formula (VIcc):

(VIcc)

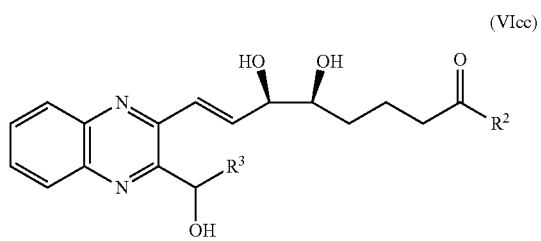

wherein R² is OH or a C₁₋₄ alkoxy group and wherein R³ is an optionally substituted alkyl group.

Suitably the compound of this first aspect has the formula (VIc):

(VIc)

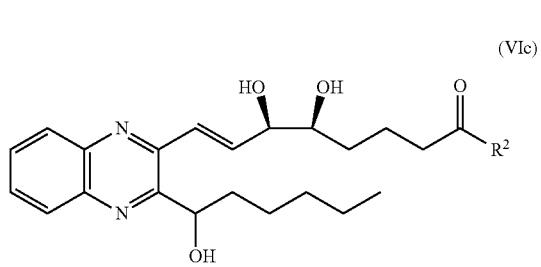

wherein R² is OH or a C₁₋₄ alkoxy group.

Suitably the compound of this first aspect has the formula (VId):

(VId)

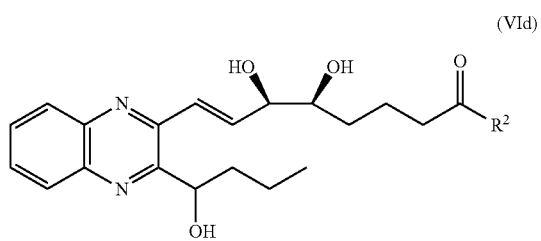

wherein R² is OH or a C₁₋₄ alkoxy group.

Suitably the compound of this first aspect has the formula (VIe):

(VIe)

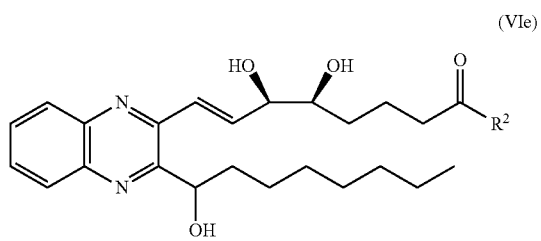

wherein R² is OH or a C₁₋₄ alkoxy group.

Suitably the compound of this first aspect has the formula (VIff):

(VIff)

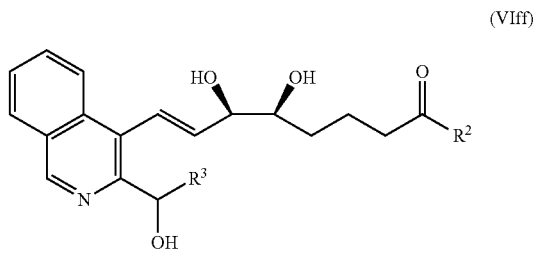

wherein R² is OH or a C₁ alkoxy group and wherein R³ is an optionally substituted alkyl group.

Suitably the compound of this first aspect has the formula (VIf):

(VIf)

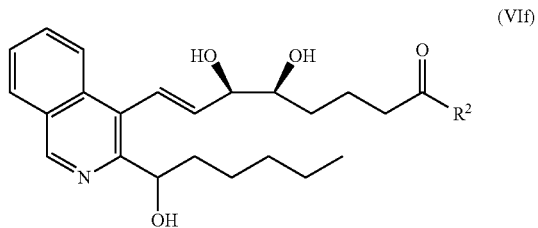

wherein R² is OH or a C₁₋₄ alkoxy group.

Suitably the compound of this first aspect has the formula (VIgg):

(VIgg)

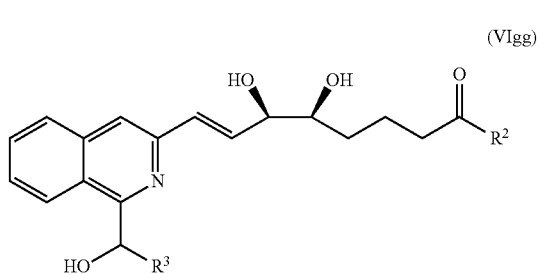

wherein R² is OH or a C₁₋₄ alkoxy group and wherein R³ is an optionally substituted alkyl group.

Suitably the compound of this first aspect has the formula (Vg):

(VIg)

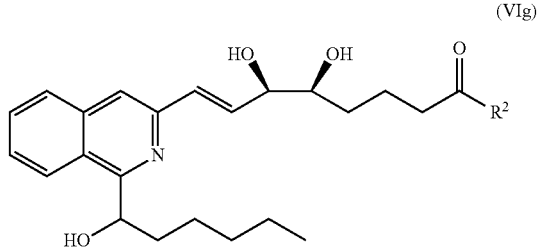

wherein R² is OH or a C₁₋₄ alkoxy group.

Suitably the compound of this first aspect has the formula (VIhh):

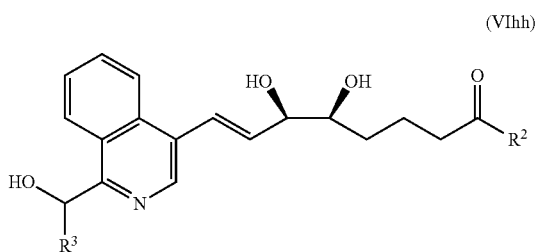

(VIhh)

wherein $R^2$ is OH or a $C_{1-4}$ alkoxy group and wherein $R^3$ is an optionally substituted alkyl group.

Suitably the compound of this first aspect has the formula (VIh):

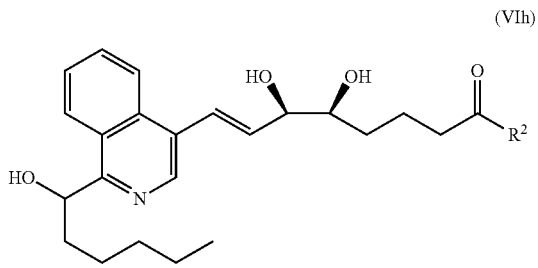

(VIh)

wherein $R^2$ is OH or a $C_{1-4}$ alkoxy group.

Suitably the compound of this first aspect has the formula (VIii):

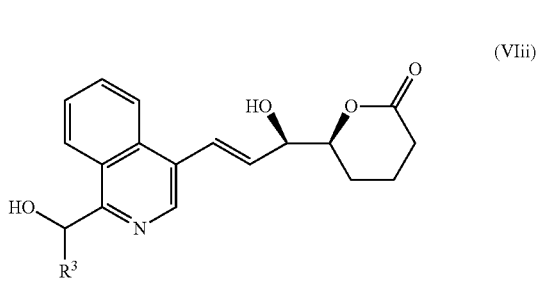

(VIii)

wherein $R^2$ is OH or a $C_{1-4}$ alkoxy group and wherein $R^3$ is an optionally substituted alkyl group.

Suitably the compound of this first aspect has the formula (VIi):

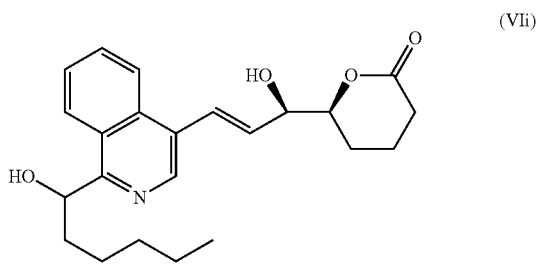

(VIi)

wherein $R^2$ is OH or a $C_{1-4}$ alkoxy group.

Suitably the compound of this first aspect has the formula (VIjj):

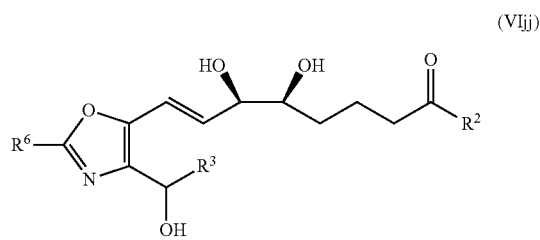

(VIjj)

wherein $R^2$ is OH or a $C_{1-4}$ alkoxy group; wherein $R^3$ is an optionally substituted alkyl group and wherein $R^6$ is H or an optionally substituted alkyl or aryl group.

Suitably the compound of this first aspect has the formula (VIj):

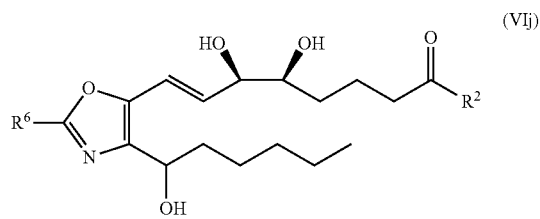

(VIj)

wherein $R^2$ is OH or a $C_{1-4}$ alkoxy group and wherein $R^6$ is H or an optionally substituted alkyl or aryl group.

Suitably the compound of this first aspect has the formula (VIjj2):

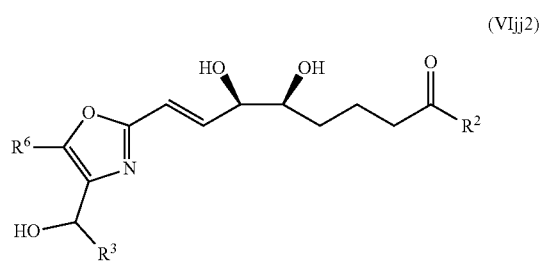

(VIjj2)

wherein $R^2$ is OH or a $C_{1-4}$ alkoxy group; wherein $R^3$ is an optionally substituted alkyl group and wherein $R^6$ is H or an optionally substituted alkyl or aryl group.

Suitably the compound of this first aspect has the formula (VIj2):

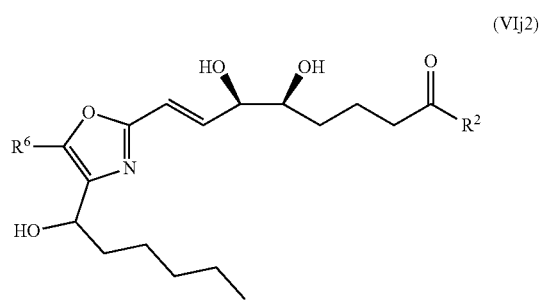

(VIj2)

wherein $R^2$ is OH or a $C_{1-4}$ alkoxy group and wherein $R^6$ is H or an optionally substituted alkyl or aryl group.

Suitably the compound of this first aspect has the formula (VIkk):

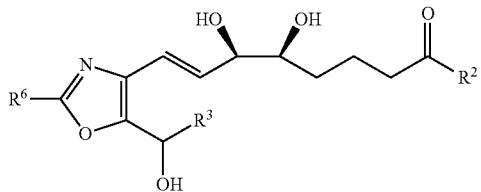

(VIkk)

wherein $R^2$ is OH or a $C_{1-4}$ alkoxy group; wherein $R^3$ is an optionally substituted alkyl group and wherein $R^6$ is H or an optionally substituted alkyl or aryl group.

Suitably the compound of this first aspect has the formula (VIk):

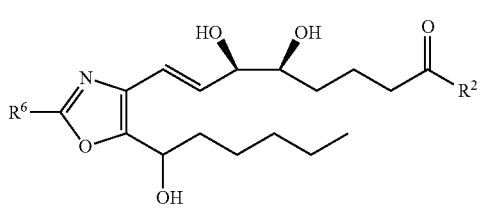

(VIk)

wherein $R^2$ is OH or a $C_{1-4}$ alkoxy group and wherein $R^6$ is H or an optionally substituted alkyl or aryl group.

Suitably the compound of this first aspect has the formula (VImm):

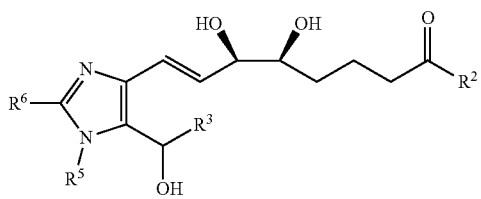

(VImm)

wherein $R^2$ is OH or a $C_{1-4}$ alkoxy group; wherein $R^3$ is an optionally substituted alkyl group; wherein $R^6$ is H or an optionally substituted alkyl or aryl group; and wherein $R^5$ is H or an optionally substituted alkyl or aryl group.

Suitably the compound of this first aspect has the formula (VIm):

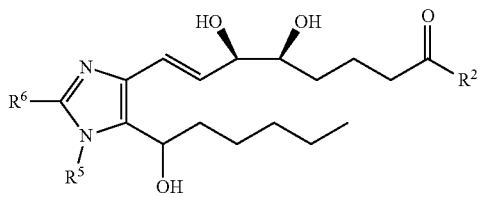

(VIm)

wherein $R^2$ is OH or a $C_{1-4}$ alkoxy group; wherein $R^6$ is H or an optionally substituted alkyl or aryl group; and wherein $R^5$ is H or an optionally substituted alkyl or aryl group.

Suitably the compound of this first aspect has the formula (VImm2):

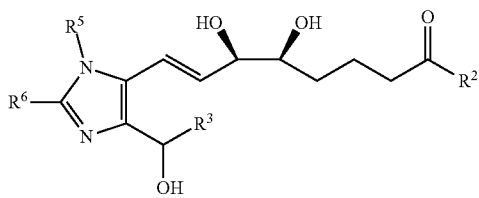

(VImm2)

wherein $R^2$ is OH or a $C_{1-4}$ alkoxy group; wherein $R^3$ is an optionally substituted alkyl group; wherein $R^6$ is H or an optionally substituted alkyl or aryl group; and wherein $R^5$ is H or an optionally substituted alkyl or aryl group.

Suitably the compound of this first aspect has the formula (VIm2):

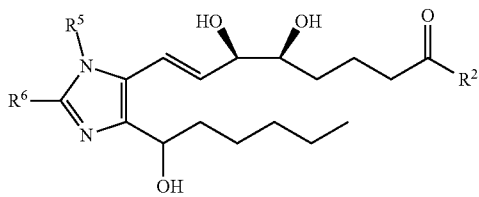

(VIm2)

wherein $R^2$ is OH or a $C_{1-4}$ alkoxy group; wherein $R^6$ is H or an optionally substituted alkyl or aryl group; and wherein $R^5$ is H or an optionally substituted alkyl or aryl group.

Suitably the compound of this first aspect has the formula (VInn):

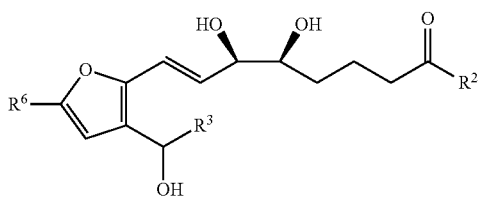

(VInn)

wherein $R^2$ is OH or a $C_{1-4}$ alkoxy group; wherein $R^3$ is an optionally substituted alkyl group; and wherein $R^6$ is H or an optionally substituted alkyl or aryl group.

Suitably the compound of this first aspect has the formula (Vn):

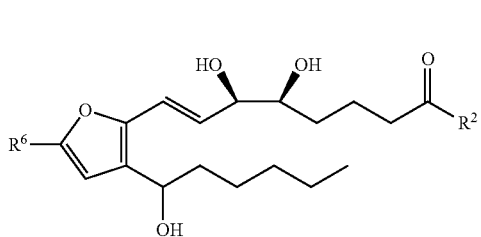

(VIn)

wherein $R^2$ is OH or a $C_{1-4}$ alkoxy group; and wherein $R^6$ is H or an optionally substituted alkyl or aryl group.

Suitably the compound of this first aspect has the formula (VIoo):

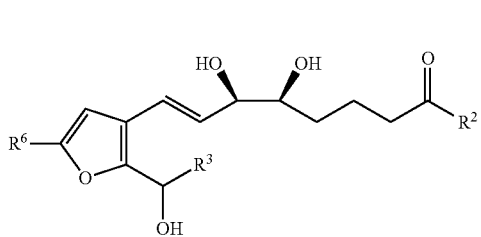

(VIoo)

wherein $R^2$ is OH or a $C_{1-4}$ alkoxy group; wherein $R^3$ is an optionally substituted alkyl group; and wherein $R^6$ is H or an optionally substituted alkyl or aryl group.

Suitably the compound of this first aspect has the formula (VIo):

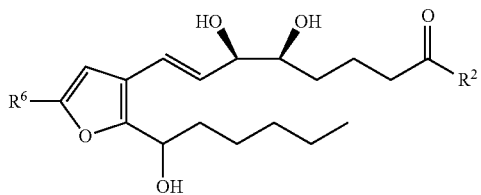

(VIo)

wherein $R^2$ is OH or a $C_{1-4}$ alkoxy group; and wherein $R^6$ is H or an optionally substituted alkyl or aryl group.

Suitably the compound of this first aspect has the formula (VIoo2):

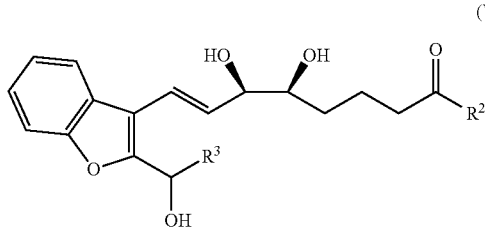

(VIoo2)

wherein $R^2$ is OH or a $C_{1-4}$ alkoxy group and wherein $R^3$ is an optionally substituted alkyl group.

Suitably the compound of this first aspect has the formula (VIo2):

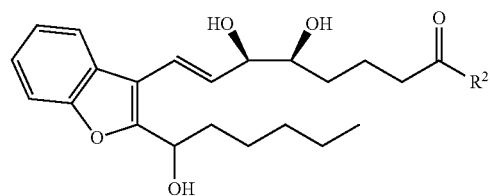

(VIo2)

wherein $R^2$ is OH or a $C_{1-4}$ alkoxy group.

Suitably the compound of this first aspect has the formula (VIpp):

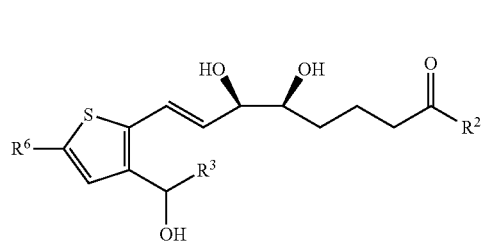

(VIpp)

wherein $R^2$ is OH or a $C_{1-4}$ alkoxy group; wherein $R^3$ is an optionally substituted alkyl group; and wherein $R^6$ is H or an optionally substituted alkyl or aryl group.

Suitably the compound of this first aspect has the formula (VIp):

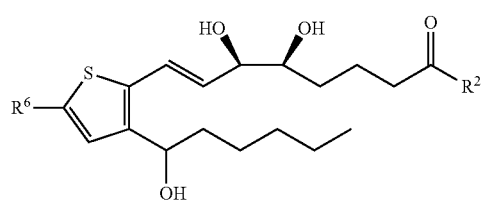

(VIp)

wherein $R^2$ is OH or a $C_{1-4}$ alkoxy group; and wherein $R^6$ is H or an optionally substituted alkyl or aryl group.

Suitably the compound of this first aspect has the formula (VIqq):

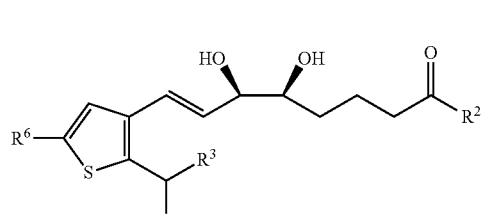

(VIqq)

wherein $R^2$ is OH or a $C_{1-4}$ alkoxy group; wherein $R^3$ is an optionally substituted alkyl group; and wherein $R^6$ is H or an optionally substituted alkyl or aryl group.

Suitably the compound of this first aspect has the formula (VIq):

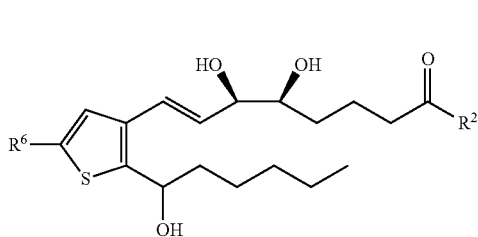

(VIq)

wherein $R^2$ is OH or a $C_{1-4}$ alkoxy group; and wherein $R^6$ is H or an optionally substituted alkyl or aryl group.

Suitably the compound of this first aspect has the formula (VIqq2):

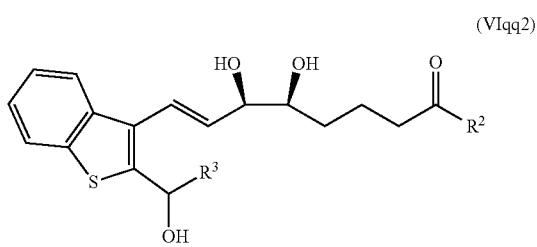

(VIqq2)

wherein $R^2$ is OH or a $C_{1-4}$ alkoxy group and wherein $R^3$ is an optionally substituted alkyl group.

Suitably the compound of this first aspect has the formula (VIq2):

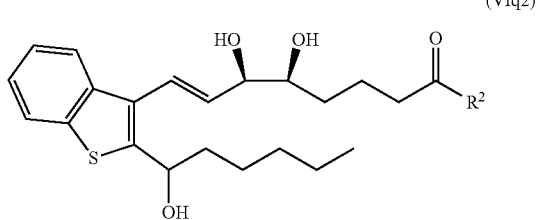

(VIq2)

wherein $R^2$ is OH or a $C_{1-4}$ alkoxy group.

Suitably the compound of this first aspect has the formula (VIrr):

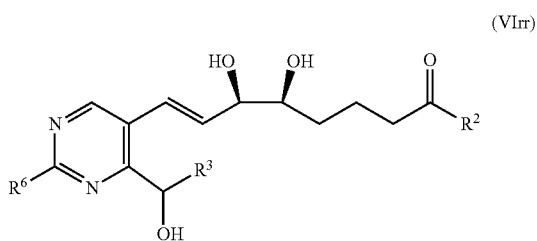

(VIrr)

wherein $R^2$ is OH or a $C_{1-4}$ alkoxy group; wherein $R^3$ is an optionally substituted alkyl group; and wherein $R^6$ is H or an optionally substituted alkyl or aryl group.

Suitably the compound of this first aspect has the formula (VIr):

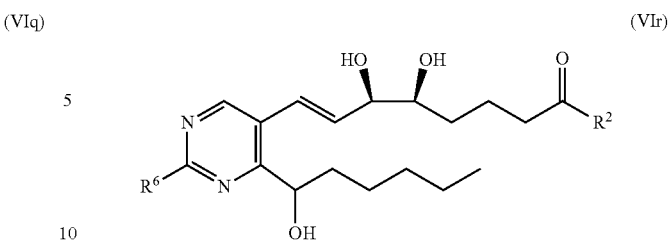

(VIr)

wherein $R^2$ is OH or a $C_{1-4}$ alkoxy group; and wherein $R^6$ is H or an optionally substituted alkyl or aryl group.

According to a second aspect of the present invention, there is provided a composition comprising a compound according to the first aspect and a pharmaceutically acceptable diluent, lubricant or carrier.

Suitable diluents, lubricants and carriers would be known to a person skilled in the relevant art.

According to a third aspect of the present invention, there is provided a compound according to the first aspect or a composition according to the second aspect for use as a medicament.

The compound for use as a medicament of this third aspect may be for use in the treatment or prophylaxis of asthma and/or glomerulonephritis and/or atherosclerosis.

The compound for use as a medicament of this third aspect may be for use in the treatment or prophylaxis of the macro and/or microvascular complications associated with metabolic diseases, for example diabetes.

According to a fourth aspect of the present invention, there is provided a compound according to the first aspect or a composition according to the second aspect for use in the treatment or prophylaxis of a disease or condition in which inhibition of acute inflammation and/or promotion of its resolution and/or suppression of fibrosis is beneficial.

According to a further aspect of the present invention, there is provided the use of a compound according to the first aspect for the manufacture of a medicament.

The medicament may be for use in the treatment or prophylaxis of asthma and/or glomerulonephritis and/or atherosclerosis.

The medicament may be for use in the treatment or prophylaxis of of the macro and/or microvascular complications associated with metabolic diseases, for example diabetes.

According to a further aspect of the present invention, there is provided the use of a compound according to the first aspect for the manufacture of a medicament for the treatment or prophylaxis of a disease or condition in which inhibition of acute inflammation and/or promotion of its resolution and/or suppression of fibrosis is beneficial.

According to a further aspect of the present invention, there is provided a method of treatment or prophylaxis of asthma and/or glomerulonephritis and/or atherosclerosis, the method comprising administering a therapeutically effective amount of a compound according to the first aspect or a composition according to the second aspect.

According to a further aspect of the present invention, there is provided a method of treatment or prophylaxis of a disease or condition in which inhibition of acute inflammation and/or promotion of its resolution and/or suppression of fibrosis is beneficial, the method comprising administering a therapeutically effective amount of a compound according to the first aspect or a composition according to the second aspect.

According to a further aspect of the present invention, there is provided a compound, composition, use or method substantially as described herein.

DETAILED DESCRIPTION OF THE EXAMPLE EMBODIMENTS

Embodiments of the present invention will now be described, by way of example only, with reference to the accompanying figures, in which:

FIGS. 1A-1C are graphs showing imidazole-lipoxin analogues (1R)-9 and (1S)-9 attenuating LPS-induced NFkB-driven luciferase activity. $1 \times 10^5$ THP-1 LUCIA monocytes were pre-treated for 30 min with native $LXA_4$ 1 (FIG. 1A), imidazole analogues 9 [(1R)-epimer (FIG. 1B) and (1S)-epimer (FIG. 1C)], vehicle or appropriate controls, at increasing doses ranging from $10^{-12}$ M up to $10^{-6}$ M. $10^8$ HKLM was used as positive control for NFkB activation. After 24 h from stimulation with 50 ng/ml of LPS, supernatants were collected and NFkB-driven luciferase was measured. (d) Data are expressed as % Relative Luminescence Unit relative to LPS alone ±SEM (n=3), *=p<0.05, =p<0.01, *=p<0.001. Graphs display the statistical analysis of the tested compound vs LPS.

Legend

Unt=Untreated cells (neg ctr)
Veh=Vehicle ctr (0.1% EtOH)
HKLM=Heat Killed *Listeria monocytogenes* (NFkB activation ctr) ($10^8$/ml)
LPS=Lipopolysaccharide (NFkB activation ctr) (50 ng/ml)
Dex=Dexamethasone ($10^{-6}$ M)
1=$LXA_4$ (native compound) ($10^{-12}$ M-$10^{-6}$ M)
(1R)-5=(1R) epimer of $LXA_4$-benzoanalogue ($10^{-12}$ M)
(1R)-9=(1R) epimer of $LXA_4$-imidazole analogue ($10^{-12}$ M-$10^{-6}$ M)
(1S)-9=(1S) epimer of $LXA_4$-imidazole analogue ($10^{-12}$ M-$10^{-6}$ M)

FIG. 2A-2E are graphs showing imidazole-lipoxin analogues (1R)-9 and (1S)-9 reduce LPS-induced Th1 cytokine release. $1 \times 10^5$ THP-1 LUCIA monocytes were pre-treated for 30 min with $10^{-1}$ M, $10^{-9}$ M or $10^{-7}$ M of LXA4 1 and imidazole-lipoxin analogues (1R)-9 and (1S)-9, vehicle or appropriate controls. After 24 h from stimulation with 50 ng/ml of LPS, supernatants were collected and IL1@ (FIG. 2A), IL6 (FIG. 2B), IL12p70 (FIG. 2C), IFNγ (FIG. 2D), and TNF-α (FIG. 2E) levels were measured. Data are expressed as % cytokine secretion relative to LPS alone ±SEM (n=3), *=p<0.05, =p<0.01, *=p<0.001.

Legend

Unt=Untreated cells (neg ctr)
Veh=Vehicle ctr (0.1% EtOH)
LPS=Lipopolysaccharide (NFkB activation ctr) (50 ng/ml)
Dex=Dexamethasone ($10^{-6}$ M)
1=$LXA_4$ (native compound) ($10^{-11}$ M; $10^{-9}$ M; $10^{-7}$ M)
(1R)-5=(1R) epimer of $LXA_4$-benzoanalogue ($10^{-2}$ M)
(1R)-9=(1R) epimer of $LXA_4$-imidazole analogue ($10^{-11}$ M; $10^{-9}$ M; $10^{-7}$ M)
(1S)-9=(1S) epimer of $LXA_4$-imidazole analogue ($10^{-11}$ M; $10^{-9}$ M; $10^{-7}$ M)

FIGS. 3A-3B are graphs illustrating that the imidazole-lipoxin analogues (1R)-9 and (1S)-9 do not elicit NFkB-driven luciferase activity in resting conditions. $1 \times 10^5$ THP-1 LUCIA monocytes were treated for 30 min with native (a) $LXA_4$ 1, its stable imidazole-lipoxin analogues (1R)-9 and (1S)-9, vehicle or appropriate controls, at increasing doses ranging from $10^{-12}$ M up to $10^{-6}$ M. After 24 h, supernatants were collected and NFkB-driven luciferase was measured. Data are expressed as % Relative Luminescence Unit relative to LPS alone ±SEM (n=3).

Legend

Unt=Untreated cells (neg ctr)
Veh=Vehicle ctr (0.1% EtOH)
HKLM=Heat Killed *Listeria monocytogenes* (NFkB activation ctr) ($10^8$/ml)
LPS=Lipopolysaccharide (NFkB activation ctr) (50 ng/ml)
Dex=Dexamethasone ($10^{-6}$ M)
1=$LXA_4$ (native compound) ($10^{-9}$ M)
(1R)-5=(1R) epimer of $LXA_4$-benzoanalogue ($10^{-2}$ M)
(1R)-9=(1R) epimer of $LXA_4$-imidazole analogue ($10^{-12}$ M-$10^{-6}$ M)
(1S)-9=(1S) epimer of $LXA_4$-imidazole analogue ($10^{-12}$ M-$10^{-6}$ M)

FIG. 4 shows formula and a graph showing quinoxaline-lipoxin analogue (1R)-CT-4-43 attenuating LPS-induced NFkB-driven luciferase activity. $1 \times 10^5$ THP-1 LUCIA monocytes were pre-treated for 30 min with native (a) $LXA_4$, (b) quinoxaline analogues (1R)-CT-4-43, vehicle or appropriate controls, at increasing doses ranging from $10^{-12}$ M up to $10^{-6}$ M. $10^7$ HKLM was used as positive control for NFkB activation. After 24 h from stimulation with 50 ng/ml of LPS, supernatants were collected and NFkB-driven luciferase was measured. (c) Data are expressed as % Relative Luminescence Unit relative to LPS alone ±SEM (n=3), *=p<0.05, =p<0.01, *=p<0.001. Graph displays the statistical analysis of the tested compound vs LPS (*) or of the quinoxaline analogue vs the same dose of $LXA_4$ ($).

Legend

Unt=Untreated cells (neg ctr)
Veh=Vehicle ctr (0.1% EtOH)
HKLM=Heat Killed *Listeria monocytogenes* (NFkB activation ctr) ($10^7$/ml)
LPS=Lipopolysaccharide (NFkB activation ctr) (50 ng/ml)
Dex=Dexamethasone ($10^{-6}$ M)
$LXA_4$=native compound ($10^{-2}$ M-$10^{-6}$ M)
(1R)-BLX=(1R) epimer of $LXA_4$-benzoanalogue ($10^{-2}$ M)
(1R)-CT-4-43=(1R) epimer of $LXA_4$-quinoxaline analogue ($10^{-2}$ M-$10^{-6}$ M)

FIG. 5 is a graph showing that the quinoxaline-lipoxin analogue (1R)-CT-4-43 does not elicit NFkB-driven luciferase activity in resting conditions. $1 \times 10^5$ THP-1 LUCIA monocytes were treated for 30 min with native (a) $LXA_4$, its stable imidazole-lipoxin analogues (1R)-CT-4-43, vehicle or appropriate controls, at increasing doses ranging from $10^{-12}$ M up to $10^{-6}$ M. After 24 h, supernatants were collected and NFkB-driven luciferase was measured. Data are expressed as % Relative Luminescence Unit relative to LPS alone ±SEM (n=3).

Legend

Unt=Untreated cells (neg ctr)
Veh=Vehicle ctr (0.1% EtOH)
HKLM=Heat Killed *Listeria monocytogenes* (NFkB activation ctr) ($10^7$/ml)

LPS=Lipopolysaccharide (NFkB activation ctr) (50 ng/ml)
Dex=Dexamethasone ($10^{-6}$ M)
LXA$_4$=native compound ($10^{-2}$ M-$10^{-6}$ M)
(1R)-BLX=(1R) epimer of LXA$_4$-benzoanalogue ($10^{-2}$ M)
(1R)-CT-4-43=(1R) epimer of LXA$_4$-quinoxaline analogue ($10^{-2}$ M-$10^{-6}$ M)

FIG. 6A-6C are graphs showing that quinoxaline-lipoxin analogue (1R)-CT-4-43 inhibits LPS-induced Th1 cytokine release. $1\times10^5$ THP-1 LUCIA monocytes were pre-treated for 30 min with $10^{-1}$ M, $10^{-9}$ M or $10^{-7}$ M of LXA$_4$ and quinoxaline-lipoxin analogue (1R)-CT-4-43, vehicle or appropriate controls. After 24 h from stimulation with 50 ng/ml of LPS, supernatants were collected and IL13 (FIG. 6A), IL6 (FIG. 6B), and IFNγ (FIG. 6C) levels were measured. Data are expressed as % cytokine secretion relative to LPS alone ±SEM (n=3), *=p<0.05, =p<0.01, *=p<0.001.

Legend

Unt=Untreated cells (neg ctr)
Veh=Vehicle ctr (0.1% EtOH)
LPS=Lipopolysaccharide (NFKB activation ctr) (50 ng/ml)
Dex=Dexamethasone ($10^{-6}$ M)
1=LXA$_4$ (native compound) ($10^{-11}$ M; $10^{-9}$ M; $10^{-7}$ M)
(1R)-5=(1R) epimer of LXA$_4$-benzoanalogue ($10^{-12}$ M)
(1R)-CT-4-43=(1R) epimer of LXA$_4$-quinoxaline analogue ($10^{-11}$ M; $10^{-9}$ M; $10^{-7}$ M)

FIG. 7 is of formula and a graph showing that the isoquinoline-lipoxin analogue RB3 attenuates LPS-induced NFkB-driven luciferase activity. $1\times10^5$ THP-1 LUCIA monocytes were pre-treated for 30 min with native (a) LXA$_4$, (b) isoquinoline analogues RB3, vehicle or appropriate controls, at increasing doses ranging from $10^{-12}$ M up to $10^{-6}$ M. $10^7$ HKLM was used as positive control for NFkB activation. After 24 h from stimulation with 50 ng/ml of LPS, supernatants were collected and NFkB-driven luciferase was measured. (c) Data are expressed as % Relative Luminescence Unit relative to LPS alone ±SEM (n=3), *=p<0.05, =p<0.01, *=p<0.001. Graph displays the statistical analysis of the tested compound vs LPS (*) or of the isoquinoline analogue vs the same dose of LXA$_4$ ($^\$$).

Legend

Unt=Untreated cells (neg ctr)
Veh=Vehicle ctr (0.1% EtOH)
HKLM=Heat Killed Listeria monocytogenes (NFkB activation ctr) ($10^7$/ml)
LPS=Lipopolysaccharide (NFkB activation ctr) (50 ng/ml)
Dex=Dexamethasone ($10^{-6}$ M)
LXA$_4$=native compound ($10^{12}$ M-$10^{-6}$ M)
(1R)-BLX=(1R) epimer of LXA$_4$-benzoanalogue ($10^{12}$ M)
(1R)-RB3=(1R) epimer of LXA$_4$-isoquinoline analogue ($10^{12}$ M-$10^{-6}$ M)

FIG. 8 is a graph showing that the isoquinoline-lipoxin analogue RB3 did not elicit NFkB-driven luciferase activity in resting conditions. $1\times10^5$ THP-1 LUCIA monocytes were treated for 30 min with native (a) LXA$_4$, its stable imidazole-lipoxin analogues (1R)-RB3, vehicle or appropriate controls, at increasing doses ranging from $10^{-12}$ M up to $10^{-6}$ M. After 24 h, supernatants were collected and NFkB-driven luciferase was measured. Data are expressed as % Relative Luminescence Unit relative to LPS alone ±SEM (n=3).

Legend

Unt=Untreated cells (neg ctr)
Veh=Vehicle ctr (0.1% EtOH)
HKLM=Heat Killed Listeria monocytogenes (NFkB activation ctr) ($10^7$/ml)
LPS=Lipopolysaccharide (NFkB activation ctr) (50 ng/ml)
Dex=Dexamethasone ($10^{-6}$ M)
LXA$_4$=native compound ($10^{-2}$ M-$10^{-6}$ M)
(1R)-BLX=(1R) epimer of LXA$_4$-benzoanalogue ($10^{-2}$ M)
(1R)-RB3=(1R) epimer of LXA$_4$-isoquinoline analogue ($10^{-1}$ M-$10^{-6}$ M)

FIG. 9A-9C are graphs showing that the isoquinoline-lipoxin analogue RB3 inhibit LPS-induced Th1 cytokine release. $1\times10^5$ THP-1 LUCIA monocytes were pre-treated for 30 min with $10^{-11}$ M, $10^{-9}$ M or $10^{-7}$ M of LXA$_4$ and isoquinoline-lipoxin analogue (1R)-RB3, vehicle or appropriate controls. After 24 h from stimulation with 50 ng/ml of LPS, supernatants were collected and IL1β(FIG. 9A), IL6 (FIG. 9B), and IL12p70 (FIG. 9C) levels were measured. Data are expressed as % cytokine secretion relative to LPS alone ±SEM (n=3), *=p<0.05, =p<0.01, *=p<0.001.

Legend

Unt=Untreated cells (neg ctr)
Veh=Vehicle ctr (0.1% EtOH)
LPS=Lipopolysaccharide (NFKB activation ctr) (50 ng/ml)
Dex=Dexamethasone ($10^{-6}$ M)
1=LXA$_4$ (native compound) ($10^{-11}$ M; $10^{-9}$ M; $10^{-7}$ M)
(1R)-5=(1R) epimer of LXA$_4$-benzoanalogue ($10^{-12}$ M)
RB3=(1R) epimer of LXA$_4$-isoquinoline analogue ($10^{-11}$ M; $10^{-9}$ M; $10^{-7}$ M)

Figure 15:
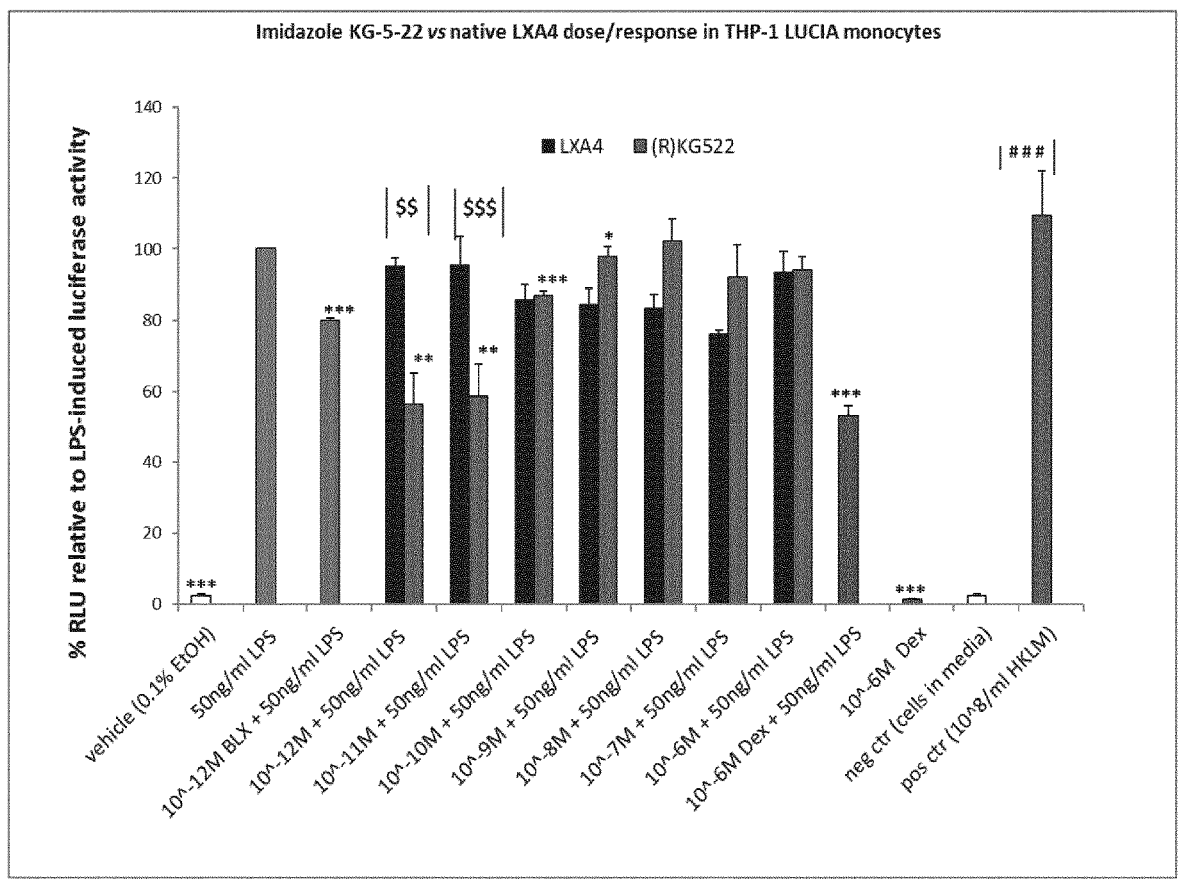
Figure 15:
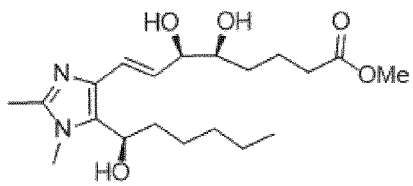

FIG. 15 shows the imidazole compound designated KG-5-22 attenuating LPS-induced NFkB-driven luciferase activity. $1\times10^5$ THP-1 LUCIA monocytes were pre-treated for 30 min with native LXA$_4$ 1 imidazole analogue KG-5-22 vehicle or appropriate controls, at increasing doses ranging from $10^{-1}$ M up to $10^{-6}$ M. $10^8$ HKLM was used as positive control for NFkB activation. After 24 h from stimulation with 50 ng/ml of LPS, supernatants were collected and NFkB-driven luciferase was measured. (d) Data are expressed as % Relative Luminescence Unit relative to LPS alone ±SEM (n=3), *=p<0.05, =p<0.01, *=p<0.001. Graphs display the statistical analysis of the tested compound vs LPS.

Legend

Figure 16:
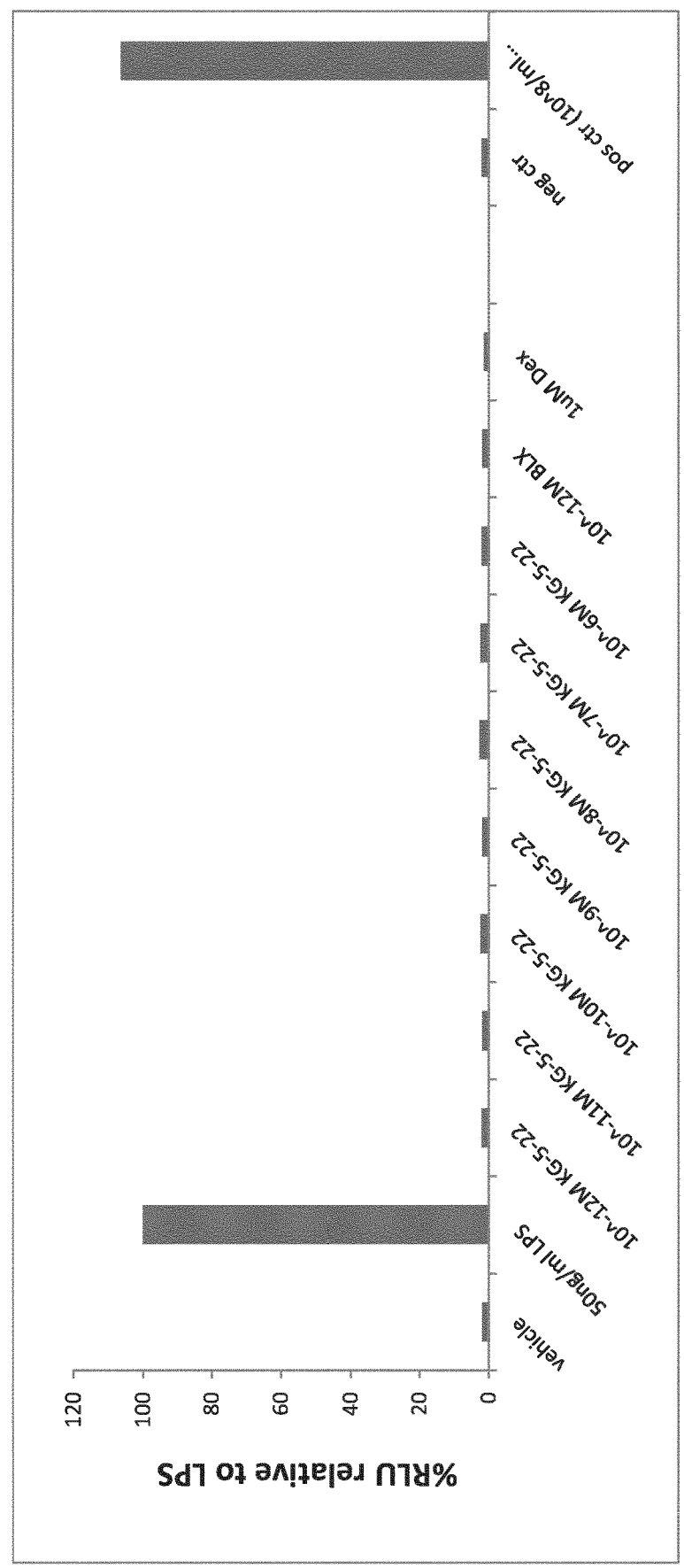

Untr=Untreated cells [neg ctrl]
Veh=Vehicle ctr (0.1% EtOH)
HKLM=heat killed *Listeria monocytogenes* (NFkB activation control]
LPS=Lipopolysaccharide (NFkB activation control; 50 ng/ml)
Dex=Dexamethasone (10-6)
BLx=Benzo LXA$_4$
LXA4 10-12 M-10-6 M
KG5-22 10-12 M-10-6 M FIG. 16 illustrates that the imidazole-lipoxin analogue KG5-22 (referred to as IM 6-R-6 in the experimental section below) does not elicit NFkB-driven luciferase activity in resting conditions. 1×105 THP-1 LUCIA monocytes were treated for 30 min with BenzoLXA4 1×10-12 M, the stable imidazole-lipoxin analogue KG-5-22, vehicle or appropriate controls, at increasing doses ranging from $10^{-12}$ M up to $10^{-6}$ M. After 24 h, supernatants were collected and NFkB-driven luciferase was measured. Data are expressed as % Relative Luminescence Unit relative to LPS alone ±SEM (n=3).

Legend

Figure 17:
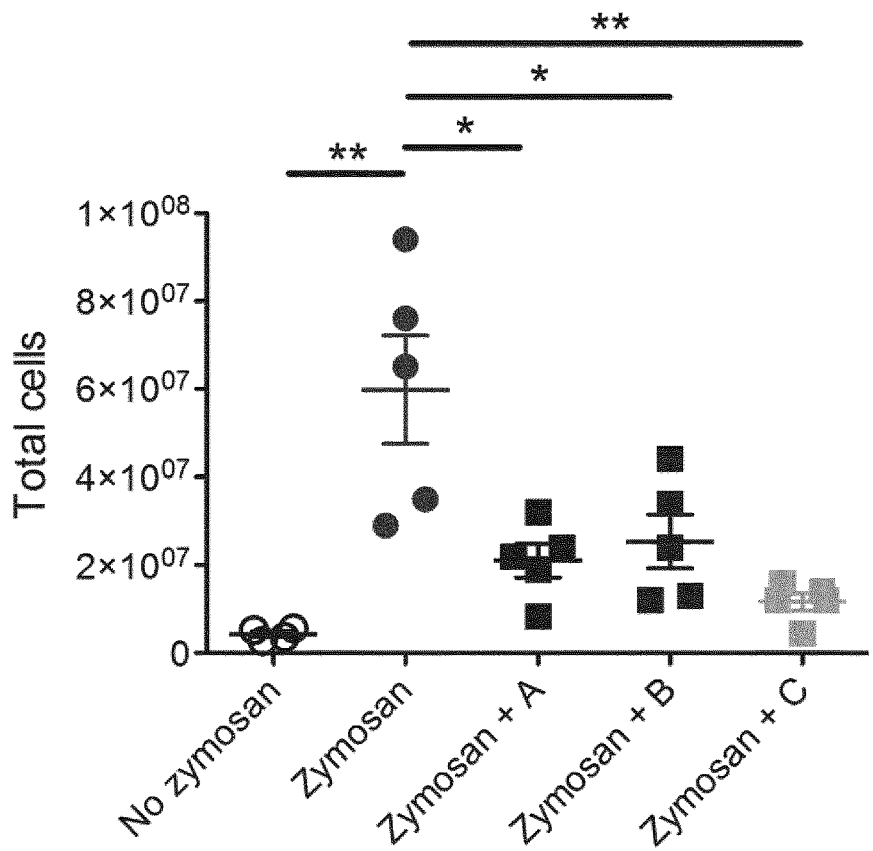

Untr=Untreated cells [neg ctrl]
Veh=Vehicle ctr (0.1% EtOH)
HKLM=heat killed *Listeria monocytogenes* (NFkB activation control]
LPS=Lipopolysaccharide (NFkB activation control; 50 ng/ml)
Dex=Dexamethasone (10-6)
BLx=Benzo LXA4
KG5-22 $10^{-12}$ M-$10^{-6}$ M FIG. 17 shows that the imidazole analogues X and Y attenuate acute inflammation in murine zymosan-induced peritonitis As shown in FIG. 17 zymosan [1 mg per mouse in 200 µl H2O] induced a massive influx of leukocytes detected in lavage 24 h post-zymosan. Pre-treatment of the animals with LXA4 [5 ng/g, 200 µl i.p. 30 minutes prior to zymosan injection and again, 1 hour after zymosan injection] significantly [p=0.0169] attenuated this response. Mean of total cell numbers=4.27×106/ml [basal]; 5.9×107 [vehicle pretreatment and zymosan]; 2.18×107 [LXA4 pretreatment and zymosan]. Pretreatment with (R) and (S) epimers of 9 also attenuated cell influx: 2.5×107/ml [pretreatment with (1R)-9 and zymosan; p=0.0368, relative to zymosan alone]; 1.16× 107 (1S)-9 [p=0.0048 relative to zymosan alone]. Importantly, (1R)-9 and (1S)-9 were administered at doses of 1.7 ng/g using the same regimen as LXA4. As anticipated the leukocyte influx was predominantly neutrophil [PMN]. PMN numbers were reduced to 35, 44 and 20% maximum response by LXA4, (1R)-9 and (1S)-9 epimers respectively.

Legend

Effect of LXA4 1 and imidazole-lipoxin analogues (1R)-9 and (1S)-9 on murine zymosan-induced peritonitis. Peritonitis was induced in groups of 5 male C57BL6/J mice by injection of zymosan (Sigma) i.p. (1 mg per mouse in 200 µl H2O). Mice were treated with LXA4 1; (5 ng/g); (1R)-9 (1.7 ng/g) or (1S)-9 (1.7 ng/g) (200 µl i.p.) 30 minutes prior to zymosan injection and again, 1 hour after zymosan injection. Treatments with LXA4 1, (1R)-9 and (1S)-9 are designated A, B and C respectively. Peritoneal cells were collected by lavage 24 hours after injection of zymosan. Cells were incubated with LIVE/DEAD Fixable Aqua stain (Molecular probes, Invitrogen) to isolate dead cells. Data shown are total cell counts/ml. Surface marker expression on peritoneal cells was assessed by flow cytometry with data collection on a CyAn (Beckman Coulter). Data were analyzed using FlowJo software (Tree Star). Cells were stained with BD Biosciences mAbs; Siglec-F-PE (E50-2440), F4/80-FITC (BM8), eBiosciences mAb; CD11b-PerCP (M1/70) and BioLegend mAbs; CD206-PECy7 (C068C2) and Ly6G-APCCy7 (1A8). Using appropriate isotype-controls, quadrants were drawn and data plotted on logarithmic scale density- or dot-plots to investigate the relative % of PMN, eoisiophils, M1 and M2 macrophgaes. The relative proportion of each cell type was unchanged by treatment with LX or LX analogues.

Figure 18:
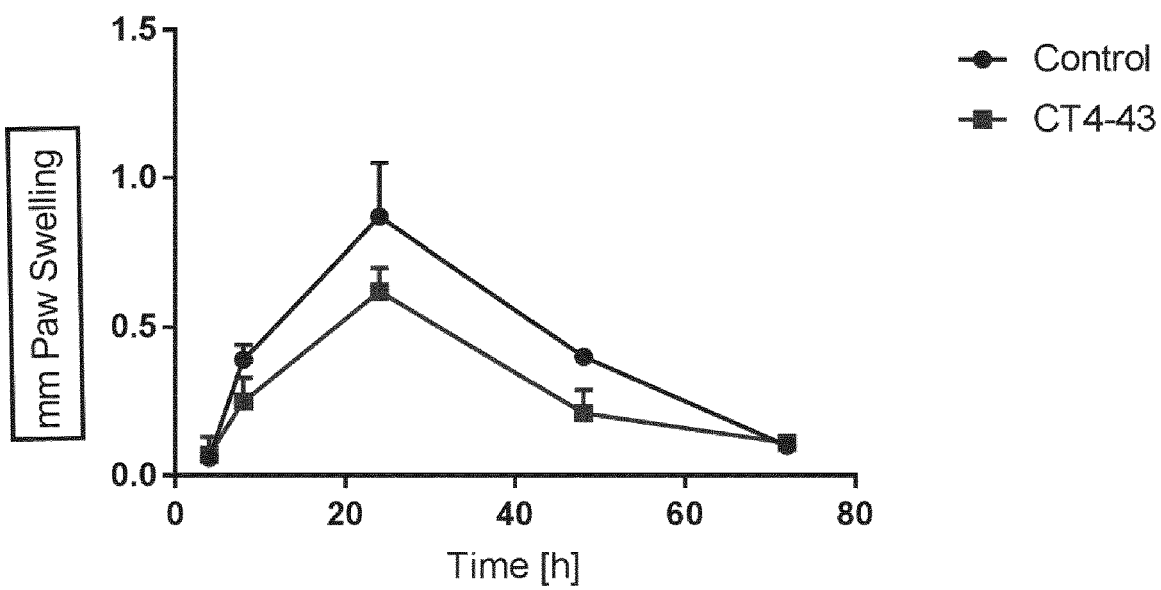

FIG. 18 shows that the quinoxaline analogue (1R)-CT-4-43 attenuates acute inflammation as measured in a murine model of carrageenan-induce paw swelling Legend CT4-43 attenuates carageenan-induced paw swelling—Mice [male C57Bl/6] were administered vehicle [0.01% EtOH] or CT4-4 [45 ng/mouse i.p] 30 mins before intrapaw injection of 1% carageenan. Paw swelling was monitored over time [4-72 h] using an external lever gauge [Kroeplin]. Data are presented as mean+/−SEM, n=3 mice/treatment group.

EXAMPLES—TESTING

The aims of the experiments were to evaluate the anti-inflammatory, pro-resolving and anti-fibrotic properties of stable LXA$_4$ analogues using a series of in vitro models of inflammation, resolution and fibrosis in order to find useful leads for the development of novel therapeutic modalities.

The structure of LXA$_4$ was modified to prevent: (i) reduction of the $C_9$-$C_{14}$ unit (at $C_{13}$-$C_{14}$); and (ii) oxidation of the $C_{15}$-$C_{20}$ unit (at $C_{15}$ and $C_{20}$).

The LX analogues were obtained by modifying the native compound as follows:

a) methyl esterification at C1 or lactonization of the upper chain;

b) replacing of the triene core with the heteroaromatic quinoxaline or isoquinoline groups; and c) shortening or extending the length of the lower chain (from 6C of LXA4 □ to 4C or 8C).

In particular, quinoxaline- and isoquinoline-derivatives (as shown in Table A below) were tested for their anti-inflammatory properties.

TABLE A

| Name | Aromatic moiety C₁-C₈ Unit | C₉-C₁₄ unit | C₁₅-C₂₀ unit | OH— in C₁₅ | Structure |
|---|---|---|---|---|---|
| (1R)-CT4-43 | Quinoxaline | LXA₄ ester derivative (methyl insertion) 8C chain (same length as LXA₄) | "2,3-quinoxaline" core insertion | 6C chain (same length as LXA₄) | (R) configuration | |
| (1S)-CT4-93 | Quinoxaline | LXA₄ ester derivative (methyl insertion) 8C chain (same length as LXA₄) | "2,3-quinoxaline" core insertion | 6C chain (same length as LXA₄) | (S) configuration | |
| (1R)-CT4-63 | Quinoxaline | LXA₄ ester derivative (methyl insertion) 8C chain (same length as LXA₄) | "2,3-quinoxaline" core insertion | 8C chain (2C longer than LXA₄) | (R) configuration | |
| (1S)-CT4-53 | Quinoxaline | LXA₄ ester derivative (methyl insertion) 8C chain (same length as LXA₄) | "2,3-quinoxaline" core insertion | 8C chain (2C longer than LXA₄) | (S) configuration | |
| (1R)-CT4-68 | Quinoxaline | LXA₄ ester derivative (methyl insertion) 8C chain (same length as LXA₄) | "2,3-quinoxaline" core insertion | 4C chain (2C shorter than LXA₄) | (R) configuration | |
| (1S)-CT4-73 | Quinoxaline | LXA₄ ester derivative (methyl insertion) 8C chain (same length as LXA₄) | "2,3-quinoxaline" core insertion | 4C chain (2C shorter than LXA₄) | (S) configuration | |

TABLE A-continued

| Name | Aromatic moiety | $C_1$-$C_8$ Unit | $C_9$-$C_{14}$ unit | $C_{15}$-$C_{20}$ unit | OH— in $C_{15}$ | Structure |
|---|---|---|---|---|---|---|
| (1R)-DM-163-RB3 | Isoquinoline | LXA$_4$ ester derivative (methyl insertion) 8C chain (same length as LXA$_4$) | "1,3-isoquinoline" core insertion | 6C chain (same length as LXA$_4$) | (R) configuration | 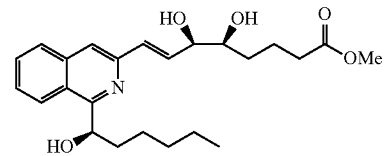 [SMILES: CCCCC[C@@H](O)c1nc(/C=C/[C@@H](O)[C@@H](O)CCCC(=O)OC)cc2ccccc12] |
| (1S)-DM-162 | Isoquinoline | LXA$_4$ ester derivative (methyl insertion) 8C chain (same length as LXA$_4$) | "1,3-isoquinoline" core insertion | 6C chain (same length as LXA$_4$) | (S) configuration | 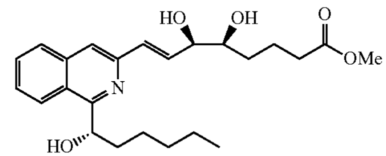 [SMILES: CCCCC[C@H](O)c1nc(/C=C/[C@@H](O)[C@@H](O)CCCC(=O)OC)cc2ccccc12] |
| (1S)-DM-178-SB4 | Isoquinoline | LXA$_4$ lactone derivative 8C cyclized chain (same length as LXA$_4$) | "1,4-isoquinoline" core insertion | 6C chain (same length as LXA$_4$) | (S) configuration | 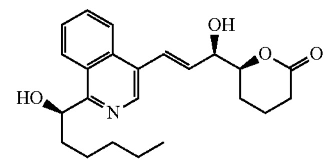 [SMILES: CCCCC[C@@H](O)c1ncc(/C=C/[C@@H](O)[C@@H]2CCCC(=O)O2)c2ccccc12] |
| (1S)-DM-178-SA4 | Isoquinoline | LXA$_4$ lactone derivative 8C cyclized chain (same length as LXA$_4$) | "1,4-isoquinoline" core insertion | 6C chain (same length as LXA$_4$) | (S) configuration | 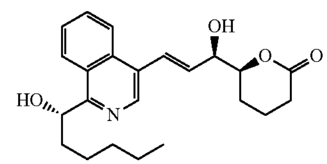 [SMILES: CCCCC[C@H](O)c1ncc(/C=C/[C@@H](O)[C@@H]2CCCC(=O)O2)c2ccccc12] |

Compound (1R)-CT4-43 is referred to as (1R)-6 in the experimental section below.

Compound (1S)-CT4-93 is referred to as (1S)-6 in the experimental section below.

Compound (1R)-CT4-63 is referred to as (1R)-7 in the experimental section below.

Compound (1S)-CT4-53 is referred to as (1S)-7 in the experimental section below.

Compound (1R)-CT4-68 is referred to as (1R)-5 in the experimental section below.

Compound (1S)-CT4-73 is referred to as (1S)-5 in the experimental section below.

Compound (1R)-DM-163-RB3 is referred to as (1R)-16 in the experimental section below.

Compound (1S)-DM-162 is referred to as (1S)-16 in the experimental section below.

Compound (1R)-DM-178-SB4 is referred to as (1R)-48 in the experimental section below.

Compound (1S)-DM-178-SA4 is referred to as (1S)-48 in the experimental section below.

Experimental Design

The experiments were based around a model which utilised $1 \times 10^5$/ml THP-1 monocytes stably expressing NFkB luciferase reporter gene (LUCIA).

Anti-Inflammatory Activity

Anti-inflammatory activity was assessed by testing 10 analogues (6 quinoxalines & 4 isoquinolines) in presence & absence of lipopolysaccharide (LPS). For each analogue, a dose-response from $10^{-12}$ M up to $10^{-6}$ M was performed. The vehicle control corresponded to 0.1% Ethanol. NFkB activator, Heat-Killed *Listeria Monocytogenes* (HKLM) ($10^7$ cells/ml), were used as positive control for luciferase induction. $10^{-6}$ M Dexamethasone (Dex) was used as positive control for luciferase inhibition. $10^{-1}$ M Benzo-lipoxin A4 (BLX) was used as positive control for $LXA_4$ analogues.

Cytotoxicity Prior to functional assay testing, all compounds were screened for any cytotoxic effect, in the presence & absence of LPS, measuring the level of lactate dehydrogenase (LDH) released at $A_{490nm}$.

Statistical Analysis

A 2-tailed, assuming unequal variance T-test analysis was performed on three independent experiments for each assay. P-values were considered significant when $p<0.05$. If $p<0.05$, then * or $; if $p<0.01$, then  or $$ or ##; if $p<0.001$, then * or $$$ or ###.

Results

The results of the experiments are shown in the appended figures.

Figure 1A:
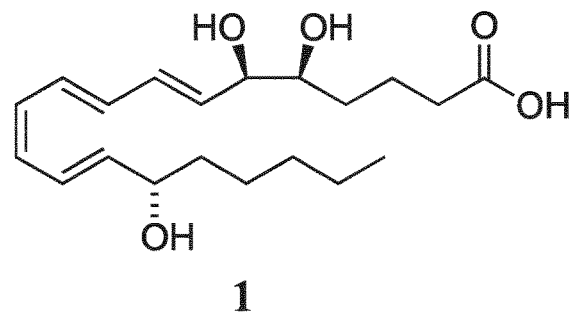
Figure 1A:
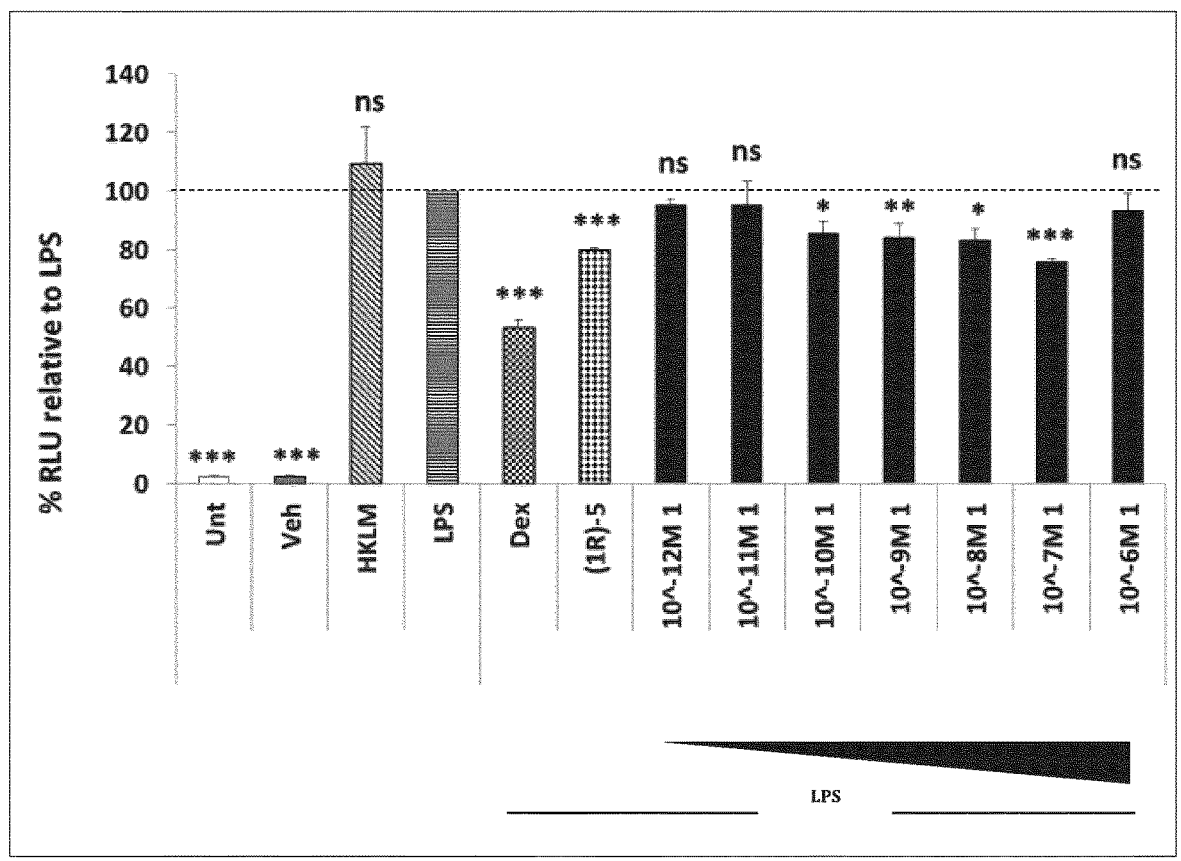
Figure 1B:
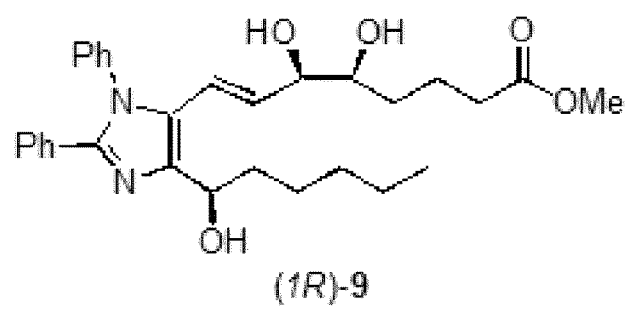
Figure 1B:
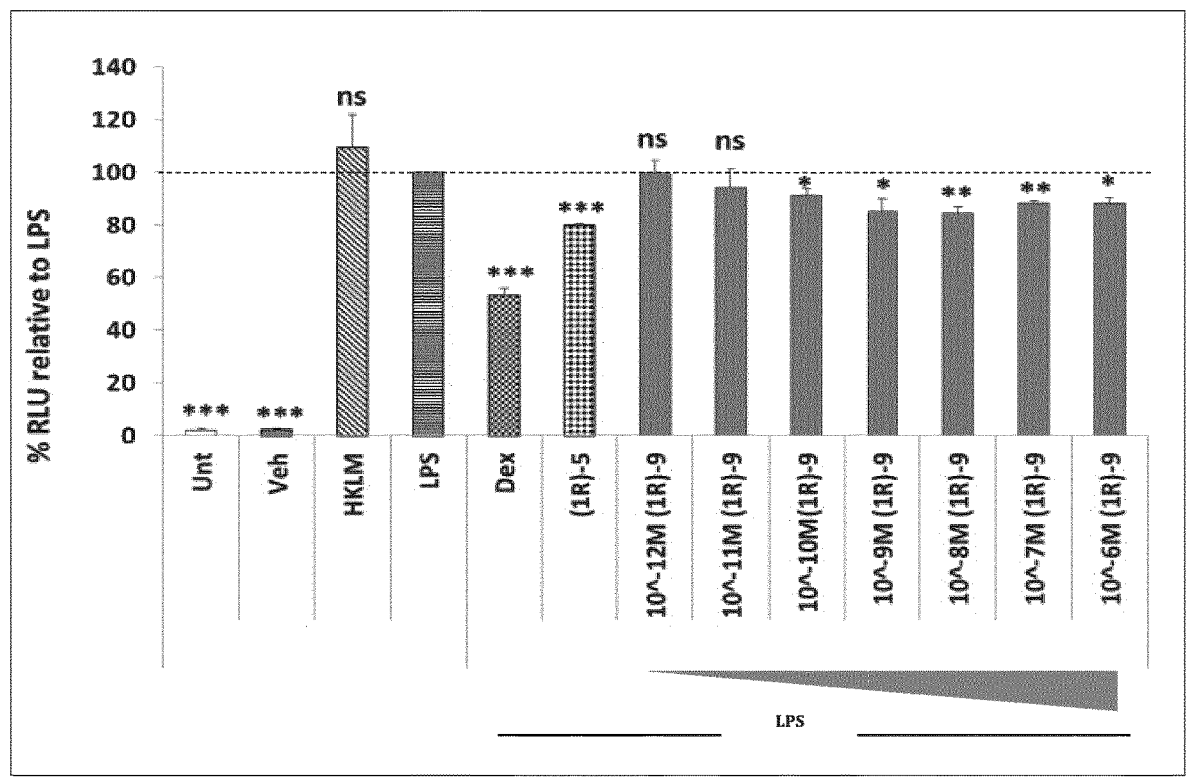
Figure 1C:
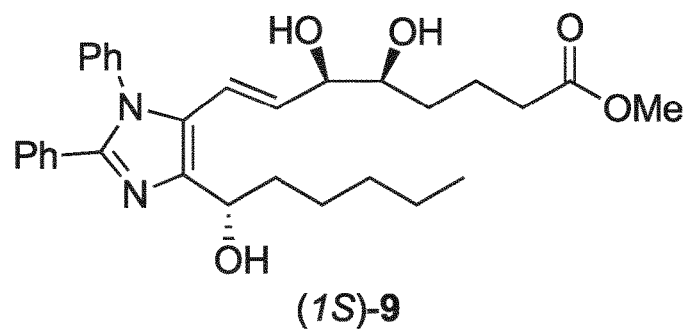
Figure 1C:
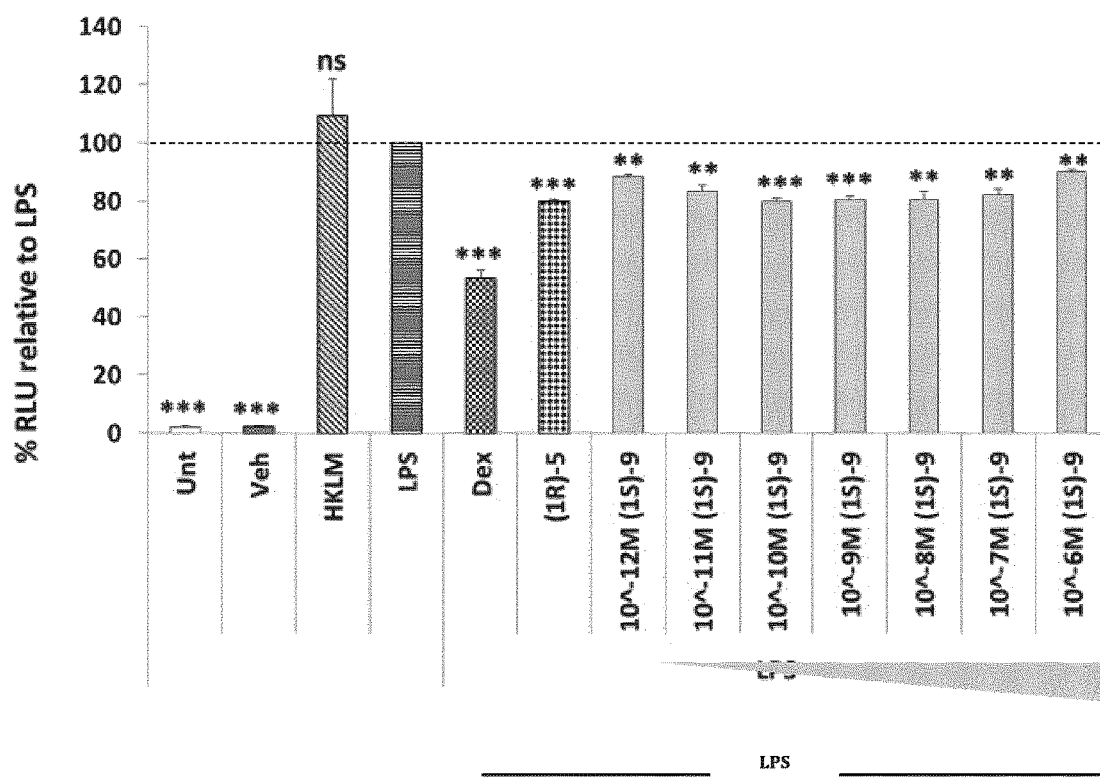
Figure 2A:
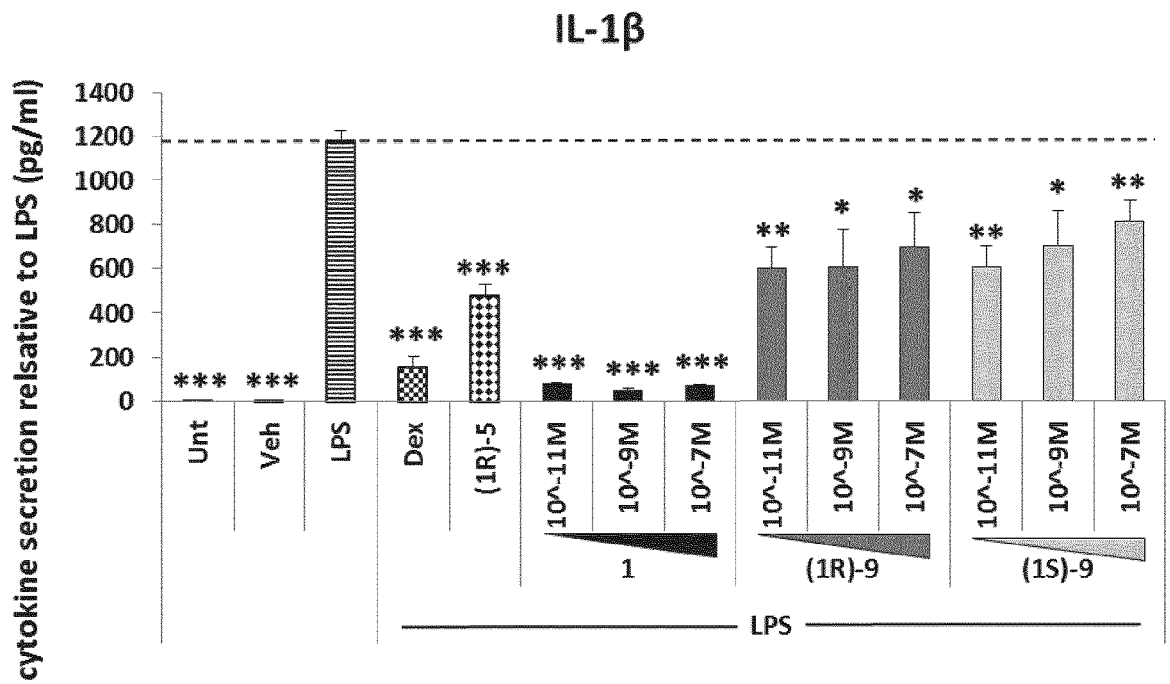
Figure 2B:
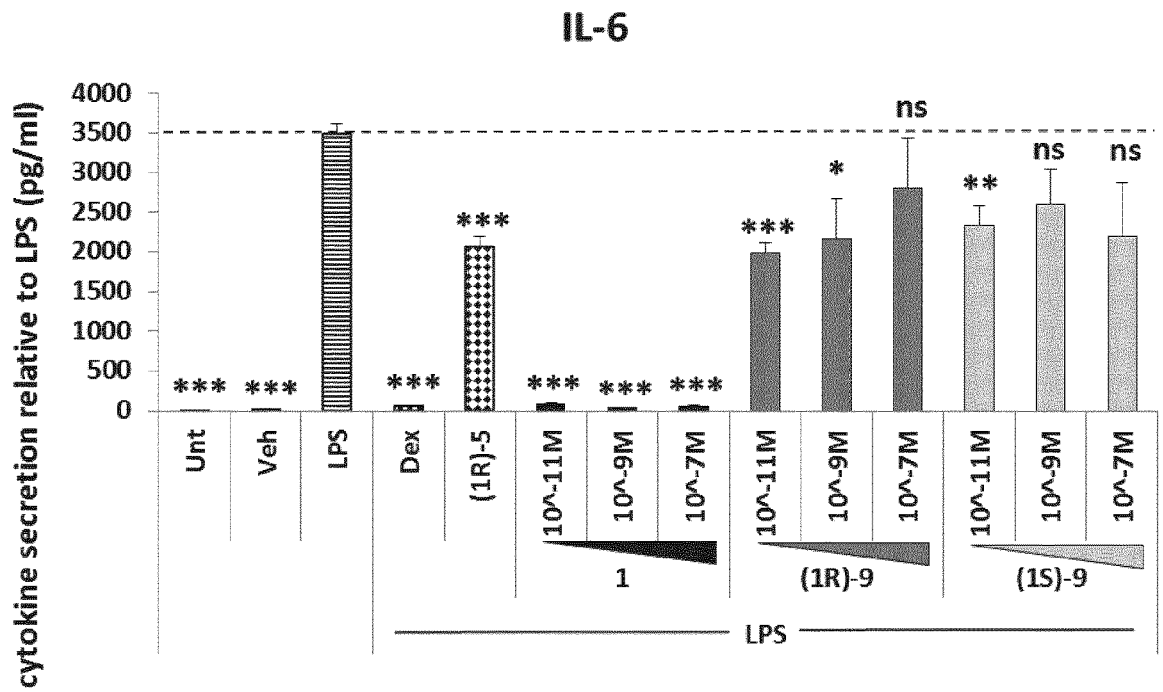
Figure 2C:
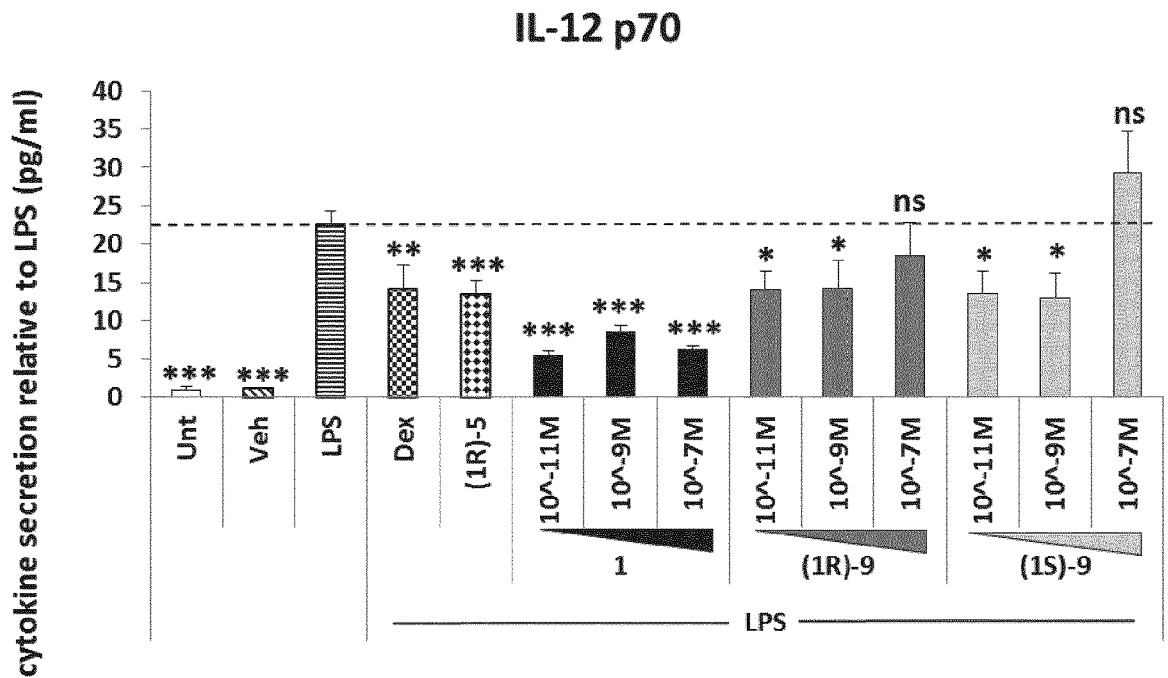
Figure 2D:
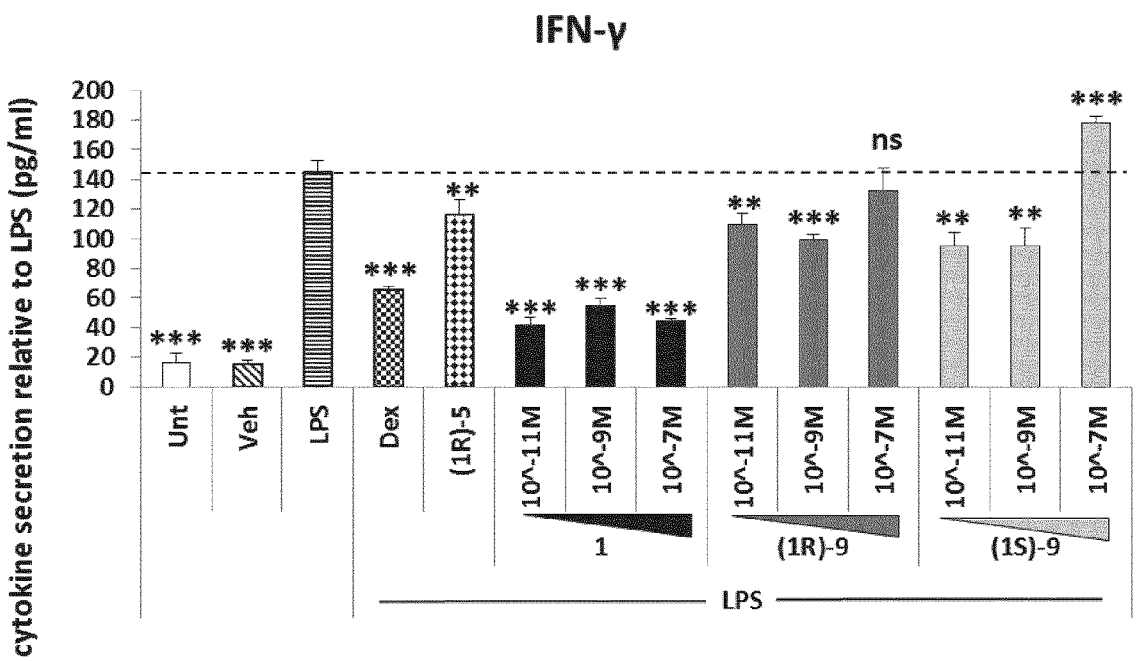
Figure 2E:
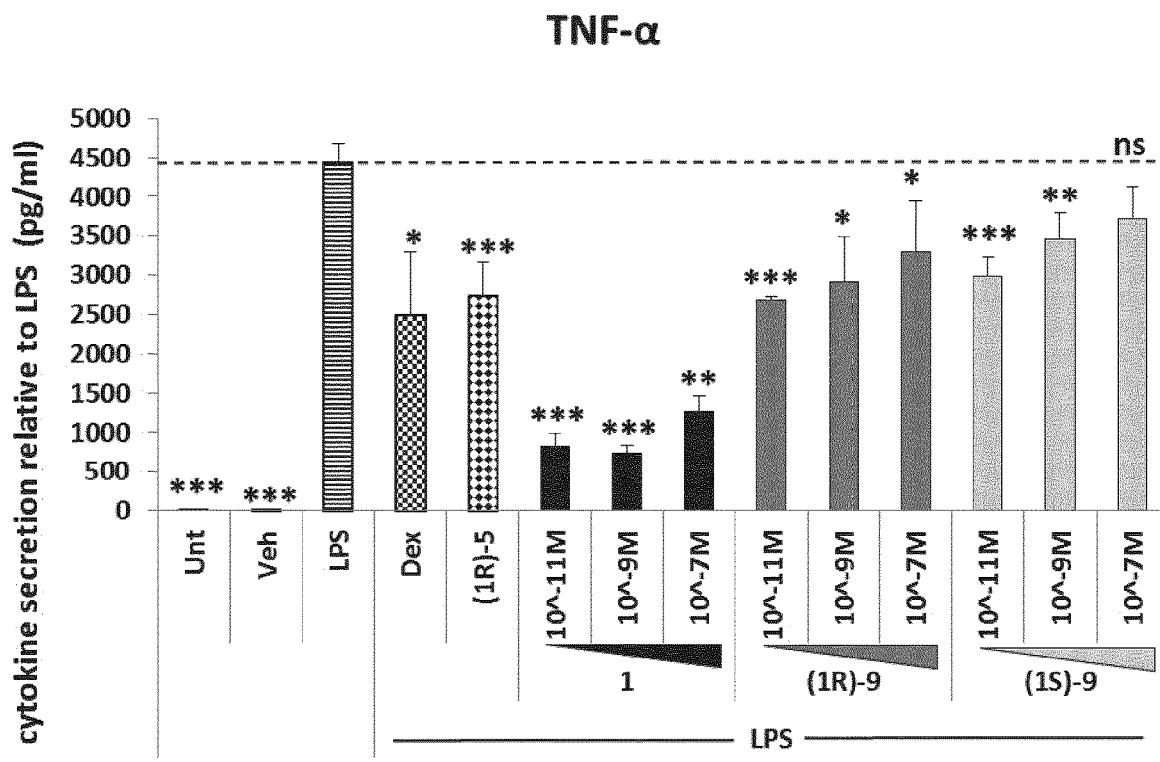
Figure 3A:
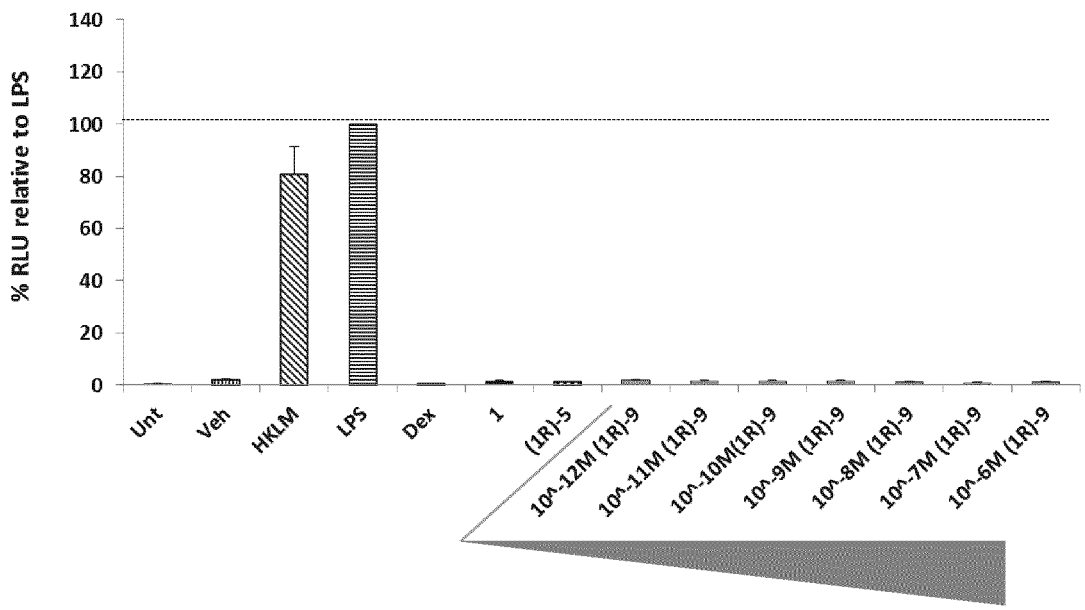
Figure 3B:
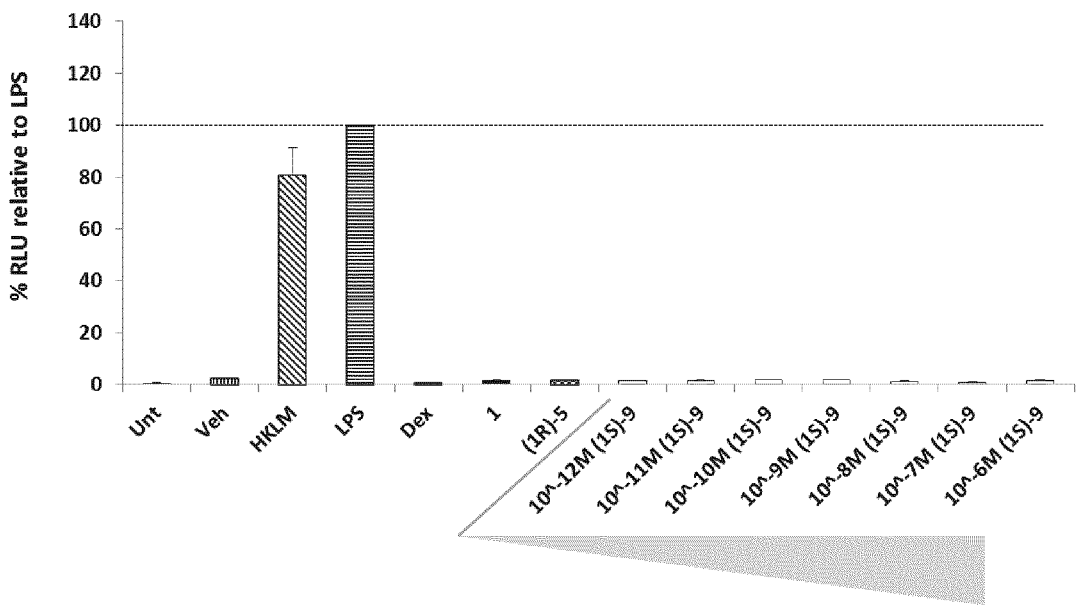
Figure 4:
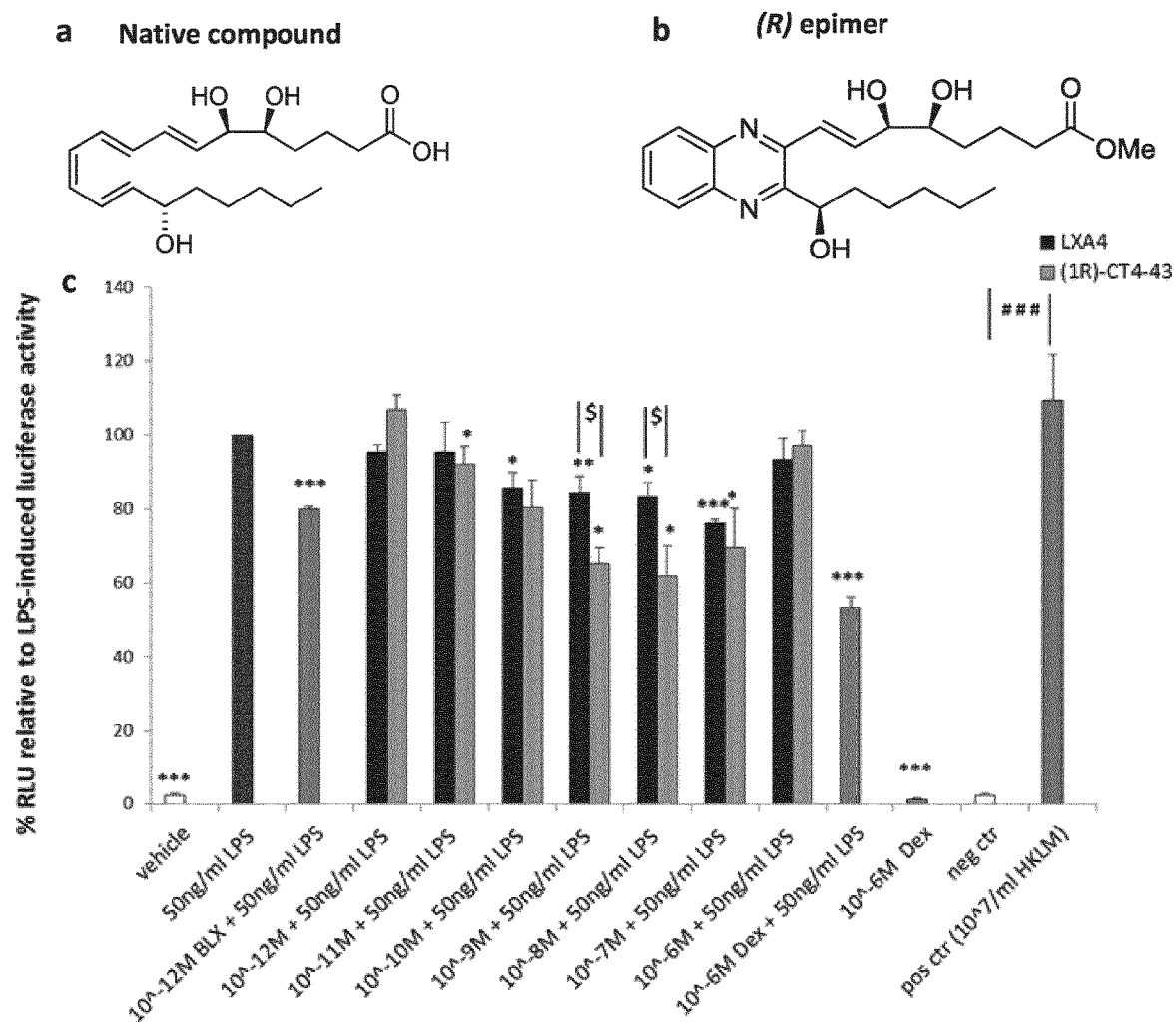
Figure 5:
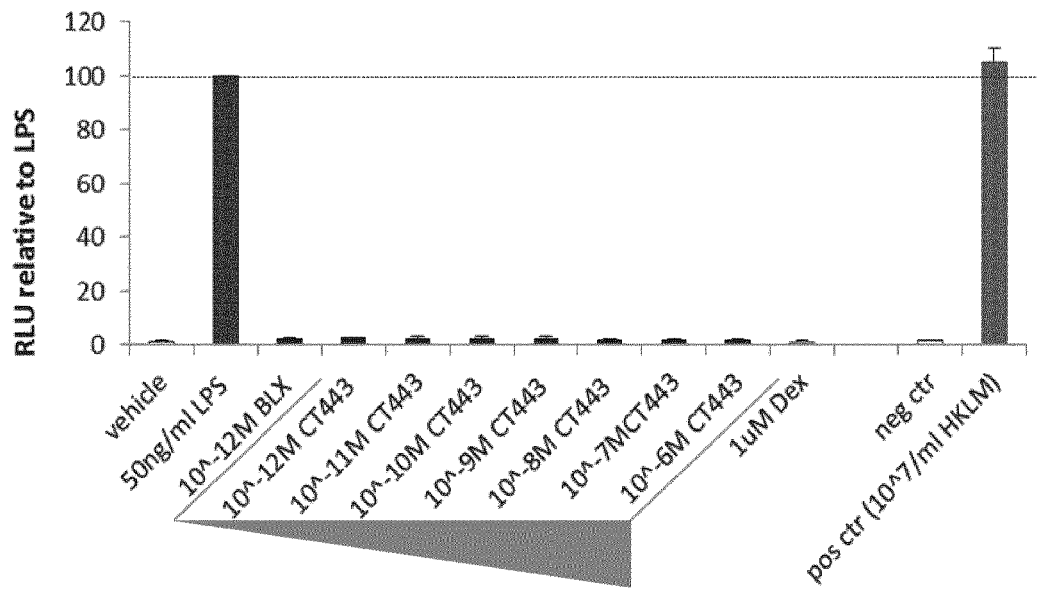
Figure 6A:
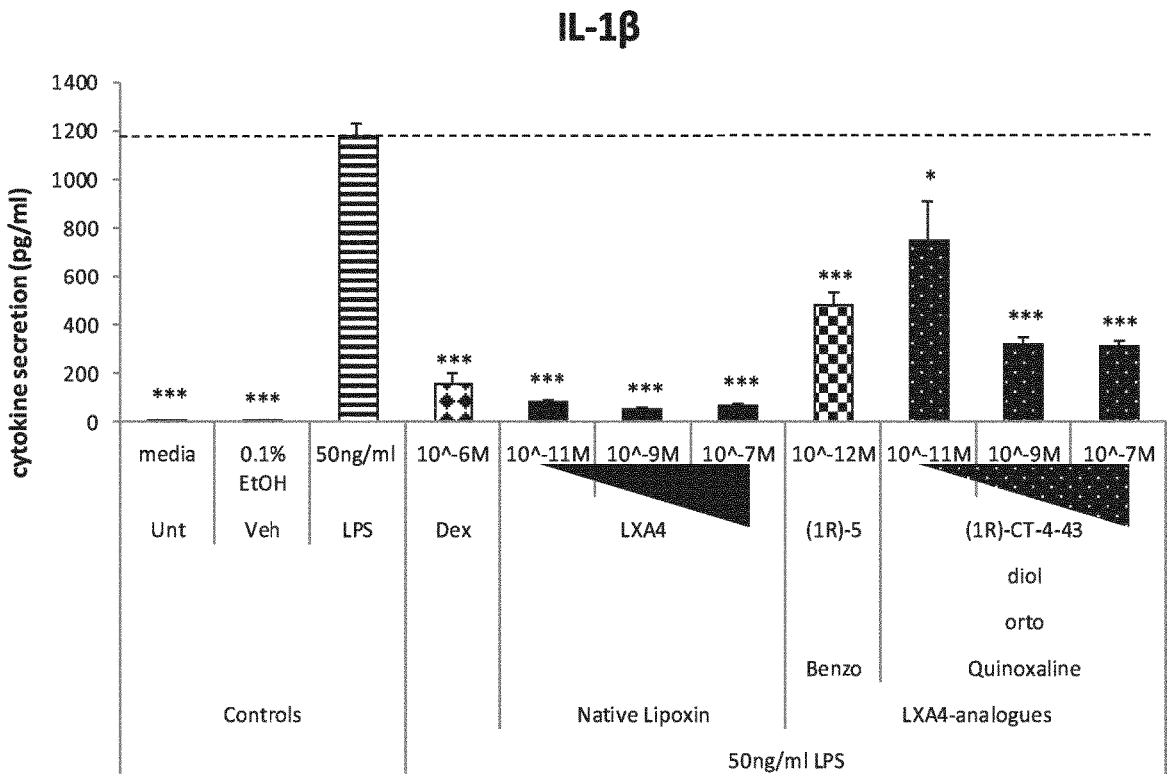
Figure 6B:
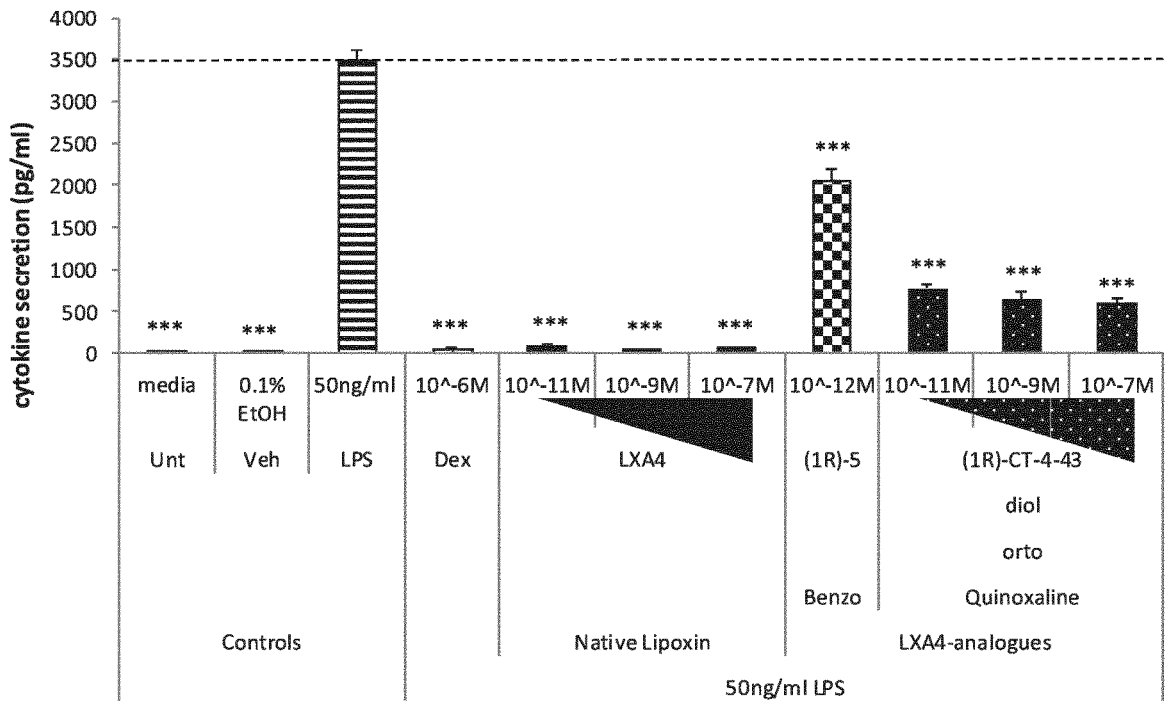
Figure 6C:
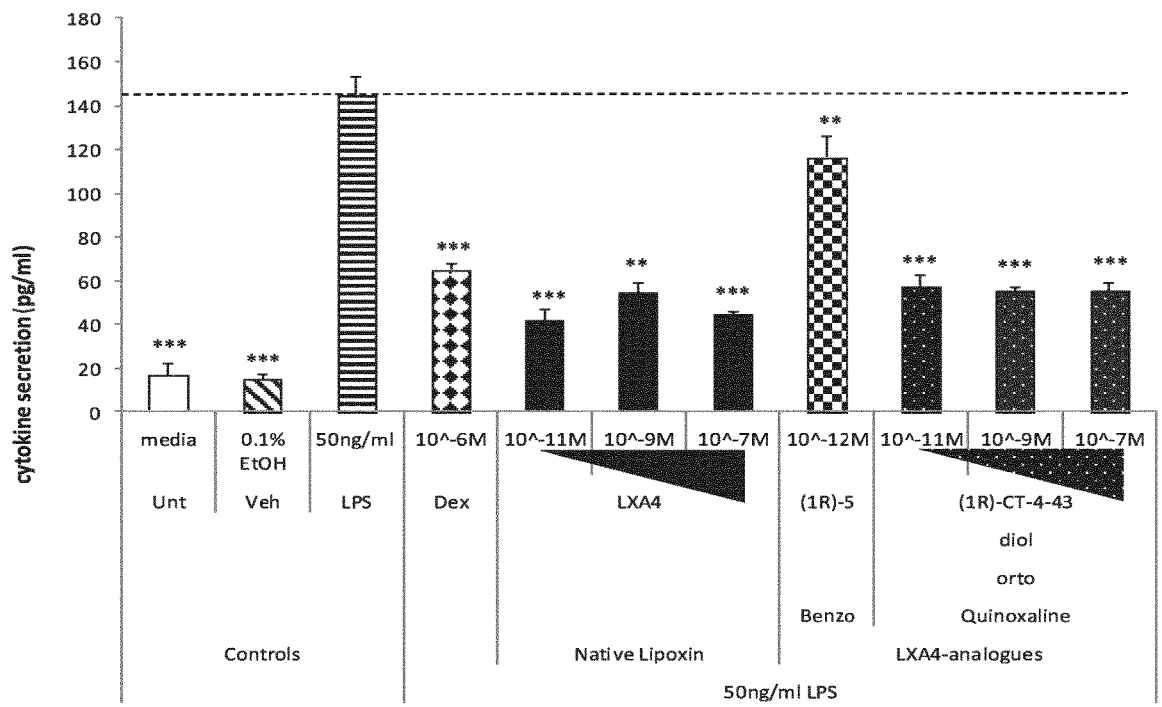
Figure 10:
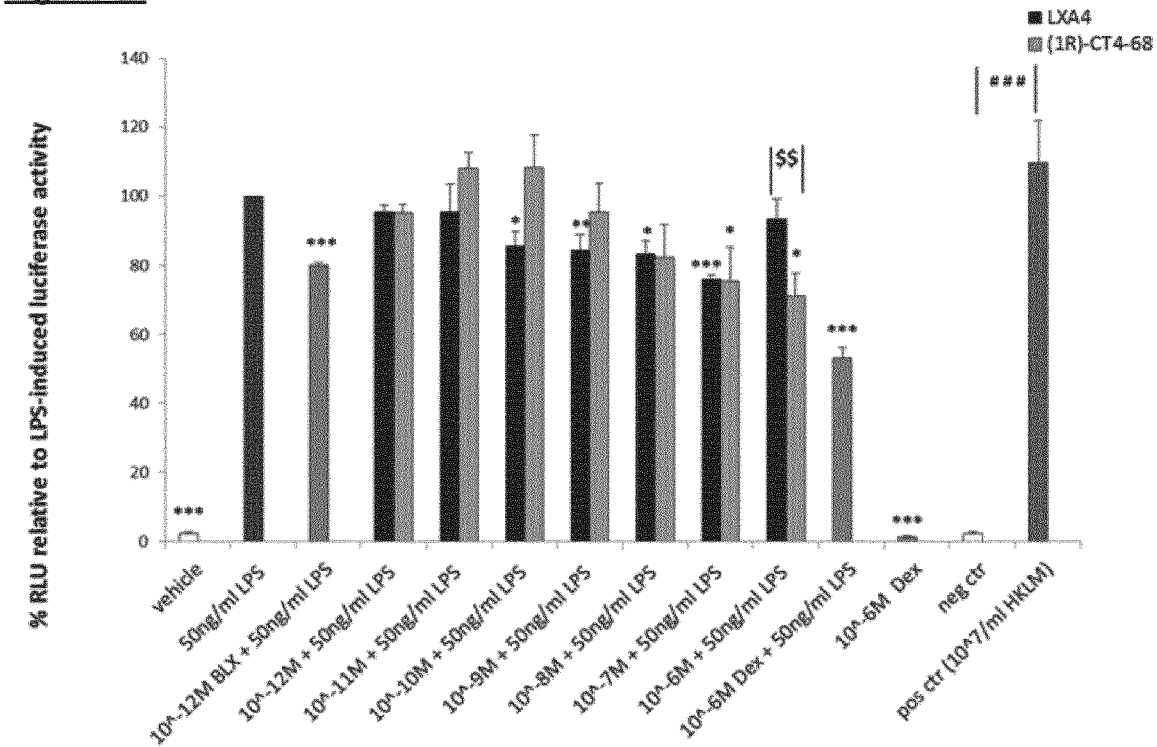
FIG. 10 is a graph showing that the quinoxaline-lipoxin analogue (1R)-CT4-68 attenuates LPS-induced NFkB-driven luciferase activity.
Figure 11:
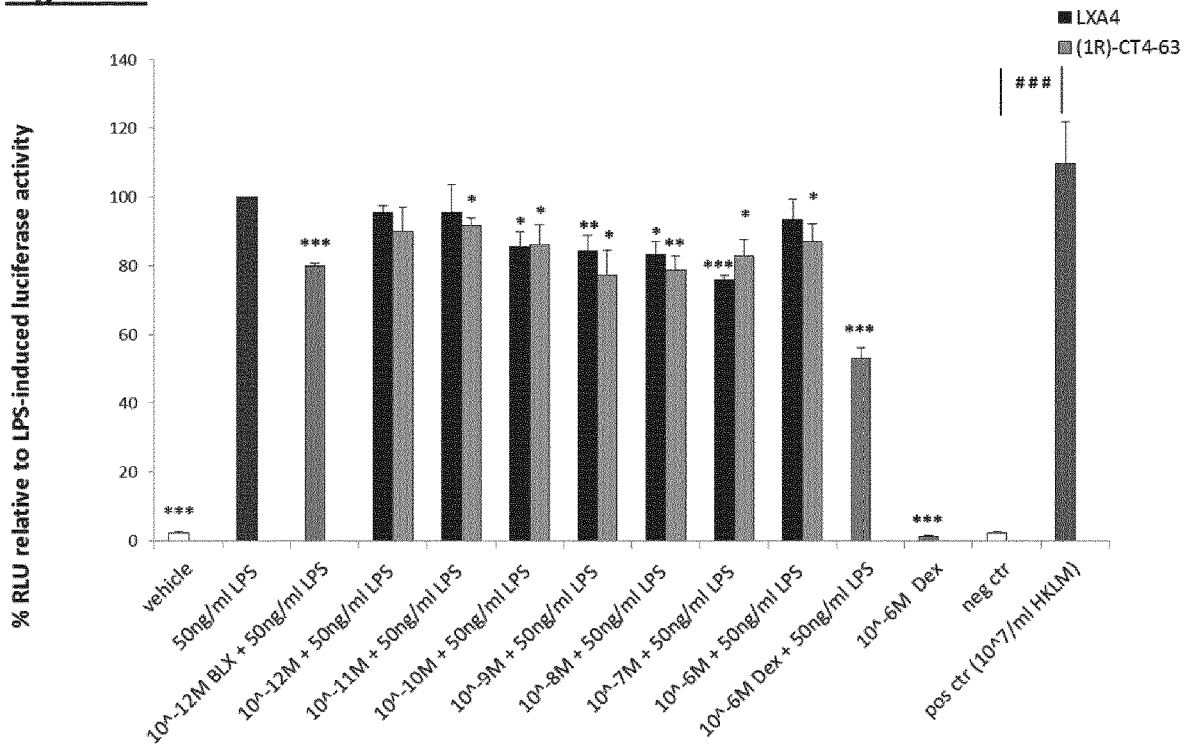
FIG. 11 is a graph showing that the quinoxaline-lipoxin analogue (1R)-CT4-63 attenuates LPS-induced NFkB-driven luciferase activity.

In particular, with reference to FIGS. 4, 10 and 11, the dose-response for $LXA_4$ vs quinoxaline-derivatives for LPS-induced NFKB luciferase activity is shown. Cells were seeded in 96-well plates and pre-treated with increasing doses of $LXA_4$, analogues or controls for 30 min, followed by 24 h of co-incubation with 50 ng/ml LPS. $LXA_4$ (denoted by black bars in the figures) maximal inhibition is reached at 100 nM (by 24±1.1% relative to LPS). CT4-43 significantly reduced ($=p<0.05$) NFkB activity, compared to the corresponding $LXA_4$ dosage, at 1 and 10 nM (respectively, by 38.2±8.2% and by 34.8±4.2%). CT4-68 significantly reduced ($$=p<0.01$) NFkB activity, compared to $LXA_4$, at 1 uM (by 28.9±6.6%). CT4-63 had its maximum inhibition at 1 nM (by 22.8±7.4%), but not significantly different from $LXA_4$. The relative "S" epimers presented similar or slightly less potent response (data not shown). (*=statistical analysis vs LPS; $=statistical analysis vs $LXA_4$)

Figure 7:
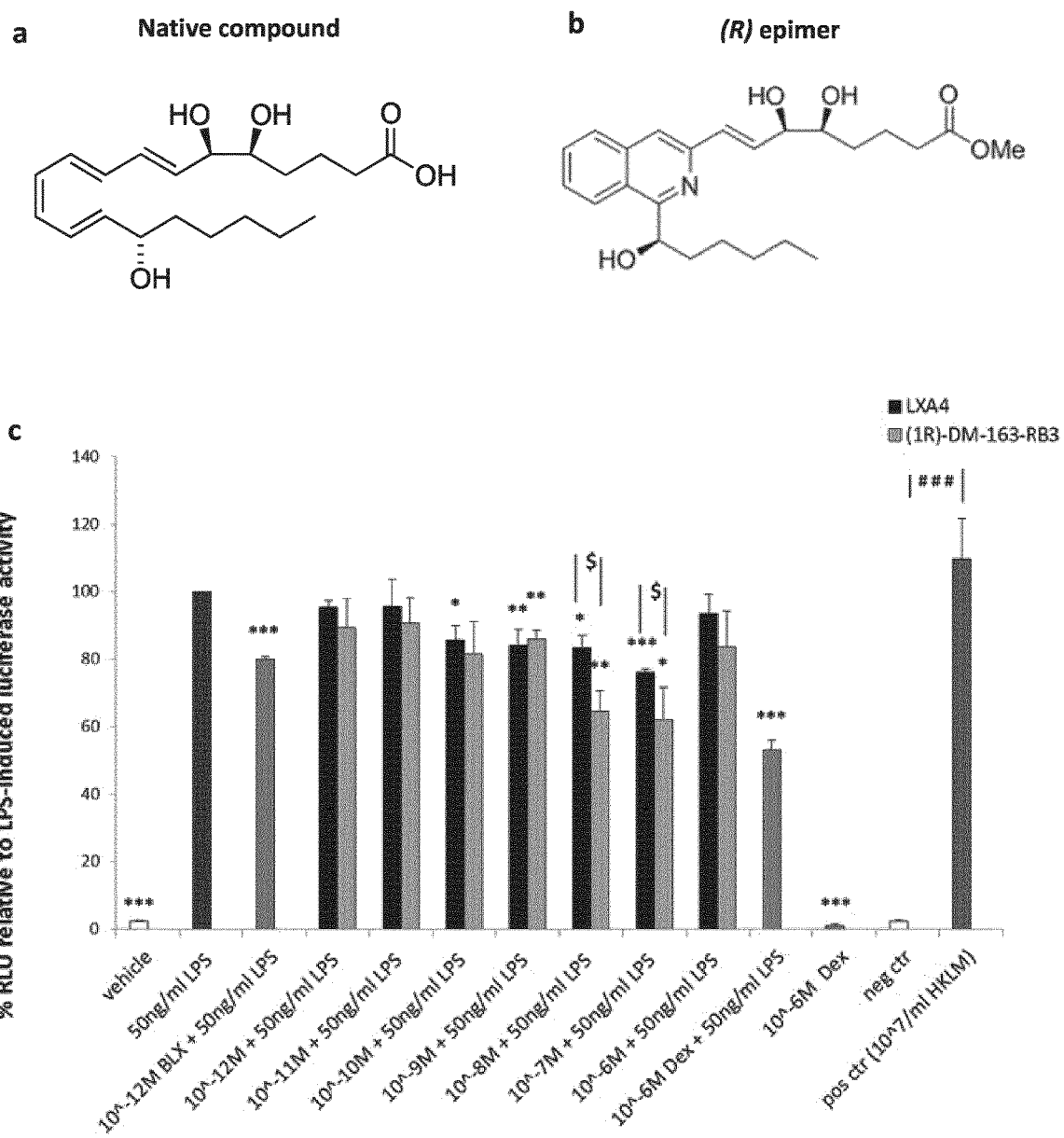
Figure 8:
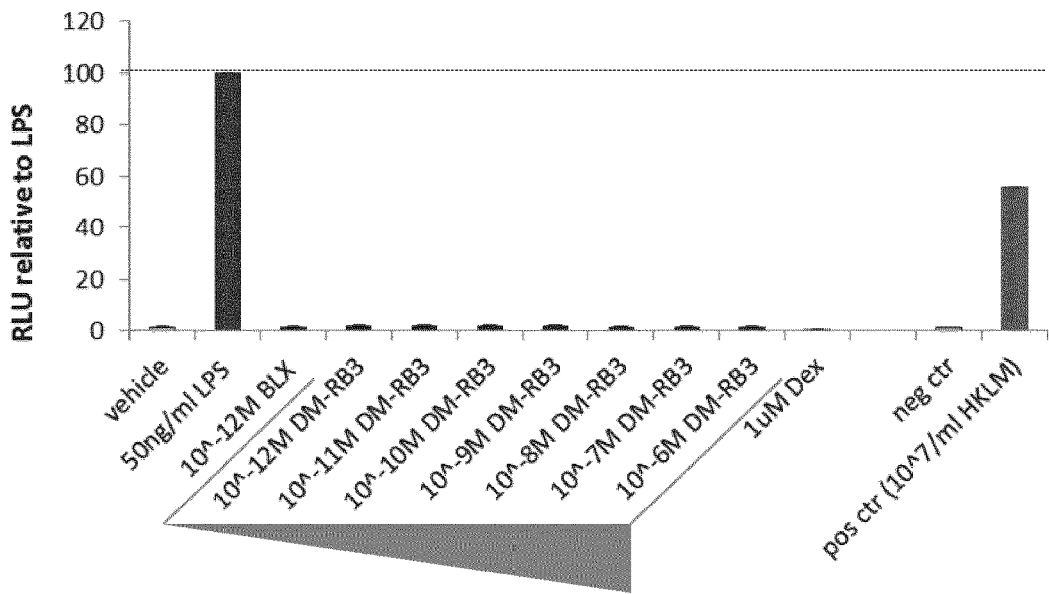
Figure 9A:
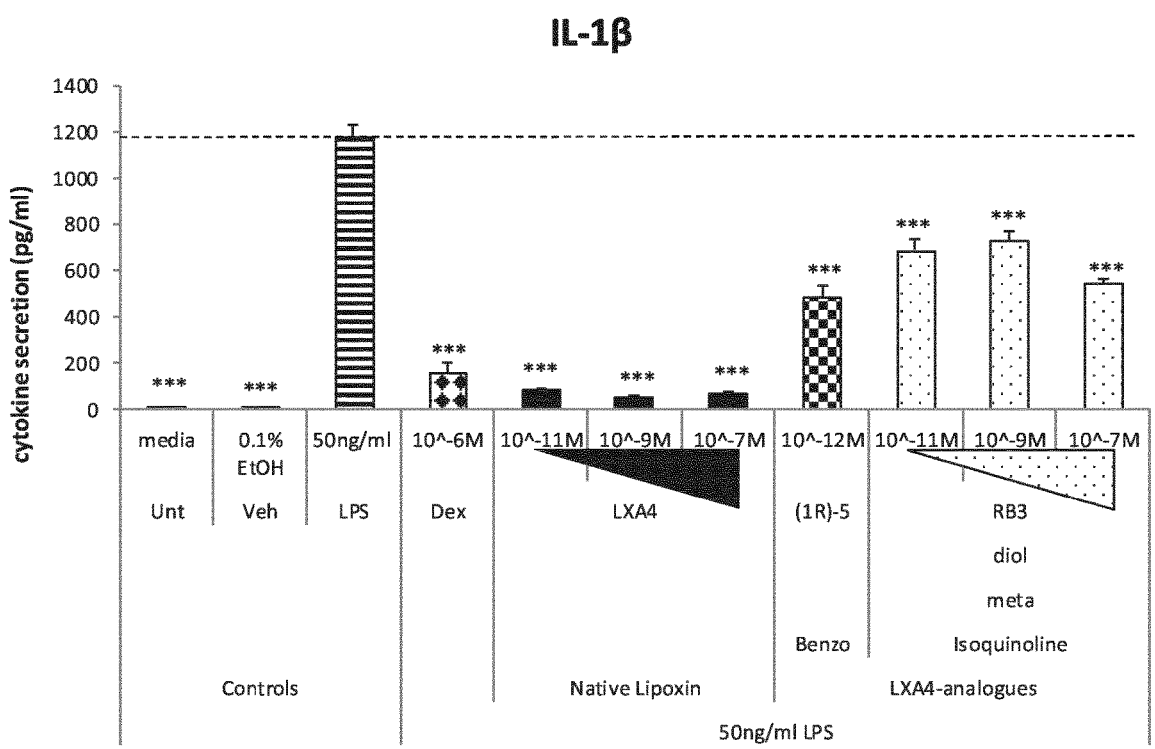
Figure 9B:
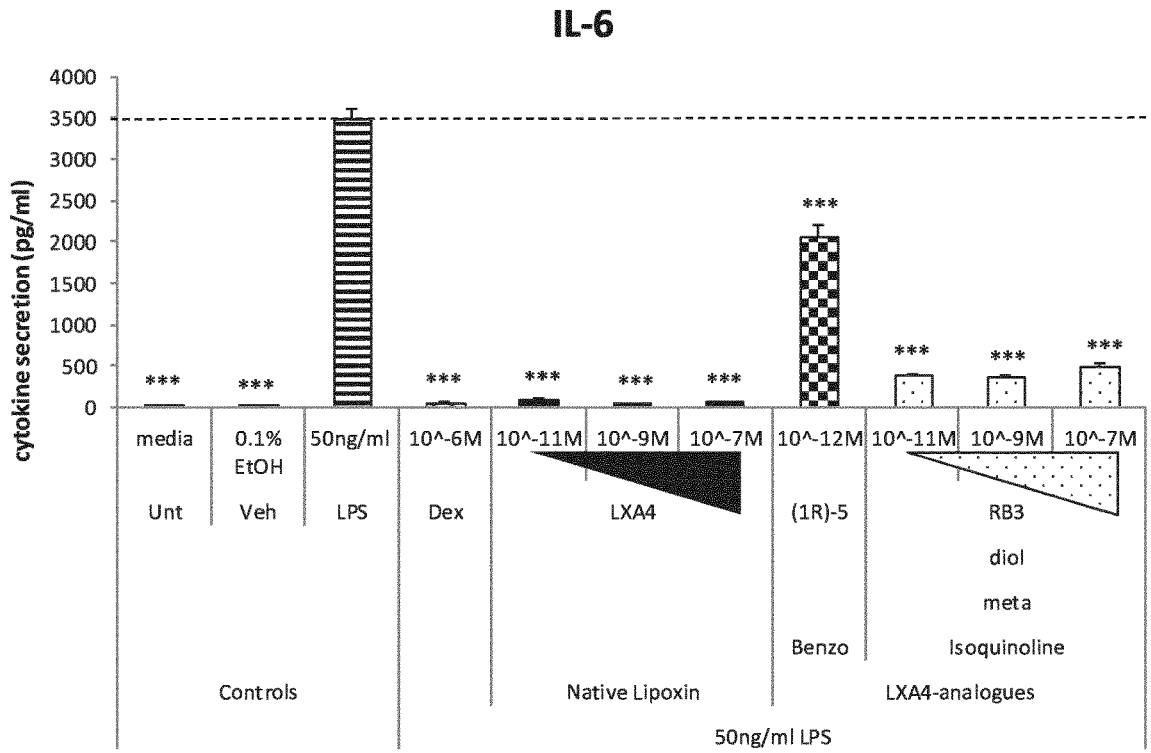
Figure 9C:
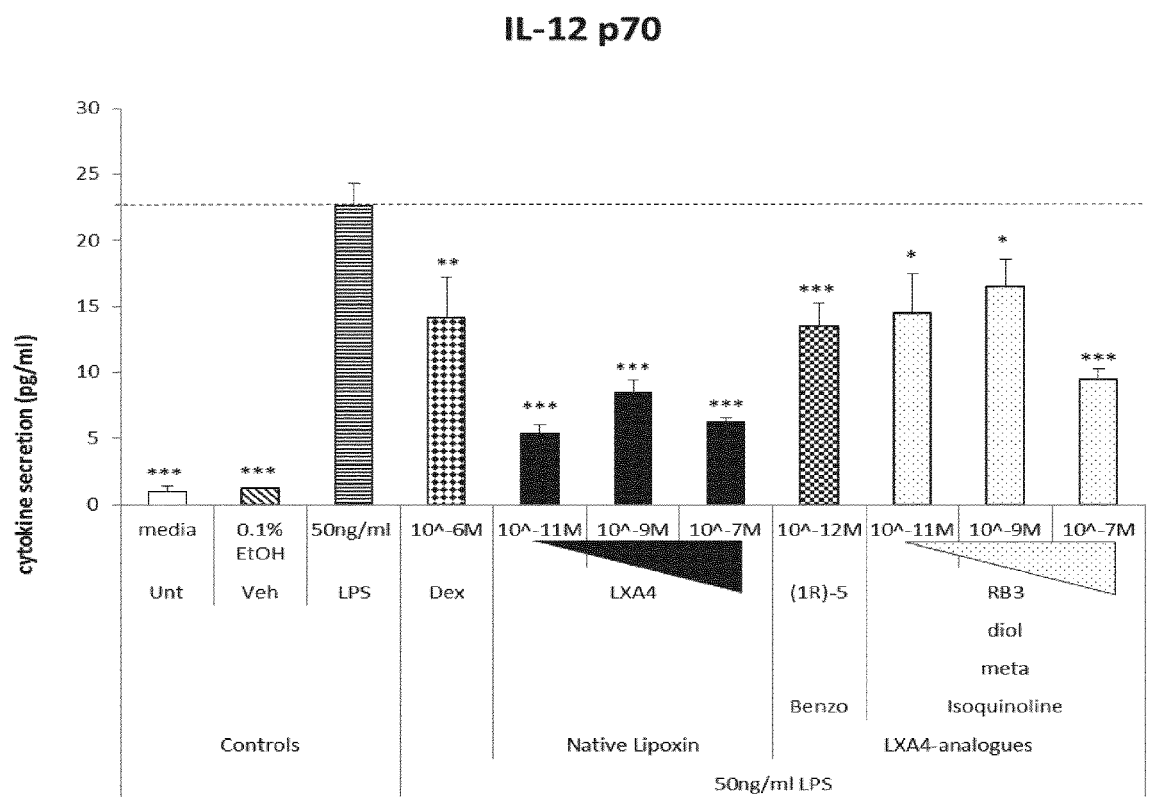
Figure 12:
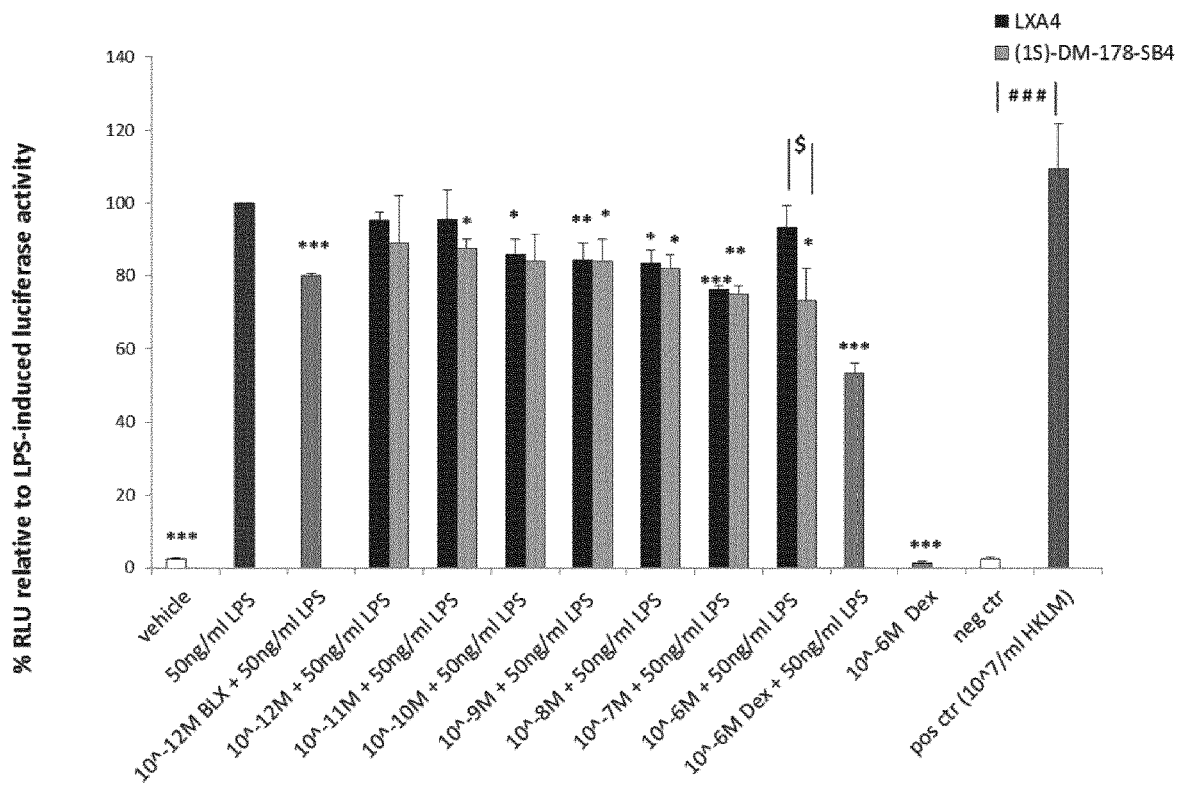
FIG. 12 is a graph showing that the isoquinoline-lipoxin analogue (1S)-DM-178-SB4 attenuates LPS-induced NFkB-driven luciferase activity.

With reference to FIGS. 7 and 12, the dose-response for $LXA_4$ vs isoquinoline-derivatives for LPS-induced NFkB luciferase activity is shown. In particular, it was shown that DM-163-RB3 significantly reduced ($=p<0.05$) NFkB activity, compared to the corresponding LXA4 dosage, at 10 nM and 100 nM (respectively, by 35.4±6.1% and by 37.9±9.7%). DM-178-SB4 significantly reduced ($=p<0.05$) NFkB activity, compared to $LXA_4$, at 1 uM (by 26.8±8.7%). Furthermore, in the absence of LPS-challenge all the quinoxalines and isoquinolines tested did not induce NFkB activity, in contrast to HKLM stimulation (data not shown). (*=statistical analysis vs LPS; $=statistical analysis vs $LXA_4$)

Figure 13:
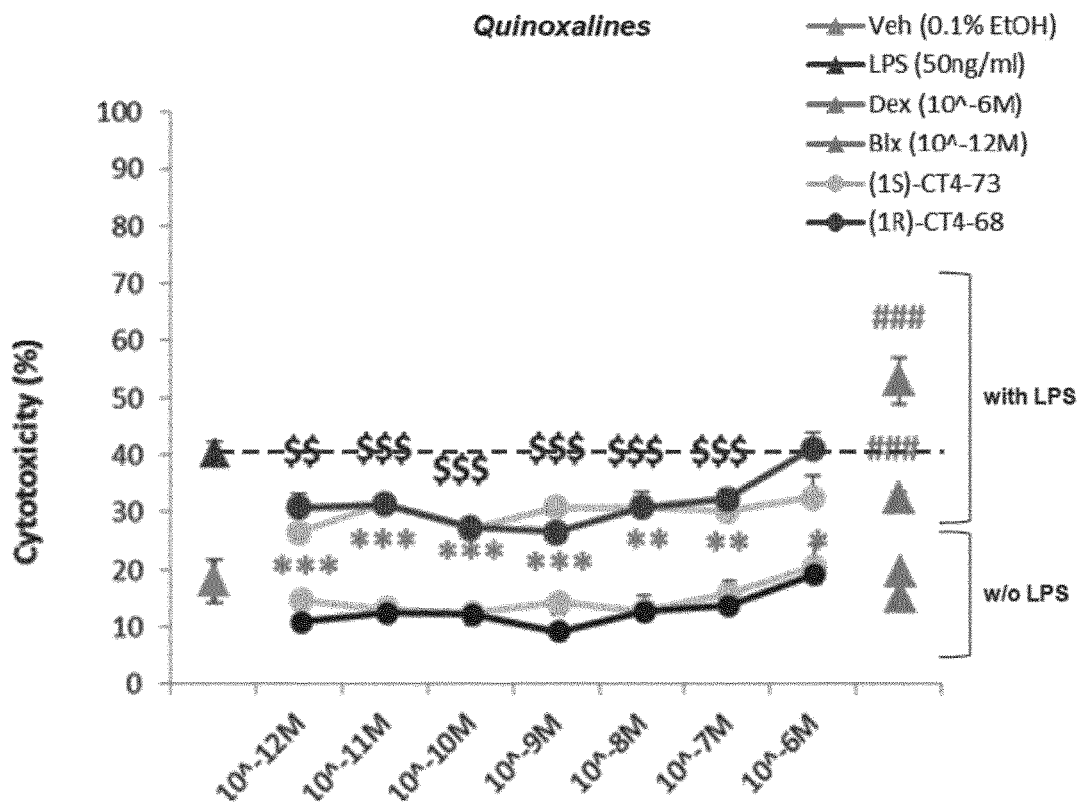
FIG. 13 is a graph showing cytotoxicity of quinoxaline-derivatives in presence and absence of LPS-challenge.
Figure 14:
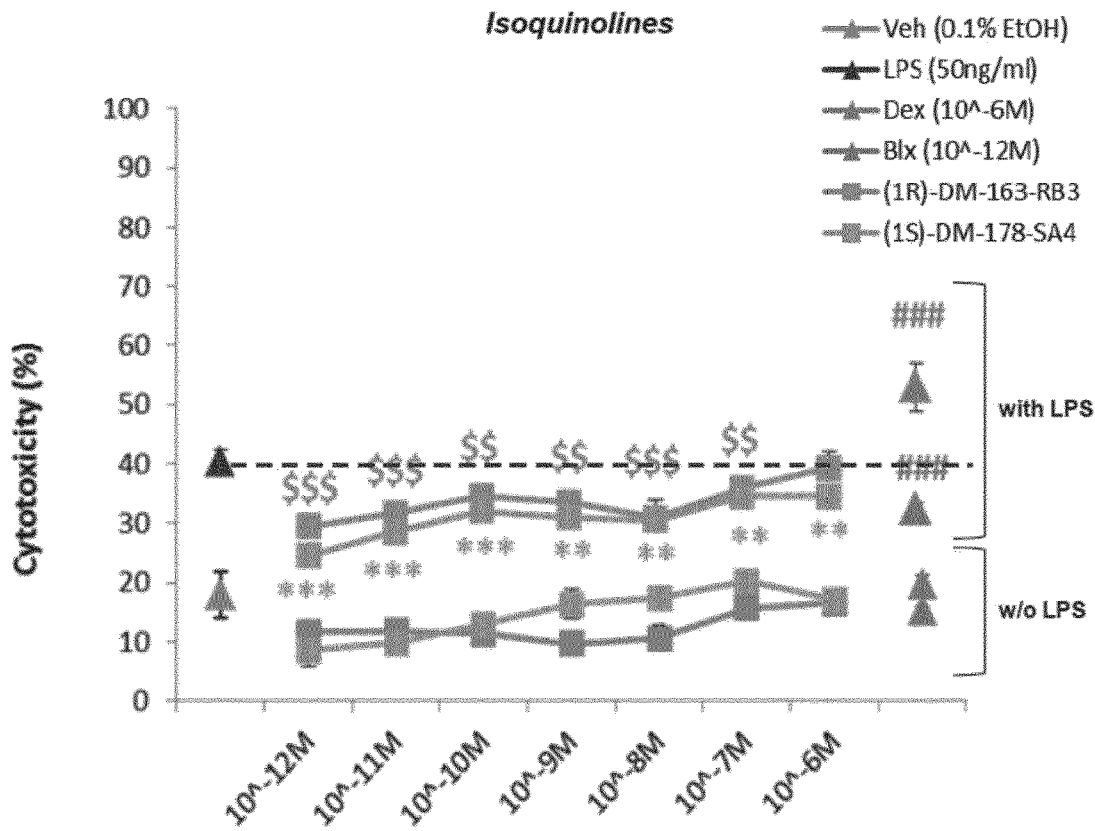
FIG. 14 is a graph showing cytotoxicity of isoquinoline-derivatives in presence and absence of LPS-challenge.

With reference to FIGS. 13 and 14, there is shown the cytotoxicity of quinoxaline- and isoquinoline-derivatives in presence and absence of LPS-challenge. The cells were treated as described above and, after 24 h, supernatant was collected and LDH activity assayed. LPS was associated with a 40% induction of LDH activity. This response was found to be significantly attenuated by $LXA_4$ analogues. Similarly, the benzo-lipoxin $A_4$ (Blx) analogue significantly ($p<0.001$) decreased LPS activity. In contrast, Dexamethasone (Dex) significantly ($p<0.001$) increased LPS response, due to an additive effect. (* or $=statistical analysis vs LPS)

SUMMARY

The most effective analogue identified in the experiment was the quinoxaline-derivative (1R)-CT4-43, which was found to be significantly more potent than $LXA_4$ in reducing LPS-induced NFkB inflammatory activity. Variation of the lower chain length (longer or shorter) did not appear to lead to enhanced activity of quinoxalines. Among the isoquinolines, (1R)-DM-163-RB3 was found to be the most potent and, overall, 1,3-isoquinolines displayed stronger anti-inflammatory properties than 1,4-derivatives. Cytotoxicity of all the analogues analysed suggests protection from LPS-induced damage.

With reference to FIG. 15, there is shown the dose-response for $LXA_4$ vs the imidazole-derivative KG-5-22 for LPS-induced NFkB luciferase activity. In particular, it was shown that KG-5-22 significantly reduced (respectively, $$=p<0.01$ and $$$=p<0.001$) NFkB activity, compared to the corresponding LXA4 dosage, at 1 pM and 10 pM (respectively, by 43.7±8.9% and by 41.3±9.0%). Furthermore, with reference to FIG. 16, it is shown that in the absence of LPS-challenge the tested imidazole-derivative did not induce NFkB activity, in contrast to HKLM stimulation (data not shown). (*=statistical analysis vs LPS; $=statistical analysis vs $LXA_4$).

EXAMPLES—COMPOUND PREPARATIONS

Compounds (1R)-1 and (1S)-1 of Formula (VIa)

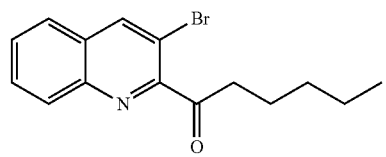

8

3-Bromoquinoline (0.27 mL, 1.99 mmol), hexanal (0.98 mL, 7.97 mmol) and EtOAc (55 mL) were placed in a 100 mL round bottom flask followed by $TMSN_3$ (0.53 mL, 4.03 mmol). $PhI(OCOCF_3)_2$ (1.72 g, 4.0 mmol) was added slowly at room temperature. The reaction was stirred for 2.5 h open to air. Triethylamine (7 mL) was added slowly after this time. The solvent was removed in vacuo and the resulting crude product was purified by column chromatography (pentane:CH$_2$Cl$_2$; 98:2) to give ketone 8 (231 mg, 38%) as an orange oil.

Methyl(5S,6R)-bis(tert-butyldimethylsilyloxy)-8-((E)-2-hexanoylquinolin-3-yl)oct-7-enoate (7)

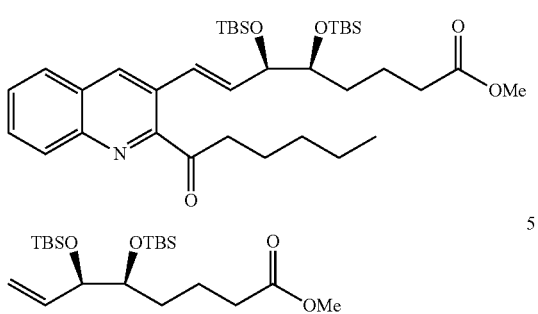

[η-(C$_3$H$_5$)PdCl]$_2$ (8 mg, 0.022 mmol, 6.6 mol %), P(o-tolyl)$_3$ (15 mg, 0.05 mmol, 15.1 mol %) and NaOAc (78 mg, 0.951 mmol, 2.87 mol %) were added to a 10 mL Schlenk tube followed by dry toluene (0.8 mL). Ketone 8 (101.3 mg, 0.331 mmol) was added in dry toluene (0.4 mL) followed by olefin 5 (166 mg, 0.399 mmol, 121 mol %) (prepared according to a published procedure (19)) in dry toluene (0.4 mL). DMA (0.52 mL) was added to the reaction flask and the reaction mixture was heated to 115° C. for 38 h. The reaction mixture was then cooled and filtered through a Celite plug with CH$_2$Cl$_2$ (100 mL). The product was purified by column chromatography (CH$_2$Cl$_2$:pentane; 1:1) to give coupled product 7 (145 mg, 68%) as a yellow oil. R$_f$=0.26 (pentane:CH$_2$Cl$_2$; 9:1); [α]$_D^{20}$=−5.315 (c=0.715, CH$_2$Cl$_2$); $^1$H NMR (500 MHz, CDCl$_3$) δ 8.23 (s, 1H), 8.10 (d, J=8.0 Hz, 1H), 7.83 (d, J=8.0 Hz, 1H), 7.73-7.69 (m, 1H), 7.62-7.58 (m, 1H), 7.17 (d, J=15.9 Hz, 1H), 6.20 (dd, J=15.9, 7.1 Hz, 1H), 4.23-4.20 (m, 1H), 3.75-3.72 (m, 1H), 3.66 (s, 3H), 3.33-3.21 (m, 2H), 2.34 (t, J=7.5 Hz, 2H), 1.80-1.68 (m, 4H), 1.58-1.54 (m, 2H), 1.42-1.38 (m, 4H), 0.93-0.90 (m, 12H), 0.88 (s, 9H), 0.07 (s, 12H); $^{13}$C NMR (126 MHz, CDCl$_3$) δ 204.67, 174.16, 151.78, 146.23, 134.57, 134.10, 129.95, 129.84, 129.76, 128.38, 127.80, 127.68, 109.69, 77.30, 76.50, 51.60, 40.37, 34.47, 33.24, 31.71, 26.17, 26.14, 23.93, 22.70, 20.90, 18.43, 18.36, 14.14, −3.82, −3.86, −4.40, −4.52; IR (neat): ν$_{max}$=3055, 2987, 2958, 2930, 2858, 2305.9, 1733, 1699, 1552, 1422.3, 1266 cm$^{-1}$; HRMS (ES+) C$_{36}$H$_{59}$NO$_5$Si$_2$ [M+Na] requires 664.3830, found 664.3827.

Methyl (5S,6R)-bis(tert-butydimethylsilyloxy)-8-((E)-2-((R/S)-1-hydroxyhexyl)quinolin-3-yl)oct-7-enoate (37)

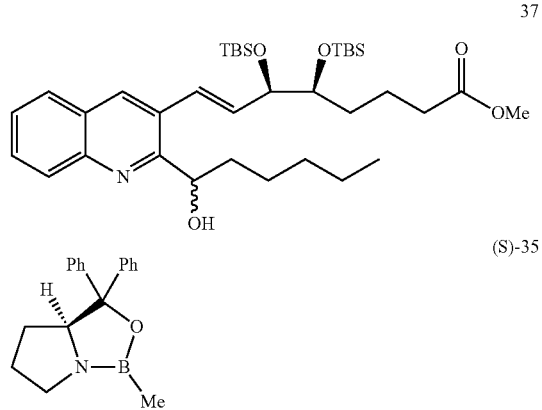

(S)-Me-CBS (S)-35 (11 mg, 0.04 mmol, 27 mol %) was placed in a 10 mL Schlenk tube followed by THF (0.2 mL) at −20° C. BH$_3$.SMe$_2$ (0.23 mL, 1 M in THF, 0.23 mmol, 1.5 equiv.) was added and the reaction mixture was stirred for 5 min. Ketone 8 (45 mg, 0.15 mmol) was added in THF (0.2 mL). The reaction mixture was stirred at −20° C. for 48 h, over which time the reaction turned red. The reaction was quenched with NH$_4$Cl sat. sol. (2 mL), extracted with CH$_2$Cl$_2$ (3×5 mL), dried over magnesium sulfate and filtered and concentrated in vacuo. The product was purified by preparative TLC (pentane:CH$_2$Cl$_2$; 1:1) to give alcohol 37 (2 mg, 4%, 11 ee % (1S)) as a yellow oil. R$_f$=0.2 (pentane:CH$_2$Cl$_2$; 1:1); [α]$_D^{20}$=−19.02 (c=0.315, CH$_2$Cl$_2$); [As this compound is a 50:50 mixture of epimers the NMR spectra have been analysed considering each epimer as an individual entity, therefore having an integration of 1 for each proton in each molecule.] $^1$H NMR (500 MHz, CDCl$_3$) δ 8.18 (s, 1H), 8.15 (s, 1H), 8.03 (d, J=8.4 Hz, 2H), 7.83-7.81 (m, 2H), 7.68 (ddd, J=8.2, 6.9, 1.3 Hz, 2H), 7.52 (ddd, J=8.2, 6.9, 1.3 Hz, 2H), 6.76-6.71 (m, 2H), 6.37 (dd, J=15.7, 6.3 Hz, 1H), 6.32 (dd, J=15.7, 6.3 Hz, 1H), 5.08-5.03 (m, 2H), 4.27-4.23 (m, 2H), 3.77-3.70 (m, 2H), 3.67-3.66 (m, 6H), 2.34-2.31 (m, 4H), 1.87-1.75 (m. 4H), 1.62-1.51 (m, 10H), 1.39-1.19 (m, 12H), 0.95-1.94 (m, 18H), 0.89-0.88 (m, 24H), 0.09-0.05 (m, 24H); $^{13}$C NMR (126 MHz, CDCl$_3$) (174.04, 174.02), (161.24, 160.21), (145.56, 145.51), (135.31, 135.23), (133.30, 133.09), (129.63, 129.61), (128.55, 128.53), (127.67, 127.67), (127.25, 127.10), (126.70, 126.68), (125.32, 125.30), (124.89, 124.66), (77.27, 77.06), (76.61, 76.49), (70.26, 70.26), (51.65, 51.64), (38.65, 38.43), (34.42, 34.35), (33.15, 33.08), (32.06, 32.03), (26.15, 26.13), (26.11, 26.11), (25.47, 25.46), (22.84, 22.84), (21.09, 20.81), (18.41, 18.40), (18.37, 18.34), (14.22, 14.22), (−3.84, −3.89), (−4.34, −4.37), (−4.41, −4.41), (−4.46, −4.48); IR (neat): ν$_{max}$=3449 (br.), 3054, 2955, 2931, 2857, 1733, 1463, 1439, 1265, 1106, 1007 cm$^{-1}$; HRMS (ES+) C$_{36}$H$_{61}$NO$_5$Si$_2$ [M+H] requires 644.4167, found 644.4169; HPLC: Chiralcel IA, (Heptane: EtOH; 98:2, 1 mL/min): R$_t$=6.95 min (55.71% area), R$_t$=9.07 min (44.29% area).

Methyl 4-((4S,5R)-2,2-dimethyl-5-vinyl-1,3-dioxolan-4-yl)butanoate (59)

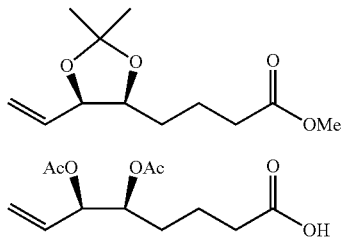

Carboxylic acid 14 (520 mg, 2.02 mmol) (prepared according to a variation of the published procedure (19)) was placed in a 100 mL round bottom flask followed by $ZrCl_4$ (180 mg, 0.77 mmol) and dry MeOH (1 mL). The reaction mixture was stirred under nitrogen at room temperature for 48 h. The resulting crude mixture was flushed through a plug of silica ($CH_2Cl_2$:MeOH; 9:1, 300 mL) and filtered. The solvent was removed in vacuo to give a colourless oil. A stirring bar was added along with $CH_2Cl_2$ (30 mL) and para-TsOH (35 mg, 0.202 mmol). 2,2-Dimethoxypropane (0.39 mL, 3.17 mmol) was then added, giving a red reaction solution. The reaction mixture was stirred under nitrogen for 18 hours after which $NaHCO_3$ sat. sol. (5 mL) was added followed by $H_2O$ (10 mL). This was extracted with $CH_2Cl_2$ (4×30 mL). The combined organic layers were washed with brine (30 mL), dried over magnesium sulfate and the solvent was removed in vacuo. The crude product was purified by flash chromatography (pentane:EtOAc; 4:1) to give 59 (277 mg, 60%) as a pale yellow oil. $R_f$=0.71 (1:1 pentane:EtOAc); $[\alpha]_D^{20}$=+4.6 (c=0.9, $CH_2Cl_2$); $^1$H NMR (500 MHz, $CDCl_3$) δ 5.80 (ddd, J=17.1, 10.3, 7.8 Hz, 1H), 5.34-5.20 (m, 2H), 4.52-4.47 (m, 1H), 4.17-4.11 (m, 1H), 3.67 (s, 3H), 2.35 (dt, J=7.6, 4.14 Hz, 2H), 1.88-1.74 (m, 1H), 1.73-1.63 (m, 1H), 1.56-1.38 (m, 5H), 1.36 (s, 3H); $^{13}$C NMR (126 MHz, $CDCl_3$) δ 173.96, 134.40, 118.52, 108.38, 79.89, 78.03, 51.65, 33.96, 30.01, 28.36, 25.78, 21.85; IR (neat): $v_{max}$=3055, 2988, 1733, 1606 cm$^{-1}$; HRMS (ES+) $C_{12}H_{20}O_4$ [M+Na] requires 251.1259, found 251.1264.

Methyl 4-((4S,5R)-2,2-dimethyl-5-((E)-2-(4,4,5,5-tetramethyl-1,3,2-dioxaborolan-2-yl)vinyl)-1,3-dioxolan-4-yl)butanoate (61)

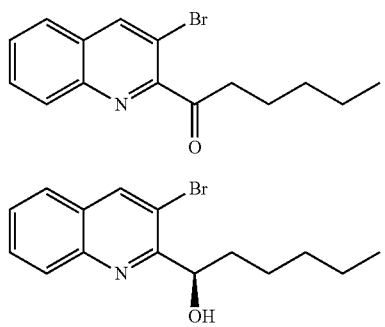

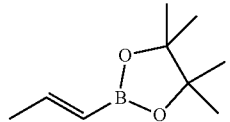

Acetonide 59 (50 mg, 0.22 mmol) was placed in a 5 mL vial containing Hoveyda-Grubbs' catalyst (7 mg, 0.011 mmol, 5 mol %) and dry $CH_2Cl_2$ (1.1 mL). Boronic ester 56 (0.08 mL, 0.42 mmol, 190 mol %) was added and the reaction mixture was stirred at 40° C. under $N_2$ for 24 h. The reaction was cooled, the solvent removed in vacuo. The crude mixture was purified by column chromatography (pentane:EtOAc; 95:5) to give 61 (28 mg, 35%) as a yellow liquid. $R_f$=0.7 (pentane:EtOAc; 6:1); $[\alpha]_D^{20}$=−5.1 (c=0.35, $CH_2Cl_2$); $^1$H NMR (500 MHz, $CDCl_3$) δ 6.49 (dd, J=18.0, 6.8 Hz, 1H), 5.71 (d, J=18.0 Hz, 1H), 4.54 (app. t, J=6.8 Hz, 1H), 4.19-4.15 (m, 1H), 3.67 (s, 3H), 2.37-2.33 (m, 2H), 1.87-1.61 (m, 4H), 1.49 (s, 3H), 1.36 (s, 3H), 1.27 (s, 12H); $^{13}$C NMR (126 MHz, $CDCl_3$) δ 173.94, 148.13, 121.98, 108.64, 83.47, 80.51, 78.14, 51.62, 33.89, 29.98, 29.84, 28.25, 25.78, 24.99, 24.96, 24.87, 24.84, 21.96; $^{11}$B NMR (128 MHz, $CDCl_3$) δ 29.42 (br., s); IR (neat): $v_{max}$=3055, 2986, 2854, 1732, 1422, 1265 cm$^{-1}$; HRMS (ES+) $C_{18}H_{31}BO_6$ [M+Na] requires 377.2111, found 377.2128.

Synthesis of (1R)-20 and (1S)-20

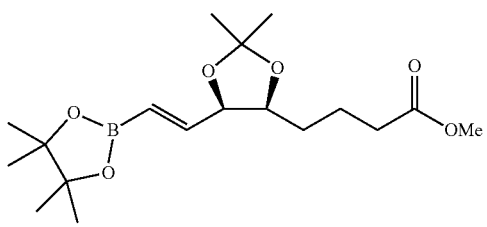

Ketone 8 (50 mg, 0.16 mmol) was added to a dry 10 mL conical flask under N2 containing $RuCl_2$[(S)-(DM-BINAP)][(S)-DAIPEN] (20 mg, 0.016 mmol, 10 mol %), KOt-Bu (21 mg, 0.17 mmol, 100 mol %). Dry iso-propanol (5 mL) was added followed by a drop of B(OiPr)$_3$. The reaction flask was flushed with $H_2$ (15 bar×3) and the reaction mixture was held at 10 bar $H_2$ pressure for 24 h at room temperature. The solvent was removed in vacuo and the crude mixture was purified by column chromatography (pentane:$CH_2Cl_2$; 98:2) giving (1R)-20 (32 mg, 65%, 96.7% ee) as a yellow oil. Using $RuCl_2$[(R)-DM-BINAP][(R)-DAIPEN] gave (1S)-20 (30.3 mg, 61.4%, 95.5% ee) as a yellow oil. $R_f$=0.21 (Pentane:EtOAc; 9:1); $[\alpha]_D^{20}$=(R)−5.74 (c=0.38, $CH_2Cl_2$); $^1$H NMR (500 MHz, $CDCl_3$) δ 8.36 (s, 1H), 8.06 (d, J=8.4 Hz, 1H), 7.76-7.75 (m, 2H), 7.58-7.55 (m, 1H), 5.14-5.11 (m, 1H), 4.69 (d, J=7.7 Hz, 1H), 2.03-1.99 (m, 1H), 1.59-1.52 (m, 3H), 1.41-1.28 (m, 4H), 0.89 (t, J=6.9 Hz, 3H); $^{13}$C NMR (125 MHz, CDCl$_3$) δ 160.37, 145.27, 139.89, 130.30, 128.87, 128.81, 127.44, 126.77, 115.79, 71.88, 37.46, 31.80, 25.56, 22.77, 14.20; IR (neat): v$_{max}$=3583 (br.), 2955, 2924, 2854, 1460, 1265 cm$^{-1}$; HRMS (ES+) C$_{15}$H$_{18}$$^{79}$BrNO [M+H] requires 308.0650, found 308.0639; UPC$^2$ Chiralcel IC (CO$_2$:MeOH; 99:1 to 70:30 over 5 min, 3 mL/min): R$_t$=3.14 min (S), R$_t$=3.27 min (R).

(1S)-20 was prepared in an identical manner using the enantiomeric catalyst RuCl$_2$[(R)-(DM-BINAP)][(R)-DAIPEN], identical in all aspects of physical data to (1R)-20 apart from [α]$_D$$^{20}$ (S)=+26.6 (c=0.415, CH$_2$Cl$_2$).

Methyl 4-((4S,5R)-5-((E)-2-(2-((R)-1-hydroxyhexyl)quinolin-3-yl)vinyl)-2,2-dimethyl-1,3-dioxolan-4-yl)butanoate ((1R)-66)

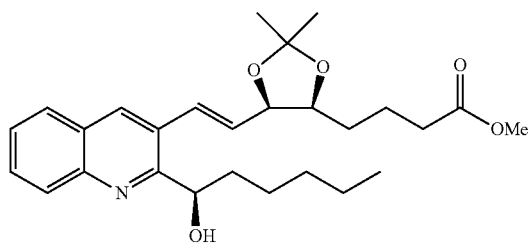

(1R)-66

Bromide (1R)-20 (50 mg, 0.162 mmol, 96% ee (R)) was added to a 10 mL Schlenk tube containing KF (27 mg, 0.465 mmol, 287 mol %), Pd(OAc)$_2$ (1 mg, 0.0045 mmol, 3 mol %), JohnPhos (3 mg, 0.01 mmol, 6 mol %). Boronic ester 61 (84 mg, 0.237 mmol, 150 mol %) was added in THF (0.8 mL) followed by deionised H$_2$O (0.1 mL). The reaction mixture was heated to 80° C. for 12 h after which time Et$_2$O (3 mL) was added followed by a NaOH 5% (w/v) solution (2 mL). The organic product was extracted into Et$_2$O (4×3 mL) and the combined organic phases were washed with brine (3 mL) and dried over magnesium sulfate. The product was purified by preparative TLC (CH$_2$Cl$_2$:MeOH; 9:1) to give coupled product (1R)-66 (50 mg, 67%) as an orange oil. R$_f$=0.7 (CH$_2$Cl$_2$:MeOH; 9:1); [α]$_D$$^{20}$=−0.32 (c=0.75, CH$_2$Cl$_2$); $^1$H NMR (500 MHz, CDCl$_3$) δ 8.21 (s, 1H), 8.03 (d, J=8.4 Hz, 1H), 7.83 (d, J=8.0 Hz, 1H), 7.69 (ddd, J=8.4, 6.9, 1.4 Hz, 1H), 7.53 (ddd, J=8.0, 6.9, 1.4 Hz, 1H), 6.90-6.84 (m, 1H), 6.26 (dd, J=15.5, 7.4 Hz, 1H), 5.09-5.04 (m, 1H), 4.81-4.74 (m, 1H), 4.30-4.26 (m, 1H), 3.64 (s, 3H), 2.41-2.33 (m, 2H), 1.92-1.67 (m, 5H), 1.57 (s, 3H), 1.55-1.48 (m, 4H), 1.43 (s, 3H), 1.34-1.24 (m, 4H), 0.87 (t, J=7.0 Hz, 3H); $^{13}$C NMR (126 MHz, CDCl$_3$) δ 173.79, 160.10, 145.73, 133.75, 130.38, 129.80, 128.54, 127.85, 127.70, 127.67, 127.64, 126.76, 108.77, 79.05, 78.38, 70.22, 51.63, 38.16, 33.79, 31.85, 30.22, 28.39, 25.72, 25.29, 22.72, 21.94, 14.16; IR (neat): v$_{max}$=3423 (br.), 3054, 2987, 1641, 1422, 1265 cm$^{-1}$; HRMS (ES+) C$_{27}$H$_{37}$NO$_5$ [M+H] requires 456.2750, found 456.2734.

Methyl(5S,6R)-dihydroxy-8-((E)-2-((R)-1-hydroxyhexyl)quinolin-3-yl)oct-7-enoate ((1R)-1)

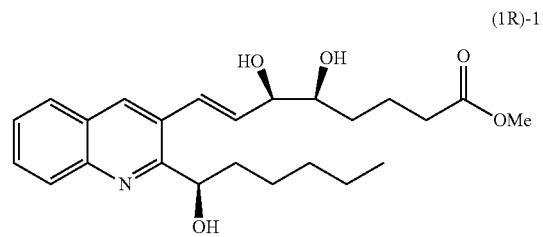 [SMILES: CCCCC[C@@H](O)c1nc2ccccc2cc1/C=C/[C@@H](O)[C@@H](O)CCCC(=O)OC]

(1R)-1

Protected compound (1R)-66 (45 mg, 0.10 mmol) in dry MeOH (1 mL) was placed in a 10 mL Schlenk tube containing ZrCl$_4$ (73 mg, 0.31 mmol, 310 mol %). The reaction mixture was stirred at room temperature for 24 h. The crude product was purified by preparative TLC (CH$_2$Cl$_2$:MeOH; 9:1) to give triol (1R)-1 (14 mg, 36%) as a yellow wax. R$_f$=0.5 (CH$_2$Cl$_2$:MeOH; 9:1); [α]$_D$$^{20}$=−4.63 (c=0.65, CH$_2$Cl$_2$); $^1$H NMR (500 MHz, CDCl$_3$) δ 8.15 (s, 1H), 8.02 (d, J=8.3 Hz, 1H), 7.75 (d, J=8.1 Hz, 1H), 7.69-7.66 (m, 1H), 7.52-7.48 (m, 1H), 6.86 (d, J=14.8 Hz, 1H), 6.38 (dd, J=14.0, 5.9 Hz, 1H), 5.10-5.03 (m, 1H), 4.38-4.32 (m, 1H), 3.84 (dt, J=8.2, 3.6 Hz, 1H), 3.73-3.61 (m, 4H), 2.39 (td, J=7.2, 3.4 Hz, 2H), 1.92-1.74 (m, 3H), 1.62-1.46 (m, 5H), 1.32-1.27 (m, 4H), 0.86 (t, J=6.9 Hz, 3H); $^{13}$C NMR (126 MHz, CDCl$_3$) δ 174.29, 159.95, 145.66, 133.65, 131.92, 129.85, 128.48, 127.68, 127.66, 127.65, 127.47, 126.81, 75.73, 74.00, 70.22, 51.79, 38.14, 33.76, 31.92, 31.72, 25.26, 22.75, 21.21, 14.19; IR (neat): v$_{max}$=3432 (br.), 3054, 2954, 2938, 2859, 1734, 1438, 1422, 1266 cm$^{-1}$; HRMS (ES+) C$_{24}$H$_{33}$NO$_5$ [M+Na] requires 438.2256, found 438.2257.

Methyl 4-((4S,5R)-5-((E)-2-(2-((S)-1-hydroxyhexyl)quinolin-3-yl)vinyl)-2,2-dimethyl-1,3-dioxolan-4-yl)butanoate ((1S)-66)

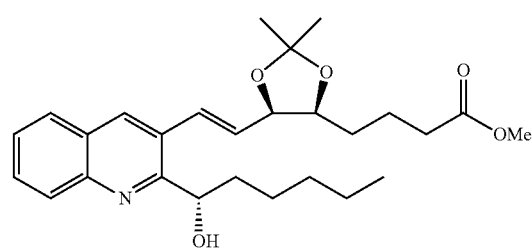

(1S)-66

Bromide (1S)-20 (71 mg, 0.23 mmol, 96% ee (S)) was added to a 10 mL Schlenk tube containing KF (38 mg, 0.65 mmol, 283 mol %), Pd(OAc)$_2$ (1 mg, 0.0045 mmol, 2 mol %), JohnPhos (4 mg, 0.0134 mmol, 6 mol %). Boronic ester 61 (112 mg, 0.316 mmol, 137 mol %) was added in THF (1.14 mL) followed by deionised H$_2$O (0.14 mL). The reaction mixture was heated to 80° C. for 16 h after which time Et$_2$O (4 mL) was added followed by a NaOH 5% (w/v) solution (3 mL). The organic product was extracted in Et$_2$O (4×5 mL) and the combined organic phases were washed with brine (5 mL) and dried over magnesium sulfate. The product was purified by preparative TLC (CH$_2$Cl$_2$:MeOH;

9:1) to give coupled product (1S)-66 (43 mg, 41%) as an orange oil. $R_f$=0.7 (CH$_2$Cl$_2$:MeOH; 9:1); $[\alpha]_D^{20}$=+2.45 (c=0.645, CH$_2$Cl$_2$); $^1$H NMR (500 MHz, CDCl$_3$) δ 8.21 (s, 1H), 8.04 (d, J=8.3 Hz, 1H), 7.83 (d, J=8.3 Hz, 1H), 7.69 (ddd, J=8.3, 7.2, 1.0 Hz, 1H), 7.53 (ddd, J=8.3, 7.2, 1.0 Hz, 1H), 6.86 (d, J=15.6 Hz, 1H), 6.26 (dd, J=15.6, 7.1 Hz, 1H), 5.10-5.03 (m, 1H), 4.77 (dd, J=7.1, 6.1 Hz, 1H), 4.31-4.25 (m, 1H), 3.64 (d, J=0.9 Hz, 3H), 2.41-2.34 (m, 2H), 1.91-1.64 (m, 5H), 1.57 (s, 3H), 1.55-1.47 (m, 4H), 1.43 (s, 3H), 1.35-1.27 (m, 4H), 0.87 (t, J=6.8 Hz, 5H); $^{13}$C NMR (126 MHz, CDCl$_3$) δ 173.84, 160.20, 145.77, 133.58, 130.45, 129.82, 128.58, 127.73, 127.68, 127.66, 127.35, 126.78, 108.75, 79.09, 78.46, 70.30, 51.67, 38.27, 33.82, 31.89, 30.31, 28.35, 25.71, 25.44, 22.78, 21.91, 14.19; IR (neat): $v_{max}$=3424 (br.), 3054, 2987, 2954, 2932, 1735, 1438, 1422, 1266 cm$^{-1}$; HRMS (ES+) C$_{27}$H$_{37}$NO$_5$ [M+H] requires 456.2750, found 456.2761.

Methyl(5S,6R)-dihydroxy-8-((E)-2-((S)-1-hydroxy-hexyl)quinolin-3-yl)oct-7-enoate ((1S)-CT4-93)

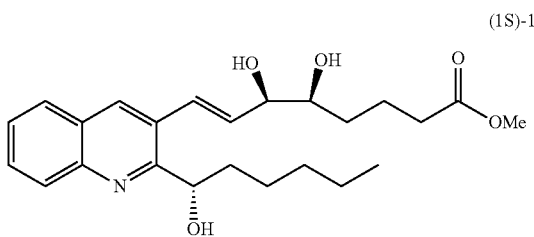 [SMILES: CCCCC[C@H](O)c1nc2ccccc2cc1/C=C/[C@@H](O)[C@@H](O)CCCC(=O)OC]

(1S)-1

Protected compound (1S)-66 (32 mg, 0.07 mmol) in dry MeOH (1 mL) was placed in a 10 mL Schlenk tube containing ZrCl$_4$ (49 mg, 0.211 mmol, 301 mol %). The reaction mixture was stirred at room temperature for 24 h. The crude product was purified by column chromatography (pentane:CH$_2$Cl$_2$; 9:1 to 1:9, then CH$_2$Cl$_2$:MeOH; 9:1) to give triol (1S)-1 (23 mg, 78%) as a yellow wax. $R_f$=0.5 (CH$_2$Cl$_2$:MeOH; 9:1); $[\alpha]_D^{20}$=+4.18 (c=0.16, CH$_2$Cl$_2$); $^1$H NMR (500 MHz, CDCl$_3$) δ 8.20 (s, 1H), 8.04 (d, J=8.4 Hz, 1H), 7.82 (d, J=8.1 Hz, 1H), 7.73-7.66 (m, 1H), 7.54-7.51 (m, 1H), 6.89 (d, J=15.7 Hz, 1H), 6.37 (dd, J=15.7, 6.5 Hz, 1H), 5.09-5.06 (m, 1H), 4.38-4.36 (m, 1H), 3.85-3.81 (m, 1H), 3.73-3.61 (m, 4H), 2.45-2.35 (m, 3H), 1.91-1.73 (m, 4H), 1.60-1.58 (m, 5H), 1.32-1.28 (m, 4H), 0.87 (t, J=6.7 Hz, 3H); $^{13}$C NMR (126 MHz, CDCl$_3$) δ 174.32, 160.16, 145.78, 133.62, 131.91, 129.85, 128.59, 127.78, 127.74, 127.66, 127.36, 126.82, 75.68, 74.05, 70.30, 51.81, 38.21, 33.77, 31.64, 29.85, 25.35, 22.77, 21.14, 14.20; IR (neat): $v_{max}$=3394 (br.), 2977, 2901, 2885, 1659, 1644, 1454, 1412, 1382, 1329, 1274, 1086, 1047 cm$^{-1}$; HRMS (ES+) C$_{24}$H$_{33}$NO$_5$ [M+Na] calculated 438.2256, found 438.2262.

Compound 1 of Formula (VIb) and Compound 2 of Formula (VIb2)

1-(2-Chloroquinolin-3-yl)hexan-1-one (5)

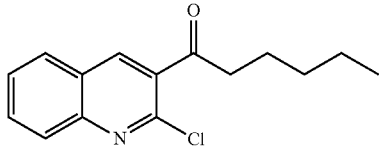

5

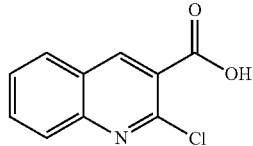

11

In a dry 250 mL Schlenk tube, oxalyl chloride (1.6 mL, 18 mmol) was added slowly at room temperature to known carboxylic acid 11 (830 mg, 4.0 mmol) in CH$_2$Cl$_2$ (35 mL), followed by DMF (0.1 mL, 1.5 mmol, 38 mol %). The solution was stirred at room temperature for 3 h, during which time the reaction mixture went from a suspension to yellow transparent solution. While this reaction was proceeding, Mg turnings (430 mg, 17.7 mmol) were placed in a 50 mL Schlenk tube and heated under vacuum for 10 min. THF (10 mL) and an iodine crystal were added followed by 1-bromopentane (2.35 mL, 19 mmol, 4.75 equiv.). The mixture was heated to reflux for 2.5 h and then brought to room temperature. Bis[2-(N,N-dimethylamino)ethyl]ether (3.35 mL, 17.5 mmol, 4.4 equiv.) was placed in a dry 100 mL round bottom flask containing THF (9 mL) and the solution was brought to 0° C. The Grignard reagent was added slowly in THF (5 mL) to this chelating ether 10 solution. The solution was stirred for 15 min at 0° C., producing a white suspension. The CH$_2$Cl$_2$ and oxalyl chloride were removed in vacuo from the 250 mL Schlenk tube. THF (10 mL) was added and the reaction was brought to −78° C. The Grignard was slowly added to the acid chloride solution and this mixture stirred was at −78° C. for 18 h, giving a yellow solution.

The reaction was quenched in a separating funnel containing NH$_4$Cl sat. sol. (40 mL) and the organic phase was extracted with EtOAc (6×50 mL). The combined organic phase was washed with brine (30 mL), dried over magnesium sulfate and the solvent was removed under reduced pressure. The product was purified by column chromatography (CH$_2$Cl$_2$:pentane; 1:1) to give ketone 5 (890 mg, 85%) as a yellow oil. $R_f$=0.26 (cyclohexane:EtOAc; 9:1); $^1$H NMR (500 MHz, CDCl$_3$) δ 8.26 (s, 1H), 8.05 (d, J=8.3 Hz, 1H), 7.88 (d, J=8.3 Hz, 1H), 7.81 (ddd, J=8.3, 7.0, 1.4 Hz, 1H), 7.62 (ddd, J=8.3, 7.0, 1.4 Hz, 1H), 3.05 (t, J=7.4 Hz, 2H), 1.77 (p, J=7.4 Hz, 2H), 1.43-1.32 (m, 4H), 0.92 (t, J=7.1 Hz, 3H); $^{13}$C NMR (126 MHz, CDCl$_3$) δ 202.16, 148.09, 145.96, 138.41, 133.89, 132.14, 128.62, 128.38, 127.95, 126.34, 43.09, 31.46, 24.12, 22.58, 14.03; IR (neat): $v_{max}$=3055, 2987, 2960, 2932, 1703.2, 1266 cm$^{-1}$; HRMS (ES+) C$_{15}$H$_{16}^{35}$ClNO [M+H] requires 262.0999, found 262.1003.

(E)-Methyl 3-(3-hexanoylquinolin-2-yl)acrylate (15)

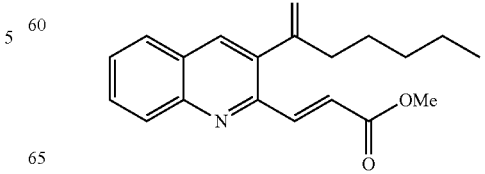

15

[η-(C₃H₅)PdCl]₂ (25 mg, 0.069 mmol, 20 mol %), P(o-tolyl)₃ (47 mg, 0.155 mmol, 45 mol %), NaOAc (85 mg, 1.032 mmol, 300 mol %) were placed in a dry 15 mL Schlenk tube. Chloride 5 (90 mg, 0.344 mmol) was added in dry toluene (0.5 mL) followed by dry toluene (0.8 mL) and dry DMA (43 mL), followed by methyl acrylate (0.06 mL, 0.67 mmol, 194 mol %). The reaction mixture was heated to 115° C. for 48 h. The reaction mixture was filtered through a plug of celite with CH₂Cl₂ (100 mL). The solvent was removed in vacuo and the product was purified by column chromatography (pentane:CH₂Cl₂; 94:6 then 100% CH₂Cl₂) to give 15 (6 mg, 5%) as a red oil. $R_f$=0.1 (CH₂Cl₂:pentane; 1:1); ¹H NMR (500 MHz, CDCl₃) δ 8.45 (s, 1H), 8.20 (d, J=15.3 Hz, 1H), 8.12 (d, J=8.5 Hz, 1H), 7.89 (d, J=8.5 Hz, 1H), 7.83 (ddd, J=8.5, 6.9, 1.4 Hz, 1H), 7.65-7.60 (m, 1H), 7.20 (d, J=15.3 Hz, 1H), 3.84 (s, 3H), 3.05 (t, J=7.4 Hz, 2H), 1.80 (p, J=7.4 Hz, 2H), 1.47-1.34 (m, 4H), 0.93 (t, J=7.1 Hz, 3H); ¹³C NMR (126 MHz, CDCl₃) δ 202.98, 167.15, 150.91, 148.53, 141.54, 137.11, 132.41, 132.05, 130.00, 128.38, 128.16, 126.86, 125.12, 52.01, 41.79, 31.57, 24.22, 22.65, 14.09; IR (neat): $v_{max}$=3430 (br.), 3055, 2988, 1720, 1688, 1422, 1266 cm⁻¹; HRMS (ES+) C₁₉H₂₁NO₃ [M+H] requires 312.1600, found 312.1596.

1-(2-Vinylquinolin-3-yl)hexan-1-one (23)

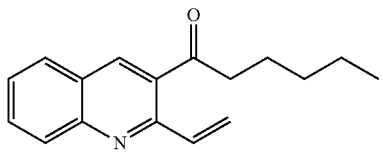

23

Chloride 5 (890 mg, 3.4 mmol) was placed in a dry 100 mL Schlenk tube followed by Pd(PPh₃)₄ (75 mg, 0.065 mmol, 1.9 mol %) and dry 1,4-dimethoxyethane (15 mL). The reaction mixture was stirred for 30 min after which time a solution of K₂CO₃ (540 mg, 3.91 mmol, 115 mol %) in deionized H₂O (5 mL) was added. O'Shea's reagent (544 mg, 2.26 mmol, 66 mol %) was added and the reaction mixture was brought to 96° C. (reflux) for 20 h. The reaction was quenched in a separatory funnel containing H₂O (100 mL) and extracted with CH₂Cl₂ (6×50 mL), filtered through a plug of magnesium sulfate and dried in vacuo. The product was purified by column chromatography (CH₂Cl₂:pentane; 1:1) giving vinylated compound 23 (710 mg, 82%) as a brown oil. $R_f$=0.2 (pentane:CH₂Cl₂; 1:1); ¹H NMR (400 MHz, CDCl₃) δ 8.32 (s, 1H), 8.10 (d, J=8.5 Hz, 1H), 7.83 (d, J=8.1 Hz, 1H), 7.77 (ddd, J=8.4, 7.0, 1.4 Hz, 1H), 7.57-7.52 (m, 1H), 7.30 (dd, J=17.0, 10.7 Hz, 1H), 6.52 (dd, J=17.0, 2.0 Hz, 1H), 5.63 (dd, J=10.7, 2.0 Hz, 1H), 2.99 (t, J=7.4 Hz, 2H), 1.76 (p, J=7.4 Hz, 3H), 1.40-1.33 (m, 4H), 0.91 (t, J=7.1 Hz, 3H); ¹³C NMR (101 MHz, CDCl₃) δ 204.22, 153.15, 148.46, 136.57, 134.67, 132.21, 131.50, 129.60, 128.24, 127.15, 126.27, 122.06, 42.31, 31.52, 24.28, 22.61, 14.05; IR (neat): $v_{max}$=3055, 2988, 1707, 1423, 1266 cm⁻¹; HRMS (ES+) C₁₇H₁₉NO [M+H] requires 254.1545, found 254.1535.

Methyl 4-((4S,5R)-5-((E)-2-(3-hexanoylquinolin-2-yl)vinyl)-2,2-dimethyl-1,3-dioxolan-4-yl)butanoate (34)

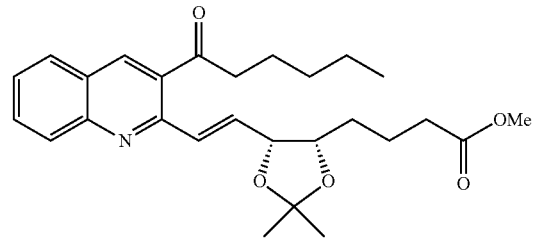

34

Chloride 5 (220 mg, 0.85 mmol) was placed in a 50 mL Schlenk tube containing Pd(PPh₃)₄ (23 mg, 0.02 mmol, 2.5 mol %) and DME (4.5 mL) and the mixture was stirred at room temperature for 30 min. K₂CO₃ (153 mg, 1.11 mmol, 130 mol %), Boronic ester 61 (330 mg, 0.93 mmol, 110 mol %), DME (2.6 mL) were added followed by deionized H₂O (1.5 mL). The reaction mixture was heated to 93° C. for 14 h after which time CH₂Cl₂ (5 mL) was added along with NaHCO₃ sat. sol. (15 mL). The aqueous phase was extracted with CH₂Cl₂ (4×20 mL) and the combined organic phases were washed with brine (30 mL) and dried over magnesium sulfate. The product was purified by column chromatography (pentane:CH₂Cl₂; 4:1 to 1:1, then pentane:EtOAc; 6:1) to give coupled product 34 (190 mg, 49%) as a yellow liquid. $R_f$=0.3 (pentane:EtOAc; 6:1); $[\alpha]_D^{20}$=−9.27 (c=0.15, CH₂Cl₂); ¹H NMR (500 MHz, CDCl₃) δ 8.31 (s, 1H), 8.07 (d, J=8.4 Hz, 1H), 7.82 (d, J=7.9 Hz, 1H), 7.77 (ddd, J=8.4, 6.9, 1.4 Hz, 1H), 7.58-7.51 (m, 1H), 7.22 (d, J=15.2 Hz, 1H), 7.04 (dd, J=15.2, 7.2 Hz, 1H), 4.82-4.79 (m, 1H), 4.29-4.25 (m, 1H), 3.63 (s, 3H), 2.99 (t, J=7.5 Hz, 2H), 2.36 (t, J=7.7 Hz, 2H), 1.79-1.70 (m, 4H), 1.66-1.59 (m, 2H), 1.58 (s, 3H), 1.41 (s, 3H), 1.39-1.36 (m, 4H), 0.92 (t, J=7.1 Hz, 3H); ¹³C NMR (126 MHz, CDCl₃) δ 202.70, 178.55, 152.06, 148.52, 136.51, 134.02, 132.28, 131.48, 130.03, 129.64, 128.23, 127.10, 126.17, 108.77, 79.06, 78.62, 51.62, 42.42, 33.96, 31.58, 30.24, 28.41, 25.90, 24.29, 22.65, 22.04, 14.09; IR (neat): $v_{max}$=3054, 2986, 2959, 2932, 2863, 1732, 1688, 1422, 1265 cm⁻¹; HRMS (ES+) C₂₇H₃₅NO₅ [M+H] requires 454.2593, found 454.2606.

Methyl 4-((4S,5R)-5-((E)-2-(3-((R)-1-hydroxyhexyl)quinolin-2-yl)vinyl)-2,2-dimethyl-1,3-dioxolan-4-yl)butanoate ((1R)-41)

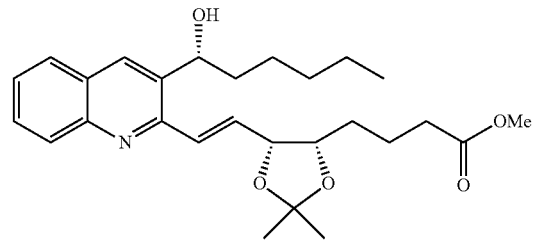

(1R)-41

Ketone 34 (23 mg, 0.05 mmol) was added to a dry 10 mL conical flask containing RuCl$_2$[(S)-(DM-BINAP)][(S)-DAIPEN] (7 mg, 0.0057 mmol, 11 mol %), KOt-Bu (7 mg, 0.06 mmol, 125 mol %) and 2-propanol (4 mL). A few drops of B(Oi-Pr)$_3$ were added and the reaction vessel was flushed with H$_2$ (3×15 bar) and stirred at room temperature for 15 h under 15 bar pressure of H$_2$. The crude mixture was purified by preparative TLC (CH$_2$Cl$_2$:MeOH; 9:1) to give alcohol (1R)-41 (13 mg, 54%, 70% de) as an orange oil. R$_f$=0.2 (CH$_2$Cl$_2$:MeOH; 9:1); [α]$_D^{20}$=+2.57 (c=0.56, CH$_2$Cl$_2$); $^1$H NMR (500 MHz, CDCl$_3$) δ 8.18 (s, 1H), 8.03 (d, J=8.5 Hz, 1H), 7.74 (d, J=8.1 Hz, 1H), 7.67-7.62 (m, 1H), 7.48-7.44 (m, 1H), 7.13 (d, J=15.1 Hz, 1H), 7.01 (dd, J=15.1, 6.4 Hz, 2H), 5.14-5.12 (m, 1H), 4.84-4.82 (m, 1H), 4.30-4.26 (m, 1H), 3.60 (s, 3H), 2.36-2.32 (m, 2H), 1.91-1.75 (m, 4H), 1.75-1.49 (m, 5H), 1.47-1.19 (m, 11H), 0.88 (t, J=6.3 Hz, 3H); $^{13}$C NMR (126 MHz, CDCl$_3$) δ 174.06, 152.40, 147.24, 136.09, 133.54, 133.19, 129.41, 129.26, 128.36, 127.64, 127.60, 126.34, 108.69, 78.91, 78.51, 70.75, 51.64, 38.66, 33.95, 31.77, 30.34, 28.42, 25.84, 25.81, 22.76, 21.95, 14.17; IR (neat): ν$_{max}$=3434 (br.), 3054, 2987, 1648, 1422, 1265 cm$^{-1}$; HRMS (ES+) C$_{27}$H$_{37}$NO$_5$ [M+H] requires 456.2750, found 456.2747; Chiralcel IC (CO$_2$: IPA; 99:1 to 70:30 over 5 min, 3 mL/min): R$_t$ (minor)=5.09 min, 15.2% area (1S), R$_t$ (major)=5.59 min, 84.8% area (1R).

Methyl 4-((4S,5R)-5-((E)-2-(3-((S)-1-hydroxyhexyl)quinolin-2-yl)vinyl)-2,2-dimethyl-1,3-dioxolan-4-yl)butanoate ((1S)-41)

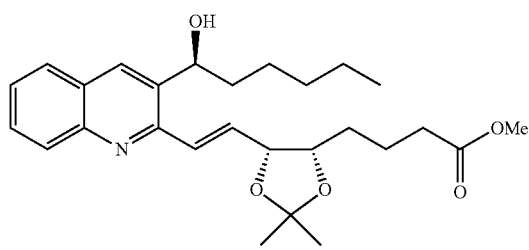

(1S)-41

Ketone 34 (28 mg, 0.062 mmol) was added to a dry 10 mL conical flask containing RuCl$_2$[(R)-(DM-BINAP)][(R)-DAIPEN] (8 mg, 0.0066 mmol, 11 mol %), KOt-Bu (8 mg, 0.065 mmol, 106 mol %) and 2-propanol (4 mL). A few drops of B(Oi-Pr)$_3$ were added and the reaction vessel was flushed with H$_2$ (3×15 bar) and stirred at room temperature for 15 h under 15 bar pressure of H$_2$. The crude mixture was purified by preparative TLC (CH$_2$Cl$_2$:pentane; 1:1 then CH$_2$Cl$_2$:MeOH; 98:2) to give alcohol (1S)-41 (8 mg, 30%, 89% de) as an orange oil. R$_f$=0.2 (CH$_2$Cl$_2$:MeOH; 9:1); [α]$_D^{20}$=−1.7 (c=0.27, CH$_2$Cl$_2$); $^1$H NMR (500 MHz, CDCl$_3$) δ 8.22 (s, 1H), 8.03 (d, J=8.3 Hz, 1H), 7.75 (d, J=8.3 Hz, 1H), 7.66-7.63 (m, 1H), 7.47-7.44 (m, 1H), 5.16 (dd, J=7.7, 4.3 Hz, 1H), 4.86-4.83 (m, 1H), 4.29 (dt, J=9.9, 5.4 Hz, 1H), 3.60 (s, 3H), 2.38-2.30 (m, 2H), 1.88-1.67 (m, 4H), 1.64-1.49 (m, 5H), 1.43 (s, 3H), 1.41-1.28 (m, 6H), 0.88 (t, J=6.1 Hz, 3H); $^{13}$C NMR (126 MHz, CDCl$_3$) δ 174.04, 152.23, 147.22, 136.15, 133.60, 132.93, 129.41, 129.25, 127.91, 127.67, 127.62, 126.33, 108.68, 78.84, 78.49, 70.25, 51.64, 38.78, 33.93, 31.83, 30.36, 28.38, 25.85, 25.83, 22.77, 21.94, 14.17; IR (neat): ν$_{max}$=3455 (br.), 3054, 2987, 1642, 1422, 1265 cm$^{-1}$; HRMS (ES+) C$_{27}$H$_{37}$NO$_5$ [M+H] requires 456.2750, found 456.2735; Chiralcel IC (CO$_2$: IPA; 99:1 to 70:30 over 5 min, 3 mL/min): R$_t$ (mayor)=5.09 min, 91.4% area (1S), R$_t$ (minor)=5.59 min, 8.6% area (1R).

Iso-propyl 4-((4S,5R)-5-((E)-2-(3-((R)-1-hydroxyhexyl)quinolin-2-yl)vinyl)-2,2-dimethyl-1,3-dioxolan-4-yl)butanoate ((1R)-42)

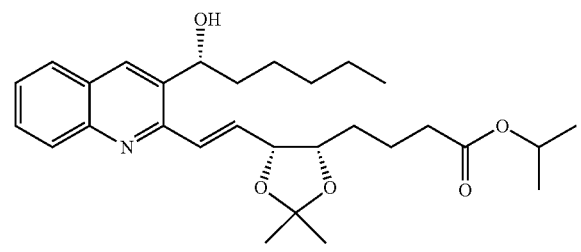

(1R)-42

Ketone 34 (105 mg, 0.23 mmol) was placed in a 10 mL conical flask containing RuCl$_2$[(S)-(DM-BINAP)][(S)-DAIPEN] (33 mg, 0.027 mmol, 12 mol %) and KOt-Bu (33 mg, 0.27 mmol, 118 mol %) in n-propanol (5 mL). A few drops of B(Oi-Pr)$_3$ were added and the reaction vessel was flushed with H$_2$ (3×15 bar) and stirred at room temperature for 22 h under 10 bar pressure of H$_2$. The product was purified by preparative TLC (CH$_2$Cl$_2$:pentane 1:1 then CH$_2$Cl$_2$:MeOH; 96:4) to give alcohol (1R)-42 (47 mg, 42%) as an orange oil. R$_f$=0.3 (CH$_2$Cl$_2$:MeOH; 9:1); [α]$_D^{20}$=+ 12.47 (c=0.83, CH$_2$Cl$_2$); $^1$H NMR (500 MHz, CDCl$_3$) 8.17 (s, 1H), 8.02 (d, J=8.5 Hz, 1H), 7.73 (d, J=8.1 Hz, 1H), 7.66-7.63 (m, 1H), 7.48-7.44 (m, 1H), 7.13 (d, J=15.1 Hz, 1H), 7.02 (dd, J=15.1, 6.4 Hz, 1H), 5.13 (dd, J=7.5, 4.9 Hz, 1H), 4.91 (sep, J=6.2 Hz, 1H), 4.83 (t, J=6.4 Hz, 1H), 4.32-4.25 (m, 1H), 2.31-2.27 (m, 2H), 1.89-1.66 (m, 4H), 1.65-1.47 (m, 5H), 1.46-1.27 (m, 9H), 1.20 (dd, J=6.2, 4.8 Hz, 2H), 1.15 (dd, J=6.2, 4.8 Hz, 4H), 0.91-0.87 (m, 3H); $^{13}$C NMR (126 MHz, CDCl$_3$) δ 173.18, 152.38, 147.24, 136.10, 133.54, 133.17, 129.37, 129.29, 128.32, 127.70, 127.63, 127.58, 126.31, 108.67, 78.91, 78.54, 70.78, 67.68, 38.67, 34.59, 31.77, 30.36, 28.44, 25.85, 25.82, 22.76, 22.04, 21.93, 14.17; IR (neat): ν$_{max}$=3400 (br.), 2980, 2932, 2858, 1730, 1458, 1215 cm$^{-1}$; HRMS (ES+) C$_{29}$H$_{41}$NO$_5$ [M+Na] requires 506.2882, found 506.2893. Separation of the diastereoisomers by HPLC (including SFC) proved difficult, therefore de has not been calculated.

Iso-propyl 4-((4S,5R)-5-((E)-2-(3-((S)-1-hydroxyhexyl)quinolin-2-yl)vinyl)-2,2-dimethyl-1,3-dioxolan-4-yl)butanoate ((1S)-42)

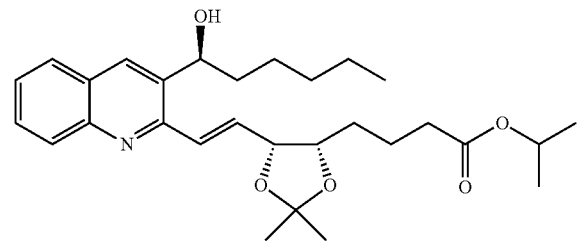

(1S)-42

Ketone 34 (25 mg, 0.055 mmol) was placed in a 10 mL conical flask containing RuCl$_2$[(R)-(DM-BINAP)][(R)-DAIPEN] (8 mg, 0.0066 mmol, 12 mol %) and KOt-Bu (8 mg, 0.065 mmol, 118 mol %) in n-propanol (5 mL). A few drops of B(Oi-Pr)$_3$ were added and the reaction vessel was flushed with H$_2$ (3×15 bar) and stirred at room temperature for 22 h under 10 bar pressure of H$_2$. The product was purified by preparative TLC (CH$_2$Cl$_2$:MeOH; 96:4) to give alcohol (1S)-42 (15 mg, 56%) as an orange oil. R$_f$=0.3 (CH$_2$Cl$_2$:MeOH; 9:1); [α]$_D^{20}$=−17.99 (c=0.59, CH$_2$Cl$_2$); $^1$H NMR (600 MHz, CDCl$_3$) δ 8.22 (s, 1H), 8.02 (d, J=8.4 Hz, 1H), 7.75 (d, J=8.0 Hz, 1H), 7.64 (ddd, J=8.4, 6.8, 1.4 Hz, 1H), 7.46 (ddd, J=8.0, 6.8, 1.4 Hz, 1H), 7.09 (d, J=15.0 Hz, 1H), 7.04 (dd, J=15.0, 6.0 Hz, 1H), 5.17 (dd, J=8.2, 4.3 Hz, 1H), 4.91 (sep, J=6.3 Hz, 1H), 4.85-4.83 (m, 1H), 4.30-4.27 (m, 1H), 2.34-2.26 (m, 2H), 1.86-1.68 (m, 4H), 1.64-1.50 (m, 5H), 1.50-1.22 (m, 9H), 1.16 (d, J=6.3 Hz, 3H), 1.13 (d, J=6.3 Hz, 3H), 0.88 (t, J=7.1 Hz, 3H); $^{13}$C NMR (151 MHz, CDCl$_3$) δ 173.16, 152.22, 147.25, 136.17, 133.63, 132.90, 129.36, 129.29, 127.89, 127.67, 127.60, 126.29, 108.66, 78.86, 78.53, 70.22, 67.68, 38.79, 34.57, 31.84, 30.37, 28.40, 25.86, 25.84, 22.78, 22.04, 21.93, 21.91, 14.17; IR (neat): ν$_{max}$=3412 (br.), 2980, 2933, 2858, 1729, 1458, 1213 cm$^{-1}$; HRMS (ES+) C$_{29}$H$_{41}$NO$_5$ [M+Na] requires 506.2882, found 506.2875. Separation of the diastereoisomers by HPLC (including SFC) proved difficult, therefore de has not been calculated.

Methyl(5S,6R)-dihydroxy-8-((E)-3-((S/R)-1-hydroxyhexyl)quinolin-2-yl)oct-7-enoate (1)

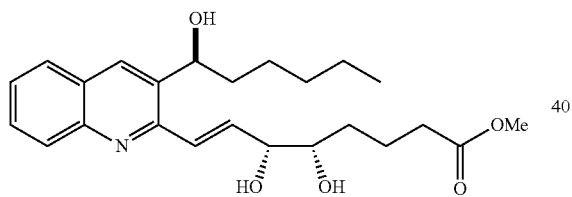

Protected compound 42 (47 mg, 0.103 mmol) was added to a 10 mL Schlenk tube containing ZrCl$_4$ (72 mg, 0.31 mmol, 301 mol %) in MeOH (1.5 mL). The reaction mixture was stirred at room temperature for 20 h. The product was purified by column chromatography (CH$_2$Cl$_2$:pentane; 1:1 to 9:1 then CH$_2$Cl$_2$:MeOH; 95:5) to give triol 1 (24 mg, 56%) as an off white waxy oil. R$_f$=0.2 (CH$_2$Cl$_2$:MeOH; 95:5); $^1$H NMR (500 MHz, (CD$_3$)$_2$CO) δ 8.99 (s, 1H), 8.67 (s, 1H), 8.14 (d, J=8.1 Hz, 1H), 7.93-7.80 (m, 2H), 7.74-7.71 (m, 1H), 7.65-7.58 (m, 1H), 7.17-7.05 (m, 1H), 5.10 (dd, J=8.7, 3.5 Hz, 1H), 4.08-4.02 (m, 1H), 3.51-3.49 (m, 1H), 3.45 (s, 3H), 2.28-2.23 (m, 2H), 1.82-1.57 (m, 5H), 1.46-1.18 (m, 8H), 0.80-0.71 (m, 3H); $^{13}$C NMR (126 MHz, (CD$_3$)$_2$CO) δ 174.07, 159.34, 143.55, 141.63, 138.19, 134.58, 134.44, 130.04, 129.55, 128.60, 121.32, 121.31, 78.38, 75.04, 68.65, 51.73, 39.68, 34.28, 32.51, 26.67, 23.47, 23.37, 22.87, 14.51. IR (neat): ν$_{max}$=3352 (br.), 2983, 2944, 2834, 2596, 2519, 2361, 2340, 2221, 2045, 1656, 1449, 1421, 1115, 1024 cm$^{-1}$; HRMS (ES+) C$_{24}$H$_{33}$NO$_5$ [M+H] requires 416.2437, found 416.2458. Separation of the diastereoisomers by HPLC (including SFC) proved difficult, therefore de has not been calculated.

Methyl(5S,6R)-dihydroxy-8-(3-((S)-1-hydroxyhexyl)quinolin-2-yl)octanoate (43)

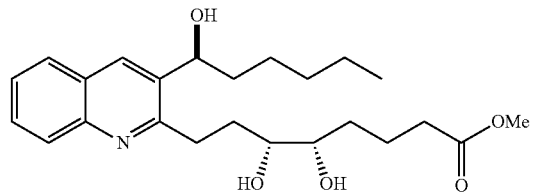

R$_f$=0.2 (CH$_2$Cl$_2$:MeOH; 9:1); $^1$H NMR (400 MHz, (CH$_3$)$_2$CO) δ 8.38-8.36 ((m, 1H), 8.01-7.88 (m, 2H), 7.73-7.66 (m, 1H), 7.57-7.49 (m, 1H), 5.23-5.15 (m, 1H), 4.46 (dd, J=14.1, 4.4 Hz, 1H), 3.79-3.78 (m, 1H), 3.64-3.56 (m, 4H), 2.38-2.33 (m, 2H), 1.96-1.46 (m, 10H), 1.36-1.28 (m, 8H), 0.92-0.87 (m, 3H); $^{13}$C NMR (101 MHz, (CH$_3$)$_2$CO) δ 172.80, 160.90, 147.83, 133.51, 129.72, 129.69, 128.90, 128.51, 128.44, 126.65, 76.33, 74.95, 70.19, 51.45, 39.61, 39.51, 34.45, 32.69, 32.48, 26.60, 26.37, 23.34, 22.33, 14.35; IR (neat): ν$_{max}$=3495 (br.), 3174, 3107, 3055, 2956, 2956, 2849, 2107, 1646, 1453, 1382, 1015 cm$^{-1}$; HRMS (ES+) C$_{24}$H$_{35}$NO$_5$ [M+H] requires 418.2593, found 418.2578.

1-(3-Bromoquinolin-4-yl)hexan-1-ol (53)

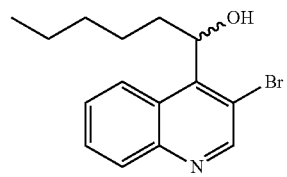

n-BuLi (3.3 mL, 1.6 M in hexanes, 5.28 mmol, 1.1 equiv.) was added to diisopropylamine (0.81 mL, 5.8 mmol, 1.21 equiv.) in THF (10 mL) in a 250 mL Schlenk at −78° C. The mixture was stirred for 15 min after which time 3-bromoquinoline (0.65 mL, 4.79 mmol) in THF (7 mL) was added over 10 min. The reaction mixture was then brought to −100° C. for 20 min. Hexanal (1.56 mL, 12.7 mmol) was added over 10 min at −100° C. The reaction mixture was stirred for 1 h at −100° C. The reaction was quenched with NH$_4$Cl sat. sol. (70 mL) and the aqueous phase was extracted in CH$_2$Cl$_2$ (4×100 mL). The combined organic phase was then washed with brine (100 mL) and dried over NaSO$_4$. The solvent was removed in vacuo and purified by column chromatography (cyclohexane:EtOAc; 95:5) to give alcohol 53 (446 mg, 30%) as a white waxy oil that solidified on standing. M.p.=53-55° C.; R$_f$=0.8 (EtOAc:pentane; 3:1); $^1$H NMR (500 MHz, CDCl$_3$) δ 8.86 (s, 1H), 8.75 (d, J=8.5 Hz, 1H), 8.08-8.06 (m, 1H), 7.70 (ddd, J=8.5, 6.9, 1.4 Hz, 1H), 7.56 (ddd, J=8.5, 6.9, 1.4 Hz, 1H), 5.66 (ddd, J=8.6, 5.2, 2.6 Hz, 1H), 2.62 (br. s, 1H), 2.24-2.12 (m, 1H), 1.94-1.88 (m, 1H), 1.73-1.62 (m, 1H), 1.39-1.28 (m, 5H), 0.89 (t, J=6.9 Hz, 3H); $^{13}$C NMR (126 MHz, CDCl$_3$) δ 152.09, 147.93, 146.70, 130.22, 129.32, 127.36, 126.74, 109.99, 75.69, 36.61, 31.53, 25.84, 22.53, 14.00. IR (neat):

1-(3-Bromoquinolin-4-yl)hexan-1-one (45)

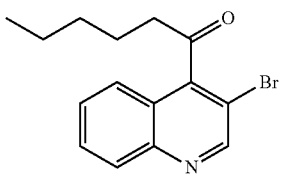

n-BuLi (0.93 mL, 1.48 M in hexanes, 1.38 mmol, 1.03 equiv) was added to diisopropylamine (0.19 mL, 1.35 mmol, 1.02 equiv.) in THF (3.2 mL) at −78° C. and stirred for 15 min. 3-Bromoquinoline (0.17 mL, 1.33 mmol) in THF (0.2 mL) was added over 10 min. The reaction mixture was then brought to −88° C. for 20 min and then −100° C. for 10 min. Hexanal (0.30 mL, 2.50 mmol, 1.88 equiv.) in THF (0.6 mL) was added over 10 min at −100° C. The mixture was stirred for 1 h at this temperature. The reaction mixture was quenched with saturated $NH_4Cl$ sat. sol. (0.6 mL), extracted in ether (3×50 mL) and dried over $NaSO_4$. The solvent was removed in vacuo and purified by column chromatography (pentane:EtOAc; 4:1) to give approximately 25% yield of a yellow oil. PCC (50 mg, 0.23 mmol) was added to $CH_2Cl_2$ (1.5 mL) at 0° C., followed by the crude alcohol 53 in $CH_2Cl_2$ (0.4 mL) and then acetic acid (0.02 mL, 0.35 mmol). The reaction mixture was stirred for 71 h with the temperature increasing to room temperature. $Et_2O$ (3.2 mL) was added, the reaction was filtered twice through filter paper and cotton wool. The crude mixture was purified by column chromatography (EtOAc:pentane; 4:1) to give 45 (16 mg, 9% over two steps) as a yellow oil product. $R_f$=0.7 (pentane:EtOAc; 4:1); $^1$H NMR (400 MHz, $CDCl_3$) δ 8.94 (s, 1H), 8.13 (d, J=8.4 Hz, 1H), 7.77 (ddd, J=8.4, 6.6, 1.7 Hz, 1H), 7.65-7.53 (m, 2H), 2.95 (t, J=7.3 Hz, 2H), 1.84 (tt, J=7.34, 7.23 Hz, 2H), 1.49-1.31 (m, 4H), 0.93 (t, J=6.9 Hz, 3H); $^{13}$C NMR (101 MHz, $CDCl_3$) δ 204.58, 151.82, 147.25, 146.70, 130.29, 128.61, 128.59, 124.11, 111.95, 44.10, 31.37, 22.88, 22.62, 14.05; IR (neat): $v_{max}$=2932, 2869, 1711, 1456 cm$^{-1}$; HRMS (E+) $C_{15}H_{16}^{79}BrNO$ [M] requires 305.0415, found 305.0416.

3-Bromoquinoline-4-carboxylic acid (54)

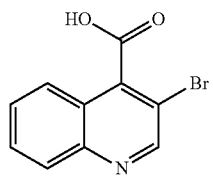

n-BuLi (1.6 M in hexanes, 3.3 mL, 5.28 mmol, 1.1 equiv) was added slowly to a 250 mL Schlenk tube containing dry THF (10 mL) and diisopropylamine (0.81 mL, 5.8 mmol, 1.1 equiv.) at −78° C. The mixture was stirred at −78° C. for 10 min after which time 3-bromoquinoline (0.65 mL, 4.8 mmol) in dry THF (7 mL) was added over 20 min. The reaction mixture was brought to −100° C. over 15 min and held at this temperature for 20 min. $CO_2$ (s) was added as a powder to the open reaction flask under a constant stream of nitrogen. The reaction mixture was allowed to come to room temperature overnight. $NaHCO_3$ sat. sol. (30 mL) was added to the reaction along with $CH_2Cl_2$ (50 mL) and the aqueous phase was brought to pH 10 by addition of $NaHCO_3$ sat. sol. (approx. 100 mL). The organic phase was extracted in $CH_2Cl_2$ (3×50 mL) and discarded and the aqueous phase was brought to pH 1 by careful addition of HCl (1 M solution, approx. 200 mL). The organic phase was extracted from this acidic aqueous phase by a 3:1 mixture of chloroform:ethanol (5×75 mL). The combined organic phase was dried over $Na_2SO_4$ and the solvent was removed in vacuo to give acid 54 (562 mg 47%) as an off-white solid. M.p.=245-247° C.; $^1$H NMR (500 MHz, $(CD_3)_2SO$) δ 9.06 (s, 1H), 8.12 (d, J=8.4 Hz, 1H), 7.89 (ddd, J=8.4, 6.8, 1.5 Hz, 1H), 7.84-7.81 (m, 1H), 7.76 (ddd, J=8.4, 6.8, 1.5 Hz, 1H); $^{13}$C NMR (126 MHz, $(CD_3)_2SO$) δ 166.53, 151.63, 145.80, 141.40, 130.61, 129.46, 128.92, 124.60, 124.06, 112.58; IR (neat): $v_{max}$=3402 (br.), 2954, 2930, 2858, 1670, 1502, 1264, 1159 cm$^{-1}$; HRMS (ES+) $C_{10}H_7NO_2^{79}Br$ [M+H] requires 251.9660, found 251.9656.

3-Bromo-N-methoxy-N-methylquinoline-4-carboxamide (60)

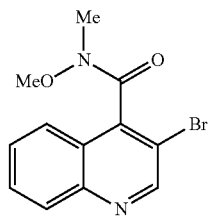

Carboxylic acid 54 (30 mg, 0.12 mmol) was added to a 10 mL Schlenk tube containing HN(OMe)Me.HCl (85 mg, 0.87 mmol, 7.25 equiv.) in dry $CH_2Cl_2$ (1 mL). The mixture was stirred for 10 min after which time 1-(3-dimethylaminopropyl)-3-ethyl-carbodiimide (80 mg, 0.417 mmol, 3.5 equiv.) and HN(OMe)Me.HCl (50 mg, 0.51 mmol, 4.25 equiv.) were added, followed by a few drops of diisopropylethylamine. The reaction mixture was stirred at room temperature for 16 h after which time the reaction was diluted with $CH_2Cl_2$ (3 mL). $NH_4Cl$ sat. sol. was added and the organic phase was extracted with $CH_2Cl_2$ (4×5 mL), The resulting organic phase was then washed with $NaHCO_3$ sat. sol. (25 mL), and brine (25 mL) and dried over $Na_2SO_4$. The resulting crude mixture was filtered through silica plug with $Et_2O$ to give 60 (25 mg, 70%) as a pale yellow oil. $R_f$=0.5 (100% $Et_2O$); $^1$H NMR (500 MHz, $CDCl_3$) δ 8.97 (s, 1H), 8.13 (d, J=8.4 Hz, 1H), 7.76 (ddd, J=8.4, 7.0, 2.6 Hz, 1H), 7.72 (d, J=8.4 Hz, 1H), 7.61 (ddd, J=8.4, 7.0, 2.6 Hz, 1H), 3.53 (s, 2H), 3.42 (s, 3H); $^{13}$C NMR (126 MHz, $CDCl_3$) 166.70, 151.65, 146.76, 142.62, 130.18, 130.06, 128.43, 124.73, 122.81, 113.96, 61.98, 32.52; IR (neat): $v_{max}$=3054, 2987, 1662, 1423, 1266, 1099 cm$^{-1}$; HRMS (ES+) $C_{12}H_{12}N_2O_2^{79}Br$ [M+H] requires 295.0082, found 295.0083.

Methyl 4-((4S,5R)-5-((E)-2-(4-(1-hydroxyhexyl)quinolin-3-yl)vinyl)-2,2-dimethyl-1,3-dioxolan-4-yl)butanoate (63)

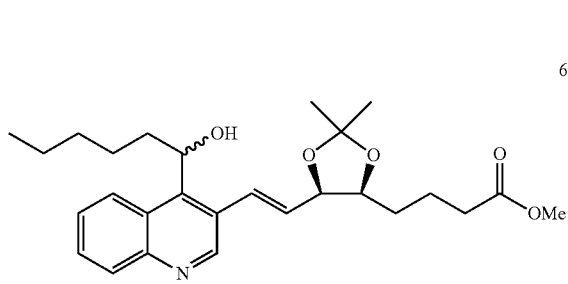

Aryl bromide 53 (49 mg, 0.16 mmol) was placed in a 10 mL Schlenk tube containing KF (28 mg, 0.482 mmol, 300 mol %), Pd(OAc)$_2$ (1 mg, 0.0045 mmol, 2.8 mol %) and JohnPhos (3 mg, 0.01 mmol, 6.3 mol %). Boronic ester 61 (82 mg, 0.23 mmol, 145 mol %) was added in dry THF (0.8 mL) followed by deionized H$_2$O (0.1 mL). The reaction mixture was heated to 80° C. for 16 h during which time the reaction mixture went darker. Et$_2$O (3 mL) was added followed by a NaOH 5% (v/v) solution (2 mL). The aqueous phase was extracted in Et$_2$O (4×3 mL) and the organic phase was washed with brine (3 mL) and dried over magnesium sulfate. The crude mixture was purified by preparative TLC (CH$_2$Cl$_2$:MeOH; 9:1) followed by an additional preparative TLC (CH$_2$Cl$_2$:MeOH; 98:2) to give the coupled product 63 (28 mg, 39%) of as an off-white wax. R$_f$=0.5 (CH$_2$Cl$_2$: pentane; 9:1); $[\alpha]_D^{20}$=-2.07 (c=0.32, CH$_2$Cl$_2$); [As this compound is a 50:50 mixture of epimers the NMR spectra have been analysed considering each epimer as an individual entity, therefore having an integration of 1 for each proton in each molecule.] $^1$H NMR (500 MHz, CDCl$_3$) 8.88 (s, 1H), 8.87 (s, 1H), 8.56 (d, J=8.6 Hz, 1H), 8.44 (d, J=8.6 Hz, 1H), 8.07 (d, J=8.6 Hz, 2H), 7.68-7.62 (m, 2H), 7.56-7.50 (m, 2H), 7.29 (d, J=15.9 Hz, 1H), 7.20 (d, J=15.9 Hz, 1H), 6.12-6.04 (m, 2H), 5.64-5.52 (m, 2H), 4.79-4.73 (m, 2H), 4.29-4.23 (m, 2H), 3.61 (s, 3H), 3.60 (s, 3H), 2.41-2.28 (m, 4H), 2.20-2.13 (m, 2H), 1.91-1.84 (m, 2H), 1.82-1.61 (m, 8H), 1.56 (s, 6H), 1.42 (s, 6H), 1.34-1.27 (m, 12H), 0.90-0.84 (m, 6H); $^{13}$C NMR (126 MHz, CDCl$_3$) δ (174.25, 174.16), (150.26, 150.04), (145.26, 145.13), (140.34, 140.34), (130.33, 130.30), (128.95, 128.95), (128.92, 128.92), (127.67, 127.61), (126.66, 126.66), (126.55, 126.55), (126.34, 126.34), (125.88, 125.66), (108.75, 108.75), (79.43, 79.39), (78.38, 78.35), (71.14, 70.99), (51.78, 51.78), (37.43, 37.39), (33.99, 33.96), (31.82, 31.80), (28.39, 28.39), (26.27, 26.27), (25.76, 25.76), (22.73, 22.73), (22.72, 21.79), (21.69, 21.69), (14.16, 14.16); IR (neat): v$_{max}$=3428 (br.), 3331, 3054, 2986, 2957, 2930, 1730, 1641, 1438, 1264 cm$^{-1}$; HRMS (ES+) C$_{27}$H$_{37}$NO$_5$ [M+H] requires 456.2750, found 456.2757; HPLC: Chiralcel IB, (Heptane:EtOH 90:10, 1 mL/min): R$_t$=8.7 min, R$_t$=11.7 min.

Methyl (5S,6R)-dihydroxy-8-((E)-4-(1-hydroxyhexyl)quinolin-3-yl)oct-7-enoate (2)

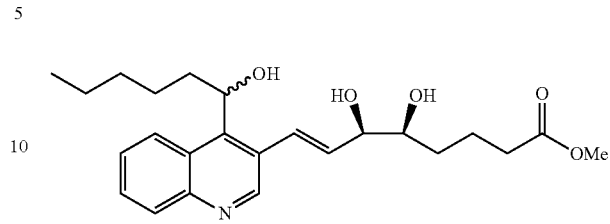

Compound 63 (28 mg, 0.0615 mmol) was added in dry MeOH (1 mL) to a 5 mL vial containing ZrCl$_4$ (43 mg, 0.18 mmol, 292 mol %). The reaction mixture was stirred overnight at room temperature. The reaction mixture was purified by preparative TLC (CH$_2$Cl$_2$:MeOH; 95:5) to give 2 (10 mg, 37%) as a white wax. R$_f$=0.2 (CH$_2$Cl$_2$:MeOH; 95:5); $[\alpha]_D^{20}$=-20.31 (c=0.65, CH$_2$Cl$_2$); [As this compound is a 50:50 mixture of epimers the NMR spectra have been analysed considering each epimer as an individual entity, therefore having an integration of 1 for each proton in each molecule.] H NMR (500 MHz, CDCl$_3$) δ 8.53 (s, 1H), 8.51-8.37 (m, 3H), 7.96 (app. t, J=8.0 Hz, 2H), 7.60-7.56 (m, 2H), 7.51-7.42 (m, 2H), 7.16 (d, J=16 Hz, 1H), 7.04 (d, J=16 Hz, 1H), 6.09-6.00 (m, 2H), 5.52-5.45 (m, 1H), 5.45-5.42 (m, 1H), 4.23-4.18 (m, 2H), 3.78-3.72 (m, 2H), 3.63 (s, 6H), 2.31 (t, J=7.3 Hz, 2H), 2.27 (t, J=7.3 Hz, 2H), 2.13-2.03 (m, 2H), 1.86-1.75 (m, 4H), 1.73-1.60 (m, 2H), 1.58-1.39 (m, 4H), 1.28-1.20 (m, 12H), 0.84-0.81 (m, 6H); $^{13}$C NMR (126 MHz, CDCl$_3$) δ (174.47, 174.43), (152.42, 152.42), (149.71, 149.58), (147.52, 147.43), (146.03, 146.03), (132.52, 132.52), (129.49, 129.47), (129.09, 129.06), (127.95, 127.79), (126.74, 126.74), (126.64, 126.64), (125.75, 125.70), (75.88, 75.78), (74.17, 74.14), (70.53, 70.53), (51.78, 51.78), (37.24, 37.17), (33.85, 33.81), (31.97, 31.97), (31.79, 31.79), (29.85, 29.85), (22.68, 22.68), (21.26, 21.21), (14.14, 14.14); IR (neat): v$_a$=3408 (br.), 2954, 2932, 2857, 1729, 1438, 1266 cm$^{-1}$; HRMS (ES+) C$_{24}$H$_{33}$NO$_5$ [M+H] requires 416.2437, found 416.2424.

Compounds (1R)-6, (1S)-6, (1R)-7, (1S)-7, (1R)-5 and (1S)-5 of formulas (VIc) (VId) and (VIe)

1-(3-Chloro-quinoxalin-2-yl)-hexan-1-one (9)

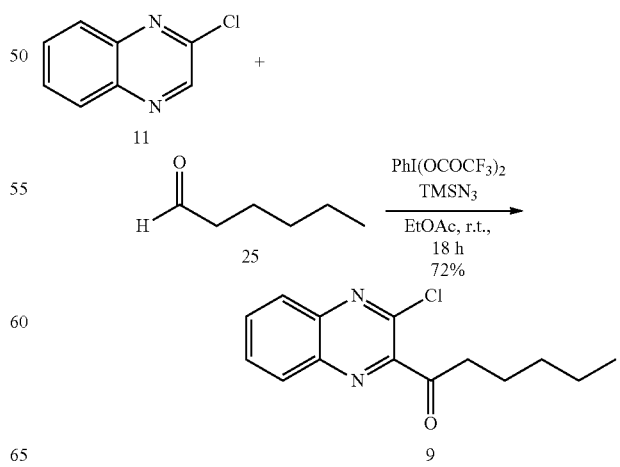

2-Chloroquinoxaline 11 (500 mg, 3.04 mmol, 1 eq) was dissolved in EtOAc (23 mL). Hexanal (1.5 mL, 12.15 mmol, 4 eq) and TMSN$_3$ (0.8 mL, 6.08 mmol, 2 eq) were added. PhI(OCOCF$_3$)$_2$ (2.61 g, 6.08 mmol, 2 eq) was added portionwise over 10 min and the mixture turned orange in colour. The mixture was stirred at room temperature for 2 h. Additional TMSN$_3$ (0.8 mL, 6.08 mmol, 2 eq) and PhI (OCOCF$_3$)$_2$ (2.61 g, 6.08 mmol, 2 eq) were added and the reaction mixture was stirred for a further 16 h. Triethylamine (7 mL) was added dropwise and the mixture was stirred for 15 min, filtered through Celite and washed with 10% CuSO$_4$ solution (3×50 mL), water (25 mL) and brine (25 mL). The organic layer was dried with MgSO$_4$, filtered and concentrated. The crude mixture was purified by silica gel column chromatography (50:1→20:1 pentane:EtOAc) to afford product 9 as a yellow solid (572 mg, 72%). R$_f$=0.4 (20:1 pentane:EtOAc); m.p.=45-48° C.; $^1$H NMR (400 MHz, CDCl$_3$) δ 8.12 (dd, J=8.0, 1.5 Hz, 1H), 8.04 (dd, J=8.0, 1.5 Hz, 1H), 7.85 (m, 2H), 3.18 (t, J=7.5 Hz, 2H), 1.82-1.72 (m, 2H), 1.44-1.31 (m, 4H), 0.91 (t, J=7.0 Hz, 3H); $^{13}$C NMR (101 MHz, CDCl$_3$) δ 200.7, 148.2, 143.7, 142.3, 139.5, 132.6, 130.8, 129.54, 128.3, 40.4, 31.3, 23.2, 22.4, 13.9; IR (neat) (ν$_{max}$, cm$^{-1}$) 3435, 1710, 1265; HRMS (ESI) [M+H]$^+$ calc 263.0951 for C$_{14}$H$_{16}$O$^{35}$Cl, found 263.0941.

1-(3-Chloroquinoxalin-2-yl)hexan-1-ol (34)

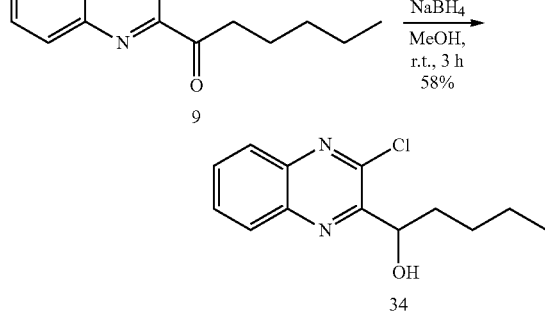

Ketone 9 (97 mg, 0.369 mmol, 1 eq) was dissolved in dry MeOH (2 mL) and cooled to 0° C. NaBH$_4$ (40 mg, 1.057 mmol, 2.9 eq) was added. The reaction was stirred at room temperature for 2 h and then was quenched by the addition of acetone (5 mL). The solvent was removed in vacuo and the mixture re-suspended in a saturated aq. NH$_4$Cl solution (25 mL) and extracted with CH$_2$Cl$_2$ (3×20 mL). The organic layer was washed with water (20 mL), brine (20 mL), dried over MgSO$_4$, filtered and concentrated. The crude product was purified by silica gel column chromatography (10:1 pentane:EtOAc) to afford the product 34 as a pale yellow solid (57 mg, 58%). R$_f$=0.50 (pentane:EtOAc 6:1); m.p.=73-79° C.; $^1$H NMR (400 MHz, CDCl$_3$) δ 8.12-8.06 (m, 1H), 8.06-8.00 (m, 1H), 7.88-7.72 (m, 2H), 5.17 (m, 1H), 4.05 (d, J=8.0 Hz, 1H), 2.06-1.98 (m, 1H), 1.65-1.54 (m, 3H), 1.41-1.25 (m, 4H), 0.88 (t, J=7.0 Hz, 3H); $^{13}$C NMR (101 MHz, CDCl$_3$) δ 156.0, 145.4, 141.8, 139.9, 130.9, 130.7, 128.6, 128.4, 70.6, 37.2, 31.7, 25.4, 22.7, 14.2; IR (CHCl$_3$) (ν$_{max}$, cm$^{-1}$) 3476, 2958, 1466, 1048; HRMS (ESI) [M+H]$^+$ calc 265.1108 for C$_{14}$H$_{18}$$^{35}$ClN$_2$O, found 265.1106.

(S)-1-(3-Chloroquinoxalin-2-yl)hexan-1-ol ((1S)-34)

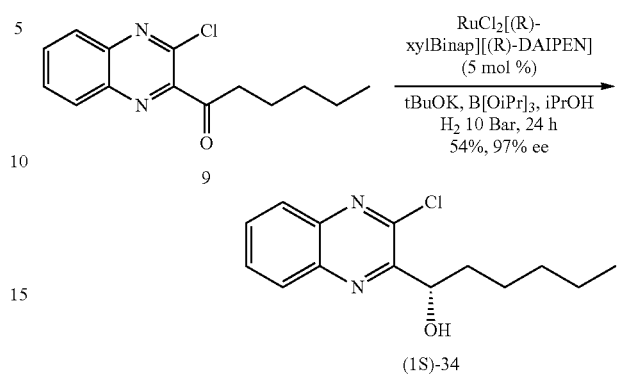

Quinoxaline ketone 9 (50 mg, 0.190 mmol, 1 eq) was dissolved in iPrOH (2.5 mL). RuCl$_2$[(R)-xylBinap][(R)-DAIPEN] (12 mg, 0.0095 mmol, 0.05 mmol), tBuOK (6 mg, 0.0535 mmol, 0.28 eq) and triisopropyl borate (0.01 mL) were added and the reaction mixture was stirred under 10 Bar of H$_2$ for 24 h. The mixture was concentrated and purified by silica gel column chromatography (10:1 pentane:EtOAc) and product (1S)-34 was isolated as a pale yellow solid (27 mg, 54%). M.p.=78-81° C.; [α]$_D$=−7.22 (c=1.5 in CHCl$_3$); ee=97% as determined by SFC using a Chiralpak IC column (CO$_2$:MeCN, gradient 99:1 0-1 min, then gradient to 60:40 until 5 min, 3 mL/min), R$_t$=3.00 min (S)-enantiomer, 3.41 min (R)-enantiomer. Identical in all other physical data to the previously prepared racemic 34.

(R)-1-(3-Chloroquinoxalin-2-yl)hexan-1-ol ((1R)-34)

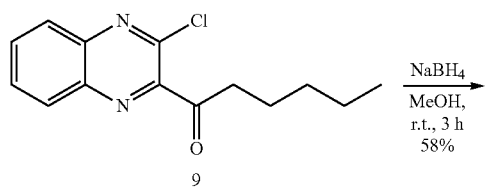

Quinoxaline ketone 9 (100 mg, 0.381 mmol, 1 eq) was dissolved in iPrOH (3 mL). RuCl$_2$[(S)-xylbinap][(S)-DAIPEN] (23 mg, 0.019 mmol, 0.05 mmol), tBuOK (11 mg, 0.095 mmol, 0.25 eq) and triisopropyl borate (0.02 mL) were added and the reaction mixture was stirred under 10 Bar of H$_2$ for 18 h. The mixture was concentrated and purified by silica gel column chromatography (10:1 pentane:EtOAc) and product (1R)-34 was isolated as a pale yellow solid (40 mg, 40%). M.p.=78-81° C.; [α]$_D$=+13.49 (c=1.5 in CHCl$_3$); ee=98% as determined by SFC using a Chiralpak IC column (CO$_2$:MeCN, gradient 99:1 0-1 min, then gradient to 60:40 until 5 min, 3 mL/min), R$_t$=3.00 min (S)- enantiomer, 3.41 min (R)-enantiomer. Identical in all other physical data to the previously prepared racemic 34.

(S)-1-(3-Chloroquinoxalin-2-yl)hexyl (R)-3,3,3-trifluoro-2-methoxy-2-phenylpropanoate ((S,R)-49)

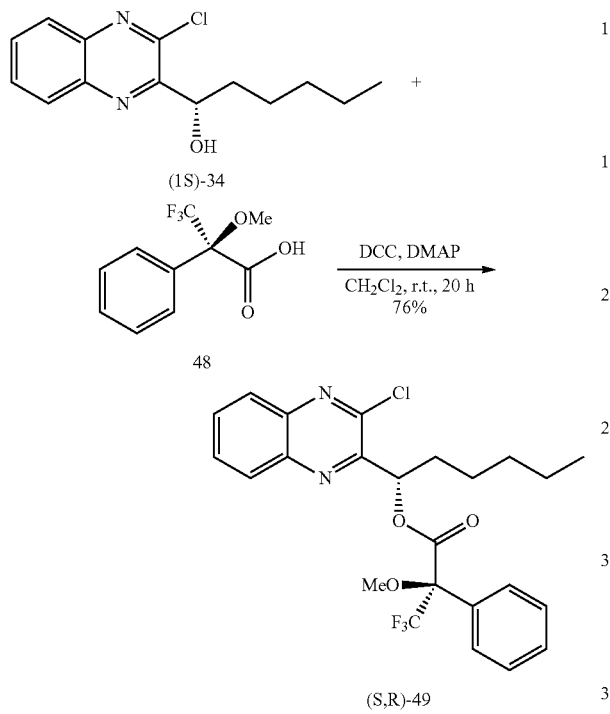

Quinoxaline alcohol (1S)-34 (35 mg, 0.432 mmol, 1 eq) and (R)-(+)-MTPA 48 (96 mg, 0.410 mmol, 3.1 eq) were dissolved in dry $CH_2Cl_2$ (2 mL). N,N'-Dicyclohexylcarbodiimide (85 mg, 0.410 mmol, 3.1 eq) and DMAP (46 mg, 0.410 mmol, 3.1 eq) were added and the reaction mixture was stirred at room temperature for 20 h. The reaction mixture was diluted with $H_2O$ (2 mL), extracted with $Et_2O$ (3×5 mL), and the extracts dried with $MgSO_4$, filtered and concentrated. The crude mixture was purified by silica gel column chromatography (9:1 cyclohexane:EtOAc) and product (S,R)-49 was isolated as a yellow oil (48 mg, 76%). $R_f$=0.46 (20:1 pentane:EtOAc); $^1$H NMR (400 MHz, $CDCl_3$) δ 8.06-8.00 (m, 1H), 7.91-7.86 (m, 1H), 7.83-7.72 (m, 2H), 7.50 (d, J=7.5 Hz, 2H), 7.44-7.38 (m, 1H), 7.37-7.30 (m, 2H), 6.32 (dd, J=8.0, 5.5 Hz, 1H), 3.62 (d, J=1.0 Hz, 3H), 2.11 (tdd, J=8.5, 6.0, 2.5 Hz, 2H), 1.63-1.52 (m, 2H), 1.41-1.30 (m, 4H), 0.89 (t, J=7.0 Hz, 3H); $^{13}$C NMR (126 MHz, $CDCl_3$) δ 166.3, 151.4, 145.2, 141.5, 140.5, 131.8, 131.1, 130.4, 129.5, 129.0, 128.2, 128.2, 127.7, 123.2 (q, J=289.0 Hz), 84.7 (q, J=28.0 Hz), 75.3, 55.7 (q, J=1.0 Hz), 32.8, 31.1, 25.2, 22.4, 13.9; $^{19}$F NMR (376 MHz, $CDCl_3$) δ −71.74; IR ($CHCl_3$) ($v_{max}$, cm$^{-1}$) 2955, 1748, 1269, 1186, 1170; $[α]_D$=−32.62 (c=1.0 in $CHCl_3$); [M+Na] calc 503.1325 for $C_{24}H_{24}N_2O_3F_3{}^{35}ClNa$, found 503.1349.

(S)-1-(3-Chloroquinoxalin-2-yl)hexyl (S)-3,3,3-trifluoro-2-methoxy-2-phenylpropanoate (S,S)-(49)

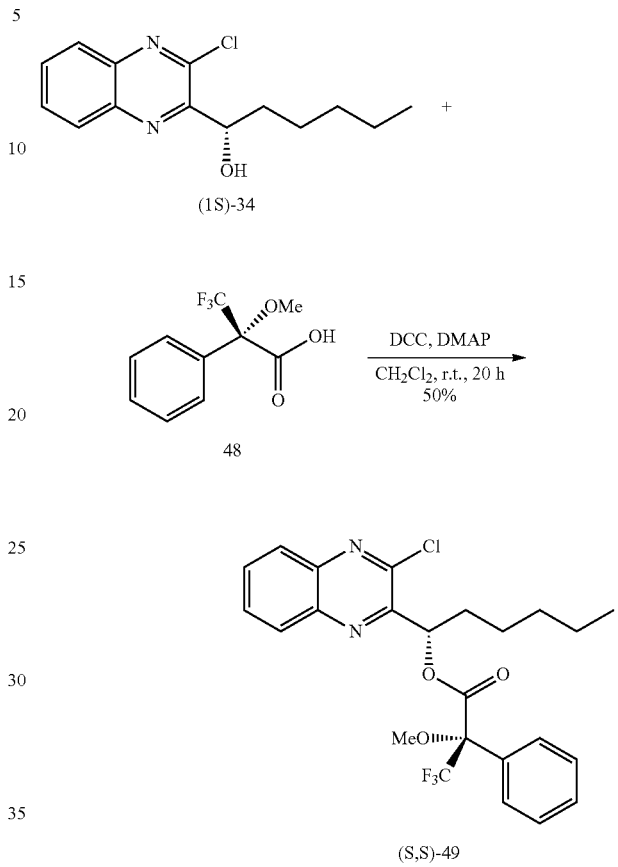

Quinoxaline alcohol (1S)-34 (20 mg, 0.076 mmol, 1 eq) and (S)-(+)-MTPA 48 (57 mg, 0.236 mmol, 3.1 eq) were dissolved in dry $CH_2Cl_2$ (2 mL). N,N'-Dicyclohexylcarbodiimide (49 mg, 0.236 mmol, 3.1 eq) and DMAP (26 mg, 0.236 mmol, 3.1 eq) were added and the reaction mixture was stirred at room temperature for 20 h. The reaction mixture was diluted with $H_2O$ (1.5 mL), extracted with $Et_2O$ (3×5 mL), and the extracts dried with $MgSO_4$, filtered and concentrated. The crude mixture was purified by preparative thin layer chromatography (20:1 cyclohexane:EtOAc) and product (S,S)-49 was isolated as a yellow oil (18 mg, 50%). $R_f$=0.46 (20:1 pentane:EtOAc); $^1$H NMR (400 MHz, $CDCl_3$) δ 8.07-8.00 (m, 2H), 7.84-7.78 (m, 2H), 7.75 (dd, J=6.5, 2.5 Hz, 2H), 7.47-7.39 (m, 3H), 6.33-6.27 (m, 1H), 3.67 (d, J=1.0 Hz, 3H), 2.04 (dd, J=14.0, 7.5 Hz, 2H), 1.47-1.20 (m, 6H), 0.85 (t, J=7.0 Hz, 3H); $^{13}$C NMR (126 MHz, $CDCl_3$) δ 166.3, 151.7, 145.0, 141.5, 140.5, 132.3, 131.1, 130.5, 129.6, 128.7, 128.4, 128.3, 127.6, 123.3 (q, J=288.8 Hz), 84.5 (q, J=27.5 Hz), 75.4, 55.7 (q, J=1.5 Hz), 33.1, 31.0, 24.9, 22.3, 13.8; $^{19}$F NMR (376 MHz, cdcl$_3$) 6-71.63; IR ($CHCl_3$) ($v_{max}$, cm$^{-1}$) 2955, 1748, 1269, 1186, 1170; $[α]_D$=−10.65 (c=0.9 in $CHCl_3$); [M+Na]$^+$ calc 503.1325 for $C_{24}H_{24}N_2O_3F_3{}^{35}ClNa$, found 503.1349.

Methyl 4-((4S,5R)-5-((E)-2-(3-((R)-1-hydroxy-hexyl)quinoxalin-2-yl)vinyl)-2,2-dimethyl-1,3-dioxolan-4-yl)butanoate ((1R)-28)

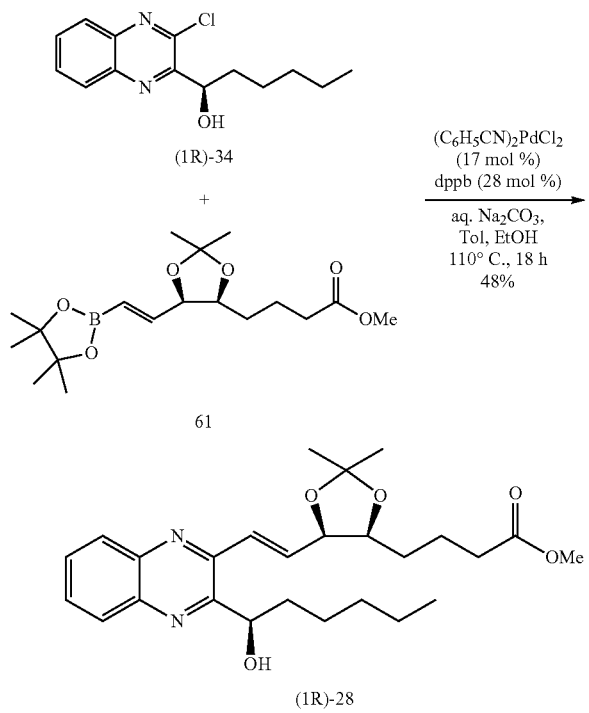

Bis(benzonitrile)Pd(II)chloride (10 mg, 0.0261 mmol, 0.17 eq) and dppb (18 mg, 0.0422 mmol, 0.28 eq) were dissolved in toluene (1 mL) and stirred at room temperature for 30 min to give a creamy orange solution. Quinoxaline alcohol (1R)-34 (40 mg, 0.151 mmol, 1 eq), dissolved in toluene (1 mL), and boronic ester 61 (62 mg, 0.180 mmol, 1.2 eq), dissolved in toluene (1 mL), were added followed by EtOH (0.05 mL) and $Na_2CO_3$ (0.17 mL of a 1 M aq. solution, 0.177 mmol, 1.2 eq). The reaction mixture was heated to 110° C. and stirred for 18 h after which time it was diluted with $H_2O$ (20 mL), extracted with EtOAc (3×15 mL), and the extracts washed with brine (20 mL), dried with $MgSO_4$, filtered and concentrated. The crude reaction mixture was purified by silica gel column chromatography (10:1→2:1 pentane:EtOAc) to give product (1R)-28 as a pale yellow oil (33 mg, 48%) $R_f$=0.2 (6:1 pentane:EtOAc); $^1$H NMR (400 MHz, $CDCl_3$) δ 8.11-7.94 (m, 2H), 7.70 (m, 2H), 7.14 (dd, J=15.0, 6.0 Hz, 1H), 6.97 (d, J=15.0 Hz, 1H), 5.16-5.10 (m, 1H), 4.84 (dd, J=11.0, 5.5 Hz, 1H), 4.64 (d, J=6.5 Hz, 1H), 4.30 (dt, J=8.5, 5.5 Hz, 1H), 3.63 (s, 3H), 2.43-2.23 (m, 2H), 1.94-1.80 (m, 2H), 1.76-1.63 (m, 2H), 1.57 (s, 3H), 1.42 (s, 3H), 1.34-1.21 (m, 8H), 0.85 (t, J=7 Hz, 3H). $^{13}$C NMR (101 MHz, $CDCl_3$) δ 173.7, 155.1, 146.9, 141.8, 139.8, 135.9, 129.7, 129.7, 129.1, 128.2, 125.3, 108.7, 78.3, 78.3, 69.8, 51.5, 38.1, 33.7, 31.5, 30.1, 28.2, 25.6, 25.2, 22.6, 21.8, 14.0; IR ($CHCl_3$) ($v_{max}$, cm$^{-1}$) 3054, 1733, 1422, 1266; $[α]_D$=+2.21 (c=0.8 in $CHCl_3$); HRMS (ESI) [M+H]$^+$ calc 457.2702 for $C_{26}H_{37}N_2O_5$, found 457.2706.

Methyl 4-((4S,5R)-5-((E)-2-(3-((S)-1-hydroxyhexyl)quinoxalin-2-yl)vinyl)-2,2-dimethyl-1,3-dioxolan-4-yl)butanoate ((1S)-28)

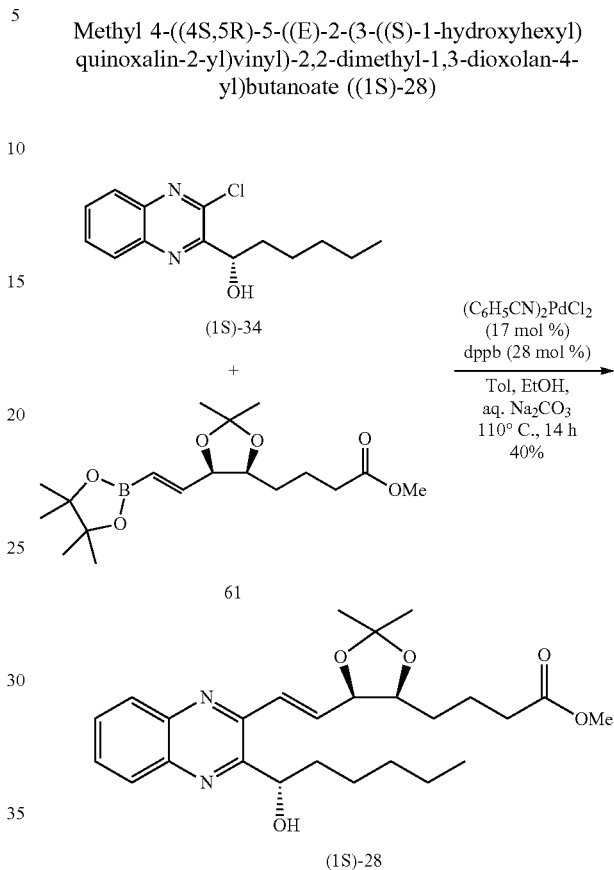

Bis(benzonitrile)Pd(II)chloride (10 mg, 0.0261 mmol, 0.17 eq) and dppb (18 mg, 0.0422 mmol, 0.28 eq) were dissolved in toluene (1 mL) and stirred at room temperature for 30 min to give a creamy orange solution. Quinoxaline alcohol (1S)-34 (39 mg, 0.147 mmol, 1 eq), dissolved in toluene (1 mL), and boronic ester 61 (70 mg, 0.198 mmol, 1.3 eq), dissolved in toluene (1 mL), were added followed by EtOH (0.05 mL) and $Na_2CO_3$ (0.17 mL of a 1 M aq. solution, 0.177 mmol, 1.2 eq). The reaction mixture was heated to 110° C. and stirred for 14 h after which time it was diluted with $H_2O$ (20 mL), extracted with EtOAc (3×20 mL), and the extracts washed with brine (20 mL), dried with $MgSO_4$, filtered and concentrated to give a crude mixture which was purified by silica gel column chromatography (10:1→2:1 pentane:EtOAc) to give product (1S)-28 as a pale yellow oil (27 mg, 40%). $R_f$=0.2 (6:1 pentane:EtOAc); $^1$H NMR (500 MHz, $CDCl_3$) δ 8.04-7.92 (m, 2H), 7.70-7.61 (m, 2H), 7.10 (dd, J=15.0, 6.0 Hz, 1H), 6.90 (d, J=15.0 Hz, 1H), 5.08 (m, 1H), 4.80 (t, J=6.0 Hz, 1H), 4.62 (d, J=7.0 Hz, 1H), 4.25 (dd, J=13.5, 6.0 Hz, 1H), 3.55 (s, 3H), 2.33-2.24 (m, 2H), 1.85-1.78 (m, 2H), 1.70-1.63 (m, 1H), 1.53 (s, 3H), 1.51-1.47 (m, 4H), 1.37 (s, 3H), 1.33-1.20 (m, 5H), 0.81 (t, J=6.8 Hz, 3H); $^{13}$C NMR (101 MHz, $CDCl_3$) δ 174.3, 155.3, 147.3, 141.9, 140.0, 137.9, 130.0, 129.9, 129.1, 128.5, 125.4, 75.2, 74.1, 70.1, 51.8, 38.1, 33.8, 31.8, 31.5, 25.3, 22.7, 21.2, 14.2; IR ($CHCl_3$) ($v_{max}$, cm$^{-1}$) 3054, 1733, 1422, 1266; $[α]_D$=+83.31 (c=0.85 in $CHCl_3$); HRMS (ESI) [M+H]$^+$ calc 457.2702 for $C_{26}H_{37}N_2O_5$, found 457.2706.

Methyl (5S,6R,E)-5,6-dihydroxy-8-(3-((S)-1-hydroxyhexyl)quinoxalin-2-yl)oct-7-enoate ((1S)-6)

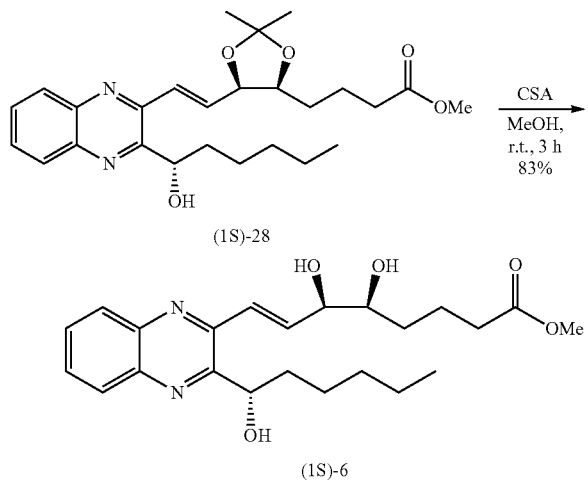

Acetonide (1S)-28 (20 mg, 0.0438 mmol, 1 eq) was dissolved in MeOH (0.5 mL), camphorsulfonic acid (9 mg, 0.0387 mmol, 0.88 eq) was added and the reaction mixture was stirred at room temperature for 3 h. The mixture was diluted with Et$_2$O (20 mL), washed with H$_2$O (20 mL), brine (20 mL), and the organic layer dried with MgSO$_4$, filtered and concentrated. The crude product was purified by preparative thin layer chromatography (96:4 CH$_2$Cl$_2$:MeOH). The product (1S)-6 was isolated as a yellow oil (15 mg, 83%). R$_f$=0.36 (96:4 CH$_2$Cl$_2$:MeOH); $^1$H NMR (500 MHz, CDCl$_3$) δ 8.07-7.99 (m, 2H), 7.74-7.69 (m, 2H), 7.22 (dd, J=15.0, 5.5 Hz, 1H), 7.04 (dd, J=15.0, 1.5 Hz, 1H), 5.16 (dd, J=7.5, 3.0 Hz, 1H), 4.51-4.47 (m, 1H), 3.85 (dt, J=8.5, 4.0 Hz, 1H), 3.66 (s, 3H), 2.37 (td, J=7.0, 2.0 Hz, 2H), 1.93-1.85 (m, 2H), 1.79-1.72 (m, 1H), 1.62-1.53 (m, 4H), 1.35-1.24 (m, 6H), 0.87 (t, J=7.0 Hz, 3H); $^{13}$C NMR (101 MHz, CDCl$_3$) δ 174.4, 155.3, 147.3, 141.8, 140.0, 137.9, 130.0, 129.9, 129.1, 128.5, 125.3, 75.2, 74.1, 70.2, 51.8, 38.1, 33.8, 31.8, 31.4, 25.3, 22.7, 21.2, 14.2; IR (CHCl$_3$) (v$_{max}$, cm$^{-1}$) 3434, 3054, 1734, 1422, 1265; [α]$_D$=−14.33 (c=0.75 in CHCl$_3$); HRMS (ESI) [M+Na]$^+$ calc 439.2209 for C$_{23}$H$_{32}$O$_5$Na, found 439.2213.

Methyl (5S,6R,E)-5,6-dihydroxy-8-(3-((R)-1-hydroxyhexyl)quinoxalin-2-yl)oct-7-enoate ((1R)-6)

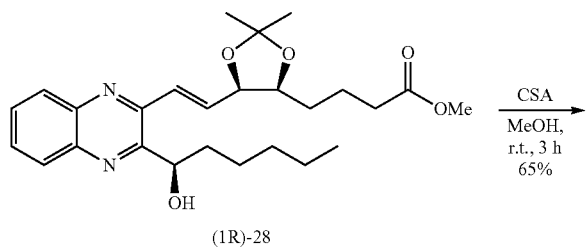

Acetonide (1R)-28 (25 mg, 0.055 mmol, 1 eq) was dissolved in MeOH (1.5 mL) and camphorsulfonic acid (14 mg, 0.060 mmol, 1.1 eq) was added and the reaction mixture was stirred at room temperature for 3 h. The mixture concentrated and was purified by preparative thin layer chromatography (96:4 CH$_2$Cl$_2$:MeOH). The product (1R)-6 was isolated as a yellow oil (15 mg, 65%). R$_f$=0.36 (96:4 CH$_2$Cl$_2$:MeOH); $^1$H NMR (400 MHz, CDCl$_3$) δ 8.07-7.95 (m, 2H), 7.75-7.67 (m, 2H), 7.25-7.19 (dd, J=15.0, 6 Hz, 1H), 7.01 (dd, J=15.0, 1.5 Hz, 1H), 5.18-5.10 (m, 1H), 4.64 (d, J=7.0 Hz, 1H), 4.49-4.44 (m, 1H), 3.89-3.82 (m, 1H), 3.66 (s, 3H), 2.75 (s, 1H), 2.63 (s, 1H), 2.38 (t, J=7.5 Hz, 2H), 1.95-1.81 (m, 2H), 1.81-1.67 (m, 2H), 1.64-1.51 (m, 4H), 1.33-1.25 (m, 4H), 0.86 (t, J=7.0 Hz, 3H); $^{13}$C NMR (101 MHz, CDCl$_3$) δ 174.2, 155.1, 147.1, 141.6, 139.9, 137.7, 129.8, 129.7, 128.9, 128.3, 125.3, 75.1, 74.0, 69.9, 51.6, 37.9, 33.6, 31.6, 31.5, 25.1, 22.6, 21.1, 14.0; IR (CHCl$_3$) (v$_{max}$, cm$^{-1}$) 3434, 3054, 1734, 1422, 1265; [α]$_D$= +36.74 (c=0.7 in CHCl$_3$); HRMS (ESI) [M]$^+$ calc 417.2389 for C$_{23}$H$_{32}$O$_5$, found 417.2371.

1-(3-Bromoquinoxalin-2-yl)octan-1-one (51)

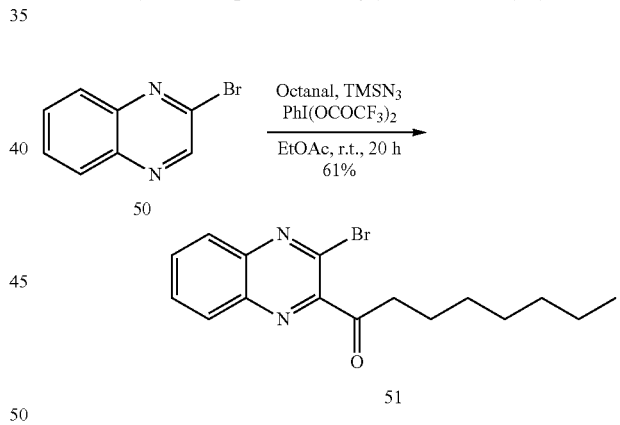

2-Bromoquinoxaline 50 (350 mg, 1.67 mmol, 1 eq) was dissolved in EtOAc (16 mL). Octanal (1.05 mL, 6.715 mmol, 4 eq) and TMSN$_3$ (0.44 mL, 6.698 mmol, 2 eq) were added. PhI(OCOCF$_3$)$_2$ (1.44 g, 6.698 mmol, 2 eq) was added portionwise over 10 min and the mixture turned orange in colour. The mixture was stirred at room temperature for 2 h. Further TMSN$_3$ (0.44 mL, 6.698 mmol, 2 eq) and PhI(OCOCF$_3$)$_2$ (1.44 g, 6.698 mmol, 2 eq) were added and reaction was stirred for 18 h. Triethylamine (2 mL) was added dropwise and the mixture was stirred for 15 min. The reaction mixture was concentrated and the crude mixture was purified by silica gel column chromatography (50:1 pentane:EtOAc) to afford product 51 as a yellow solid (259 mg, 61%). R$_f$=0.38 (10:1 cyclohexane:EtOAc); m.p.=43-48° C.; $^1$H NMR (400 MHz, CDCl$_3$) δ 8.16-8.04 (m, 2H), 7.90-7.81 (m, 2H), 3.18 (t, J=7.5 Hz, 2H), 1.83-1.75 (m, 2H), 1.44-1.28 (m, 8H), 0.89 (t, J=7.0 Hz, 3H); $^{13}$C NMR (101 MHz, CDCl$_3$) δ 201.5, 149.8, 143.3, 139.6, 134.8, 132.6, 131.2, 129.8, 128.61, 40.7, 31.8, 29.3, 29.2, 23.7, 22.8, 14.2; IR (CHCl$_3$) (v$_{max}$, cm$^{-1}$) 3429, 1708, 1560; HRMS (ESI) [M+H]$^+$ calc 335.0759 for C$_{16}$H$_{20}$N$_2$O$^{79}$Br, found 335.0759.

(R)-1-(3-Bromoquinoxalin-2-yl)octan-1-ol ((1R)-52)

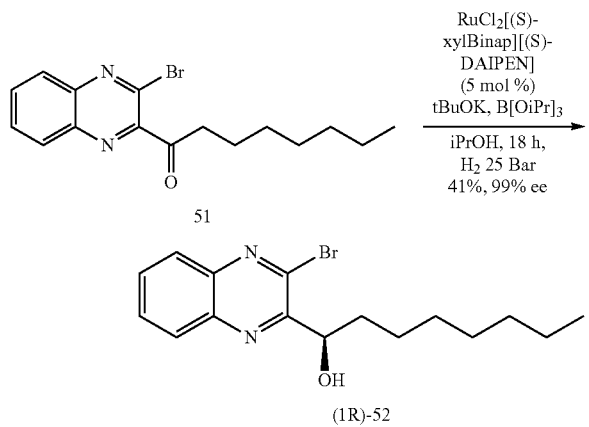

Quinoxaline ketone 51 (90 mg, 0.268 mmol, 1 eq) was dissolved in iPrOH (3 mL). RuCl$_2$[(S)-xylBinap][(S)-DAIPEN] (16 mg, 0.0134 mmol, 0.05 mmol), tBuOK (8 mg, 0.067 mmol, 0.25 eq) and triisopropyl borate (0.02 mL) were added and the reaction mixture was stirred under 25 Bar of H$_2$ for 18 h. The mixture was concentrated and purified by silica gel column chromatography (10:1 pentane:EtOAc) and product (1R)-52 was isolated as a pale yellow solid (37 mg, 41%). m.p.=48-54° C.; R$_f$=0.41 (10:1 cyclohexane:EtOAc); $^1$H NMR (300 MHz, CDCl$_3$) δ 8.15-8.04 (m, 2H), 7.88-7.76 (m, 2H), 5.24-5.15 (m, 1H), 4.04 (d, J=8.5 Hz, 1H), 2.13-2.01 (m, 1H), 1.65-1.57 (m, 3H), 1.29 (s, 8H), 0.89 (t, J=6.5 Hz, 3H); $^{13}$C NMR (101 MHz, CDCl$_3$) δ 157.0, 142.5, 139.7, 138.1, 130.7, 130.7, 128.5, 128.3, 71.4, 37.3, 31.8, 29.3, 29.2, 25.7, 22.6, 14.1; IR (CHCl$_3$) (v$_{max}$, cm$^{-1}$) 3417, 1641; [α]$_D$=+12.48 (c=1.7 in CHCl$_3$); [M+H]$^+$ calc 337.0915 for C$_{16}$H$_{22}$N$_2$O$^{79}$Br, found 337.0900; ee=99% as determined by SFC using a Chiralpak IC column (CO$_2$:MeCN, gradient 99:1 0-1 min, then gradient to 60:40 until 5 min, 3 mL/min), R$_t$=3.43 min (S)-enantiomer, 4.18 min (R)-enantiomer.

(S)-1-(3-Bromoquinoxalin-2-yl)octan-1-ol ((1S)-52)

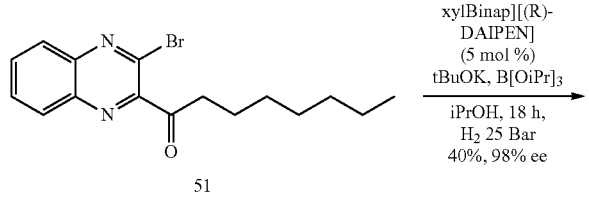

Quinoxaline ketone 51 (100 mg, 0.298 mmol, 1 eq) was dissolved in iPrOH (3 mL). RuCl$_2$[(S)-xylBinap][(S)-DAIPEN] (18 mg, 0.0145 mmol, 0.05 mmol), tBuOK (8 mg, 0.0745 mmol, 0.25 eq) and triisopropyl borate (0.02 mL) were added and the reaction mixture was stirred under 25 Bar of H$_2$ for 18 h. The mixture was concentrated and purified by silica gel column chromatography (10:1 pentane:EtOAc) and product (1S)-52 was isolated as a pale yellow solid (40 mg, 40%). [α]$_D$=−21.63 (c=0.5 in CHCl$_3$); ee=98% as determined by SFC using a Chiralpak IC column (CO$_2$:MeCN, gradient 99:1 0-1 min, then gradient to 60:40 until 5 min, 3 mL/min), R$_t$=3.43 min (S)-enantiomer, 4.18 min (R)-enantiomer; Identical in all other physical data to the previously prepared (1R)-enantiomer.

Methyl 4-((4S,5R)-5-((E)-2-(3-((R)-1-hydroxyoctyl)quinoxalin-2-yl)vinyl)-2,2-dimethyl-1,3-dioxolan-4-yl)butanoate ((1R)-53)

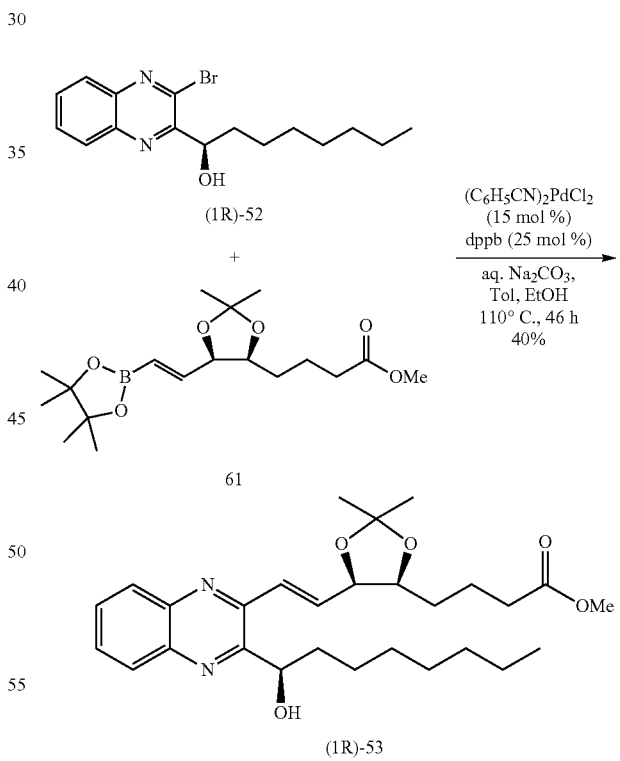

Bis(benzonitrile)Pd(II)chloride (11 mg, 0.029 mmol, 0.15 eq) and dppb (21 mg, 0.048 mmol, 0.25 eq) were dissolved in toluene (1 mL) and stirred at room temperature for 30 min to give a creamy orange solution. Quinoxaline alcohol (1R)-52 (65 mg, 0.193 mmol, 1 eq), dissolved in toluene (1 mL), and boronic ester 61 (81 mg, 0.231 mmol, 1.2 eq), dissolved in toluene (1 mL), were added followed by EtOH (0.09 mL) and Na$_2$CO$_3$ (0.22 mL of a 1 M aq. solution, 0.222 mmol, 1.15 eq). The reaction mixture was heated to 110° C. and stirred for 46 h. The reaction mixture was diluted with H$_2$O (10 mL), extracted with EtOAc (3×10 mL), and the extracts washed with brine (15 mL), dried with MgSO$_4$, filtered and concentrated. The crude product was purified by silica gel column chromatography (10:1→6:1 pentane:EtOAc) to give product (1R)-53 as a pale yellow oil (38 mg, 40%). R$_f$=0.19 (6:1 pentane:EtOAc); $^1$H NMR (400 MHz, CDCl$_3$) 8.10-7.99 (m, 2H), 7.77-7.69 (m, 2H), 7.16 (dd, J=15.0, 6.0 Hz, 1H), 6.99 (dd, J=15.0, 1.0 Hz, 1H), 5.14 (td, J=7.5, 3.0 Hz, 1H), 4.85 (td, J=6.0, 1.0 Hz, 1H), 4.61 (d, J=7.5 Hz, 1H), 4.31 (ddd, J=9.0, 6.0, 5.0 Hz, 1H), 3.63 (s, 3H), 2.41-1.81 (m, 2H), 1.94-1.81 (m, 2H), 1.78-1.68 (m, 1H), 1.59 (s, 3H), 1.58-1.52 (m, 4H), 1.44 (s, 3H), 1.37-1.19 (m, 9H), 0.87 (t, J=7.0 Hz, 3H); $^{13}$C NMR (101 MHz, CDCl$_3$) δ 173.9, 155.3, 147.0, 142.0, 140.0, 136.1, 129.9, 129.8, 129.3, 128.4, 125.5, 108.9, 78.5, 78.5, 70.0, 51.6, 38.3, 33.8, 31.9, 30.3, 29.5, 29.4, 28.4, 25.8, 25.7, 22.8, 22.0, 14.2; IR (CHCl$_3$) (v$_{max}$, cm$^{-1}$) 3461, 2910, 1737, 1645, 1381; [α]$_D$=+11.48 (c=0.9 in CHCl$_3$); HRMS (ESI) [M+H]$^+$ calc 485.3015 for C$_{28}$H$_{41}$N$_2$O$_5$, found 485.3017.

Methyl 4-((4S,5R)-5-((E)-2-(3-((S)-1-hydroxyoctyl) quinoxalin-2-yl)vinyl)-2,2-dimethyl-1,3-dioxolan-4-yl)butanoate ((1S)-53)

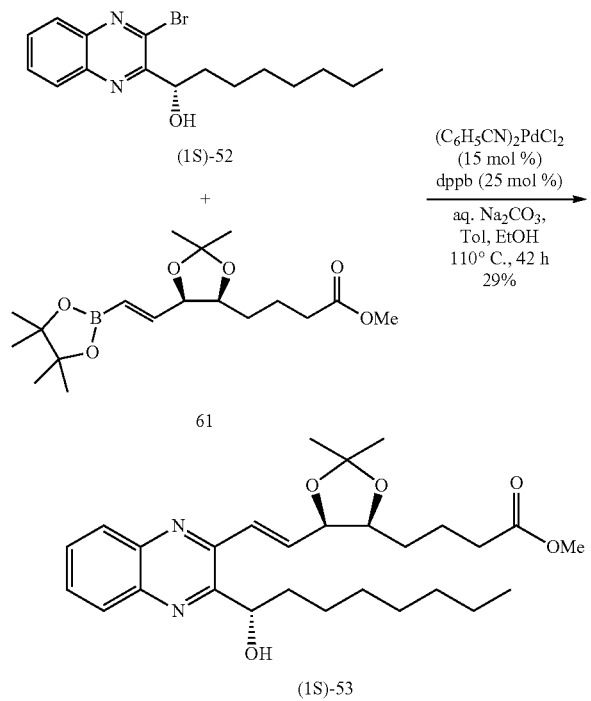

Bis(benzonitrile)Pd(II)chloride (7 mg, 0.018 mmol, 0.15 eq) and dppb (13 mg, 0.03 mmol, 0.25 eq) were dissolved in toluene (1 mL) and stirred at room temperature for 30 min to give a creamy orange solution. Quinoxaline alcohol (1S)-52 (40 mg, 0.119 mmol, 1 eq), dissolved in toluene (1 mL), and boronic ester 61 (57 mg, 0.161 mmol, 1.35 eq), dissolved in toluene (1 mL), were added followed by EtOH (0.06 mL) and Na$_2$CO$_3$ (0.14 mL of a 1 M aq. solution, 0.14 mmol, 1.15 eq). The reaction mixture was heated to 110° C. and stirred for 42 h. The reaction mixture was diluted with H$_2$O (10 mL), extracted with EtOAc (3×10 mL), and the extracts washed with H$_2$O (10 mL), brine (15 mL), dried with MgSO$_4$, filtered and concentrated. The crude product was purified by silica gel column chromatography (10:1→3:1 pentane:EtOAc) to give product (1S)-53 as a pale yellow oil (17 mg, 29%). R$_f$=0.19 (6:1 pentane:EtOAc); $^1$H NMR (400 MHz, CDCl$_3$) δ 8.09-7.99 (m, 2H), 7.76-7.68 (m, 2H), 7.17 (dd, J=15.0, 6.0 Hz, 1H), 6.97 (dd, J=15.0, 1.0 Hz, 1H), 5.15 (td, J=7.5, 3.0 Hz, 1H), 4.86 (td, J=6.5, 1.0 Hz, 1H), 4.68 (d, J=7.5 Hz, 1H), 4.32 (dt, J=8.0, 6.5 Hz, 1H), 3.62 (s, 3H), 2.43-2.27 (m, 2H), 1.93-1.82 (m, 2H), 1.78-1.69 (m, 1H), 1.59 (s, 3H), 1.57-1.51 (m, 5H), 1.44 (s, 3H), 1.32-1.24 (m, 8H), 0.86 (t, J=7.0 Hz, 3H); $^{13}$C NMR (101 MHz, CDCl$_3$) δ 173.9, 155.3, 147.0, 142.0, 140.0, 136.0, 129.9, 129.9, 129.3, 128.4, 125.3, 108.9, 78.5, 78.5, 70.0, 51.7, 38.5, 33.8, 32.0, 30.4, 29.7, 29.4, 28.3, 25.9, 25.8, 22.8, 22.0, 14.2; IR (CHCl$_3$) (v$_{max}$, cm$^{-1}$) 3461, 2910, 1737, 1645, 1381; [α]$_D$=−75.51 (c=0.9 in CHCl$_3$); HRMS (ESI) [M+H]$^+$ calc 485.3015 for C$_{28}$H$_{41}$N$_2$O$_5$, found 485.2994.

Methyl (5S,6R,E)-5,6-dihydroxy-8-(3-((R)-1-hydroxyoctyl)quinoxalin-2-yl)oct-7-enoate ((1R)-7)

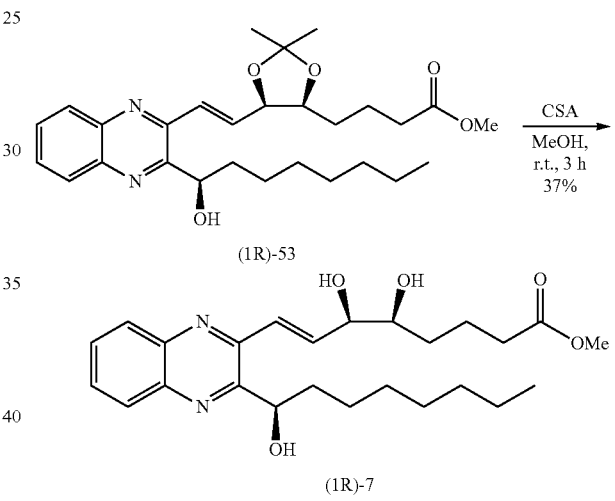

Acetonide (1R)-53 (33 mg, 0.068 mmol, 1 eq) was dissolved in MeOH (1.5 mL), camphorsulfonic acid (13 mg, 0.055 mmol, 0.8 eq) was added and the reaction mixture was stirred at room temperature for 2 h. Further camphorsulfonic acid (13 mg, 0.055 mmol, 0.8 eq) was added and the reaction mixture was stirred for 1 h. The mixture was concentrated and was purified by preparative thin layer chromatography (96:4 CH$_2$Cl$_2$:MeOH). The product (1R)-7 was isolated as a yellow oil (11 mg, 37%). R$_f$=0.31 (96:4 CH$_2$Cl$_2$:MeOH); $^1$H NMR (400 MHz, CDCl$_3$) δ 8.06-7.97 (m, 2H), 7.74-7.67 (m, 2H), 7.24 (dd, J=15.0, 5.5 Hz, 1H), 7.02 (dd, J=15.0, 1.5 Hz, 1H), 5.18-5.11 (m, 1H), 4.63 (d, J=7.0 Hz, 1H), 4.51-4.43 (m, 1H), 3.89-3.82 (m, 1H), 3.66 (s, 3H), 2.65 (s, 1H), 2.54 (s, 1H), 2.38 (t, J=7.5 Hz, 2H), 1.95-1.84 (m, 2H), 1.81-1.66 (m, 2H), 1.63-1.52 (m, 4H), 1.29-1.21 (m, 8H), 0.85 (t, J=7.0 Hz, 3H); $^{13}$C NMR (101 MHz, CDCl$_3$) δ 174.1, 155.1, 147.0, 141.7, 139.9, 137.7, 129.8, 129.7, 129.0, 128.3, 125.3, 75.1, 74.0, 69.9, 51.6, 38.0, 33.6, 31.8, 31.4, 29.4, 29.2, 25.4, 22.6, 21.1, 14.1; IR (CHCl$_3$) (v$_{max}$, cm$^{-1}$) 3386, 3020, 2254, 1720, 1216; [α]$_D$=+33.52 (c=0.7 in CHCl$_3$); HRMS (ESI) [M+H]$^+$ calc 445.2702 for C$_{25}$H$_{37}$N$_2$O$_5$, found 445.2704.

Methyl (5S,6R,E)-5,6-dihydroxy-8-(3-((S)-1-hydroxyoctyl)quinoxalin-2-yl)oct-7-enoate ((1S)-7)

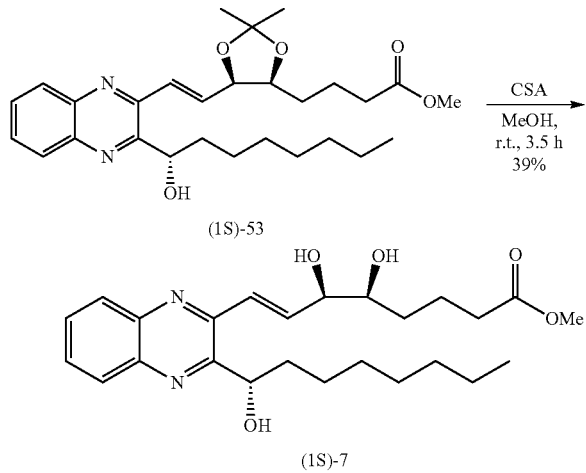

Acetonide (1S)-53 (20 mg, 0.041 mmol, 1 eq) was dissolved in MeOH (1.5 mL), camphorsulfonic acid (8 mg, 0.034 mmol, 0.8 eq) was added and the reaction mixture was stirred at room temperature for 3.5 h. The mixture was concentrated and was purified by preparative thin layer chromatography (96:4 $CH_2Cl_2$:MeOH). The product (1S)-7 was isolated as a yellow oil (7 mg, 39%). $R_f$=0.31 (96:4 $CH_2Cl_2$:MeOH); $^1$H NMR (400 MHz, $CDCl_3$) δ 8.08-7.98 (m, 2H), 7.75-7.68 (m, 2H), 7.22 (dd, J=15.0, 6.5 Hz, 1H), 7.03 (dd, J=15.0, 1.5 Hz, 1H), 5.19-5.14 (m, 1H), 4.66 (d, J=6.5 Hz, 1H), 4.54-4.45 (m, 1H), 3.91-3.80 (m, 1H), 3.66 (s, 3H), 2.58 (s, 1H), 2.47 (s, 1H), 2.37 (td, J=7.0, 1.5 Hz, 2H), 1.94-1.84 (m, 2H), 1.81-1.65 (m, 2H), 1.61-1.51 (m, 4H), 1.31-1.23 (m, 8H), 0.86 (t, J=7.0 Hz, 3H); $^{13}$C NMR (101 MHz, $CDCl_3$) δ 174.2, 155.2, 147.1, 141.7, 139.9, 137.7, 129.8, 129.7, 129.0, 128.3, 125.2, 75.1, 73.9, 70.0, 51.6, 38.0, 33.6, 31.8, 31.3, 29.4, 29.2, 25.5, 22.6, 21.0, 14.1; IR ($CHCl_3$) ($v_{max}$, cm$^{-1}$) 3386, 3020, 2254, 1720, 1216; $[α]_D$=−69.52 (c=0.7 in $CHCl_3$); HRMS (ESI) [M+H]$^+$ calc 445.2702 for $C_{25}H_{37}N_2O_5$, found 445.2722.

1-(3-Chloroquinoxalin-2-yl)butan-1-one (54)

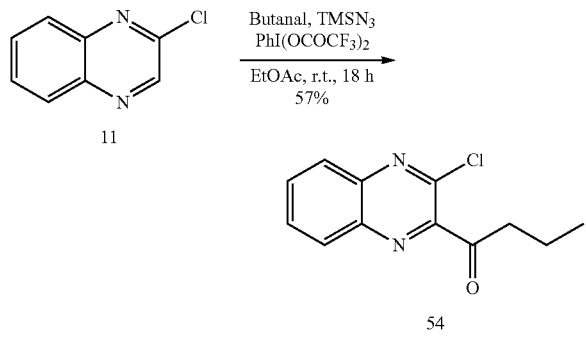

2-Chloroquinoxaline 11 (300 mg, 1.82 mmol, 1 eq) was dissolved in EtOAc (14 mL). Butyraldehyde (0.66 mL, 7.29 mmol, 4 eq) and $TMSN_3$ (0.48 mL, 3.65 mmol, 2 eq) were added. $PhI(OCOCF_3)_2$ (1.57 g, 3.65 mmol, 2 eq) was added portionwise over 15 min and the mixture turned orange in colour. The mixture was stirred at room temperature for 2 h. Further $TMSN_3$ (0.48 mL, 3.65 mmol, 2 eq) and $PhI(OCOCF_3)_2$ (1.57 g, 3.65 mmol, 2 eq) were added and reaction was stirred for 16 h. Triethylamine (2 mL) was added dropwise and the mixture was stirred for 10 min. The reaction mixture was concentrated and the crude mixture was purified by silica gel column chromatography (50:1 cyclohexane:EtOAc) to afford the product 54 as a yellow solid (234 mg, 57%). $R_f$=0.42 (10:1 cyclohexane:EtOAc); m.p.=33-36° C.; $^1$H NMR (400 MHz, $CDCl_3$) δ 8.18-8.11 (m, 1H), 8.09-8.03 (m, 1H), 7.86 (m, 2H), 3.19 (t, J=7.0 Hz, 2H), 1.87-1.78 (m, 2H), 1.06 (t, J=7.5 Hz, 3H); $^{13}$C NMR (101 MHz, $CDCl_3$) δ 200.6, 148.5, 143.7, 142.3, 139.5, 132.6, 130.8, 129.6, 128.3, 42.3, 17.1, 13.7; IR ($CHCl_3$) ($v_{max}$, cm$^{-1}$) 2983, 1710, 1260; HRMS (ESI) [M]$^+$ calc 234.0560 for $C_{12}H_{11}N_2O^{35}Cl$, found 234.0560.

(R)-1-(3-Bromoquinoxalin-2-yl)butan-1-ol ((1R)-55)

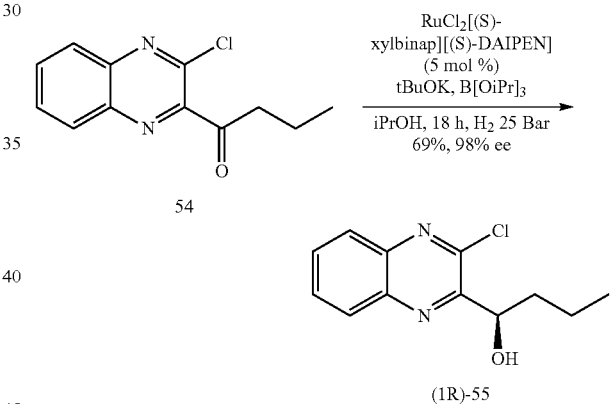

Quinoxaline ketone 54 (107 mg, 0.439 mmol, 1 eq) was dissolved in iPrOH (2.5 mL). $RuCl_2$[(S)-xylBinap][(S)-DAIPEN] (26 mg, 0.0212 mmol, 0.048 mmol), tBuOK (12 mg, 0.107 mmol, 0.24 eq) and triisopropyl borate (0.02 mL) were added and the reaction mixture was stirred under 25 Bar of $H_2$ for 18 h. The mixture was concentrated and purified by silica gel column chromatography (20:1→10:1 cyclohexane:EtOAc) and product (1R)-55 was isolated as a pale yellow solid (75 mg, 69%). $R_f$=0.31 (20:1 cyclohexane:EtOAc); m.p.=100-104° C.; $^1$H NMR (400 MHz, $CDCl_3$) δ 8.09-8.04 (m, 1H), 8.04-7.99 (m, 1H), 7.79-7.73 (m, 2H), 5.19 (td, J=8.0, 3.0 Hz, 1H), 4.10 (d, J=8.0 Hz, 1H), 2.04-1.94 (m, 1H), 1.65-1.54 (m, 3H), 0.98 (t, J=7.0 Hz, 3H); $^{13}$C NMR (101 MHz, $CDCl_3$) δ 155.9, 145.3, 141.7, 139.8, 130.8, 130.6, 128.5, 128.4, 70.3, 39.2, 18.9, 13.9; IR ($CHCl_3$) ($v_{max}$, cm$^{-1}$) 3449, 3020, 1641, 1050; $[α]_D$=−41.16 (c=2.0 in $CHCl_3$); ee=98% as determined by SFC using a Chiralpak IC column ($CO_2$:MeCN, gradient 99:1 0-1 min, then gradient to 60:40 until 5 min, 3 mL/min), $R_t$=3.02 min (S)-enantiomer, 3.45 min (R)-enantiomer.

65

(S)-1-(3-Bromoquinoxalin-2-yl)butan-1-ol ((1S)-55)

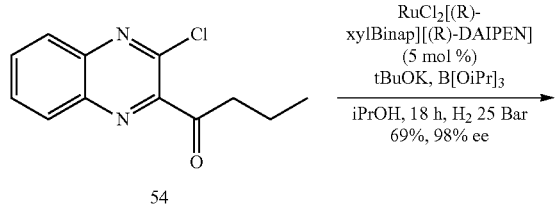

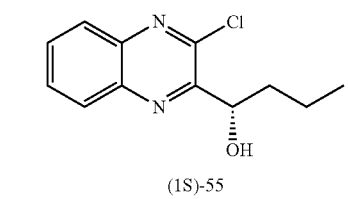

Quinoxaline ketone 54 (107 mg, 0.439 mmol, 1 eq) was dissolved in iPrOH (2.5 mL). RuCl$_2$[(R)-xylBinap][(R)-DAIPEN] (26 mg, 0.0212 mmol, 0.048 mmol), tBuOK (12 mg, 0.107 mmol, 0.24 eq) and triisopropyl borate (0.02 mL) were added and the reaction mixture was stirred under 25 Bar of H$_2$ for 18 h. The mixture was concentrated and purified by silica gel column chromatography (20:1→10:1 cyclohexane:EtOAc) and product (1S)-55 was isolated as a pale yellow solid (75 mg, 69%). [α]$_D$=−41.16 (c=2 in CHCl$_3$); ee=98% as determined by SFC using a Chiralpak IC column (CO$_2$:MeCN, gradient 99:1 0-1 min, then gradient to 60:40 until 5 min, 3 mL/min), R$_t$=3.02 min (S)-enantiomer, 3.45 min (R)-enantiomer; Identical in all other physical data to the previously prepared (1R)-enantiomer.

Methyl 4-((4S,5R)-5-((E)-2-(3-((R)-1-hydroxybutyl)quinoxalin-2-yl)vinyl)-2,2-dimethyl-1,3-dioxolan-4-yl)butanoate ((1R)-56)

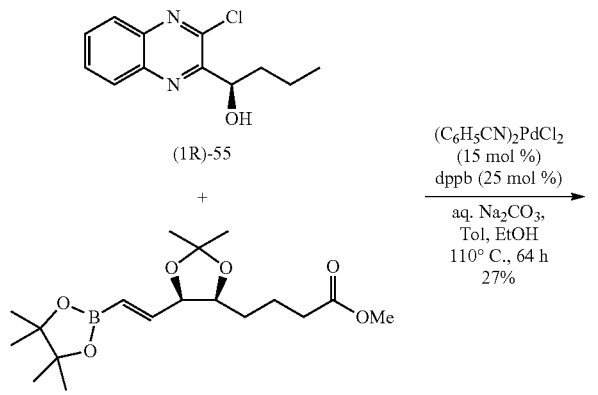

66

-continued

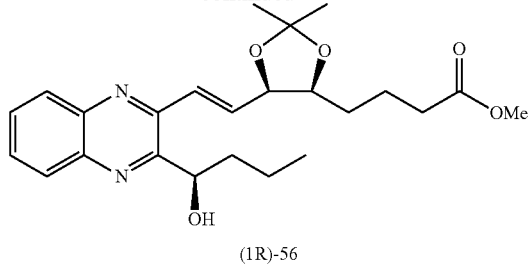

Bis(benzonitrile)Pd(II)chloride (18 mg, 0.048 mmol, 0.15 eq) and dppb (34 mg, 0.079 mmol, 0.25 eq) were dissolved in toluene (1 mL) and stirred at room temperature for 30 min to give a creamy orange solution. Quinoxaline alcohol (1R)-55 (75 mg, 0.317 mmol, 1 eq), dissolved in toluene (1 mL), and boronic ester 61 (130 mg, 0.367 mmol, 1.16 eq), dissolved in toluene (1 mL), were added followed by EtOH (0.09 mL) and Na$_2$CO$_3$ (0.37 mL of a 1 M aq. solution, 0.37 mmol, 1.15 eq). The reaction mixture was heated to 110° C. and stirred for 64 h. It was diluted with H$_2$O (10 mL), extracted with EtOAc (3×10 mL), and the extracts washed with brine (15 mL), dried with MgSO$_4$, filtered and concentrated. The crude product was purified by silica gel column chromatography (10:1→3:1 cyclohexane:EtOAc) to give product (1R)-56 as a pale yellow oil (36 mg, 27%). R$_f$=0.15 (6:1 pentane:EtOAc); $^1$H NMR (400 MHz, CDCl$_3$) δ 8.09-7.99 (m, 2H), 7.75-7.68 (m, 2H), 7.16 (dd, J=15.0, 6.0 Hz, 1H), 6.99 (d, J=15.0 Hz, 1H), 5.16 (td, J=7.0, 3.0 Hz, 1H), 4.85 (t, J=6.0 Hz, 1H), 4.62 (d, J=7.0 Hz, 1H), 4.32 (dt, J=8.5, 6.0 Hz, 1H), 3.63 (s, 3H), 2.39-2.32 (m, 2H), 1.91-1.72 (m, 3H), 1.62-1.50 (m, 8H), 1.44 (s, 3H), 0.98 (t, J=7.0 Hz, 3H); $^{13}$C NMR (101 MHz, CDCl$_3$) δ 173.9, 155.3, 147.0, 142.0, 140.1, 136.1, 129.9, 129.8, 129.3, 128.4, 125.5, 108.9, 78.5, 78.5, 69.7, 51.7, 40.4, 33.8, 30.3, 28.4, 25.8, 22.0, 18.9, 14.0; IR (CHCl$_3$) (v$_{max}$, cm$^{-1}$) 3316, 2960, 1729, 1650, 1216; [α]$_D$=+12.14 (c=1.0 in CHCl$_3$); HRMS (ESI) [M+H]$^+$ calc 429.2389 for C$_{24}$H$_{33}$N$_2$O$_5$, found 429.2396.

Methyl 4-((4S,5R)-5-((E)-2-(3-((S)-1-hydroxybutyl)quinoxalin-2-yl)vinyl)-2,2-dimethyl-1,3-dioxolan-4-yl)butanoate ((1S)-56)

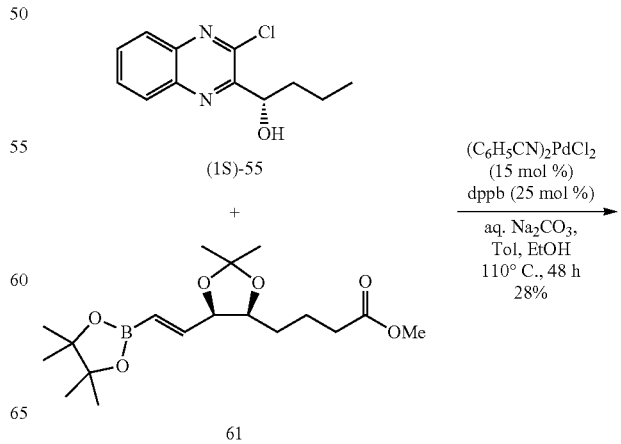

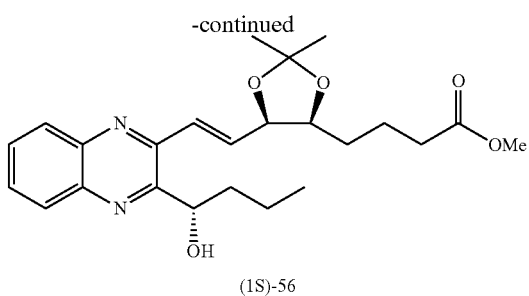

(1S)-56

Bis(benzonitrile)Pd(II)chloride (15 mg, 0.038 mmol, 0.15 eq) and dppb (27 mg, 0.063 mmol, 0.25 eq) were dissolved in toluene (1 mL) and stirred at room temperature for 30 min to give a creamy orange solution. Quinoxaline alcohol (1S)-55 (60 mg, 0.253 mmol, 1 eq), dissolved in toluene (1 mL), and boronic ester 61 (113 mg, 0.319 mmol, 1.26 eq), dissolved in toluene (1 mL), were added followed by EtOH (0.08 mL) and Na$_2$CO$_3$ (0.29 mL of a 1 M aq. solution, 0.29 mmol, 1.15 eq). The reaction mixture was heated to 110° C. and stirred for 48 h. The reaction mixture was diluted with H$_2$O (10 mL), extracted with EtOAc (3×10 mL), and the extracts washed with brine (15 mL), dried with MgSO$_4$, filtered and concentrated. The crude product was purified by silica gel column chromatography (6:1→3:1 cyclohexane:EtOAc) to give product (1S)-56 as a pale yellow oil (30 mg, 28%). R$_f$=0.15 (6:1 pentane:EtOAc); $^1$H NMR (400 MHz, CDCl$_3$) δ 8.10-7.98 (m, 2H), 7.77-7.67 (m, 2H), 7.17 (dd, J=15.0, 5.5 Hz, 1H), 6.98 (dd, J=15.0, 1.5 Hz, 1H), 5.21-5.13 (m, 1H), 4.86 (td, J=6.5, 1.0 Hz, 1H), 4.69 (d, J=7.0 Hz, 1H), 4.32 (ddd, J=8.5, 6.5, 5.5 Hz, 1H), 3.62 (s, 3H), 2.40-2.31 (m, 2H), 1.92-1.81 (m, 2H), 1.78-1.68 (m, 1H), 1.59 (s, 3H), 1.59-1.50 (m, 5H), 1.44 (s, 3H), 0.96 (t, J=7.0 Hz, 3H); $^{13}$C NMR (101 MHz, CDCl$_3$) δ 173.7, 155.1, 146.9, 141.8, 139.8, 135.7, 129.7, 129.7, 129.1, 128.2, 125.1, 108.7, 78.3, 78.3, 69.6, 51.5, 40.3, 33.7, 30.2, 28.1, 25.6, 21.8, 18.9, 13.9; IR (CHCl$_3$) (ν$_{max}$, cm$^{-1}$) 3316, 2960, 1729, 1650, 1216; [α]$_D$=−94.53 (c=1.5 in CHCl$_3$); HRMS (ESI) [M+H]$^+$ calc 429.2389 for C$_{24}$H$_{33}$N$_2$O$_5$, found 429.2392.

Methyl (5S,6R,E)-5,6-dihydroxy-8-(3-((R)-1-hydroxybutyl)quinoxalin-2-yl)oct-7-enoate ((1R)-5)

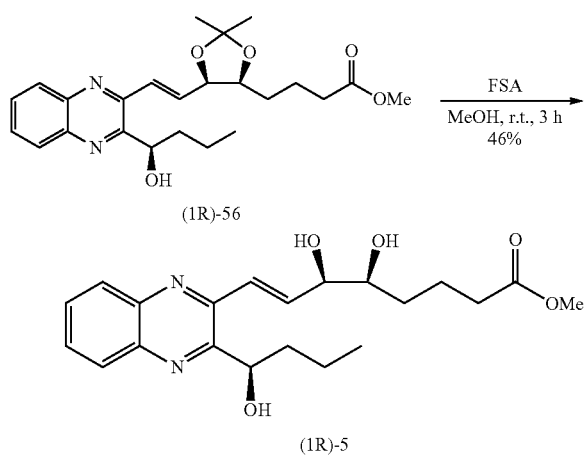

Acetonide (1R)-56 (29 mg, 0.068 mmol, 1 eq) was dissolved in MeOH (1.5 mL), camphorsulfonic acid (16 mg, 0.068 mmol, 1 eq) was added and the reaction mixture was stirred at room temperature for 3 h. The mixture was diluted with Et$_2$O (15 mL), washed with H$_2$O (10 mL), brine (10 mL), and the organic layer dried with MgSO$_4$, filtered and concentrated. The crude product was purified by preparative thin layer chromatography (96:4 CH$_2$Cl$_2$:MeOH). The product (1R)-5 was isolated as a yellow oil (12 mg, 46%). R$_f$=0.41 (96:4 CH$_2$Cl$_2$:MeOH); $^1$H NMR (400 MHz, CDCl$_3$) δ 8.05-7.93 (m, 2H), 7.72-7.65 (m, 2H), 7.22 (dd, J=15.0, 5.5 Hz, 1H), 7.01 (dd, J=15.0, 1.5 Hz, 1H), 5.14 (dd, J=7.5, 6.5 Hz, 1H), 4.65 (d, J=6.5 Hz, 1H), 4.49-4.42 (m, 1H), 3.88-3.82 (m, 1H), 3.65 (s, 3H), 2.94 (s, 1H), 2.79 (s, 1H), 2.37 (t, J=7.2 Hz, 2H), 2.02-1.40 (m, 8H), 0.94 (t, J=7.1 Hz, 3H); $^{13}$C NMR (101 MHz, CDCl$_3$) δ 174.3, 155.3, 147.3, 141.8, 140.0, 138.1, 130.0, 129.9, 129.1, 128.4, 125.4, 75.3, 74.2, 69.8, 51.8, 40.1, 33.8, 31.7, 21.3, 18.8, 14.0; IR (CHCl$_3$) (ν$_{max}$, cm$^{-1}$) 3020, 2976, 1734, 1216, 1095; [α]$_D$=+27.63 (c=1.2 in CHCl$_3$); HRMS (ESI) [M+H]$^+$ calc 389.2076 for C$_{21}$H$_{29}$N$_2$O$_5$, found 389.2096.

Methyl (5S,6R,E)-5,6-dihydroxy-8-(3-((S)-1-hydroxybutyl)quinoxalin-2-yl)oct-7-enoate ((1S)-5)

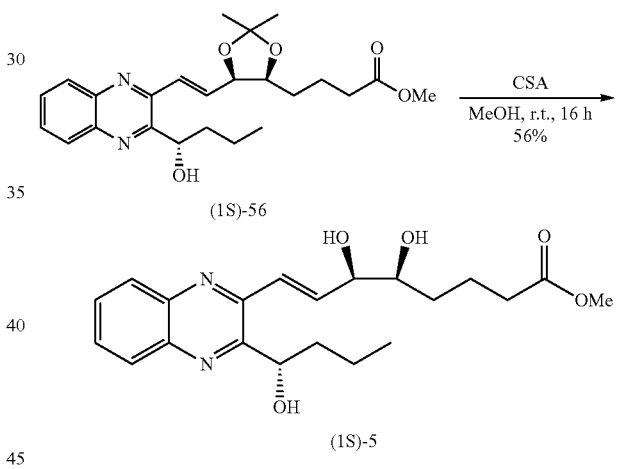

Acetonide (1S)-56 (28 mg, 0.065 mmol, 1 eq) was dissolved in MeOH (1.5 mL), camphorsulfonic acid (16 mg, 0.069 mmol, 1.05 eq) was added and the reaction mixture was stirred at room temperature for 16 h The mixture was diluted with Et$_2$O (15 mL), washed with H$_2$O (10 mL), brine (10 mL), and the organic layer dried with MgSO$_4$, filtered and concentrated. The crude product was purified by preparative thin layer chromatography (96:4 CH$_2$Cl$_2$:MeOH). The product (1S)-5 was isolated as a yellow oil (14 mg, 56%). R$_f$=0.41 (96:4 CH$_2$Cl$_2$:MeOH); $^1$H NMR (400 MHz, CDCl$_3$) δ 8.07-7.95 (m, 2H), 7.75-7.64 (m, 2H), 7.21 (dd, J=15.5, 5.5 Hz, 1H), 7.04 (d, J=15.5 Hz, 1H), 5.22-5.10 (m, 1H), 4.72-4.61 (m, 1H), 4.53-4.45 (m, 1H), 3.90-3.81 (m, 1H), 3.65 (s, 3H), 2.93-2.55 (m, 2H), 2.37 (t, J=7.0 Hz, 2H), 1.96-1.67 (m, 4H), 1.59-1.48 (m, 4H), 0.95 (t, J=7.0 Hz, 3H); $^{13}$C NMR (101 MHz, CDCl$_3$) δ 174.2, 155.2, 147.2, 141.6, 139.8, 137.8, 129.8, 129.7, 128.9, 128.3, 125.2, 75.1, 74.0, 69.8, 51.6, 40.0, 33.6, 31.3, 21.1, 18.7, 13.9; IR (CHCl$_3$) (ν$_{max}$, cm$^{-1}$) 3020, 2976, 1734, 1216, 1095; [α]$_D$=−60.02 (c=1.4 in CHCl$_3$); HRMS (ESI) [M+H]$^+$ calc 389.2076 for C$_{21}$H$_{29}$N$_2$O$_5$, found 389.2076.

Compounds 1R-17 and 1S-17 of Formula (VIh),
Compounds 1R-16 and 1S-16 of Formula (VIg)
and Compounds 1R-48 and 1S-48 of Formula (Vii)

1-(4-Bromoisoquinolin-1-yl)hexan-1-one

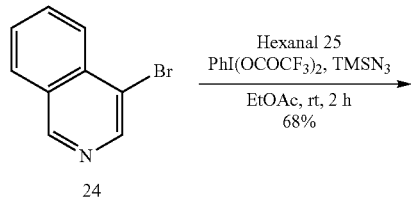

4-Bromoisoquinoline 24 (0.5 g, 2.40 mmol) was dissolved in EtOAc (20 mL) and hexanal (1.18 mL, 9.61 mmol) and TMSN$_3$ (0.63 mL, 4.81 mmol) were added. (Bis(trifluoroacetoxy)iodo)benzene (2.07 g, 4.81 mmol) was added slowly over 10 min and the mixture was stirred at room temperature for 2 h. Triethylamine (6.25 mL) was added and the reaction was stirred for 10 min. After removal of the solvents in vacuo the residue was purified by silica gel column chromatography (cyclohexane/MeOH, 99:1) to yield the ketone 22 (0.5 g, 68%) as an orange solid. TLC: R$_f$=0.52 (pentane/EtOAc, 19:1); $^1$H NMR (400 MHz, CDCl$_3$) 8.85 (d, J=8.6 Hz, 1H), 8.73 (s, 1H), 8.20 (d, J=8.5 Hz, 1H), 7.79 (dd, J=8.5, 7.6 Hz, 1H), 7.69 (dd, J=8.6, 7.6 Hz, 1H), 3.26 (t, J=7.4 Hz, 2H), 1.80-1.71 (m, 2H), 1.41-1.35 (m, 4H), 0.91 (t, J=6.9 Hz, 3H); $^{13}$C NMR (101 MHz, CDCl$_3$) δ 204.3, 152.6, 143.0, 135.7, 131.6, 129.8, 127.3, 127.0, 126.3, 123.6, 40.5, 31.6, 24.0, 22.7, 14.1; IR (v$_{max}$) 3053, 2957, 1697, 1560, 1490, 1265 cm$^{-1}$; HRMS (ESI) Found 306.0498 [M+H] C$_{15}$H$_{17}$NOBr requires 306.0494.

(5S,6R,E)-Methyl 5,6-bis((tert-butyldimethylsilyl)
oxy)-8-(1-hexanoylisoquinolin-4-yl)oct-7-enoate

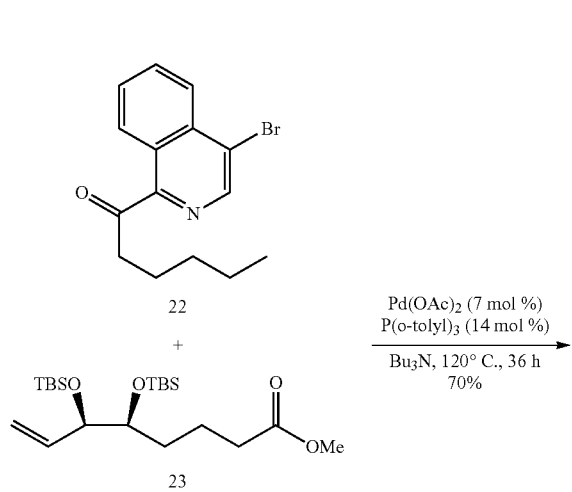

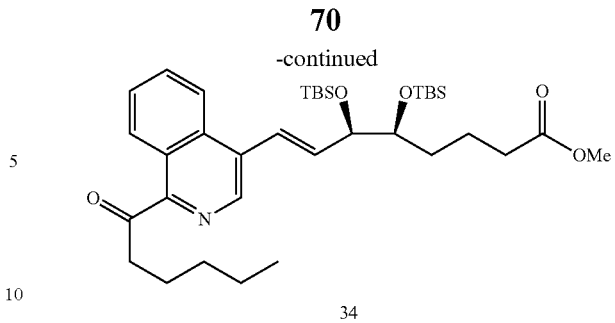

Pd(OAc)$_2$ (2.5 mg, 0.01 mmol), P(o-tolyl)$_3$ (7 mg, 0.02 mmol) and tributylamine (0.85 mL, 3.59 mmol) were sealed under nitrogen and stirred at 80° C. for 10 min. Ketone 22 (50 mg, 0.163 mmol) and alkene 23 (74 mg, 0.179 mmol) were added and the reaction mixture was stirred at 120° C. for 36 h. After filtering through a pad of silica with EtOAc (250 mL) most of the solvent (200 mL) was removed in vacuo and the remaining solution was washed with 10% (w/v) CuSO$_4$ solution (3×20 mL). The organic layer was separated and washed with water (50 mL) and brine (50 mL) and dried over MgSO$_4$. The solvent was removed in vacuo and the residue was purified by silica gel column chromatography (pentane/EtOAc, 19:1) to afford 34 (74 mg, 70%) as an orange oil. TLC: R$_f$=0.31 (pentane/EtOAc, 19:1); [α]$_D^{20}$ −16.3 (c=0.55, CHCl$_3$); $^1$H NMR (400 MHz, CDCl$_3$) δ 8.93-8.89 (d, J=8.3 Hz, 1H), 8.65 (s, 1H), 8.11 (d, J=8.3 Hz, 1H), 7.76-7.71 (m, 1H), 7.70-7.65 (m, 1H), 7.16 (d, J=15.9 Hz, 1H), 6.40 (dd, J=15.9, 6.7 Hz, 1H), 4.31-4.26 (m, 1H), 3.77 (m, 1H), 3.66 (s, 3H), 3.31 (t, J=7.5 Hz, 2H), 2.34 (t, J=7.2 Hz, 2H), 1.81-1.73 (m, 4H), 1.66-1.54 (m, 2H), 1.42-1.38 (m, 4H), 0.95 (s, 9H), 0.92 (t, J=7.1 Hz, 3H), 0.87 (s, 9H), 0.09 (4×s, 12H); $^{13}$C NMR (101 MHz, CDCl$_3$) δ 205.0, 174.1, 152.5, 138.8, 137.4, 134.7, 131.9, 130.4, 128.8, 127.3, 125.5, 125.0, 123.3, 77.2, 76.2, 51.6, 40.4, 34.4, 33.4, 31.7, 26.1, 26.1, 24.1, 22.7, 20.7, 18.5, 18.3, 14.1, −3.8, −3.8, −4.4, −4.4; IR (neat) (v$_{max}$) 3054, 2963, 2928, 2855, 1735, 1677, 1420, 1265 cm$^{-1}$; HRMS (ESI) Found 642.3979 [M+H]$^+$ C$_{36}$H$_{60}$NO$_5$Si$_2$ requires 642.4010.

(5S,6R,E)-Methyl 5,6-bis((tert-butyldimethylsilyl)
oxy)-8-(1-(1-hydroxyhexyl)isoquinolin-4-yl)oct-7-enoate

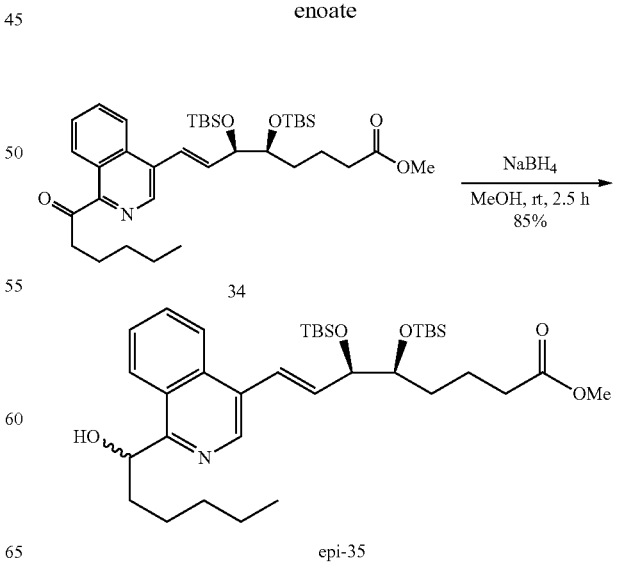

Ketone 34 (70 mg, 0.11 mmol) was dissolved in dry methanol (4 mL) and sodium borohydride (8.4 mg, 0.22 mmol) was added at 0° C. The reaction was stirred at room temperature for 2.5 h and quenched with acetone (4 mL). The solvent was evaporated and saturated NH$_4$Cl solution (20 mL) and Et$_2$O (10 mL) were added. The organic phase was separated and the aqueous phase extracted with Et$_2$O (3×10 mL). The combined organic layers were washed with water (20 mL) and brine (20 mL) and dried over MgSO$_4$. The solvent was removed in vacuo and the yellow residue was purified by silica gel chromatography (pentane/EtOAc, 19:1) to afford epi-35 (60 mg, 85%) as a yellow oil. TLC: R$_f$=0.57 (pentane/EtOAc, 15:1); $^1$H NMR (400 MHz, CDCl$_3$) δ 8.51 (s, 1H), 8.12-8.02 (m, 2H), 7.77-7.68 (m, 1H), 7.66-7.60 (m, 1H), 7.10 (d, J=15.8 Hz, 1H), 6.29 (dd, J=15.8, 6.1 Hz, 1H), 5.47-5.42 (m, 1H), 5.17-4.93 (s, br, 1H), 4.30-4.24 (m, 1H), 3.79-3.73 (m, 1H), 3.66 (s, 3H), 2.33 (t, J=7.4 Hz, 2H), 1.76-1.60 (m, 4H), 1.38-1.26 (m, 8H), 0.95 (s, 9H), 0.88-0.86 (m, 12H), 0.12-0.03 (4×s, 12H); $^{13}$C NMR (101 MHz, CDCl$_3$) δ 174.1, 160.7, 138.1, 135.6, 134.5, 130.3, 128.3, 127.2, 125.2, 124.6, 124.4, 124.1, 77.3, 76.3, 69.8, 51.6, 39.5, 34.5, 33.3, 32.0, 29.9, 29.8, 26.1, 26.1, 25.5, 22.8, 20.8, 18.5, 18.4, 14.2, −3.8, −3.8, −4.4, −4.4; HRMS (ESI) Found 666.3990 [M+Na]$^+$ C$_{36}$H$_{61}$NO$_5$NaSi$_2$ requires 666.3986.

(5S,6R,E)-Methyl 5,6-bis((tert-butyldimethylsilyl)oxy)-8-(1-((R)-1-hydroxyhexyl)isoquinolin-4-yl)oct-7-enoate

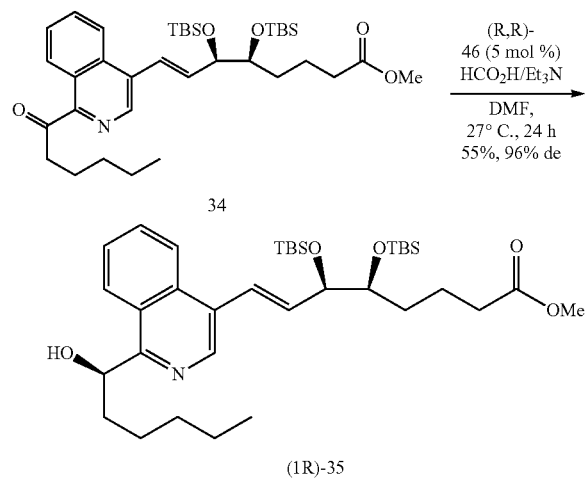

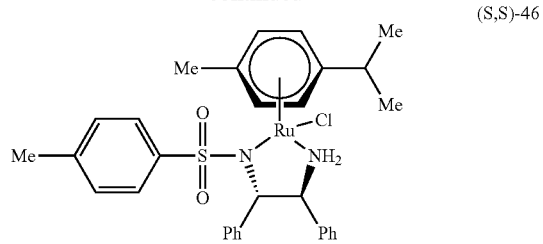

A mixture of formic acid (0.03 mL, 670 μmol) and triethylamine (0.05 mL, 390 μmol) was added to ketone 34 (100 mg, 0.16 μmol) with RuCl-(p-cymene)[R,R-TsDPEN], (R,R)-46, (5 mg, 8 μmol) in anhydrous DMF (1 mL). The mixture was degassed by freeze-thaw cycles and stirred at 27° C. for 24 h. The mixture was neutralised with saturated NaHCO$_3$ solution (5 mL) and diluted with EtOAc (10 mL). The organic phase was separated and the aqueous phase extracted with EtOAc (3×20 mL). The combined organic layers were washed with water (20 mL) and brine (20 mL) and dried over MgSO$_4$. The solvent was removed in vacuo and the residue was purified by silica gel column chromatography (pentane/EtOAc, 9:1) to afford (1R)-35 (55 mg, 55%) as an orange oil. de=96%, as determined by chiral SFC using a Chiralpak IC column (CO$_2$: 2-PrOH, 99:1 to 85:15 after 1 min); flow rate: 3 mL/min; R$_t$-(1S)=1.91 min, R$_t$-(1R)=2.24 min; TLC: R$_f$=0.36 (pentane/EtOAc, 9:1); [α]$_D^{20}$+1.9 (c=1.00, CHCl$_3$); $^1$H NMR (400 MHz, CDCl$_3$) δ 8.51 (s, 1H), 8.10 (d, J=8.5 Hz, 1H), 8.04 (d, J=8.4 Hz, 1H), 7.74-7.70 (m, 1H), 7.66-7.61 (m, 1H), 7.10 (d, J=15.8 Hz, 1H), 6.30 (dd, J=15.8, 6.8 Hz, 1H), 5.47 (t, J=6.2 Hz, 1H), 5.08 (s, 1H), 4.27 (dd, J=6.8, 4.9 Hz, 1H), 3.76 (m, 1H), 3.66 (s, 3H), 2.33 (t, J=7.5 Hz, 2H), 2.01-1.92 (m, 1H), 1.83-1.56 (m, 6H), 1.53-1.44 (m, 1H), 1.34-1.26 (m, 4H), 0.94 (s, 9H), 0.89-0.84 (m, 12H), 0.16-0.04 (4×s, 12H); $^{13}$C NMR (101 MHz, CDCl$_3$) δ 174.1, 160.8, 138.1, 135.6, 134.5, 130.3, 128.3, 127.2, 125.1, 124.6, 124.4, 124.1, 77.3, 76.3, 69.8, 51.6, 39.6, 34.5, 33.3, 32.0, 26.2, 26.1, 25.5, 22.8, 20.8, 18.5, 18.4, 14.2, −3.8, −3.8, −4.4, −4.4; IR (v$_{max}$) 3623, 3054, 2928, 2852, 1734, 1450, 1266 cm$^{-1}$; HRMS (ESI) Found 644.4145 [M+H]$^+$ C$_{36}$H$_{62}$NO$_5$Si$_2$ requires 644.4167.

(5S,6R,E)-Methyl 5,6-bis((tert-butyldimethylsilyl)oxy)-8-(1-((S)-1-hydroxyhexyl)isoquinolin-4-yl)oct-7-enoate

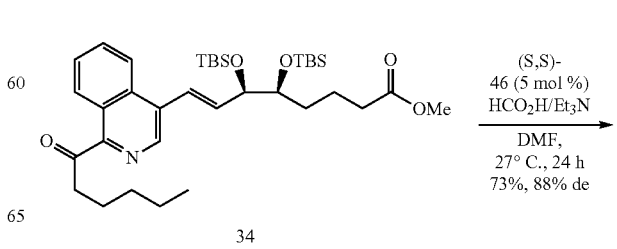

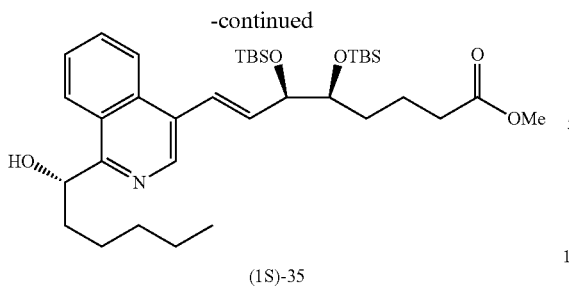

(1S)-35

A mixture of formic acid (0.03 mL, 670 μmol) and triethylamine (0.05 mL, 390 μmol) was added to a mixture of ketone 34 (100 mg, 0.16 μmol) and RuCl-(p-cymene)[S,S-TsDPEN] (S,S)-46, (5 mg, 8 μmol) in anhydrous DMF (1 mL). The mixture was degassed by freeze-thaw cycles and then stirred at 27° C. for 48 h. The mixture was neutralised with saturated NaHCO$_3$ solution (5 mL) and diluted with EtOAc (10 mL). The organic phase was separated and the aqueous phase extracted with EtOAc (3×20 mL). The combined organic phase was washed with water (20 mL) and brine (20 mL) and dried over MgSO$_4$. The solvent was removed in vacuo and the residue was purified by silica gel column chromatography (pentane/EtOAc, 9:1) to afford (1S)-35, (73 mg, 73%) as an orange oil. de=88%, as determined by chiral SFC using a Chiralpak IC column (CO$_2$: 2-PrOH, 99:1 to 85:15 after 1 min); flow rate: 3 mL/min; R$_t$-(S)=2.03 min, R$_t$-(R)=2.37 min; TLC: R$_f$=0.42 (pentane/EtOAc, 9:1); [α]$_D^{20}$−21.9 (c=1.00, CHCl$_3$); $^1$H NMR (400 MHz, CDCl$_3$) δ 8.51 (s, 1H), 8.10 (d, J=8.4 Hz, 1H), 8.04 (d, J=8.4 Hz, 1H), 7.76-7.71 (m, 1H), 7.66-7.60 (m, 1H), 7.10 (d, J=15.8 Hz, 1H), 6.28 (dd, J=15.8, 6.8 Hz, 1H), 5.48-5.42 (m, 1H), 4.27 (dd, J=6.8, 4.5 Hz, 1H), 3.79-3.73 (m, 1H), 3.66 (s, 3H), 2.33 (t, J=7.4 Hz, 2H), 2.01-1.92 (m, 1H), 1.83-1.70 (m, 2H), 1.66-1.46 (m, 5H), 1.33-1.22 (m, 4H), 0.96-0.93 (m, 9H), 0.87 (s, 12H) 0.17-0.02 (4×s, 12H); $^{13}$C NMR (101 MHz, CDCl$_3$) δ 174.1, 160.8, 138.1, 135.6, 134.5, 130.3, 128.3, 127.2, 125.2, 124.6, 124.4, 124.1, 77.3, 76.2, 69.8, 51.6, 39.6, 34.5, 33.3, 32.0, 26.1, 26.1, 25.6, 22.8, 20.8, 18.5, 18.3, 14.2, −3.8, −3.8, −4.4, −4.4; IR (ν$_{max}$) 3428, 3055, 2929, 2852, 1735, 1642, 1450, 1265 cm$^{-1}$; HRMS (ESI) Found 644.4195 [M+H]$^+$ C$_{36}$H$_{62}$NO$_5$Si$_2$ requires 644.4167.

(5S,6R,E)-Methyl 5,6-dihydroxy-8-(1-((R)-1-hydroxyhexyl)isoquinolin-4-yl)oct-7-enoate Tetra-n-butylammonium fluoride (0.20 mL, 1.0 M in THF, 0.20 mmol) was added to alcohol (1R)-35 (50 mg, 0.08 mmol) in anhydrous THF (3 mL) and the solution was stirred at room temperature for 16 h. The solvent was removed in vacuo at 25° C. and the residue was purified by preparative TLC (CH$_2$Cl$_2$/MeOH, 96:4) to afford diol (1R)-17 (14 mg, 40%) as a yellow wax. TLC: R$_f$=0.13 (CH$_2$Cl$_2$/MeOH, 96:4); [α]$_D^{20}$+22.9 (c=0.32, CHCl$_3$); $^1$H NMR (500 MHz, CD$_3$CN) δ 8.58 (s, 1H), 8.24 (m, 2H), 7.85 (t, J=7.5 Hz, 1H), 7.73 (t, J=7.8 Hz, 1H), 7.29 (d, J=15.6 Hz, 1H), 6.44 (dd, J=15.6, 6.2 Hz, 1H), 5.47-5.42 (m, 1H), 4.27 (dd, J=5.1, 4.8 Hz, 1H), 3.69-3.64 (m, 1H), 3.63 (s, 3H), 3.34 (s, 1H), 2.99 (s, 1H), 2.37 (t, J=6.9 Hz, 2H), 1.87-1.26 (m, 12H) 0.89 (t, J=6.9 Hz, 3H); $^{13}$C NMR (126 MHz, CD$_3$CN) δ 174.8, 162.0, 138.8, 135.5, 135.1, 131.5, 129.3, 128.2, 125.9, 125.8, 125.2, 124.8, 76.3, 74.8, 70.6, 51.8, 39.7, 34.4, 32.6, 32.4, 26.1, 23.3, 22.2, 14.3; IR (ν$_{max}$) 3392, 2959, 2930, 1733, 1649, 1569, 1487, 1462, 1380 cm$^{-1}$; HRMS (ESI) Found 416.2444 [M+H]$^+$ C$_{24}$H$_{34}$NO$_5$ requires 416.2437.

(S)-6-((R,E)-1-Hydroxy-3-(1-((R)-1-hydroxyhexyl)isoquinolin-4-yl)allyl)tetrahydro-2H-pyran-2-one The lactone was isolated by preparative TLC (CH$_2$Cl$_2$/MeOH, 96:4) to afford (1R)-48 (14 mg, 16%) as a yellow oil. TLC: R$_f$=0.14 (CH$_2$Cl$_2$/MeOH, 96:4); [α]$_D^{20}$+15.8 (c=0.95, CHCl$_3$); $^1$H NMR (500 MHz, CD$_3$CN) δ 8.57 (s, 1H), 8.25-8.14 (m, 2H), 7.85 (t, J=7.3 Hz, 1H), 7.75-7.66 (m, 1H), 7.27 (d, J=15.0 Hz, 1H), 6.37 (dd, J=15.0, 5.0 Hz, 1H), 5.57-5.42 (m, 1H), 4.53 (dd, J=5.0, 3.6 Hz, 1H), 4.49-4.40 (m, 1H), 3.41 (s, br, 1H), 3.15 (s, br, 1H), 2.56-2.39 (m, 2H), 1.87-1.63 (m, 4H), 1.52-1.20 (m, 8H), 0.87 (t, J=7.1 Hz 3H); $^{13}$C NMR (126 MHz, CD$_3$CN) δ 171.4, 161.8, 138.2, 134.8, 131.0, 130.9, 128.5, 127.6, 127.1, 124.9, 124.5, 124.3, 83.1, 73.5, 70.0, 39.6, 31.9, 30.0, 25.6, 22.9, 21.9, 18.6, 14.3; IR (ν$_{max}$) 3675, 3409, 3221, 2968, 1731, 1650, 1569, 1461, 1393 cm$^{-1}$; HRMS (ESI) Found 384.2188 [M+H]$^+$ C$_{23}$H$_{30}$NO requires 384.2175.

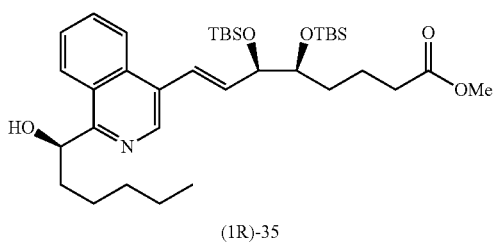

(1R)-35

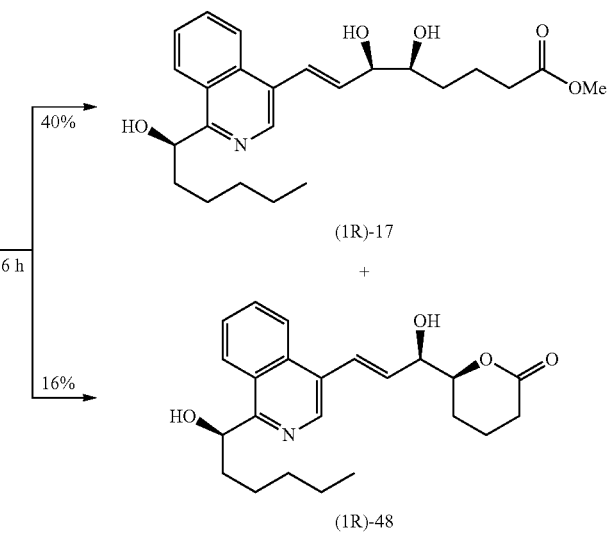

(1R)-17

+

(1R)-48

(5S,6R,E)-Methyl 5,6-dihydroxy-8-(1-((S)-1-hydroxyhexyl)isoquinolin-4-yl)oct-7-enoate

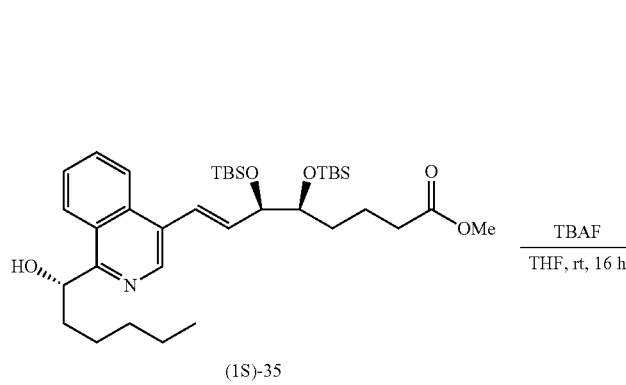

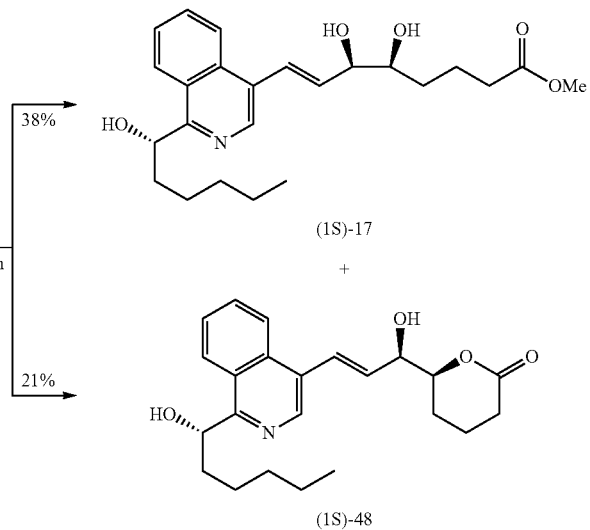

Tetra-n-butylammonium fluoride (0.20 mL, 1 M in THF, 0.20 mmol) was added to a solution of alcohol (1S)-35 (50 mg, 0.08 mmol) in anhydrous THF (3 mL) and the solution was stirred at room temperature for 16 h. The solvent was removed in vacuo at 25° C. and the residue was purified by preparative TLC (CH$_2$Cl$_2$/MeOH, 96:4) to afford diol (1S)-17 (13 mg, 38%) as a yellow wax. TLC: R$_f$=0.13 (CH$_2$Cl$_2$/MeOH, 96:4); $[\alpha]_D^{20}$ −29.8 (c=3.00, CHCl$_3$); $^1$H NMR (500 MHz, CDCl$_3$) δ 8.52 (s, 1H), 8.10 (d, J=8.5 Hz, 1H), 8.04 (d, J=8.4 Hz, 1H), 7.74 (dd, J=8.4, 7.5 Hz, 1H), 7.63 (dd, J=8.5, 7.5 Hz, 1H), 7.27 (d, J=15.7 Hz, 1H), 6.36 (dd, J=15.7, 6.0 Hz, 1H), 5.45 (dd, J=7.8, 2.8 Hz, 1H), 4.42 (dd, J=6.0, 3.9 Hz, 1H), 3.84 (td, J=6.9, 3.9 Hz, 1H), 3.66 (s, 3H), 3.00 (s, br, 1H), 2.39 (t, J=7.2 Hz, 2H), 1.98-1.87 (m, 2H), 1.83-1.23 (m, 12H), 0.87 (t, J=7.0 Hz, 3H); $^{13}$C NMR (126 MHz, CDCl$_3$) δ 174.3, 161.2, 138.1, 134.4, 132.4, 130.5, 127.9, 127.4, 126.7, 124.6, 124.3, 124.1, 75.8, 74.0, 69.8, 51.8, 39.5, 33.8, 31.9, 31.7, 25.5, 22.8, 21.2, 14.2; IR (v$_{max}$) 3420, 3054, 2987, 2927, 1729, 1648, 1421, 1265 cm$^{-1}$; HRMS (ESI) Found 416.2422 [M+H]$^+$ C$_{24}$H$_{34}$NO$_5$ requires 416.2437.

(S)-6-((R,E)-1-Hydroxy-3-(1-((S)-1-hydroxyhexyl)isoquinolin-4-yl)allyl)tetrahydro-2H-pyran-2-one The lactone was isolated by preparative TLC (CH$_2$Cl$_2$/MeOH, 96:4) to yield (1S)-48 (8 mg, 21%) as a yellow oil. TLC: R$_f$=0.14 (CH$_2$Cl$_2$/MeOH, 96:4); $[\alpha]_D^{20}$ −26.2 (c=0.85, CHCl$_3$); $^1$H NMR (500 MHz, CDCl$_3$) δ 8.52 (s, 1H), 8.16-8.04 (m, 2H), 7.83-7.73 (m, 1H), 7.71-7.64 (m, 1H), 7.40 (d, J=15.8 Hz, 1H), 6.30 (dd, J=15.8, 5.8 Hz, 1H), 5.53-5.43 (m, 1H), 4.72 (dd, J=6.9, 5.8 Hz, 1H), 4.59-4.46 (m, 1H), 2.78-2.43 (m, 2H), 2.11-1.85 (m, 5H), 1.74-1.24 (m, 9H), 0.89 (t, J=5.9 Hz, 3H); $^{13}$C NMR (126 MHz, CDCl$_3$) δ 171.4, 161.4, 138.0, 134.4, 130.7, 130.7, 127.8, 127.5, 127.0, 124.7, 124.3, 124.1, 82.9, 73.3, 69.8, 39.5, 31.9, 29.9, 25.5, 22.8, 21.9, 18.5, 14.2; IR (v$_{max}$) 3675, 3408, 2966, 1730, 1651, 1568, 1381, 1251 cm$^{-1}$; HRMS (ESI) Found 384.2185 [M+H]$^+$ C$_{23}$H$_{30}$NO requires 384.2175.

1-(3-Bromoisoquinolin-1-yl)hexan-1-one

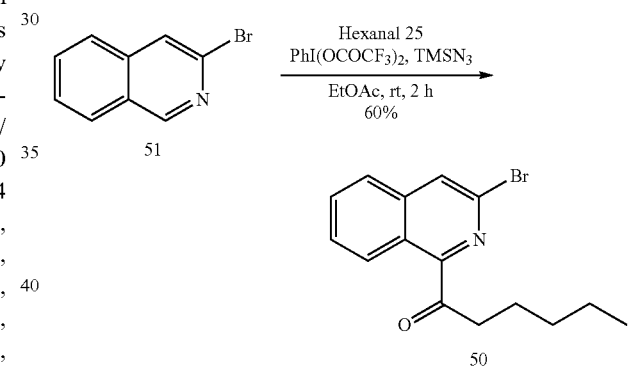

3-Bromoisoquinoline 51 (0.5 g, 2.40 mmol) was dissolved in EtOAc (20 mL) and hexanal 25 (1.18 mL, 9.61 mmol) and TMSN$_3$ (0.63 mL, 4.81 mmol) were added. (Bis(trifluoroacetoxy)iodo)benzene (2.07 g, 4.81 mmol) was added slowly over 45 min and the mixture was stirred at room temperature for 2 h. Triethylamine (6.25 mL) was added and the reaction was stirred for 10 min. After removal of the solvents in vacuo the residue was purified by silica gel column chromatography (pentane/EtOAc, 19:1) to yield the ketone 50 (0.44 g, 60%) as an orange oil. TLC: R$_f$=0.65 (pentane/EtOAc, 19:1); $^1$H NMR (400 MHz, CDCl$_3$) δ 8.81 (d, J=8.3 Hz, 1H), 8.03 (s, 1H), 7.83-7.63 (m, 3H), 3.29 (t, J=7.4 Hz, 2H), 1.81-1.73 (m, 2H), 1.42-1.37 (m, 4H), 0.92 (t, J=7.1 Hz, 3H); $^{13}$C NMR (101 MHz, CDCl$_3$) δ 203.7, 153.8, 139.4, 133.8, 131.4, 129.5, 127.8, 127.2, 126.2, 124.8, 40.4, 31.6, 23.9, 22.7, 14.1; IR (v$_{max}$) 3056, 2986, 2957, 1700, 1560, 1490, 1266, 1046 cm$^{-1}$; HRMS (ESI) Found 306.0489 [M+H] C$_{15}$H$_{17}$NOBr requires 306.0494.

(5S,6R,E)-Methyl 5,6-bis((tert-butyldimethylsilyl)oxy)-8-(1-hexanoylisoquinolin-3-yl)oct-7-enoate (5S,6R,E)-Methyl 5,6-bis((tert-butyldimethylsilyl)oxy)-8-(1-((R)-1-hydroxyhexyl)isoquinolin-3-yl)oct-7-enoate

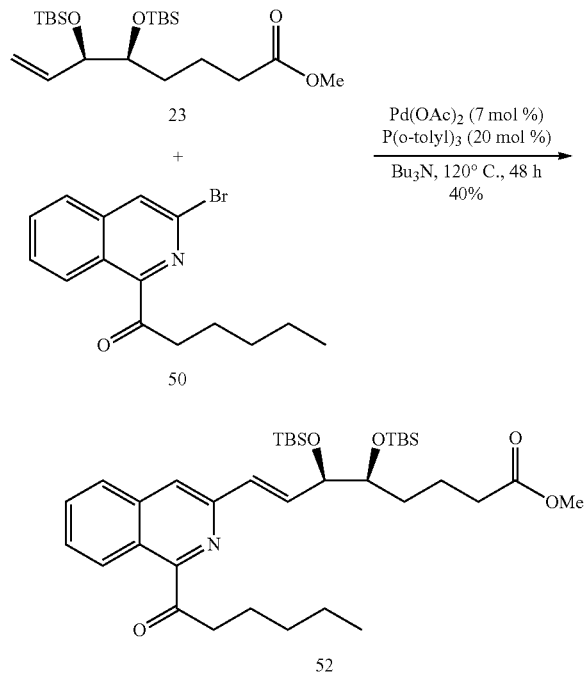

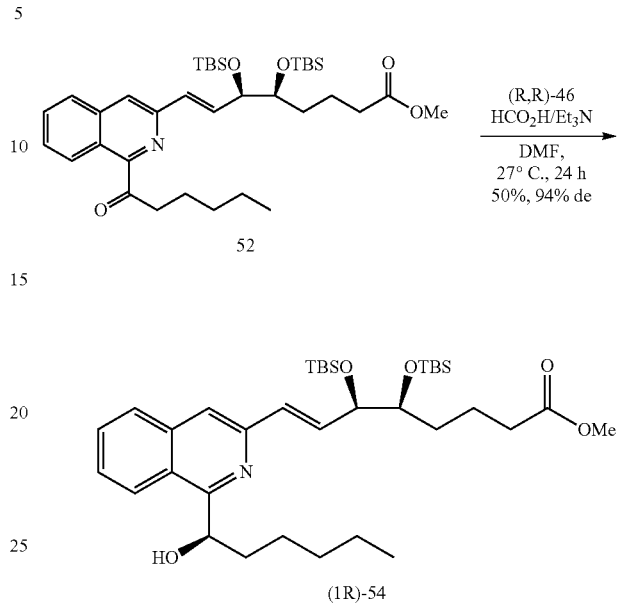

Pd(OAc)$_2$ (11 mg, 0.05 mmol), P(o-tolyl)$_3$ (41 mg, 0.14 mmol) and tributylamine (3.55 mL, 15.0 mmol) were sealed under nitrogen and stirred at 80° C. for 10 min. Alkene 23 (341 mg, 0.82 mmol) and ketone 50 (208 mg, 0.68 mmol) were added and the reaction mixture was stirred at 120° C. for 72 h. After filtering through silica with EtOAc (250 mL) most of the solvent (200 mL) was removed in vacuo and the remaining solution was washed with 10% (w/v) CuSO$_4$ solution (3×20 mL). The organic layer was separated and washed with water (50 mL) and brine (50 mL) and dried over MgSO$_4$. The solvent was removed in vacuo and the residue was purified by silica gel column chromatography (pentane/EtOAc, 19:1) to afford 52 (255 mg, 40%) as an orange oil. TLC: R$_f$=0.38 (pentane/EtOAc, 19:1); [α]$_D^{20}$–10.0 (c=1.00, CHCl$_3$); $^1$H NMR (400 MHz, CDCl$_3$) δ 8.80 (d, J=8.8 Hz, 1H), 7.80 (d, J=8.1 Hz, 1H), 7.68-7.63 (m, 1H), 7.61-7.55 (m, 2H), 6.94 (dd, J=15.5, 7.1 Hz, 1H), 6.70 (d, J=15.5 Hz, 1H), 4.24 (dd, J=7.1, 5.4 Hz, 1H), 3.72 (dt, J=6.4, 5.4 Hz, 1H), 3.66 (s, 3H), 3.34 (t, J=7.5, 2H), 2.33 (t, J=7.3 Hz, 2H), 1.81-1.74 (m, 4H), 1.68-1.58 (m, 2H) 1.43-1.37 (m, 4H), 0.96-0.90 (m, 15H) 0.86 (s, 9H), 0.13-0.00 (4×s, 12H); $^{13}$C NMR (101 MHz, CDCl$_3$) δ 205.4, 174.2, 153.2, 147.4, 138.0, 135.9, 130.4, 130.2, 128.4, 127.2, 127.0, 125.0, 121.5, 76.9, 76.0, 51.6, 40.4, 34.6, 33.2, 31.8, 26.1, 26.1, 24.2, 22.7, 20.5, 18.4, 18.3, 14.2, −3.7, −3.9, −4.3, −4.5; IR (ν$_{max}$) 3054, 2929, 2852, 1734, 1680, 1422, 1265 cm$^{-1}$; HRMS (ESI) Found 664.3820 [M+Na]$^+$ C$_{36}$H$_{59}$NO$_5$NaSi$_2$ requires 664.3830.

A mixture of formic acid (0.06 mL, 1.61 mmol) and triethylamine (0.13 mL, 0.94 mmol) was added to ketone 52 (240 mg, 0.37 mmol) and RuCl-(p-cymene)[R,R-TsDPEN], (R,R)-46, (19 mg, 0.02 mmol). Anhydrous DMF (1.8 mL) was added and the mixture was degassed by freeze-thaw cycles and then stirred at 27° C. for 24 h. The mixture was neutralised with saturated NaHCO$_3$ solution (5 mL) and diluted with EtOAc (10 mL). The organic phase was separated and the aqueous phase extracted with EtOAc (3×20 mL). The combined organic phase was washed with water (20 mL) and brine (20 mL) and dried over MgSO$_4$. The solvent was removed in vacuo and the residue was purified by silica gel column chromatography (pentane/EtOAc, 9:1) to afford (1R)-54 (119 mg, 50%) as an orange oil. de=94%, as determined by chiral UPLC using a Chiralpak OD column (heptane:2-PrOH, 98.5:1,5); flow rate: 1 mL/min; R$_t$-(1S)= 3.93 min, R$_t$-(1R)=5.69 min; TLC: R$_f$=0.44 (pentane/EtOAc, 9:1); [α]$_D^{20}$+6.0 (c=1.00, CHCl$_3$); $^1$H NMR (400 MHz, CDCl$_3$) δ 7.97 (d, J=8.4 Hz, 1H), 7.81 (d, J=8.1 Hz, 1H), 7.70-7.62 (m, 1H), 7.58-7.51 (m, 1H), 7.39 (s, 1H), 6.86 (dd, J=15.5, 7.0 Hz, 1H), 6.67 (d, J=15.5 Hz, 1H), 5.46-5.39 (m, 1H), 5.36-5.30 (m, 1H), 4.22 (dd, J=7.6, 6.1 Hz, 1H), 3.73-3.67 (m, 1H), 3.66 (s, 3H), 2.32 (t, J=7.3 Hz, 2H), 2.01-1.54 (m, 6H), 1.37-1.27 (m, 6H), 0.94-0.82 (m, 21H), 0.15-0.04 (4×s, 12H); $^{13}$C NMR (101 MHz, CDCl$_3$) δ 174.2, 161.4, 146.5, 137.5, 135.4, 130.5, 130.2, 127.8, 126.9, 124.4, 124.2, 118.1, 77.4, 75.9, 69.7, 51.6, 39.4, 34.6, 33.0, 32.0, 29.9, 26.1, 26.1, 22.8, 20.5, 18.4, 18.3, 14.2, −3.7, −3.9, −4.3, −4.5; IR (ν$_{max}$) 3445, 3054, 2986, 2929, 2852, 1734, 1450, 1422, 1265 cm$^{-1}$; HRMS (ESI) Found 644.4144 [M+H]$^+$ C$_{36}$H$_{62}$NO$_5$Si$_2$ requires 644.4167.

(5S,6R,E)-Methyl 5,6-bis((tert-butyldimethylsilyl)oxy)-8-(1-((S)-1-hydroxyhexyl)isoquinolin-3-yl)oct-7-enoate

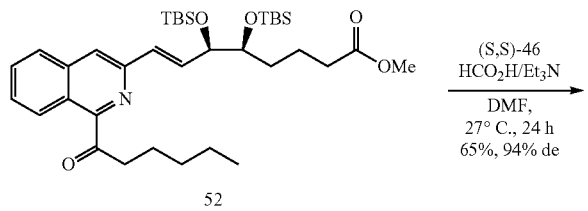

A mixture of formic acid (0.03 mL, 0.67 mmol) and triethylamine (0.06 mL, 0.39 mmol) was added to ketone 52 (100 mg, 0.16 mmol) and RuCl-(p-cymene)[S,S-TsDPEN], (S,S)-46, (5 mg, 0.01 mmol). Anhydrous DMF (0.7 mL) was added and the mixture was degassed by freeze-thaw cycles and then stirred at 27° C. for 24 h. The mixture was neutralised with saturated NaHCO$_3$ (5 mL) and diluted with EtOAc (10 mL). The organic phase was separated and the aqueous phase extracted with EtOAc (3×20 mL). The combined organic phase was washed with water (20 mL) and brine (20 mL) and dried over MgSO$_4$. The solvent was removed in vacuo and the residue was purified by silica gel column chromatography (pentane/EtOAc, 9:1) to afford (1S)-54 (65 mg, 65%) as an orange oil. de=94%, as determined by chiral UPLC using a Chiralpak OD column (heptane:2-PrOH, 98.5:1.5); flow rate: 1 mL/min; R$_t$-(1S)=3.95 min, R$_t$-(1R)=5.65 min; TLC: R$_f$=0.41 (pentane/EtOAc, 9:1); [α]$_D^{20}$−14.0 (c=1.00, CHCl$_3$); $^1$H NMR (400 MHz, CDCl$_3$) δ 7.97 (d, J=8.4 Hz, 1H), 7.81 (d, J=8.2 Hz, 1H), 7.69-7.62 (m, 1H), 7.57-7.51 (m, 1H), 7.40 (s, 1H), 6.89 (dd, J=15.5, 6.7 Hz, 1H), 6.68 (d, J=15.5 Hz, 1H), 5.47-5.37 (m, 1H), 4.23 (t, J=5.7 Hz, 1H), 3.73-3.67 (m, 1H), 3.65 (s, 3H), 3.38-3.24 (m, 1H), 2.32 (t, J=7.3 Hz, 2H), 1.82-1.53 (m, 6H), 1.51-1.18 (m, 6H), 0.97-0.81 (m, 21H), 0.13-0.02 (m, 12H); $^{13}$C NMR (101 MHz, CDCl$_3$) δ 174.2, 161.3, 146.5, 137.4, 135.3, 130.5, 130.0, 127.8, 126.9, 124.4, 124.2, 118.1, 76.7, 76.0, 69.7, 51.6, 39.4, 34.6, 33.0, 32.0, 29.8, 26.1, 26.1, 22.8, 20.5, 18.4, 18.3, 14.2, −3.8, −3.9, −4.3, −4.5; IR (v$_{max}$) 3407, 3055, 2968, 2928, 2856, 1734, 1643, 1450, 1422, 1265 cm$^{-1}$; HRMS (ESI) Found 644.4156 [M+H]$^+$ C$_{36}$H$_{62}$NO$_5$Si$_2$ requires 644.4167.

(5S,6R,E)-Methyl 5,6-dihydroxy-8-(1-(R)-1-hydroxyhexyl)isoquinolin-3-yl)oct-7-enoate

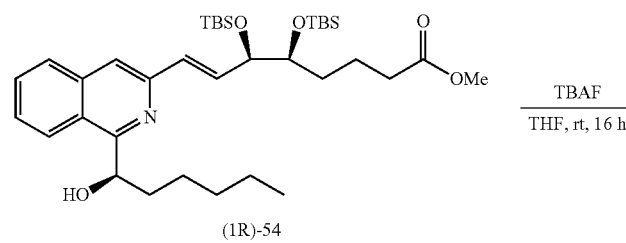

Tetra-n-butylammonium fluoride (0.23 mL, 1.0 M in THF, 0.23 mmol) was added to alcohol (1R)-54 (60 mg, 0.09 mmol) in anhydrous THF (3.6 mL) and the solution was stirred at room temperature for 16 h. The solvent was removed in vacuo at 25° C. and the residue was purified by preparative TLC (CH$_2$Cl$_2$/MeOH, 96:4) to afford (1R)-16 (11.6 mg, 30%) as a yellow oil. TLC: R$_f$=0.16 (CH$_2$Cl$_2$/MeOH, 96:4); [α]$_D^{20}$+17.5 (c=0.11, CHCl$_3$); $^1$H NMR (400 MHz, CD$_3$CN) δ 8.13 (d, J=8.4 Hz, 1H), 7.89 (d, J=8.2 Hz, 1H), 7.76-7.69 (m, 1H), 7.63-7.56 (m, 2H), 7.00 (dd, J=15.6, 6.0 Hz, 1H), 6.82 (d, J=15.6 Hz, 1H), 5.43-5.35 (m, 1H), 4.26-4.13 (m, 1H), 3.65-3.60 (m, 1H), 3.59 (s, 3H), 2.32 (t, J=7.2 Hz, 2H), 1.85-1.24 (m, 15H), 0.86 (t, J=7.0 Hz, 3H); $^{13}$C NMR (101 MHz, CD$_3$CN) δ 174.8, 162.7, 147.4, 138.3, 134.2, 131.6, 130.8, 128.6, 127.9, 125.6, 125.0, 119.0, 76.0, 74.8, 70.6, 51.8, 39.8, 34.4, 32.5, 32.4, 26.2, 23.3, 22.2, 14.3; IR ($v_{max}$) 3402, 3055, 2956, 2854, 1724, 1645, 1462, 1378 cm$^{-1}$; HRMS (ESI) Found 416.2420 [M+H]$^+$ C$_{24}$H$_{34}$NO$_5$ requires 416.2437.

(S)-6-((R,E)-1-Hydroxy-3-(1-(R)-1-hydroxyhexyl)isoquinolin-3-yl)allyl)tetrahydro-2H-pyran-2-one The lactone was isolated by preparative TLC (CH$_2$Cl/MeOH, 96:4) to yield (1R)-55 (7 mg, 18%) as a yellow oil. TLC: R$_f$=0.26 (CH$_2$Cl/MeOH, 96:4); [α]$_D^{20}$+5.5 (c=0.24, CHCl$_3$); $^1$H NMR (500 MHz, CDCl$_3$) δ 7.98 (d, J=8.3 Hz, 1H), 7.82 (d, J=8.4 Hz, 1H), 7.71-7.65 (m, 1H), 7.61-7.55 (m, 1H), 7.46 (s, 1H), 7.00-6.85 (m, 2H), 5.45-5.41 (m, 1H), 4.75-4.70 (m, 1H), 4.53-4.48 (m, 1H), 2.69-2.45 (m, 2H), 2.34 (s, br, 1H), 2.21 (s, br, 1H), 2.04-1.82 (m, 4H), 1.68-1.49 (m, 2H), 1.37-1.27 (m, 6H), 0.88 (t, J=6.5 Hz, 3H); $^{13}$C NMR (126 MHz, CDCl$_3$) δ 171.7, 161.6, 145.6, 137.3, 132.3, 131.3, 130.7, 128.7, 127.9, 127.3, 124.4, 119.0, 83.0, 73.0, 69.9, 39.5, 31.9, 29.9, 25.7, 22.8, 21.5, 18.5, 14.2; IR ($v_{max}$) 3430, 3055, 2928, 1730, 1641, 1432, 1266 cm$^{-1}$; HRMS (ESI) Found 384.2179 [M+H]$^+$ C$_{23}$H$_{30}$NO$_4$ requires 384.2175.

(5S,6R,E)-Methyl 5,6-dihydroxy-8-(1-(S)-1-hydroxyhexyl)isoquinolin-3-yl)oct-7-enoate

(S)-6-((R,E)-1-Hydroxy-3-(1-(S)-1-hydroxyhexyl)isoquinolin-3-yl)allyl)tetrahydro-2H-pyran-2-one The lactone was isolated by preparative TLC (CH$_2$Cl$_2$/MeOH, 96:4) to yield (1S)-55 (6 mg, 19%) as a yellow oil. TLC: R$_f$=0.28 (CH$_2$Cl$_2$/MeOH, 96:4); [α]$_D^{20}$−11.2 (c=0.75, CHCl$_3$); $^1$H NMR (400 MHz, CDCl$_3$) δ 7.99 (d, J=8.3 Hz, 1H), 7.83 (d, J=8.2 Hz, 1H), 7.69 (m, 1H), 7.58 (m, 1H), 7.47 (s, 1H), 6.96-6.86 (m, 2H), 5.42 (dd, J=6.1, 4.9 Hz, 1H), 4.83 (dd, J=5.0, 4.2 Hz, 1H), 4.69 (ddd, J=7.7, 6.3, 4.2 Hz, 1H), 3.64 (s, br, 1H), 2.68-2.48 (m, 2H), 2.35 (s, br, 1H), 2.04-1.84 (m, 4H), 1.67-1.49 (m, 2H) 1.35-1.22 (m, 6H), 0.88 (t, J=7.1 Hz, 3H); $^{13}$C NMR (126 MHz, CDCl$_3$) δ 171.7, 161.6, 145.5, 137.4, 132.3, 131.4, 130.7, 128.7, 127.8, 127.3, 124.4, 119.0, 83.0, 73.0, 69.9, 39.6, 31.8, 29.8, 25.7, 22.8, 21.5, 18.6, 14.2; IR ($v_{max}$) 3433, 3056, 2924, 1730, 1642, 1427 cm$^{-1}$; HRMS (ESI) Found 384.2185 [M+H]$^+$ C$_{23}$H$_{30}$NO$_4$ requires 384.2175.

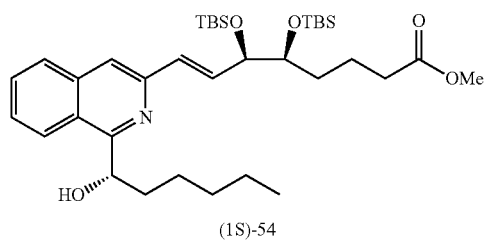

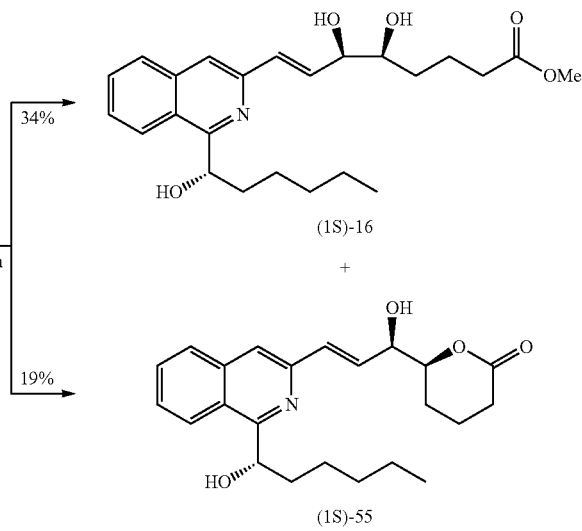

Tetra-n-butylammonium fluoride (0.20 mL, 1.0 M in THF, 0.20 mmol) was added to alcohol (1S)-54 (50 mg, 0.08 mmol) in anhydrous THF (3 mL) and the solution was stirred at room temperature for 16 h. The solvent was removed in vacuo at 25° C. and the residue was purified by preparative TLC (CH$_2$Cl$_2$/MeOH, 96:4) to afford (1S)-16 (11 mg, 34%) as a yellow oil. TLC: R$_f$=0.21 (CH$_2$Cl/MeOH, 96:4); [α]$_D^{20}$−2.6 (c=0.45, CHCl$_3$); $^1$H NMR (400 MHz, CD$_3$CN) δ 8.13 (d, J=8.4 Hz, 1H), 7.89 (d, J=8.2 Hz, 1H), 7.75-7.69 (m, 1H), 7.63-7.57 (m, 2H), 6.99 (dd, J=15.5, 6.2 Hz, 1H), 6.81 (d, J=15.5 Hz, 1H), 5.41-5.37 (m, 1H), 4.20 (m, 1H), 3.65-3.60 (m, 1H), 3.59 (s, 3H), 3.20 (s, br, 1H), 2.90 (s, br, 1H), 2.32 (t, J=7.2 Hz, 2H), 1.84-1.74 (m, 1H), 1.69-1.28 (m, 12H), 0.86 (t, J=7.0 Hz, 3H); $^{13}$C NMR (101 MHz, CD$_3$CN) δ 174.8, 162.7, 147.4, 138.3, 134.2, 131.6, 130.9, 128.6, 128.0, 125.6, 125.0, 119.0, 76.1, 74.9, 70.6, 51.8, 39.8, 34.4, 32.5, 32.5, 26.2, 23.3, 22.2, 14.3; IR ($v_{max}$)

Compounds Ox_10 and Ox_11 of Formula (VIj) and Compounds Ox_13 and Ox_14 of Formula (VIj2)

Ethyl 2-aminooxazole-4-carboxylate

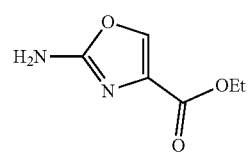

Ox_2

The compound was synthesised in two steps from Ethyl 2-aminooxazole-4-carboxylate using a known published procedure.

Ethyl 2-chlorooxazole-4-carboxylate

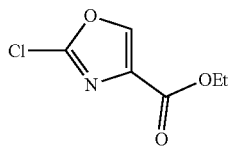

Ox_3

The compound was synthesised in one step from Ethyl 2-aminooxazole-4-carboxylate using a known published procedure.

Ethyl 2-phenyloxazole-4-carboxylate

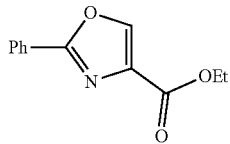

Ox_4

The compound was synthesised from Ethyl 2-aminooxazole-4-carboxylate using a known published procedure.

N-Methoxy-N-methyl-2-phenyloxazole-4-carboxamide

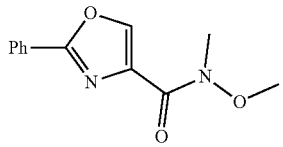

Ox_5

In a round bottom flask (50 mL), known phenyloxazole Ox_4 (0.31 g, 1.40 mmoL) and $CH_3ONHCH_3 \cdot HCl$ (0.21 g, 2.22 mmol) were dissolved in dry THF (10 mL). The solution was cooled to −20° C. in a NaCl ice bath. $^iPrMgCl$ (2.23 mL, 2 M in THF, 4.50 mmol) was added dropwise. After 2 h, $NH_4Cl$ (4 mL) and EtOAc (5 mL) were added. The solution was left to warm to room temperature and the layers were separated. The aqueous layer was extracted with EtOAc (3×5 mL). Afterwards the organic layers were combined, washed with brine (20 mL), dried over $MgSO_4$ and concentrated in vacuo. The compound was purified by column chromatography using silica gel (96:4 $CH_2Cl_2$:MeOH) affording the Weinreb amide Ox_5 as a yellow oil (0.267 g, 83%), $R_f$: 0.74 (96:4 $CH_2Cl_2$:MeOH); m.p.=93-95° C.; HRMS calculated for $C_{12}H_{13}N_2O_3$: 233.0926, found: 233.0930. IR ($v_{max}$)=1026.01, 1120.80, 1216.04, 1483.86, 1561.76, 1648.50, 2400.73, 2874.89, 2937.96, 2973.11, 3018.56 $cm^{-1}$; $^1H$ NMR (400 MHz, $CDCl_3$) δ 8.21 (s, 1H), 8.08 (m, 2H), 7.42 (m, 3H), 3.78 (s, 3H), 3.41 (s, 3H). $^{13}C$ NMR (101 MHz, $CDCl_3$) δ 161.39, 156.35, 142.48, 134.58, 130.91, 129.44, 128.74, 128.71, 61.41, 33.29.

1-(2-Phenyloxazol-4-yl)hexan-1-one

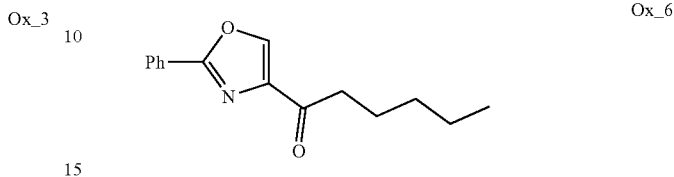

Ox_6

In a round bottom flask (150 mL), activated magnesium turnings (0.19 g, 7.80 mmol, 3 eq), bromopentane (0.97 mL, 7.8 mmol), a crystal of iodine were dissolved in dry THF (20 mL). The reaction was refluxed for 1.5 h. The Weinreb amide Ox_5 was dissolved in dry THF (30 mL) and added via cannula to the reaction mixture which was refluxed for another 1.5 h. The solution was left to cool down to room temperature then saturated ammonium chloride (100 mL) was added. The layers were separated and the aqueous layer was extracted with $Et_2O$ (2×50 mL). The organic layers were combined, washed with $H_2O$ (100 mL) and brine (100 mL), dried over $MgSO_4$ and concentrated in vacuo. The product was purified by column chromatography using silica gel (9:1 pentane:EtOAc) giving the product Ox_6 as a yellow oil (0.44 g, 69%); $R_f$: 0.78 (9:1 Pentane:EtOAc); m.p.=180° C. decomposition; HRMS calculated for $C_{15}H_{18}NO_2$: 244.1338, found: 244.1332. IR ($v_{max}$)=1057.93, 1448.99, 1678.56, 2346.42, 2862.19, 2922.60, 2957.76, 3119.31 $cm^{-1}$; $^1H$ NMR (500 MHz, $CDCl_3$) δ=8.24 (s, 1H), 8.10 (m, 2H), 7.50 (m, 3H), 2.97 (t, J=7.5 Hz, 2H), 1.76 (p, J=7.5 Hz, 2H), 1.38 (m, 4H), 0.92 (t, J=7.0 Hz, 3H). $^{13}C$ NMR (126 MHz, $CDCl_3$) δ 195.75, 161.95, 141.82, 141.75, 131.07, 128.87, 126.80, 126.67, 39.92, 31.45, 23.58, 22.48, 13.95.

1-(5-Bromo-2-phenyloxazol-4-yl)hexan-1-one

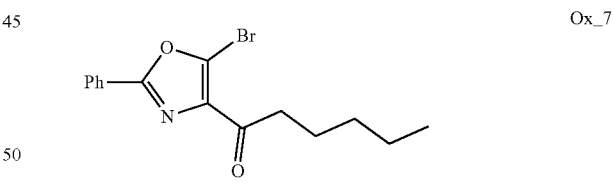

Ox_7

In a flame dried round bottom flask (150 mL), the ketone Ox_6 (0.44 g, 1.80 mmol) was dissolved in acetonitrile (25 mL). NBS (1.28 g, 7.2 mmol) was added and the reaction was refluxed for 16 h. Saturated sodium carbonate (80 mL) and $CH_2Cl_2$ (80 mL) were added. The layers were separated and the organic layer was washed with brine (80 mL), dried over $MgSO_4$ and concentrated in vacuo. The product was purified by column chromatography using silica gel (9:1 pentane:EtOAc) yielding the product Ox_7 as a white solid (0.404 g, 70%); $R_f$: 0.88 (9:1 Pentane:EtOAc); m.p.=72-73° C.; HRMS calculated for $C_{15}H_{16}NO_2NaBr$: 344.0262, found: 344.0265. IR ($v_{max}$)=689.99, 909.24, 1127.97, 1449.87, 1691.04, 2253.96, 2334.75, 2860.01, 2929.73, 2958.32 $cm^{-1}$; $^1H$ NMR (400 MHz, $CDCl_3$) δ=8.05 (m, 2H), 6=7.50 (m, 3H), 3.01 (t, J=7.4 Hz, 2H), 1.74 (p, J=7.4 Hz, 2H), 1.39 (m, 4H), 0.90 (m, 3H). $^{13}$C NMR (101 MHz, CDCl$_3$) δ 195.09, 161.88, 137.30, 131.35, 128.92 (2 C), 126.49 (2 C), 125.97, 125.58, 40.11, 31.37, 23.27, 22.47, 13.93.

Methyl 4-((4S,5R)-5-((E)-2-(4-hexanoyl-2-phenyloxazol-5-yl)vinyl)-2,2-dimethyl-1,3-dioxolan-4-yl)butanoate

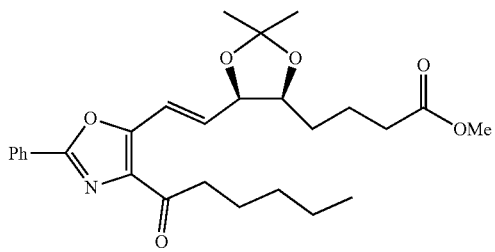

In a 25 mL flame dried round bottom flask the boronic ester 61 (50 mg, 0.14 mmol, 1.1 eq), the oxazole Ox_7 (41 mg, 0.13 mmol, 1 eq) and Pd(PPh$_3$)$_4$ (15 mg, 0.013 mmol, 10 mol %) were set under N$_2$ atmosphere. DMF (2.5 mL) and 1 M Na$_2$CO$_3$ (0.7 mL) were freeze-pump-thaw degassed and then the solution was added to the reaction flask. The reaction mixture was heated to reflux for 16 h. The solution was left to cool, then 1 M HCl (15 mL) and EtOAc (30 mL) were added. The layers were separated, the organic layer was washed with 1 M HCl (5 mL), brine (5 mL) and dried over MgSO$_4$. Concentration in vacuo and purification by column chromatography using silica gel (4:1 pentane:EtOAc) yielded the product Ox_8 as a dark orange oil (45 mg, 74%). R$_f$: 0.75 (4:1 Pentane:EtOAc); HRMS calculated for C$_{27}$H$_{35}$NO$_6$Na: 492.2362, found: 492.2363. IR (v$_{max}$)= 1026.07, 1082.38, 1215.93, 1370.88, 1449.90, 1559.29, 1684.78, 1737.41, 2869.23, 2925.79 (b) cm$^{-1}$; $^1$H NMR (400 MHz, CDCl$_3$) 8.09 (m, 2H), 7.53-7.45 (m, 3H), 7.26 (d, J=16.0 Hz, 1H), 6.57 (dd, J=16.0, 7.7 Hz, 1H), 4.73 (dd, J=7.7, 1.0 Hz, 1H), 4.25 (m, 1H), 3.63 (s, 3H), 3.03 (t, J=7.4 Hz, 2H), 2.35 (dt, J=11.3, 5.7 Hz, 2H), 1.80 (m, 2H), 1.72 (m, 2H), 1.56 (s, 3H), 1.50 (m, 2H), 1.40 (s, 3H), 1.39-1.35 (m, 4H), 0.91 (t, J=6.9 Hz, 3H). $^{13}$C NMR (101 MHz, CDCl$_3$) δ 197.63, 173.70, 159.22, 150.99, 141.72, 135.27, 132.92, 131.00, 128.83 (2 C), 126.76 (2 C)n, 126.62, 118.88, 108.84, 78.77, 78.31, 40.19, 33.65, 31.44, 29.92, 28.22, 25.58 (2 C), 23.47, 22.49, 21.80, 13.94. [α]$_D$=1.97 (c=1 in CHCl$_3$).

(5S,6R,E)-methyl 8-(4-hexanoyl-2-phenyloxazol-5-yl)-5,6-dihydroxyoct-7-enoate

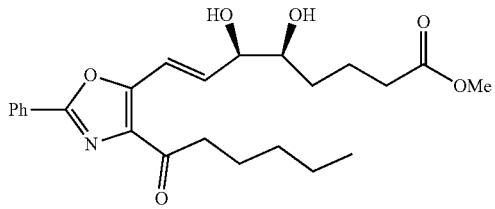

In a 10 mL round bottom flask Oxazole Ox_8 (0.046 g, 0.980 mmol), ZrCl$_4$ (0.046 g, 0.199 mmol) were dissolved in dry methanol (2 mL). The reaction was stirred at room temperature for 2 h. The mixture was concentrated at room temperature in vacuo and purified by preparative thin layer chromatography (1:1 pentane:EtOAc) to give the product as a yellow oil (0.024 g, 56%). R$_f$: 0.4 (1:1 Pentane:EtOAc); $^1$H NMR (400 MHz, CDCl$_3$) δ 8.08 (m, 2H), 7.55 (m, 3H), 7.17 (dd, J=16.4, 1.6 Hz, 1H), 6.82 (dd, J=16.4, 5.6 Hz, 1H), 4.22 (ddd, J=10, 5.2, 1.0 Hz, 1H), 3.60 (s, 3H), 3.37 (m, 1H), 2.98 (t, J=7.4 Hz, 2H), 2.32 (dt, J=7.6, 1.2 Hz, 2H), 1.80 (m, 2H), 1.69 (m, 2H), 1.56 (m, 2H), 1.40 (m, 2H), 1.36 (m, 2H), 0.92 (t, J=7.0 Hz, 3H). $^{13}$C NMR (101 MHz, CDCl$_3$) δ 197.07, 173.75, 158.76, 151.69, 137.94, 134.46, 131.07, 129.08, 126.65, 126.40, 116.13, 74.54, 73.72, 50.88, 39.73, 33.38, 31.60, 31.17, 23.26, 22.22, 21.15, 13.25. [α]$_D$=−7.57 (c=1 in CHCl$_3$).

(5S,6R,E)-isopropyl 5,6-dihydroxy-8-(4-((S)-1-hydroxyhexyl)-2-phenyloxazol-5-yl)oct-7-enoate

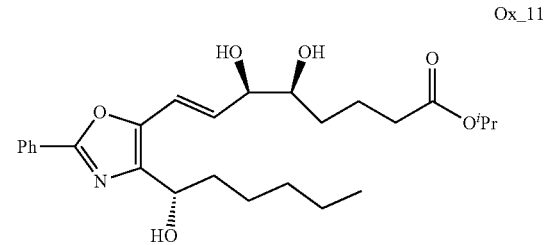 [SMILES: CCCCC[C@H](O)c1nc(-c2ccccc2)oc1/C=C/[C@@H](O)[C@@H](O)CCCC(=O)OC(C)C]

In a 10 mL conical flask the ketone Ox_9 (0.03 g, 0.177 mmol), RuCl$_2$[(R)-(DM-BINAP)] (0.0106 g, 0.0064 mmol, 5 mol %) and potassium tert-butoxide (0.0199 g, 0.177 mmol) were dissolved in iso-propanol (2 mL). Tri-isopropyl borate (0.01 mL, 0.04 mmol) was added and the solution was stirred in a Parr hydrogenator at 8 bar for 24 h. The solution was concentrated in vacuo. The product was purified by preparative thin layer chromatography (1:2 pentane:EtOAc) to give the product Ox_11 as a white wax (0.009 g, 28%, 98.4% de). R$_f$: 0.36 (1:2 Pentane:EtOAc); HRMS calculated for C$_{26}$H$_{37}$NO$_6$Na: 482.2519 found: 482.2525. IR (v$_{max}$)=1107.82, 1260.12, 1374.76, 1486.42, 1550.04, 1668.28, 1729.21, 2065.79, 2181.16, 2870.60, 2926.52, 3379.56 cm$^{-1}$; $^1$H NMR (500 MHz, CD$_3$CN) δ 8.04 (m, 2H), 7.51 (m, 3H), 6.72 (d, J=16.0 Hz, 1H), 6.36 (dd, J=16.0, 6.0 Hz, 1H), 4.96 (sep, 5 Hz, 1H), 4.70 (m, 1H), 4.14 (m, 1H), 3.56 (m, 1H), 2.26 (m, 2H), 1.79 (m, 2H), 1.60 (m, 2H), 1.52 (m, 2H), 1.37 (m, 2H), 1.29 (m, 2H), 1.17 (d, J=5 Hz, 6H), 0.88 (m, 3H). $^{13}$C NMR (126 MHz, CD$_3$CN) δ 173.62, 160.11, 145.75, 141.16, 131.18, 130.65, 129.72, 127.94, 126.69, 116.27, 75.45, 74.40, 67.81, 66.74, 37.05, 34.66, 32.14, 32.02, 25.69, 23.13, 21.96, 21.72, 14.14. [α]$_D$=−3.26 (c=1 in CHCl$_3$).

(5S,6R,E)-isopropyl 5,6-dihydroxy-8-(4-((S)-1-hydroxyhexyl)-2-phenyloxazol-5-yl)oct-7-enoate

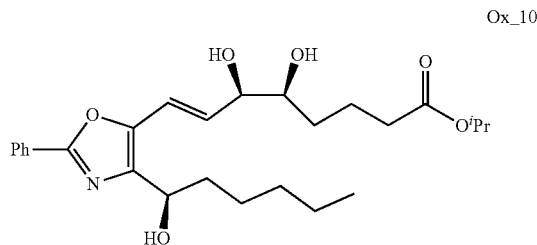 [SMILES: CCCCC[C@@H](O)c1nc(-c2ccccc2)oc1/C=C/[C@@H](O)[C@@H](O)CCCC(=O)OC(C)C]

Ox_10

In a 10 mL conical flask the ketone Ox_9 (0.119 g, 0.277 mmol), RuCl$_2$[(R)-(DM-BINAP)] (0.0348 g, 0.021 mmol, 5 mol %) and potassium tert-butoxide (0.0327 g, 0.290 mmol) were dissolved in iso-propanol (2 mL). Tri-isopropyl borate (0.02 mL, 0.08 mmol) was added and the solution was stirred in a Parr hydrogenator at 8 bar for 24 h. The solution was concentrated in vacuo. The product was purified by preparative thin layer chromatography (1:2 pentane:EtOAc) to give the product as a white wax (0.016 g, 12%, 96% de). R$_f$: 0.36 (1:2 Pentane:EtOAc); $^1$H NMR (400 MHz, CDCl$_3$) δ 8.03 (m, 2H), 7.54-7.33 (m, 3H), 6.68 (d, J=15.7 Hz, 1H), 6.31 (dd, J=15.7, 6.5 Hz, 1H), 4.97 (sep, J=5 Hz, 1H), 4.74 (s, 1H), 4.31 (s, 1H), 3.78 (s, 1H), 2.32 (m, 2H), 1.83 (m, 2H), 1.71 (m, 2H), 1.58-1.39 (m, 2H), 1.30 (m, 4H), 1.24 (m, 2H), 1.20 (m, 3H), 1.18 (m, 3H), 0.89 (m, 3H). $^{13}$C NMR (101 MHz, CDCl$_3$) δ 173.32, 160.51, 144.19, 140.89, 130.53, 128.68, 127.68, 127.06, 126.50, 117.10, 75.16, 73.78, 67.65, 67.29, 37.19, 34.20, 31.59, 31.38, 29.66, 25.16, 22.55, 21.77, 20.97, 14.03.

Methyl 4-((4S,5R)-5-((E)-2-(4-hexanoyloxazol-2-yl)vinyl)-2,2-dimethyl-1,3-dioxolan-4-yl)butanoate

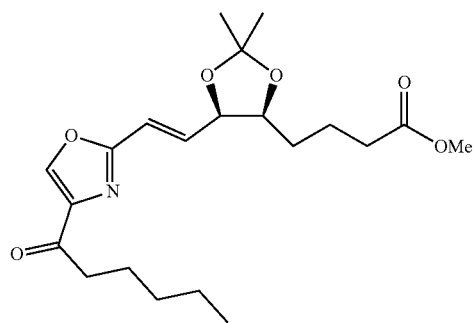

Ox_12

In a 100 mL round bottom flask, Chlorooxazole Ox_3 (0.5 g, 2.848 mmol) was dissolved in dry toluene (25 mL). The reaction was cooled to −78° C. and DIBAL-H (2.35 mL of 25 wt % in toluene) was slowly added. A magnesium n-pentane bromide solution (24 mL, 0.36 M) was slowly added to the reaction at −78° C. The reaction was stirred for 2 h prior quenching by adding water (5 mL). The layers were separated and the aqueous layer was extracted with EtOAc (2×50 mL). The organic layers were combined, dried over MgSO$_4$ and concentrated in vacuo. The crude mixture was dissolved in toluene (20 mL) in a 50 mL flame dried round bottom flask with boronic ester (0.56 g, 1.57 mmol) and Pd(PPh$_3$)$_4$ (0.083 g, 0.0718 mmol). 2 M K$_2$CO$_3$ (1.4 mL) was added to the reaction flask and the reaction mixture was heated to reflux for 16 h. The solution was left to cool to r.t, then water (15 mL) and EtOAc (10 mL) were added. The layers were separated, the aqueous layer was extracted with EtOAc (2×30 mL) and dried over MgSO$_4$. Concentration in vacuo and filtration with a silica plug (3:2 cyclohexane:EtOAc) to give a crude mixture. The off yellow crude mixture (0.156 g) was dissolved in CH$_2$Cl$_2$ (30 mL), Dess-Martin reagent (0.198 g, 0.468 mmol) was added and the reaction was stirred at room temperature for 2 h. A saturated solution of Na$_2$S$_2$O$_3$ (15 mL) was added. The solution was vigorously stirred for 0.5 h. The layers were separated and the aqueous layer was extracted with CH$_2$Cl$_2$, (2×20 mL). The organic layers were combined, dried over MgSO$_4$ and concentrated in vacuo. The product was purified by column chromatography using silica gel (3:2 Cyclohexane:EtOAc) yielding the product Ox_12 as a white wax (0.120 g, 10.1% over 4 steps) R$_f$: 0.67 (3:2 Pentane:EtOAc); HRMS calculated for C$_{21}$H$_{33}$NO$_6$: 394.2230 found: 394.2235. IR (ν$_{max}$)= 862.14, 882.62, 949.30, 982.05. 1052.95, 1082.05, 1116.23, 1216.51, 1372.13, 1437.72, 1457.88, 1559.77, 1691.06, 1734.91, 2009.08, 2259.46, 2871.37, 2932.89, 2954.37, 2984.79, 3141.62, 3248.56, 3367.79 cm$^{-1}$; $^1$H NMR (400 MHz, CDCl$_3$) δ 8.11 (s, 1H), 6.69 (dd, J=15.9, 6.3 Hz, 1H), 6.56 (dd, J=16.0, 0.9 Hz, 1H), 4.70 (td, J=6.3, 0.9 Hz, 1H), 4.25 (ddd, J=8.9, 6.3, 4.7 Hz, 1H), 3.64 (s, 3H), 2.91-2.83 (m, 2H), 2.41-2.30 (m, 2H), 1.83 (m, 2H), 1.70 (m, 4H), 1.51 (s, 3H), 1.50-1.43 (m, 2H), 1.38 (s, 3H), 1.36-1.29 (m, 4H), 0.89 (dd, J=9.6, 4.5 Hz, 3H). $^{13}$C NMR (101 MHz, CDCl$_3$) δ 195.36, 173.63, 160.46, 141.55, 141.49, 136.53, 117.71, 108.93, 78.05, 77.77, 51.51, 39.83, 33.59, 31.35, 29.94, 28.04, 25.49, 23.43, 22.42, 21.78, 13.89. [α]$_D$=0.34 (c=1 in CHCl$_3$).

(5S,6R,E)-methyl 5,6-dihydroxy-8-(4-((S)-1-hydroxyhexyl)oxazol-2-yl)oct-7-enoate

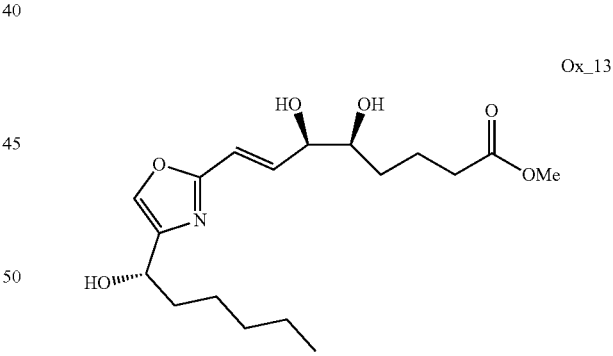

Ox_13

In a 10 mL conical flask the ketone Ox_12 (0.018 g, 0 0.0457 mmol), RuCl$_2$[(R)-(DM-BINAP)] (0.006 g, 0.0036 mmol, 5 mol %) and potassium tert-butoxide (0.008 g, 0.071 mmol) were dissolved in iso-propanol (2 mL). Tri-isopropyl borate (0.01 mL, 0.04 mmol) was added and the solution was stirred in a Parr hydrogenator at 5 bar for 24 h. The solution was concentrated in vacuo. The product was purified by preparative thin layer chromatography (3:2 pentane:EtOAc) to give a mixture of Isopropyl and Methyl ester. The mixture was dissolved in dry methanol (5 mL) and stirred at r.t. with CSA (0.018 g, 0.07 mmol) for 3 h. The reaction was concentrated in vacuo at r.t. and the product was purified by preparative thin layer chromatography (1:10 MeOH:

CH$_2$Cl$_2$) as a white wax (0.006 g, 27% over 2 steps). $^1$H NMR (400 MHz, D20) δ 7.60 (s, 1H), 6.72-6.62 (m, 1H), 6.52-6.34 (m, 1H), 4.60-4.54 (m, 1H), 4.20 (m, 1H), 3.65-3.59 (m, 1H), 3.22 (3.52 (s, 3H), 2.30 (t, J=7.4 Hz, 2H), 1.71-1.64 (m, 2H), 1.57-1.41 (m, 4H), 1.31 (m, 2H), 1.15 (m, 4H), 0.72 (d, J=6.8 Hz, 3H). $^{13}$C NMR (101 MHz, D20) δ 177.12, 137.81, 128.84, 117.57, 116.92, 74.03, 73.27, 66.10, 52.02, 34.78, 33.34, 30.89, 30.66, 24.11, 21.76, 20.64, 13.14.

(5S,6R,E)-methyl 5,6-dihydroxy-8-(4-((R)-1-hydroxyhexyl)oxazol-2-yl)oct-7-enoate

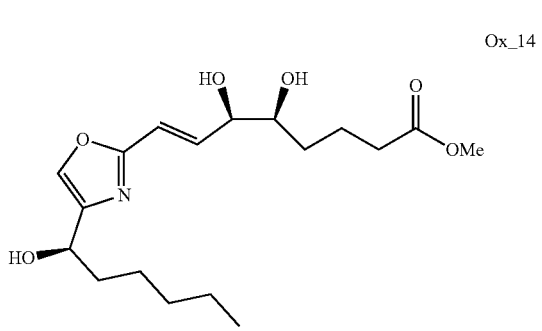 [SMILES: CCCCC[C@@H](O)c1coc(/C=C/[C@@H](O)[C@@H](O)CCCC(=O)OC)n1]

Ox_14

In a 10 mL conical flask the ketone Ox_12 (0.040 g, 0.102 mmol), RuCl$_2$[(R)-(DM-BINAP)] (0.012 g, 0.0072 mmol, 5 mol %) and potassium tert-butoxide (0.016 g, 0.142 mmol) were dissolved in iso-propanol (2 mL). Tri-isopropyl borate (0.01 mL, 0.04 mmol) was added and the solution was stirred in a Parr hydrogenator at 5 bar for 24 h. The solution was concentrated in vacuo. The product was purified by preparative thin layer chromatography (3:2 pentane:EtOAc) to give a mixture of Isopropyl and Methyl ester. The mixture was dissolved in dry methanol (5 mL) and stirred at r.t. with CSA (0.020 g, 0.077 mmol) for 3 h. The reaction was concentrated in vacuo at room temperature and the product was purified by preparative thin layer chromatography (1:10 MeOH:CH$_2$Cl$_2$) as a white wax (0.012 g, 32% over 2 steps)$^1$H NMR (400 MHz, CD$_3$CN) δ 7.59 (s, 1H), 6.72 (dd, J=16.1, 5.5 Hz, 1H), 6.50 (d, J=16.1, 1H), 4.65-4.51 (m, 1H), 4.15 (t, J=4.6 Hz, 1H), 3.63 (s, 3H), 3.61-3.55 (m, 1H), 2.33 (t, J=7.7 Hz, 2H), 2.18 (s, 2H), 1.83-1.74 (m, 2H), 1.72-1.50 (m, 2H), 1.46-1.39 (m, 2H), 1.32 (m, 4H), 0.95-0.86 (m, 3H). $^{13}$C NMR (101 MHz, CD$_3$CN) δ 173.76, 138.29, 126.95, 117.09, 116.72, 74.24, 73.58, 66.59, 50.88, 36.17, 33.37, 31.56, 31.43, 24.80, 22.34, 21.13, 13.33.

Compounds Im 6-S-2, Im 6-R-4, Im 6-S-4, Im 6-R-6, Im 6-S-6, of Formula (VImm)

4, 5-Dibromo-1, 2-dimethyl-1H-imidazole (IM 2)

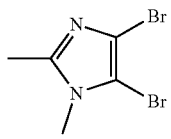

To a solution of 1,2-dimethylimidazole (8.71 g, 90.67 mmol) in CHCl3 (300 mL) was added 1,3-dibromo-5,5-dimethylhydantoin (28.51 g, 99.73 mmol) in one portion. The resulting mixture was stirred for 16 h at room temperature, following which 100 mL of 2.0 M HCl was added. The resulting mixture was extracted with water (3×100 mL), and the pH of the combined aqueous layers was adjusted to 7.0 using Aq. sat. NaHCO$_3$. The resulting white precipitate was filtered, dissolved in CH$_2$Cl$_2$ and concentrated in vacuo to afford the target dibrominated imidazole Im 2 as a white solid (12.3209 g, 48.5222 mmol 54%). mp=77-80° C. (lit 77-78° C.); IR ($v_{max}$)=3054, 2986, 1421 cm$^{-1}$; $^1$H NMR (300 MHz, CDCl$_3$) δ 3.53 (s, 3H), 2.40 (s, 3H) ppm; $^{13}$C NMR (75 MHz, CDCl$_3$) δ 145.66, 114.54, 102.96, 32.80, 14.19 ppm; HRMS calcd. for C$_5$H$_7$N$_2$Br$_2$ (ES$^+$) 252.8976 found 252.8988 (4.8 ppm).

General Procedure for Lithium-Halogen Exchange on 4, 5-dibromo-1, 2-dimethyl-1H-imidazole

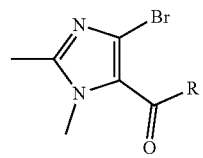

Under an atmosphere of N$_2$, 4, 5-dibromo-1, 2-dimethylimidazole (2.00 g, 7.88 mmol) in anhydrous THF (120 mL) was cooled to −78° C. and n-butyllithium solution was added dropwise (2.50 M, 3.15 mL, 7.88 mmol). The reaction was stirred at −78° C. for 10 minutes. The lithiated solution was then transferred dropwise by cannula to a reaction vessel under inert atmosphere containing a solution of the corresponding acid chloride (9.46 mmol) pre-cooled to −78° C. The reaction mixture was stirred at −78° C. for 1 hour, followed by warming to room temperature and stirring for an additional hour. Water (20 mL) was added to the reaction and the pH adjusted to 7. The organic layer was extracted with CH$_2$Cl$_2$ (3×20 mL), and the combined organic extracts were washed with water (30 mL) and brine (30 mL), dried over MgSO$_4$ and concentrated in vacuo. Purification by flash chromatography (4:1 Pent:EtOAc) yielded the target compound.

1-(4-bromo-1,2-dimethyl-1H-imidazol-5-yl)ethanone (Im 3-2)

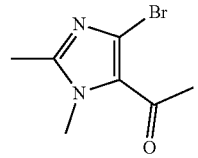

Compound Im 3-2 isolated as a colourless crystalline solid (66%). mp=70-71° C.; $v_{max}$=2995, 2957, 2859, 1801, 1741, 1649, 1487 cm$^{-1}$; $^1$H NMR (300 MHz, CDCl$_3$) δ 3.79 (s, 3H), 2.63 (s, 3H), 2.39 (s, 3H) ppm; $^{13}$C NMR (101 MHz, CDCl$_3$) δ 188.49, 149.95, 128.64, 123.65, 34.17, 30.61, 13.37. ppm; HRMS calcd. for C$_7$H$_9$BrN$_2$O (ES$^+$) 216.9976 found 216.9975 (−0.7 ppm).

1-(4-bromo-1,2-dimethyl-1H-imidazol-5-yl)butan-1-one (Im 3-4)

Compound Im 3-4 was isolated as a yellow oil (54%). $v_{max}$=2963, 2933, 2873, 1751, 1650, 1463, 1430, 1249 cm$^{-1}$; $^1$H NMR (300 MHz, CDCl$_3$) δ 3.68 (s, 3H), 2.85 (t, J=7.4 Hz, 2H), 2.28 (s, 3H), 1.59 (dt, J=9.4, 4.7 Hz, 2H), 0.88 (t, J=7.4 Hz, 3H) ppm; $^{13}$C NMR (101 MHz, CDCl$_3$) δ 191.48, 149.76, 128.43, 122.58, 43.63, 34.17, 17.74, 13.76, 13.36 ppm;

1-(4-bromo-1,2-dimethyl-1H-imidazol-5-yl)pentan-1-one (Im 3-5)

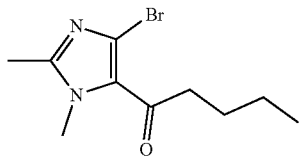

Compound Im 3-5 isolated as a yellow oil (64%). $^1$H NMR (400 MHz, CDCl$_3$) δ 3.75 (s, 3H), 2.96 (t, J=7.5 Hz, 2H), 2.36 (s, 3H), 1.72-1.55 (m, 2H), 1.43-1.30 (m, 2H), 0.91 (t, J=7.3 Hz, 3H) ppm; $^{13}$C NMR (101 MHz, CDCl$_3$) δ 191.64, 149.73, 128.44, 122.59, 41.46, 34.15, 26.36, 22.34, 13.86, 13.36 ppm; HRMS calcd. for C$_{10}$H$_{15}$BrN$_2$O (ES$^+$) 259.0446 found 259.0444 (−0.8 ppm).

1-(4-Bromo-1,2-dimethyl-1H-imidazol-5-yl)hexan-1-one (Im 3-6)

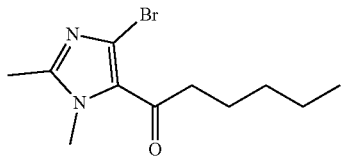

Compound Im 3-6 isolated as a yellow oil (72%); $v_{ma}$=2956, 2930, 2860, 1752, 1655, 1466, 1252 cm$^{-1}$; $^1$H NMR (500 MHz, CDCl$_3$) δ 3.80 (s, 3H), 2.99 (t, 2H), 2.40 (s, 3H), 1.72-1.66 (m, 2H), 1.39-1.34 (m, 4H), 0.93-0.90 (m, 3H) ppm; $^{13}$C NMR (126 MHz, CDCl$_3$) 191.55, 149.73, 128.39, 122.53, 41.70, 34.15, 31.40, 23.96, 22.46, 13.90, 13.34 ppm; HRMS calcd. for C$_1$H$_{18}$N$_2$OBr (ES$^+$) 273.0602 found 273.0616 (4.9 ppm).

General Procedure for Asymmetric Reduction of Bromoimidazole Ketone

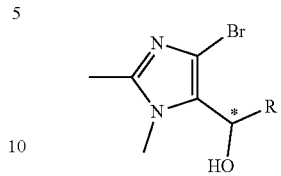

To a solution of imidazole ketone (4 mmol) in $^i$PrOH (3.0 mL) was added KO$^t$Bu (4 mmol) and RuCl2[(R)-DM-BINAP][(R)-DAIPEN] (0.08 mmol) or RuCl2[(S)-DM-BINAP][(S)-DAIPEN] (0.08 mmol). The reaction mixture was stirred in a Parr hydrogenator under 15 bar of hydrogen for 16 hours. CH$_2$Cl$_2$ (30 mL) was added and the reaction mixture then washed with aq. sat. NH$_4$Cl (30 mL), water (30 mL) and brine (30 mL), dried over MgSO4, filtered and concentrated in vacuo. Purification by flash chromatography (3:1 Pent:EtOAc) afforded target alcohol as a crystalline solid. Recrystallisation from EtOAc and pentane afforded the enantioenriched target compound.

(R)-1-(4-bromo-1,2-dimethyl-1H-imidazol-5-yl)ethanol (Im 4-R-2)

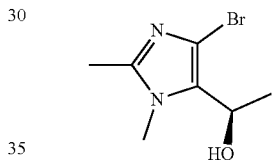

Compound Im 4-R-2 isolated as a colourless crystalline solid (32%, 99% ee).

(S)-1-(4-bromo-1,2-dimethyl-1H-imidazol-5-yl)ethanol (Im 4-S-2)

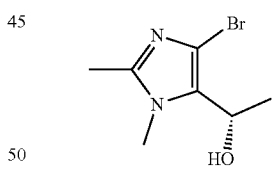

Compound Im 4-S-2 isolated as a colourless crystalline solid (33%, 98% ee).

(R)-1-(4-bromo-1,2-dimethyl-1H-imidazol-5-yl)butan-1-ol (Im 4-R-4)

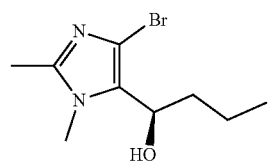

Compound Im 4-R-4 isolated as a colourless crystalline solid (63%, >99% ee) mp=162-165° C.; $v_{max}$=3178, 2956, 2931, 2868, 1724, 1560, 1403, 1237 cm$^{-1}$; $^1$H NMR (400 MHz, CDCl$_3$) δ 4.83 (t, 1H), 3.63 (t, 3H), 2.93 (s, 1H), 2.29 (s, 3H), 1.97-1.85 (m, 1H), 1.80-1.71 (m, 1H), 1.51-1.36 (m, 1H), 1.33-1.18 (m, 1H), 0.93 (t, J=7.4 Hz, 3H) ppm; $^{13}$C NMR (101 MHz, CDCl$_3$) δ 145.87, 129.43, 112.45, 66.18, 38.04, 31.97, 19.35, 13.95, 13.29 ppm; HRMS calcd. for C$_9$H$_{15}$BrN$_2$O (ES$^+$) 247.0446 found 247.0435 (−4.5 ppm); [α]$_D$=+20.56 (c=1 in CHCl$_3$)

(S)-1-(4-bromo-1,2-dimethyl-1H-imidazol-5-yl)butan-1-ol (Im 4-S-4)

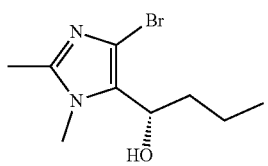

Compound Im 4-S-4 isolated as a colourless crystalline solid (62%, >99% ee) mp=163-165° C.; $^1$H NMR (400 MHz, CDCl$_3$) δ 4.84 (t, J=7.5 Hz, 1H), 3.63 (s, 3H), 2.74 (s, 1H), 2.31 (s, 3H), 1.96-1.85 (m, 1H), 1.80-1.71 (m, 1H), 1.44-1.38 (m, 1H), 1.31-1.23 (m, 1H), 0.94 (t, J=7.3, 1.9 Hz, 3H) ppm; $^{13}$C NMR (101 MHz, CDCl$_3$) 145.91, 129.38, 112.55, 66.26, 38.04, 31.97, 19.36, 13.95, 13.31 ppm; HRMS calcd. for C$_9$H$_{15}$BrN$_2$O (ES$^+$) 247.0446 found 247.0458 (+4.9 ppm); [α]$_D$=−17.56 (c=1 in CHCl$_3$).

(R)-1-(4-bromo-1,2-dimethyl-1H-imidazol-5-yl)hexan-1-ol (Im 4-R-6)

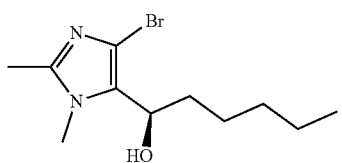

Compound Im 4-R-6 isolated as a colourless crystalline solid (56%, >99% ee)$^1$H NMR (400 MHz, CDCl$_3$) δ 4.82 (td, J=7.5, 3.5 Hz, 1H), 3.63 (s, 3H), 2.74 (d, J=3.6 Hz, 1H), 2.30 (s, 3H), 1.97-1.86 (m, 1H), 1.83-1.72 (m, 1H), 1.47-1.35 (m, 1H), 1.35-1.25 (m, 4H), 1.26-1.16 (m, 1H), 0.87 (t, J=7.0 Hz, 3H) ppm; $^{13}$C NMR (101 MHz, CDCl$_3$) δ 145.90, 129.39, 112.56, 66.50, 35.89, 31.96, 31.65, 25.77, 22.69, 14.14, 13.32 ppm; HRMS calcd. for C$_{11}$H$_{19}$BrN$_2$O (ES$^+$) 275.0759 found 275.0762 (1.1 ppm); [α]$_D$=+15.02 (c=1 in CHCl$_3$).

(S)-1-(4-Bromo-1, 2-dimethyl-1H-imidazol-5-yl)hexan-1-ol (Im 4-S-6)

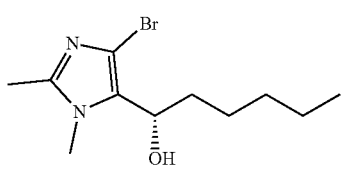

Compound Im 4-S-6 isolated as a colourless crystalline solid (55%, >99% ee) mp=135-137° C.; $v_{max}$=3237, 2950, 2858, 1477, 1431, 1404, 1321, 1238, 1062 cm$^{-1}$; $^1$H NMR (400 MHz, CDCl$_3$) δ 4.82 (t, J=7.5, 3.5 Hz, 1H), 3.63 (s, 3H), 2.77 (s, 1H), 2.30 (s, 3H), 1.95-1.86 (m, 1H), 1.81-1.72 (m, 1H), 1.45-1.35 (m, 1H), 1.33-1.25 (m, J=3.2 Hz, 4H), 1.25-1.14 (m, 1H), 0.87 (t, J=6.7, 6.1 Hz, 3H) ppm; $^{13}$C NMR (101 MHz, CDCl$_3$) δ 145.90, 129.40, 112.54, 66.49, 35.90, 31.96, 31.65, 25.77, 22.69, 14.14, 13.31 ppm; HRMS calcd. for C$_{11}$H$_{19}$BrN$_2$O (ES$^+$) 275.0759 found 275.0770 (4.0 ppm).

General Procedure for Suzuki Cross-Coupling Between Mono-Brominated Imidazole and Vinylboronic Ester

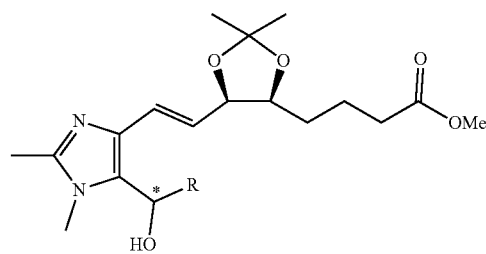

To a solution of brominated imidazole compound (200 mmol) in ethylene glycol dimethyl ether (1.0 mL) was added the vinylboronic ester 61 (240 mmol), tetrakis(triphenylphosphine) palladium (10 mmol) and K$_2$CO$_3$ (400 mmol as 2 M aqueous solution). The resulting mixture was stirred in a sealed microwave tube at 125° C., 150 W for 45 minutes, after which CH$_2$Cl$_2$ (10 mL) was added to the mixture. The solution was washed with water (10 mL) and brine (10 mL), dried over MgSO$_4$ and concentrated in vacuo. Purification by flash chromatography (1:1 Pent:EtOAc) afforded the target imidazole compound.

methyl 4-((4S,5R)-5-((E)-2-(5-((R)-1-hydroxyethyl)-1,2-dimethyl-1H-imidazol-4-yl)vinyl)-2,2-dimethyl-1,3-dioxolan-4-yl)butanoate (Im 5-R-2)

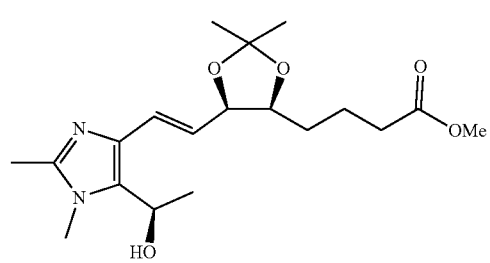 [SMILES: COC(=O)CCC[C@@H]1OC(C)(C)O[C@@H]1/C=C/c1nc(C)n(C)c1[C@@H](C)O]

Compound Im 5-R-2 was isolated as a clear yellow oil (52%)$^1$H NMR (300 MHz, CDCl$_3$) δ 6.53 (d, J=15.4 Hz, 1H), 6.22 (dd, J=15.4, 7.6 Hz, 1H), 5.15 (q, J=6.8 Hz, 1H), 4.64 (t, J=6.5 Hz, 1H), 4.21-4.10 (m, 1H), 3.63 (s, 3H), 3.62 (s, 3H), 2.32 (s, 3H), 2.36-2.28 (m, 2H), 1.81-1.65 (m, 4H), 1.55 (d, J=6.8 Hz, 3H), 1.51 (s, 3H), 1.38 (s, 3H) ppm;

methyl 4-((4S,5R)-5-((E)-2-(5-((S)-1-hydroxyethyl)-1,2-dimethyl-1H-imidazol-4-yl)vinyl)-2,2-dimethyl-1,3-dioxolan-4-yl)butanoate (Im 5-S-2)

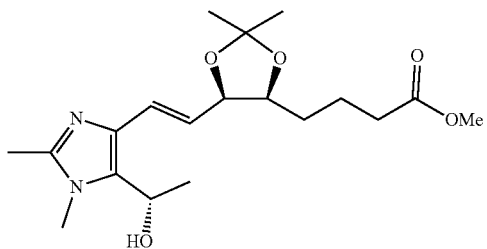 [SMILES: COC(=O)CCC[C@@H]1OC(C)(C)O[C@@H]1/C=C/c1nc(C)n(C)c1[C@H](C)O]

Compound Im 5-S-2 was isolated as a clear yellow oil (23%) $^1$H NMR (300 MHz, CDCl$_3$) δ 6.45 (d, J=15.5 Hz, 1H), 6.20 (dd, J=15.5, 7.5 Hz, 1H), 5.07 (q, J=6.8 Hz, 1H), 4.61 (t, J=5.8 Hz, 1H), 4.19-4.09 (m, 1H), 3.61 (s, 3H), 3.60 (s, 3H), 2.32 (s, 3H), 2.32-2.24 (m, 2H), 1.81-1.58 (m, 4H), 1.50 (d, J=6.8 Hz, 3H), 1.48 (s, 3H), 1.36 (s, 3H) ppm.

methyl 4-((4S,5R)-5-((E)-2-(5-((R)-1-hydroxybutyl)-1,2-dimethyl-1H-imidazol-4-yl)vinyl)-2,2-dimethyl-1,3-dioxolan-4-yl)butanoate (Im 5-R-4)

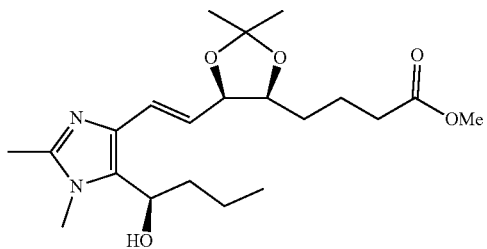 [SMILES: CCC[C@@H](O)c1c(/C=C/[C@H]2OC(C)(C)O[C@H]2CCCC(=O)OC)nc(C)n1C]

Compound Im 5-R-4 was isolated as a clear yellow oil (59%, 99% de) $^1$H NMR (400 MHz, CDCl$_3$) δ 6.36 (d, J=15.4 Hz, 1H), 6.16 (dd, J=15.4, 8.0 Hz, 1H), 4.83 (t, J=7.4 Hz, 1H), 4.60-4.55 (m, 1H), 4.15-4.09 (m, 1H), 3.61 (s, 3H), 3.57 (s, 3H), 2.33-2.27 (m, 2H), 2.23 (s, 3H), 1.94-1.83 (m, 1H), 1.82-1.74 (m, 1H), 1.69-1.60 (m, 2H), 1.57-1.51 (m, 1H), 1.49 (s, 3H), 1.45-1.41 (m, 1H), 1.42-1.38 (m, 1H), 1.36 (s, 3H), 1.21-1.19 (m, 1H), 0.89 (t, J=7.4 Hz, 3H) ppm; $^{13}$C NMR (101 MHz, CDCl$_3$) δ 174.04, 145.97, 133.21, 130.89, 123.42, 122.58, 108.18, 80.13, 78.45, 65.03, 51.56, 38.28, 33.93, 31.79, 30.11, 28.42, 25.88, 21.91, 19.56, 13.98, 12.92 ppm.

methyl 4-((4S,5R)-5-((E)-2-(5-((S)-1-hydroxybutyl)-1,2-dimethyl-1H-imidazol-4-yl)vinyl)-2,2-dimethyl-1,3-dioxolan-4-yl)butanoate (Im 5-S-4)

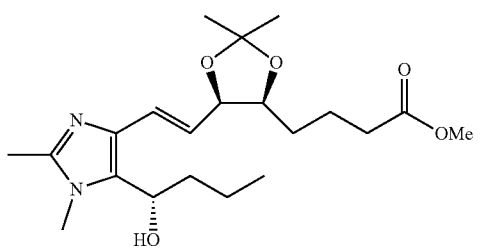 [SMILES: CCC[C@H](O)c1c(/C=C/[C@H]2OC(C)(C)O[C@H]2CCCC(=O)OC)nc(C)n1C]

Compound Im 5-S-4 was isolated as a clear yellow oil (72%, 98% de) $v_{max}$=3178.79, 2924.78, 2870.54, 1735.88, 1664.34, 1525.12 cm$^{-1}$; $^1$H NMR (400 MHz, CDCl$_3$) δ 6.39 (d, J=15.4 Hz, 1H), 6.16 (dd, J=15.4, 7.4 Hz, 1H), 4.83 (t, J=7.3 Hz, 1H), 4.65-4.56 (m, 1H), 4.12 (dt, J=13.6, 6.3 Hz, 1H), 3.60 (s, 3H), 3.55 (s, 3H), 2.79 (s, 1H), 2.35-2.27 (m, 2H), 2.25 (s, 3H), 2.01-1.71 (m, 4H), 1.70-1.52 (m, 4H), 1.47 (s, 3H), 1.35 (s, 3H), 0.93-0.83 (m, 3H) ppm; $^{13}$C NMR (75 MHz, CDCl$_3$) δ 173.91, 145.94, 133.45, 130.44, 122.87, 122.53, 108.02, 79.49, 78.33, 65.15, 51.42, 38.18, 33.78, 31.61, 29.96, 28.20, 25.72, 21.80, 19.37, 13.77, 12.99 ppm; HRMS calcd. for C$_{21}$H$_{34}$N$_2$O$_5$ (ES$^+$) 395.2546 found 395.2528 (−4.5 ppm); [α]=−1.96 (c=1 in CHCl$_3$).

methyl 4-((4S,5R)-5-((E)-2-(5-((R)-1-hydroxyhexyl)-1,2-dimethyl-1H-imidazol-4-yl)vinyl)-2,2-dimethyl-1,3-dioxolan-4-yl)butanoate (Im 5-R-6)

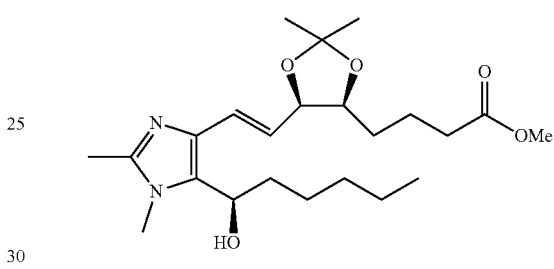

Compound Im 5-R-6 was isolated as a clear yellow oil (57%, 99% de) $v_{max}$=3271.35, 2924.79, 2855.82, 1734.71, 1657.35, 1436.39, 1377.37, 1164.80, 1057.20 cm$^{-1}$; $^1$H NMR (400 MHz, CDCl$_3$) δ 6.40 (d, J=15.4 Hz, 1H), 6.18 (dd, J=15.4, 8.0 Hz, 1H), 4.84 (t, J=7.3 Hz, 1H), 4.60 (dt, 1H), 4.18-4.09 (m, 1H), 3.62 (s, 1H), 3.57 (s, 1H), 2.31 (td, J=7.4, 3.2 Hz, 2H), 2.25 (s, 2H), 1.93-1.86 (m, 1H), 1.78 (dd, J=15.3, 7.6 Hz, 1H), 1.66 (dd, J=14.3, 6.5 Hz, 2H), 1.59-1.53 (m, 1H), 1.50 (s, 1H), 1.45-1.40 (m, 1H), 1.37 (s, 1H), 1.28-1.25 (m, J=7.6, 4.5 Hz, 4H), 0.87-0.84 (m, 3H) ppm; $^{13}$C NMR (101 MHz, CDCl$_3$) δ 174.08, 146.09, 133.64, 130.72, 123.71, 122.51, 108.20, 80.15, 78.48, 65.51, 51.59, 36.18, 33.96, 31.76, 30.16, 29.84, 28.47, 26.03, 25.92, 22.69, 21.95, 14.17, 13.10 ppm; HRMS calcd. for C$_{23}$H$_{38}$N$_2$O$_5$ (ES$^+$) 423.2859 found 423.2859 (0.0 ppm); [α]$_D$=+14.96 (c=1 in CHCl$_3$).

methyl 4-((4S,5R)-5-((E)-2-(5-((S)-1-hydroxyhexyl)-1,2-dimethyl-1H-imidazol-4-yl)vinyl)-2,2-dimethyl-1,3-dioxolan-4-yl)butanoate (Im 5-S-6)

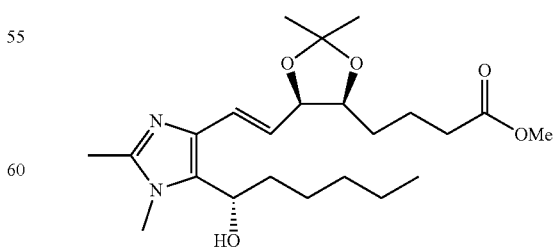

Compound Im 5-S-6 was isolated as a clear yellow oil (64%, 99% de) $^1$H NMR (300 MHz, CDCl$_3$) δ 6.35 (d, J=15.4 Hz, 1H), 6.11 (dd, J=15.4, 7.1 Hz, 1H), 4.75 (t, J=7.3

Hz, 1H), 4.60 (t, J=6.6 Hz, 1H), 4.16-4.08 (m, 1H), 3.59 (s, 3H), 3.53 (s, 3H), 2.28 (t, J=6.9 Hz, 2H), 2.22 (s, 3H), 1.94-1.71 (m, 4H), 1.70-1.57 (m, 2H), 1.59-1.49 (m, 2H), 1.46 (s, 3H), 1.34 (s, 3H), 1.29-1.15 (m, 4H), 0.89-0.78 (m, 3H) ppm; HRMS calcd. for $C_{23}H_{38}N_2O_5$ (ES$^+$) 423.2859 found 423.2845 (−3.3 ppm); $[\alpha]_D$=−4.77 (c=1 in CHCl$_3$).

General Procedure for Deprotection of Acetonide-Protected Imidazole LXA$_4$ Analogues To a solution of acetonide-protected imidazole analogue (85 mmol) in MeOH (0.5 mL) at 0° C. was added ZrCl$_4$ (25.5 mmol) in one portion. The reaction was then allowed to warm to room temperature and stirred until TLC indicated consumption of starting material. The solution was then concentrated in vacuo at room temperature. Purification by preparative thin layer chromatography (10:1 CH$_2$Cl$_2$: MeOH) afforded the desired free-diol.

(5S,6R,E)-methyl 5,6-dihydroxy-8-(5-((S)-1-hydroxyethyl)-1,2-dimethyl-1H-imidazol-4-yl)oct-7-enoate (Im 6-S-2)

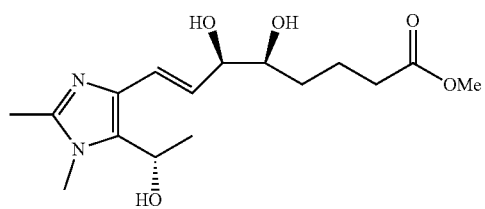 [SMILES: COC(=O)CCC[C@H](O)[C@H](O)/C=C/c1nc(C)n(C)c1[C@H](C)O]

Compound Im 6-S-2 was isolated as a dark yellow oil (31%, 98% de) $^1$H NMR (300 MHz, CD$_3$OD) δ 6.73 (d, J=16.0 Hz, 1H), 6.30 (dd, J=15.9, 5.9 Hz, 1H), 5.19 (q, J=6.8 Hz, 1H), 4.11 (t, J=5.5 Hz, 1H), 3.81 (s, 3H), 3.67 (s, 3H), 3.61-3.52 (m, 1H), 2.57 (s, 3H), 2.38 (t, J=7.3 Hz, 2H), 1.94-1.83 (m, 1H), 1.73-1.61 (m, 2H), 1.56 (d, J=6.8 Hz, 3H), 1.49-1.42 (m, 1H) ppm; HRMS calcd. for $C_{16}H_{26}N_2O_5$ (ES$^+$) 327.1920 found 327.1910 (−3.0 ppm); $[\alpha]_D$=−9.45 (c=1 in MeOH).

(5S,6R,E)-methyl 5,6-dihydroxy-8-(5-((R)-1-hydroxybutyl)-1,2-dimethyl-1H-imidazol-4-yl)oct-7-enoate (Im 6-R-4)

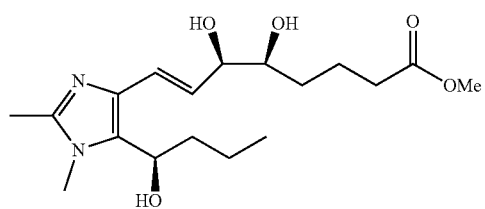 [SMILES: CCC[C@@H](O)c1c(/C=C/[C@@H](O)[C@@H](O)CCCC(=O)OC)nc(C)n1C]

Compound Im 6-R-4 isolated as a dark-coloured oil (44%, 98% de) $^1$H NMR (500 MHz, CD$_3$OD) δ 6.67 (d, J=16.0 Hz, 1H), 6.32 (dd, J=16.0, 5.5 Hz, 1H), 4.96 (t, J=7.2 Hz, 1H), 4.11 (t, J=5.5 Hz, 1H), 3.77 (s, 3H), 3.66 (s, 3H), 3.57 (dd, J=8.8, 4.0 Hz, 1H), 2.54 (s, 3H), 2.37 (t, J=7.3 Hz, 2H), 1.95-1.90 (m, 1H), 1.89-1.83 (m, 1H), 1.79-1.73 (m, 1H), 1.69-1.62 (m, 2H), 1.49-1.42 (m, 2H), 1.36-1.23 (m, 1H), 0.96 (dd, J=7.5, 6.7 Hz, 3H) ppm; $^{13}$C NMR (101 MHz, CD$_3$CN) δ 173.81, 145.51, 133.41, 131.22, 125.71, 114.76, 74.72, 73.78, 64.14, 50.94, 37.88, 33.42, 32.60, 31.71, 21.05, 18.62, 12.99, 10.58. $[\alpha]_D$=+19.61 (c=1 in MeOH).

(5S,6R,E)-methyl 5,6-dihydroxy-8-(5-((S)-1-hydroxybutyl)-1,2-dimethyl-1H-imidazol-4-yl)oct-7-enoate

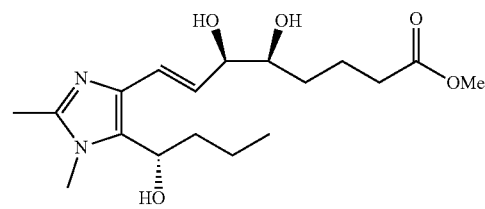 [SMILES: CCC[C@H](O)c1c(/C=C/[C@@H](O)[C@@H](O)CCCC(=O)OC)nc(C)n1C]

Compound Im 6-S-4 isolated as a dark-coloured oil (25%, 96% de) $v_{max}$=3342, 2949, 2929, 2858, 1732, 1435, 1072 cm$^{-1}$; $^1$H NMR (400 MHz, CD$_3$CN) 6.51 (d, J=15.6 Hz, 1H), 6.22 (dd, J=15.6, 6.8 Hz, 1H), 4.85 (t, J=7.4 Hz, 1H), 4.02-3.98 (m, 1H), 3.60 (s, 3H), 3.55 (s, 3H), 3.53-3.46 (m, 1H), 2.84 (s, 3H), 2.30 (t, J=6.0 Hz, 2H), 2.28 (s, 3H), 1.88-1.81 (m, 1H), 1.78-1.72 (m, 1H), 1.69-1.64 (m, 1H), 1.62-1.55 (m, 1H), 1.52-1.43 (m, 1H), 1.38-1.32 (m, 2H), 1.24-1.18 (m, 1H), 0.90 (t, J=7.4 Hz, 3H) ppm; $^{13}$C NMR (101 MHz, CD$_3$CN) δ 173.82, 145.50, 132.76, 130.36, 126.76, 121.37, 75.56, 74.00, 64.62, 50.86, 38.41, 33.48, 31.59, 31.20, 21.24, 19.03, 13.11, 12.00 ppm; HRMS calcd. for $C_{18}H_{30}N_2O_5$ (ES$^+$) 355.2233 found 355.2219 (−3.9 ppm);

(5S,6R,E)-methyl 5,6-dihydroxy-8-(5-((R)-1-hydroxyhexyl)-1,2-dimethyl-1H-imidazol-4-yl)oct-7-enoate (Im 6-R-6)

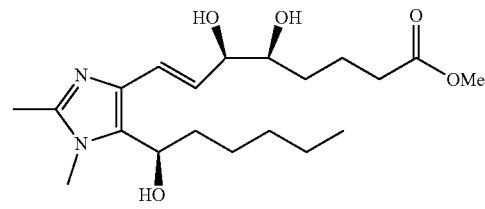 [SMILES: CCCCC[C@@H](O)c1c(/C=C/[C@@H](O)[C@@H](O)CCCC(=O)OC)nc(C)n1C]

Compound Im 6-R-6 isolated as a yellow oil (20%,99% de) $v_{max}$=3348, 2952, 2927, 2857, 1735, 1662, 1522, 1436, 1025 cm$^{-1}$; $^1$H NMR (500 MHz, CDCl$_3$) δ 6.43 (d, J=15.6 Hz, 1H), 6.26 (dd, J=15.0, 5.2 Hz, 1H), 4.83 (t, J=7.4 Hz, 1H), 3.63 (s, 3H), 3.62 (s, 3H), 3.61-3.58 (m, 1H), 2.32 (s, 3H), 2.29 (t, J=7.5 Hz, 2H), 1.91-1.84 (m, 1H), 1.83-1.73 (m, 1H), 1.71-1.59 (m, 2H), 1.52-1.34 (m, 4H), 1.33-1.19 (m, 4H), 1.18-1.11 (m, 1H), 0.84 (t, J=6.7 Hz, 3H) ppm; $^{13}$C NMR (126 MHz, CDCl$_3$) δ 174.42, 145.88, 132.73, 130.69, 127.01, 121.18, 75.83, 74.40, 65.10, 51.62, 36.16, 33.97, 31.88, 31.74, 29.82, 26.01, 22.69, 21.51, 14.16, 12.69 ppm; HRMS calcd. for $C_{20}H_{34}N_2O_5$ (ES$^+$) 383.2546 found 383.2548 (+0.5 ppm); $[\alpha]_D$=+12.47 (c=1 in CHCl$_3$).

(5S,6R,E)-methyl 5,6-dihydroxy-8-(5-((S)-1-hydroxyhexyl)-1,2-dimethyl-1H-imidazol-4-yl)oct-7-enoate (Im 6-S-6)

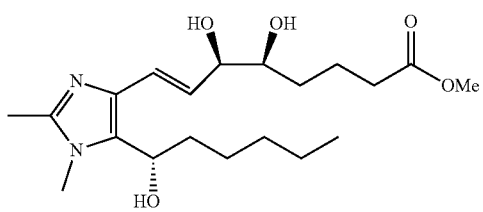 [SMILES: CCCCC[C@H](O)c1c(/C=C/[C@@H](O)[C@@H](O)CCCC(=O)OC)nc(C)n1C]

Compound Im 6-S-6 isolated as a dark yellow oil (41%, 99% de);) $v_{max}$=3342, 2929, 2858, 1732, 1522, 1435, 1048 cm$^{-1}$; $^1$H NMR (400 MHz, CD$_3$CN) δ 6.50 (d, J=15.4 Hz, 1H), 6.21 (dd, J=15.5, 6.4 Hz, 1H), 4.82 (t, J=7.4 Hz, 1H), 4.02-3.98 (m, 1H), 3.60 (s, 3H), 3.54 (s, 3H), 3.53-3.47 (m, 1H), 3.31 (s, 3H), 2.30 (t, J=7.3 Hz, 2H), 2.26 (s, 3H), 1.87-1.81 (m, 1H), 1.79-1.72 (m, 1H), 1.72-1.66 (m, 1H), 1.63-1.56 (m, 1H), 1.51-1.46 (m, 1H), 1.39-1.31 (m, 2H), 1.32-1.25 (m, 4H), 1.15 (d, J=5.2 Hz, 1H), 0.87 (t, J=6.9 Hz, 3H) ppm; $^{13}$C NMR (101 MHz, CD$_3$CN) δ 173.83, 145.60, 133.15, 130.40, 126.43, 121.71, 75.64, 74.02, 64.89, 50.87, 36.26, 33.49, 31.57, 31.29, 31.15, 25.52, 22.32, 21.27, 13.33, 12.06 ppm; HRMS calcd. for C$_{20}$H$_{34}$N$_2$O$_5$ (ES$^+$) 383.2546 found 383.2535 (−2.9 ppm); [α]=−18.91 (c=1 in CHCl$_3$).

Compounds (1S)-9 and (1R)-9 of Formula (VIm2)

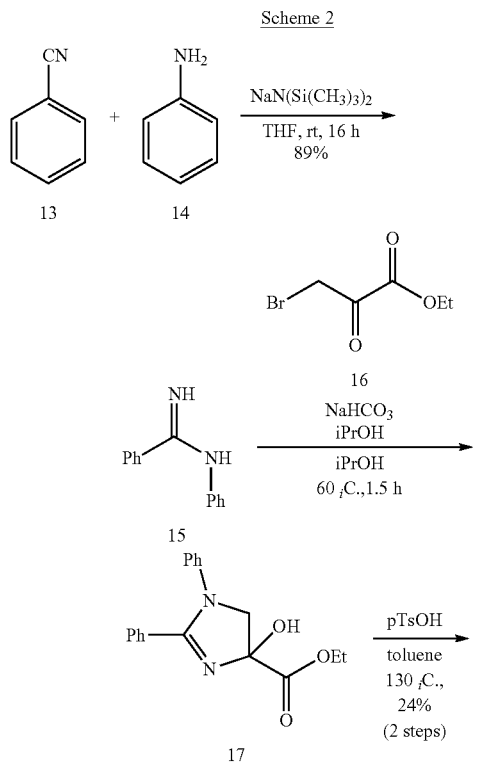

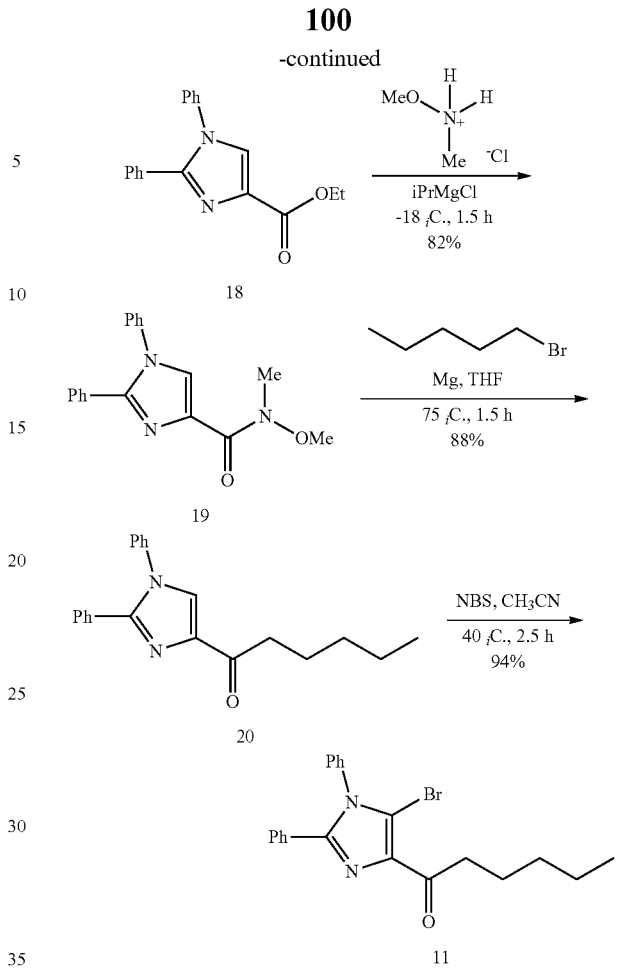

N-methoxy-N-methyl-1,2-diphenyl-1H-imidazole-4-carboxamide (19)

The ester (18) (4.45 g, 15.22 mmol, 1.00 equiv) and N,O-dimethylhydroxylamine hydrochloride (1.70 g, 19.78 mmol, 1.30 equiv) were dissolved in THF (45 mL). iPrMgCl (19.8 mL, 2 M in THF, 39.87 mmol, 2.60 equiv) was added dropwise at −18° C. and stirring was continued for 1.5 h. The reaction was allowed to warm to room temperature and Et$_2$O (50 mL) was added followed by H$_2$O (50 mL). The organic layer was washed with H$_2$O (50 mL) and brine (50 mL). The aqueous phase was then re-extracted with Et$_2$O (80 mL). The combined organic extracts were dried over MgSO$_4$, filtered and concentrated in vacuo. Purification by flash column chromatography (96:4 CH$_2$Cl$_2$:MeOH) afforded the title compound (19) as a light brown solid (4.67 g, 82%). R$_f$=0.44 (96:4 CH$_2$Cl$_2$:MeOH). mp=143-145° C. IR ($v_{max}$)= 1216, 1439, 1635, 2403, 3017 cm$^{-1}$. $^1$H NMR (400 MHz, CDCl$_3$) δ=3.55 (s, 3H), 3.87 (s, 3H), 7.23-7.30 (m, 5H), 7.41-7.43 (m, 5H), 7.80 (s, 1H) ppm. $^{13}$C NMR (101 MHz, CDCl$_3$) δ=34.8, 61.5, 126.0, 128.0, 128.3, 128.9 (2C), 129.0, 129.8, 135.0, 138.1, 146.6, 163.4, 197.4 ppm. HRMS (ESI) calcd. C$_{18}$H$_{17}$N$_3$O$_2$Na (M+Na)$^+$ 330.1218 found 330.1223 (+1.4 ppm).

1-(1,2-Diphenyl-1H-imidazol-4-yl)hexan-1-one (20)

The Grignard derivative of 1-bromopentane was prepared via the addition of bromopentane (0.32 mL, 2.60 mmol, 4.00 equiv) to preactivated magnesium turnings (0.06 g, 2.60 mmol, 4.00 equiv) in THF (10 mL) and heating to reflux for 1.25 h. The Weinreb amide (19) (0.20 g, 0.65 mmol, 1.00 equiv) in THF (5 mL) was transferred dropwise into the flask containing the Grignard reagent and heating was continued for a further 1.5 h. Aq. sat. $NH_4Cl$ (20 mL) was added to the reaction mixture which was then extracted with $Et_2O$ (20 mL) and washed with $H_2O$ (20 mL), then brine (20 mL). The aqueous layer was re-extracted with $Et_2O$ (20 mL). The combined organic extracts were dried over $MgSO_4$, filtered and concentrated in vacuo. The residue was then purified by column chromatography (9:1 Pent:EtOAc) to afford the title compound (20) as an off white solid (0.18 g, 88%). $R_f$=0.85 (94:4 $CH_2Cl_2$:MeOH). mp=92-94° C. IR ($v_{max}$)=758, 1529, 1669, 3021 $cm^{-1}$. $^1H$ NMR (400 MHz, $CDCl_3$) δ=0.90-0.94 (m, 3H), 1.22-1.45 (m, 6H), 3.08 (t, J=7.5 Hz, 2H), 7.21-7.44 (m, 10H), 7.80 (s, 1H) ppm. $^{13}C$ NMR (101 MHz, $CDCl_3$) δ=14.1, 22.7, 24.1, 31.8, 39.1, 125.9, 126.4, 128.5, 129.0, 129.1, 129.2, 129.7, 129.8, 137.9, 141.9, 147.3, 197.4 ppm. HRMS (ESI) calcd. for $C_{21}H_{23}N_2O$ $(M+H)^+$ 319.1810, found 319.1805.

1-(5-Bromo-1,2-diphenyl-1H-imidazol-4-yl)hexan-1-one (11)

The imidazole (20) (0.71 g, 2.23 mmol, 1.00 equiv) was dissolved in acetonitrile. NBS (0.87 g, 4.90 mmol, 2.20 equiv) was added and the reaction was stirred at 45° C. for 2.5 h. The reaction was concentrated and purified by flash column chromatography (9:1 Pent:EtOAc) to afford the title compound (10) as a white solid (0.84 g, 94%). $R_f$=0.88 (96:4 $CH_2Cl_2$:MeOH). mp=97-98° C. IR ($v_{max}$)=1506, 1679, 2932, 3019 $cm^{-1}$. $^1H$ NMR (400 MHz, $CDCl_3$) δ=0.92 (t, J=7.0 Hz, 3H), 1.37-1.45 (m, 6H), 3.15 (t, J=7.4 Hz, 2H), 7.16-7.53 (m, 10H) ppm. $^{13}C$ NMR (101 MHz, $CDCl_3$) δ=14.1, 22.7, 23.8, 31.7, 39.6, 110.6, 128.4, 128.5, 128.6, 129.3, 129.6, 129.8, 129.9, 136.1, 137.6, 148.0, 196.8 ppm. HRMS (ESI) calcd for $C_{21}H_{22}N_2OBr$ $(M+H)^+$ 397.0915, found 397.0907.

Methyl 4-((4S,5R)-5-((E)-2-(4-hexanoyl-1,2-diphenyl-1H-imidazol-5-yl)vinyl)-2,2-dimethyl-1,3-dioxolan-4-yl)butanoate (23)

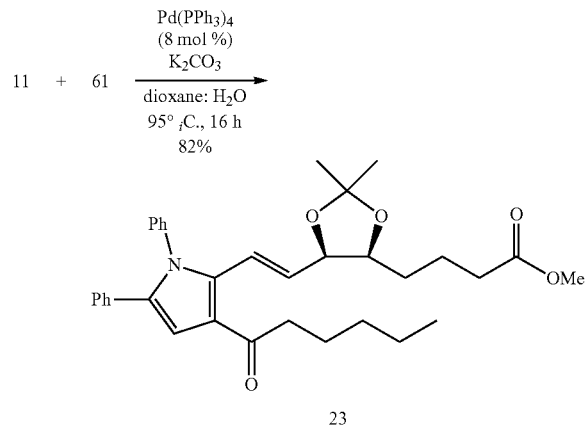

The imidazole (11) (0.10 g, 0.30 mmol, 1.00 equiv) was dissolved in 1,4-dioxane (1.5 mL). $Pd(PPh_3)_4$ (5.00 mg, 14.9 □mol, 8 mol %) was added and the reaction mixture was stirred at room temperature for 5 min. The boronic ester (61) (0.11 g, 0.30 mmol, 1.00 equiv) in 1,4-dioxane (1.5 mL) and $K_2CO_3$ (0.08 g, 0.60 mmol, 2.00 equiv) in $H_2O$ (0.30 mL) were added and the reaction was stirred under $N_2$ at 90° C. for 16 h. The reaction mixture was dissolved in $CH_2Cl_2$ (30 mL), washed with aq. sat. $NH_4Cl$ (30 mL), $H_2O$ (30 mL) and brine (30 mL). The organic extracts were dried over $MgSO_4$, filtered and concentrated in vacuo. Purification by flash column chromatography (6:1 to 1:1 Pent:EtOAc) afforded the title compound (23) as a white semi-solid (0.14 g, 87%). $R_f$=0.10 (6:1 Pent:EtOAc). $[α]_D^{20}$=−4.9 (c=1.07 in $CHCl_3$). IR ($v_{max}$)=1027, 1216, 1670, 1735, 3404 $cm^{-1}$. $^1H$ NMR (400 MHz, $CDCl_3$) δ=0.92 (t, J=7.0 Hz, 3H), 1.20-1.80 (m, 16H), 2.31 (t, J=7.5 Hz, 2H), 3.18 (t, J=7.5 Hz, 2H), 3.66 (s, 3H), 4.03-4.08 (m, 1H), 4.47 (t, J=7.0 Hz, 1H), 5.84 (dd, J=16.4, 7.0 Hz, 1H), 6.96 (d, J=16.4 Hz, 1H), 7.20-7.49 (m, 10H) ppm. $^{13}C$ NMR (101 MHz, $CDCl_3$) δ=14.2, 21.9, 22.8, 24.1, 25.8, 28.2, 29.9, 31.8, 34.0, 40.1, 51.6, 78.2, 79.9, 108.5, 119.5, 125.8, 128.3, 128.5, 129.0, 129.7, 130.1, 132.2, 134.4, 137.1, 137.9, 147.2, 173.9, 198.9 ppm. HRMS (ESI) calcd. for $C_{33}H_{40}N_2O_5Na$ (M+Na)+567.2835 found 567.2825.

(R)-1-(5-Bromo-1,2-diphenyl-1H-imidazol-4-yl)hexan-1-ol ((1R)-25)

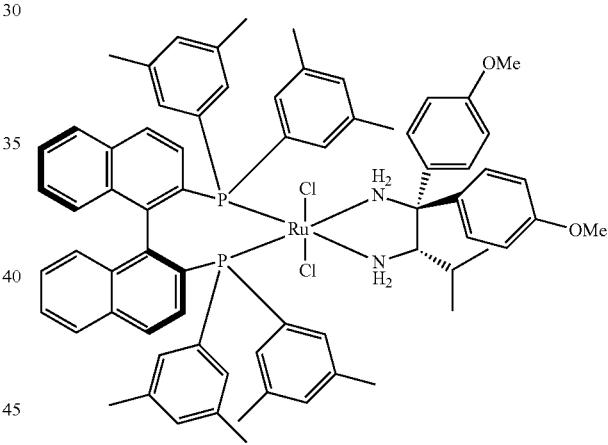

RuCl$_2$[(S)-(DM-BINAP)] [(S)-DAIPEN]

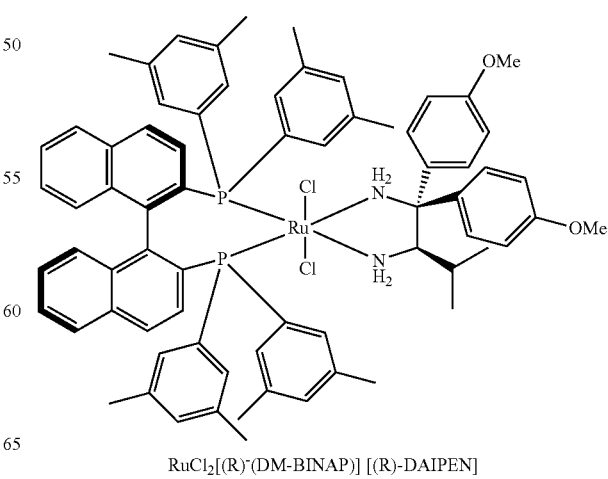

RuCl$_2$[(R)-(DM-BINAP)] [(R)-DAIPEN]

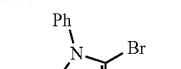

RuCl₂[(S)-(DM-BINAP)][(S)-DAIPEN] (5.00 mg, 4.00 µmol, 2.00 mol %), KOtBu (5.00 mg, 0.03 mmol, 15 mol %) and the bromo-imidazole (11) (0.08 g, 0.20 mmol, 1.00 equiv) were solubilised in iPrOH (6 mL) and 2 drops of tri-isopropyl borate were added. The reaction was stirred in a Parr hydrogenator at 40 bar for 16 h. CH₂Cl₂ (40 mL) was added and the reaction mixture was washed with aq. sat. NH₄Cl (40 mL), H₂O (40 mL) and brine (40 mL), then dried over MgSO₄, filtered and concentrated in vacuo. Purification by flash column chromatography (6:1 to 4:1 Pent:EtOAc) afforded the title compound ((1R)-25) as an off white solid (0.06 g, 69%). $[α]_D^{20}$=−1.9 (c=0.85 in CHCl₃). $R_f$=0.12 (6:1 Pent:EtOAc). mp=107-108° C. IR ($v_{max}$)=692, 1464, 1595, 2856, 3235 cm⁻¹. ¹H NMR (400 MHz, CDCl₃) δ=0.90 (t, J=6.8 Hz, 3H), 1.32-2.03 (m, 8H), 2.57 (d, J=7.4 Hz, 1H), 4.76 (dd, J=13.7, 7.4, 1H), 7.20-7.48 (m, 10H) ppm. ¹³C NMR (101 MHz, CDCl₃) δ=14.2, 22.8, 25.5, 31.8, 37.5, 67.9, 102.8, 128.3, 128.4, 128.8, 129.4, 129.6, 130.1, 136.7, 142.4, 147.1 ppm. HRMS (ESI) calcd. C₂₁H₂₄N₂OBr (M+H)⁺ 399.1072 found 399.1059. ee=96% as determined by HPLC using a Chiralpak IC column (heptane/ethanol, 98/2, 1 mL/min), $R_t$=27.6 min (S)-enantiomer, 31.7 min (R)-enantiomer.

(S)-1-(5-Bromo-1,2-diphenyl-1H-imidazol-4-yl)hexan-1-ol ((1S)-25). RuCl₂[(R)-(DM-BINAP)][(R)-DAIPEN] (0.01 g, 0.01 mmol, 5.00 mol %), KOtBu (0.02 g, 0.25 mmol, 1.00 equiv) and bromo-imidazole (10) (0.10 g, 0.25 mmol, 1.00 equiv) were solubilised in iPrOH (6 mL). Tri-isopropyl borate (0.06 mL, 0.25 mmol, 1.00 equiv) was then added. The reaction was stirred in a Parr hydrogenator at 40 bar for 16 h. CH₂Cl₂ (40 mL) was added and the reaction mixture was then washed with aq. sat. NH₄Cl (40 mL), H₂O (40 mL) and brine (40 mL), dried over MgSO₄, filtered and concentrated in vacuo. Purification by flash column chromatography (6:1 to 4:1 Pent:EtOAc) afforded the title compound ((1S)-25) as an off white solid (0.07 g, 72%). $[α]_D^{20}$=+2.3 (c=1.00 in CHCl₃); ee=89% as determined by HPLC using a Chiralpak IC column (heptane/ethanol, 98/2, 1 mL/min), $R_t$=26.7 min (S)-enantiomer, 30.8 min (R)-enantiomer; all other physical data were in agreement with a previously prepared sample.

Methyl 4-((4S,5R)-5-((E)-2-(4-((R)-1-hydroxy-hexyl)-1,2-diphenyl-1H-imidazol-5-yl)vinyl)-2,2-dimethyl-1,3-dioxolan-4-yl)butanoate ((1R)-26)

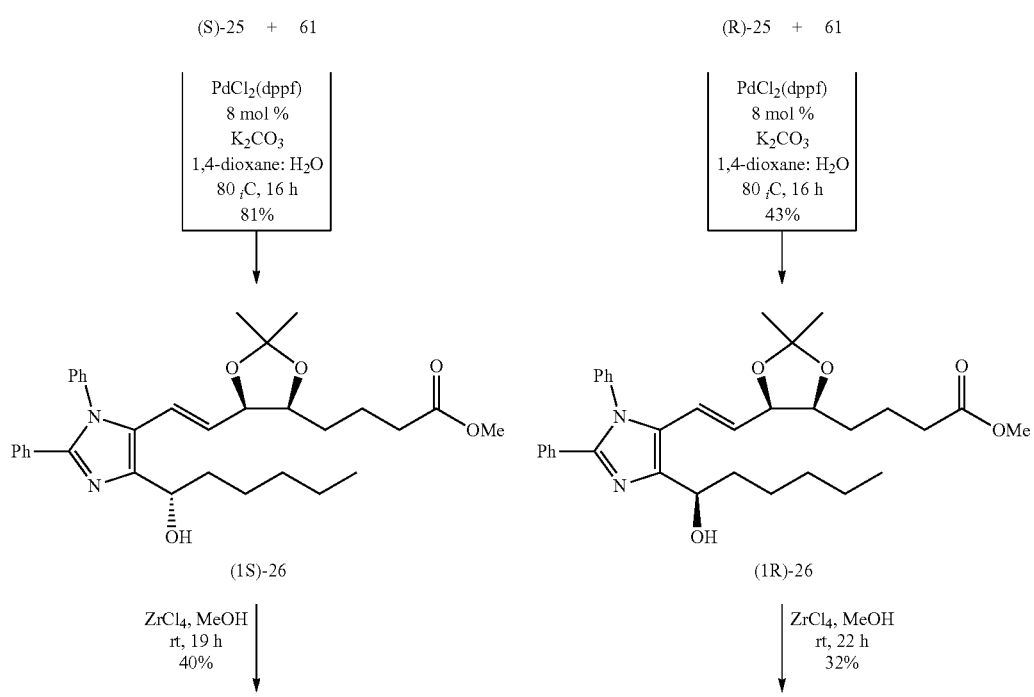

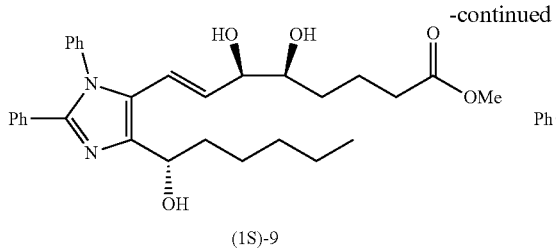

(1S)-9

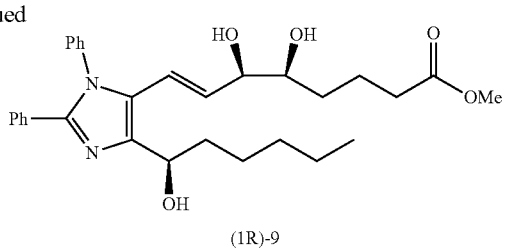

(1R)-9

Imidazole ((1R)-25) (0.06 g, 0.15 mmol, 1.00 equiv) was dissolved in 1,4-dioxane (1.4 mL). PdCl$_2$(dppf) (9.00 mg, 12.00 µmol, 8 mol %) was added and the reaction was stirred at room temperature for 5 min. The boronic ester (61) (0.07 g, 0.19 mmol, 1.26 equiv) in 1,4-dioxane (1.4 mL) and K$_2$CO$_3$ (0.06 g, 0.45 mmol, 3.00 equiv) in H$_2$O (0.34 mL) were added and the reaction was stirred under N$_2$ at 80° C. for 16 h. The reaction mixture was solubilised in CH$_2$Cl$_2$ (30 mL), washed with aq. sat. NH$_4$Cl (30 mL), H$_2$O (30 mL) then brine (30 mL). The organic extracts were dried over MgSO$_4$, filtered and concentrated in vacuo. Purification by flash column chromatography (6:1 to 1:1 Pent:EtOAc) afforded the title compound ((1R)-26) as a white semi-solid (35.3 mg, 43%). R$_f$=0.6 (7:3 EtOAc: Pent). [α]$_D^{20}$=+56.5 (c=1.17 in CHCl$_3$). IR (v$_{max}$)=1216, 1731, 2934, 3019 cm$^{-1}$. $^1$H NMR (400 MHz, CDCl$_3$)=0.90 (t, J=6.8 Hz, 3H), 1.26-2.02 (m, 18H), 2.34 (td, J=7.5, 3.7 Hz, 2H), 2.94 (br. s, 1H), 3.67 (s, 3H), 4.05-4.10 (m, 1H), 4.43 (t, J=7.0 Hz, 1H), 4.80-4.83 (m, 1H), 5.53 (dd, J=16.2, 8.0 Hz, 1H), 6.19 (d, J=16.2 Hz, 1H), 7.17-7.45 (m, 10H) ppm. $^{13}$C NMR (101 MHz, CDCl$_3$) 3=14.2, 21.9, 22.8, 25.8 (2C), 28.2, 30.1, 31.9, 33.9, 38.2, 51.7, 68.0, 78.2, 80.0, 108.4, 119.8, 126.8, 127.4, 128.2, 128.4, 128.5, 128.6, 129.1, 129.8, 130.2, 137.1, 137.9, 143.4, 146.7, 173.8 ppm. HRMS (ESI) calcd. for C$_{33}$H$_{43}$N$_2$O$_5$ [M+H] 547.3172 found 547.3160.

Methyl (5S,6R,E)-5,6-dihydroxy-8-(4-((S)-1-hydroxyhexyl)-1,2-diphenyl-1H-imidazol-5-yl)oct-7-enoate ((1S)-26). The imidazole ((1S)-25) (0.06 g, 0.14 mmol, 1.00 equiv) was dissolved in 1,4-dioxane (1.4 mL). PdCl$_2$(dppf) (8.00 mg, 11.20 µmol, 8 mol %) was added and the reaction mixture was stirred at room temperature for 5 min. The boronic ester (61) (0.10 g, 0.28 mmol, 2.00 equiv) in 1,4-dioxane (1.4 mL) and K$_2$CO$_3$ (0.06 g, 0.42 mmol, 3.00 equiv) in H$_2$O (0.34 mL) were added and the reaction was stirred under N$_2$ at 80° C. for 16 h. The reaction mixture was dissolved in CH$_2$Cl$_2$ (30 mL), washed with aq. sat. NH$_4$Cl (30 mL), H$_2$O (30 mL), brine (30 mL). The organic extracts were dried over MgSO$_4$, filtered and concentrated in vacuo. Purification by flash column chromatography (6:1 to 1:1 Pent:EtOAc) afforded the title compound ((1S)-25) as a white semi-solid (61.60 mg, 81%). R$_f$=0.60 (7:3 EtOAc: Pent). [α]$_D^{20}$=+15.2 (c=0.75 in CHCl$_3$). IR (v$_{max}$)=1216, 1731, 2933, 3019 cm$^{-1}$. $^1$H NMR (400 MHz, CDCl$_3$) δ=0.90 (t, J=7.0 Hz, 3H), 1.24-2.09 (m, 18H), 2.33 (td, J=7.6, 2.7 Hz, 2H), 2.84 (br. d, J=7.0 Hz, 1H), 3.67 (s, 3H), 4.03-4.11 (m, 1H), 4.44 (t, J=7.8 Hz, 1H), 4.78-4.84 (m, 1H), 5.58 (dd, J=16.1, 7.8 Hz, 1H), 6.22 (d, J=16.1 Hz, 1H), 7.19-7.46 (m, 10H) ppm. $^{13}$C NMR (101 MHz, CDCl$_3$) δ=14.2, 21.9, 22.8, 25.8, 25.9, 28.3, 30.0, 31.9, 33.9, 38.0, 51.7, 68.0, 78.2, 79.9, 108.4, 119.6, 127.0, 127.4, 128.2, 128.6, 128.7, 129.2, 129.8, 130.2, 137.3, 143.3, 146.9, 173.8 ppm. HRMS (ESI) calcd. for C$_{33}$H$_{42}$N$_2$O$_5$Na [M+Na]+569.2991 found 569.2997.

Methyl (5S,6R,E)-5,6-dihydroxy-8-(4-((R)-1-hydroxyhexyl)-1,2-diphenyl-1H-imidazol-5-yl)oct-7-enoate ((1R)-9). Imidazole ((1R)-26) (35.00 mg, 64.00 µmol, 1.00 equiv) was dissolved in MeOH (1 mL). ZrCl$_4$ (3.00 mg, 64.00 µmol, 0.20 equiv) was added and the reaction was stirred at room temperature for 16 h. More ZrCl$_4$ (15.00 mg, 0.06 mmol, 1.00 equiv) was added and the reaction was stirred at room temperature for a further 3 h. ZrCl$_4$ (15.00 mg, 0.06 mmol, 1.00 equiv) and MeOH (1 mL) were added and the reaction was stirred at room temperature for a further 3 h. Purification by flash column chromatography (1:1 Pent:EtOAc to 96:4 CH$_2$Cl$_2$:MeOH) followed by preparative TLC (96:4 CH$_2$Cl$_2$:MeOH) afforded the title compound ((1R)-9) as an off white semi-solid (10.6 mg, 32%). R$_f$=0.2 (96:4 CH$_2$Cl$_2$:MeOH). [α]$_D^{20}$=+10.9 (c=0.92 in CHCl$_3$). IR (v$_{max}$)=896, 1156, 1606, 1733, 2988, 3096 cm$^{-1}$. $^1$H NMR (400 MHz, CDCl$_3$) δ=0.90 (t, J=6.9 Hz, 3H), 1.26-2.15 (m, 14H), 2.33 (t, J=7.2 Hz, 2H), 2.86 (br. s, 1H), 3.58-3.62 (m, 1H), 3.67 (s, 3H), 4.04-4.07 (m, 1H), 4.79-4.4.83 (m, 1H), 5.65 (dd, J=16.3, 6.7 Hz, 1H), 6.24 (d, J=16.3 Hz, 1H), 7.10-7.32 (m, 7H), 7.44-7.46 (m, 3H) ppm. $^{13}$C NMR (101 MHz, CDCl$_3$) δ=14.2, 21.2, 22.8, 25.9, 31.5, 31.9, 33.8, 37.9, 51.8, 68.0, 74.0, 76.0, 119.2, 127.4, 128.3, 128.4, 128.6, 128.7, 129.2, 129.8, 130.0, 130.3, 137.1, 142.8, 146.7, 174.3 ppm. HRMS (ESI) calcd. for C$_{30}$H$_{39}$N$_2$O$_5$ [M+H]+ 507.2859, found 507.2860.

Methyl (5S,6R,E)-5,6-dihydroxy-8-(4-((S)-1-hydroxyhexyl)-1,2-diphenyl-1H-imidazol-5-yl)oct-7-enoate ((1S)-9). The imidazole ((1S)-26) (0.06 g, 0.10 mmol, 1.00 equiv) was dissolved in MeOH (2 mL). ZrCl$_4$ (0.04 g, 0.16 mmol, 1.50 equiv) was added and the reaction was stirred at room temperature for 16 h. ZrCl$_4$ (0.04 g, 0.16 mmol, 1.50 equiv) was added and the reaction was stirred at room temperature for a further 3 h. Purification by flash column chromatography (1:1 Pent:EtOAc to 96:4 CH$_2$Cl$_2$:MeOH) followed by preparative (TLC 96:4 CH$_2$Cl$_2$:MeOH) afforded the title compound ((1S)-9) as an off white semi-solid (20.3 mg, 40%). R$_f$=0.2 (96:4 CH$_2$Cl$_2$:MeOH). [α]$_D^{20}$=+3.6 (c=0.82 in CHCl$_3$). IR (v$_{max}$)=1156, 1606, 1733, 2988, 3090 cm$^{-1}$. $^1$H NMR (400 MHz, CDCl$_3$) δ=0.89 (t, J=6.9 Hz, 3H), 1.26-2.04 (m, 12H), 2.31 (td, J=7.4, 2.5 Hz, 2H), 2.84 (br. s, 3H), 3.58 (dd, J=8.4, 4.0 Hz, 1H), 3.67 (s, 3H), 4.03 (dd, J=5.7, 4.0 Hz, 1H), 4.80 (dd, J=7.8, 5.7 Hz, 1H), 5.68 (dd, J=16.3, 6.7 Hz, 1H), 6.20 (d, J=16.3 Hz, 1H), 7.16-7.30 (m, 7H), 7.40-7.44 (m, 3H). $^{13}$C NMR (125 MHz, CDCl$_3$) 5=14.2, 21.2, 22.8, 25.9, 31.6, 31.9, 33.9, 37.7, 51.7, 68.0, 73.9, 75.9, 119.1, 127.5, 128.3, 128.4, 128.6, 128.7, 129.2, 129.8, 130.0, 130.4, 137.1, 142.6, 146.6, 174.2 ppm. HRMS (ESI) calcd. for C$_{30}$H$_{39}$N$_2$O$_5$ (M+H)+ 507.2859, found 507.2859.

Compounds (1S)-13 and (1R)-13 of Formula (VIo) and Compounds (1S)-14 and (1R)-14 of Formula (VIo2)

1-(3-Bromofuran-2-yl)hexan-1-one (16)

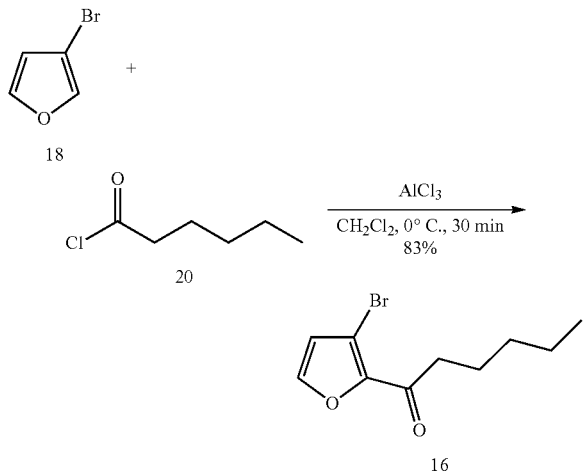

Aluminium trichloride (1.36 g, 10.21 mmol, 3 eq) was dissolved in CH$_2$Cl$_2$ (15 mL) and cooled to 0° C. Hexanoyl chloride (1.50 mL, 10.89 mmol, 3.2 eq) dissolved in CH$_2$Cl$_2$ (15 mL) was added over 5 min and stirred at 0° C. for 30 min. 3-Bromofuran (500 mg, 3.40 mmol, 1 eq) dissolved in CH$_2$Cl$_2$ (15 mL) was added over 5 min and reaction mixture was stirred while warming to room temperature for 30 min. The reaction mixture was poured into ice water (50 mL) and extracted with CH$_2$Cl$_2$ (2×50 mL), the extracts washed with sat. NaHCO$_3$ sol. (50 mL), H$_2$O (50 mL), brine (50 mL), dried over MgSO$_4$, filtered and concentrated. The crude mixture was purified by silica gel column chromatography (20:1 cyclohexane:EtOAc) to give product 16 as a yellow oil (689 mg, 83%). R$_f$=0.53 (20:1 pentane:EtOAc); $^1$H NMR (400 MHz, CDCl$_3$) δ 7.47 (d, J=2.0 Hz, 1H), 6.61 (d, J=2.0 Hz, 1H), 2.92-2.85 (t, J=7.5 Hz, 2H), 1.75-1.67 (m, 2H), 1.39-1.31 (m, 4H), 0.94-0.87 (m, 3H); $^{13}$C NMR (101 MHz, CDCl$_3$) 189.7, 148.4, 145.2, 117.5, 106.8, 39.6, 31.6, 23.6, 22.6, 14.1; IR (ATR) (v$_{max}$, cm$^{-1}$) 1677, 1474, 1379; [M+H]$^+$ calc 245.0177 for C$_{10}$H$_{14}$O$_2$$^{79}$Br, found 245.0189.

Methyl 4-((4S,5R)-5-((E)-2-(2-hexanoylfuran-3-yl)vinyl)-2,2-dimethyl-1,3-dioxolan-4-yl)butanoate (15)

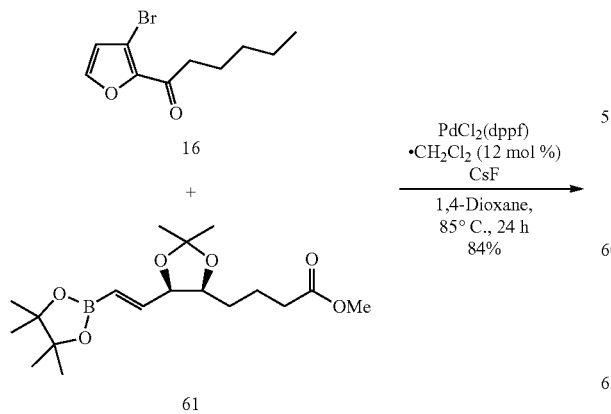

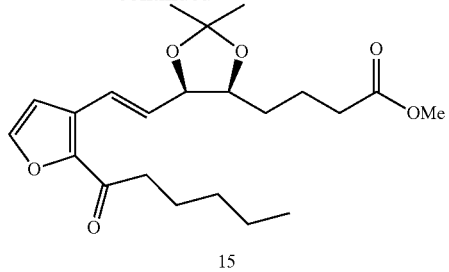

Method A: Bromide 16 (50 mg, 0.204 mmol, 1 eq) and boronic ester 61 (108 mg, 0.306 mmol, 1.5 eq) were dissolved in 1,4-dioxane (3.5 mL) in a Schlenk tube. PdCl$_2$(dppf).CH$_2$Cl$_2$ (20 mg, 0.0245 mmol, 0.12 eq) was added followed by CsF (146 mg, 0.959 mmol, 4.7 eq). The mixture was heated to 85° C., sealed under nitrogen and stirred for 24 h. The reaction mixture was allowed to cool, concentrated and was purified by silica gel column chromatography (8:1→3:1 cyclohexane:EtOAc) to afford 15 as a pale yellow oil (67 mg, 84%). R$_f$=0.12 (6:1 pentane:EtOAc); $^1$H NMR (400 MHz, CDCl$_3$) δ 7.37 (d, J=2.0, 1H), 7.33 (d, J=16.0 Hz, 1H), 6.69 (d, J=2.0, 1H), 6.12 (dd, J=16.0, 8.5 Hz, 1H), 4.67 (dd, J=8.5, 6.5, 1H), 4.17 (ddd, J=9.0, 6.5, 4.5 Hz, 1H), 3.62 (s, 3H), 2.85-2.79 (m, 2H), 2.32 (t, J=7.5 Hz, 2H), 1.84-1.75 (m, 1H), 1.72-1.63 (m, 3H), 1.50 (s, 3H), 1.49-1.37 (m, 2H), 1.36 (s, 3H), 1.35-1.30 (m, 4H), 0.92-0.85 (m, 3H); $^{13}$C NMR (101 MHz, CDCl$_3$) δ 192.2, 173.8, 147.6, 144.5, 131.2, 129.5, 124.2, 110.3, 108.6, 79.4, 78.4, 51.6, 39.4, 33.8, 31.6, 30.0, 28.4, 25.7, 23.7, 22.6, 21.9, 14.0; IR (ATR) (v$_{max}$, cm$^{-1}$) 2933, 1736, 1670, 1245, 122, 1161; [α]$_D$=−42.60 (c=0.66 in CHCl$_3$); [M+Na]$^+$ calc 415.2097 for C$_{22}$H$_{32}$O$_6$Na, found 415.2104.

Method B: Bis(benzonitrile)Pd(II)chloride (12 mg, 0.0306 mmol, 0.15 eq) and dppb (22 mg, 0.0510 mmol, 0.25 eq) were dissolved in toluene (1 mL) and stirred at room temperature for 30 min to give a creamy orange solution. Bromide 16 (50 mg, 0.204 mmol, 1 eq) and boronic ester 61 (83 mg, 0.235 mmol, 1.15 eq) dissolved in toluene (2 mL), were added followed by EtOH (0.06 mL) and Na$_2$CO$_3$ (0.24 mL of a 1 M aq. solution, 0.235 mmol, 1.15 eq). The reaction mixture was heated to 110° C. and stirred for 19 h after which time it was diluted with H$_2$O (30 mL) and extracted with EtOAc (3×15 mL). The extracts were washed with brine (30 mL), dried with MgSO$_4$, filtered and concentrated. The crude reaction mixture was purified by silica gel column chromatography (8:1→3:1 pentane:EtOAc) to afford 15 as pale yellow oil (63 mg, 79%).

Methyl (5S,6R,E)-8-(2-hexanoylfuran-3-yl)-5,6-dihydroxyoct-7-enoate (21)

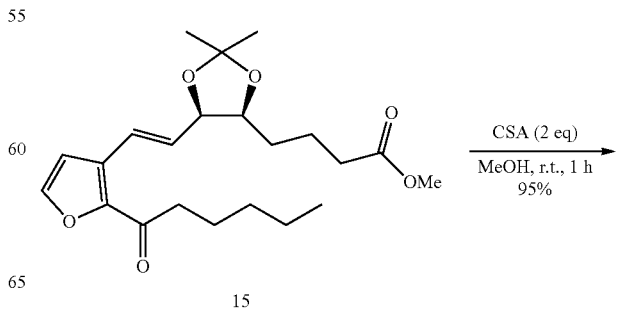

-continued

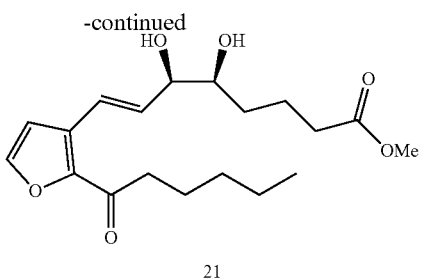

21

Acetonide 15 (50 mg, 0.127 mmol, 1 eq) was dissolved in MeOH (2 mL), camphorsulfonic acid (59 mg, 0.255 mmol, 2 eq) was added and the reaction mixture was stirred under nitrogen at room temperature for 1 h. The reaction mixture was concentrated and purified by silica gel column chromatography (96:4 $CH_2Cl_2$:MeOH) to yield 21 as a white solid (43 mg, 95%). $R_f$=0.12 (2:1 pentane:EtOAc); M.p.=82–86° C.; $^1$H NMR (400 MHz, $CDCl_3$) δ 7.37 (d, J=1.0 Hz, 1H), 7.31 (d, J=16.0 Hz, 1H), 6.69 (d, J=1.0 Hz, 1H), 6.29 (dd, J=16.0, 7.0 Hz, 1H), 4.26 (dd, J=6.5, 3.0 Hz, 1H), 3.81–3.74 (m, 1H), 3.63 (s, 3H), 2.81 (t, J=7.5 Hz, 2H), 2.33 (t, J=7.5 Hz, 2H), 1.88–1.79 (m, 1H), 1.71–1.64 (m, 3H), 1.51–1.42 (m, 2H), 1.36–1.28 (m, 4H), 0.88 (t, J=6.5 Hz, 3H); $^{13}$C NMR (101 MHz, $CDCl_3$) δ 192.3, 174.1, 147.4, 144.5, 133.0, 129.6, 123.4, 110.2, 75.7, 73.8, 51.5, 39.3, 33.7, 31.5, 31.5, 23.5, 22.4, 21.1, 13.9; IR (ATR) ($v_{max}$, cm$^{-1}$) 3237, 1738, 1663, 1235, 1152, 1120; $[\alpha]_D$=−2.83 (c=0.8 in $CHCl_3$); [M+Na]$^+$ calc 375.1784 for $C_9H_{28}O_6Na$, found 375.1767.

Methyl (5S,6R,E)-5,6-dihydroxy-8-(2-((S)-1-hydroxyhexyl)furan-3-yl)oct-7-enoate ((1S)-13)

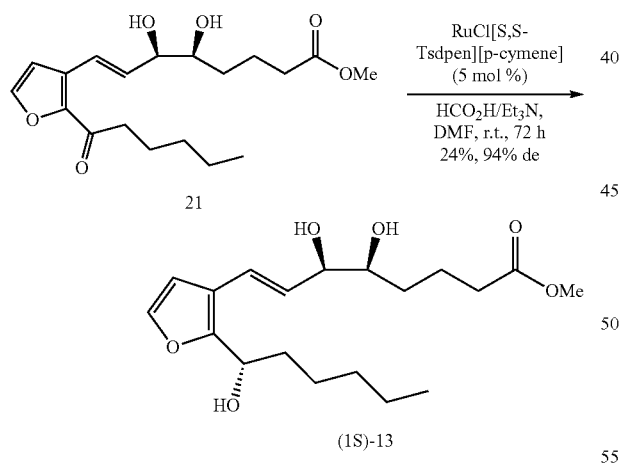

(1S)-13

Ketone 21 (80.0 mg, 0.227 mmol, 1 eq) was added to a Schlenk tube followed by RuCl[S,S-Tsdpen][p-cymene] catalyst (7.2 mg, 0.0113 mmol, 0.05 eq), $HCO_2H$ (0.037 mL, 0.976 mmol, 4.3 eq), $Et_3N$ (0.075 mL, 0.568 mmol, 2.5 eq) and DMF (0.6 mL). The reaction mixture was stirred at room temperature for 72 h, after which time it was diluted with sat. $NH_4Cl$ sol. (10 mL) and extracted with $CH_2Cl_2$ (3×10 mL). The combined organic layers were washed with $H_2O$ (15 mL), brine (15 mL), dried over $MgSO_4$, filtered and concentrated. The crude mixture was purified by silica gel column chromatography (96:4 $CH_2Cl_2$:MeOH) to give (1S)-13 as a yellow oil (20 mg, 24%). $R_f$=0.12 (96:4 $CH_2Cl_2$:MeOH); $^1$H NMR (500 MHz, $CDCl_3$) δ 7.30 (d, J=2.0 Hz, 1H), 6.61 (d, J=16.0 Hz, 1H), 6.49 (d, J=2.0 Hz, 1H), 5.96 (dd, J=16.0, 7.0 Hz, 1H), 4.79 (t, J=7.5 Hz, 1H), 4.20 (dd, J=7.0, 2.5 Hz, 1H), 3.76–3.71 (m, 1H), 3.64 (s, 3H), 2.42–2.31 (m, 4H), 1.89–1.68 (m, 4H), 1.52–1.43 (m, 2H), 1.39–1.34 (m, 1H), 1.32–1.25 (m, 5H), 0.87 (t, J=7.0 Hz, 3H); $^{13}$C NMR (126 MHz, $CDCl_3$) δ 174.5, 153.1, 142.1, 126.7, 122.8, 119.6, 108.2, 76.0, 73.9, 66.2, 51.8, 35.6, 33.9, 31.7, 31.7, 25.5, 22.7, 21.1, 14.1; IR (ATR) ($v_{max}$, cm$^{-1}$) 3393, 3020, 2953, 1730, 1661, 1215, 1055; $[\alpha]_D$=−9.15 (c=0.8 in $CHCl_3$); [M+Na]$^+$ calc 377.1940 for $C_9H_{30}O_6Na$, found 377.1952; de=94% as determined by SFC using a Chiralpak IC column ($CO_2$:MeCN:EtOH, gradient 75:12.5:12.5 0-1 min, then gradient to 60:20:20 until 6 min, 3 mL/min), $R_t$=1.190 min (1S)-epimer, 1.424 min (1R)-epimer.

Methyl(5S,6R,E)-5,6-dihydroxy-8-(2-((R)-1-hydroxyhexyl)furan-3-yl)oct-7-enoate ((1R)-13)

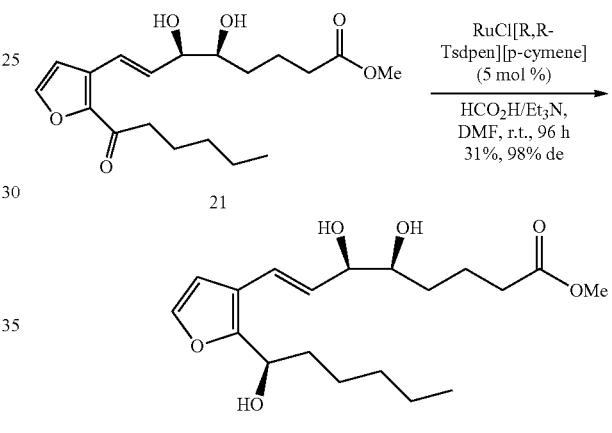

(1R)-13

Ketone 21 (80.0 mg, 0.227 mmol, 1 eq) was added to a Schlenk tube followed by RuCl[R,R-Tsdpen][p-cymene] catalyst (7.2 mg, 0.0113 mmol, 0.05 eq), $HCO_2H$ (0.037 mL, 0.976 mmol, 4.3 eq), $Et_3N$ (0.075 mL, 0.568 mmol, 2.5 eq) and DMF (0.6 mL). The reaction mixture was stirred at room temperature for 96 h, after which time it was diluted with sat. $NH_4Cl$ sol. (10 mL) and extracted with $CH_2Cl_2$ (3×10 mL). The combined organic layers were washed with $H_2O$ (15 mL), brine (15 mL), dried over $MgSO_4$, filtered and concentrated. The crude mixture was purified by silica gel column chromatography (96:4 $CH_2Cl_2$:MeOH) to give (1R)-13 was isolated as a yellow oil (25 mg, 31%). $R_f$=0.12 (96:4 $CH_2Cl_2$:MeOH); $^1$H NMR (500 MHz, $CDCl_3$) δ 7.30 (d, J=2.0 Hz, 1H), 6.62 (d, J=16.0 Hz, 1H), 6.49 (d, J=2.0 Hz, 1H), 5.97 (dd, J=16.0, 7.0 Hz, 1H), 4.79 (t, J=7.0 Hz, 1H), 4.21 (dd, J=7.0, 3.5 Hz, 1H), 3.77–3.71 (m, 1H), 3.66 (s, 3H), 2.35 (td, J=7.0, 3.5 Hz, 2H), 1.91–1.82 (m, 3H), 1.73–1.70 (m, 1H), 1.51–1.48 (m, 1H), 1.33–1.27 (m, 7H), 0.87 (t, J=6.2 Hz, 3H); $^{13}$C NMR (126 MHz, $CDCl_3$) δ 174.4, 153.0, 142.0, 126.9, 122.7, 119.7, 108.3, 75.9, 73.9, 66.2, 51.8, 35.6, 33.9, 31.7, 31.6, 25.4, 22.7, 21.2, 14.1; IR (ATR) ($v_{max}$, cm$^{-1}$) 3393, 3020, 2953, 1730, 1661, 1215, 1055; $[\alpha]_D$=+11.60 (c=0.7 in $CHCl_3$); [M+Na]$^+$ calc 377.1940 for $C_{19}H_{30}O_6Na$, found 377.1943; de=98% as determined by SFC using a Chiralpak IC column ($CO_2$:MeCN:EtOH, gradient 75:12.5:12.5 0-1 min, then gradient to 60:20:20 until 6 min, 3 mL/min), R$_t$=1.190 min (1S)-epimer, 1.424 min (1R)-epimer.

1-(3-Bromobenzofuran-2-yl)hexan-1-one (23)

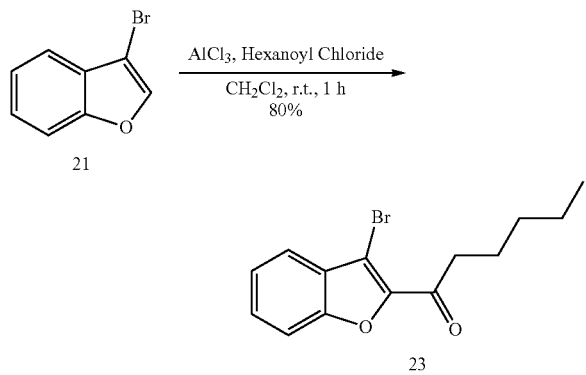

Aluminium trichloride (1.02 g, 7.614 mmol, 3 eq) was dissolved in CH$_2$Cl$_2$ (15 mL) and cooled to 0° C. Hexanoyl chloride (1.14 mL, 8.12 mmol, 3.2 eq) dissolved in CH$_2$Cl$_2$ (15 mL) was added over 5 min and stirred at 0° C. for 30 min. 3-Bromobenzofuran 22 (500 mg, 2.54 mmol, 1 eq) dissolved in CH$_2$Cl$_2$ (15 mL) was added over 5 min and the reaction mixture was stirred while warming to room temperature for 1 h. The reaction mixture was poured into ice water (50 mL) and extracted with CH$_2$Cl$_2$ (2×50 mL), the extracts washed with sat. NaHCO$_3$ sol. (50 mL), H$_2$O (50 mL), brine (50 mL), dried over MgSO$_4$, filtered and concentrated. The crude mixture was purified by silica gel column chromatography (20:1 cyclohexane:EtOAc) to yield 23 as a yellow solid (627 mg, 75%). R$_f$=0.76 (20:1 pentane:EtOAc); m.p.=55-58° C.; $^1$H NMR (400 MHz, CDCl$_3$) δ 7.70-7.64 (m, 1H), 7.58-7.51 (m, 2H), 7.38 (ddd, J=8.0, 6.5, 2.0 Hz, 1H), 3.04 (t, J=7.5 Hz, 2H), 1.83-1.74 (m, 2H), 1.43-1.36 (m, 4H), 0.95-0.90 (m, 3H); $^{13}$C NMR (101 MHz, CDCl$_3$) δ 191.6, 153.7, 147.7, 129.3, 128.5, 124.5, 122.1, 112.6, 103.8, 40.3, 31.6, 23.5, 22.6, 14.1; IR (ATR) (v$_{max}$, cm$^{-1}$) 2952, 1670, 1370; HRMS (ESI) [M]$^+$ calc 295.0334 for C$_{14}$H$_{16}$O$_2$$^{79}$Br, found 295.0344.

Methyl 4-((4S,5R)-5-((E)-2-(2-hexanoylbenzofuran-3-yl)vinyl)-2,2-dimethyl-1,3-dioxolan-4-yl)butanoate (24)

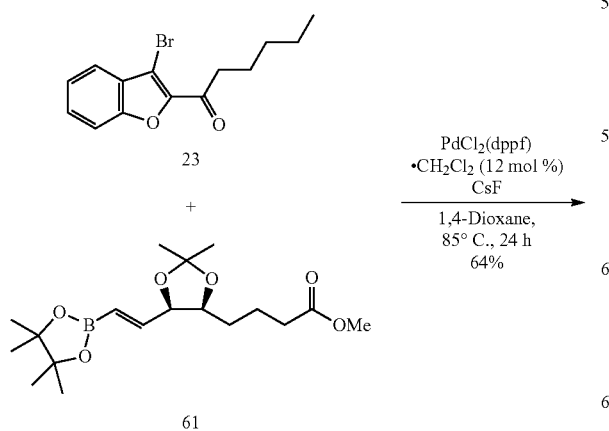

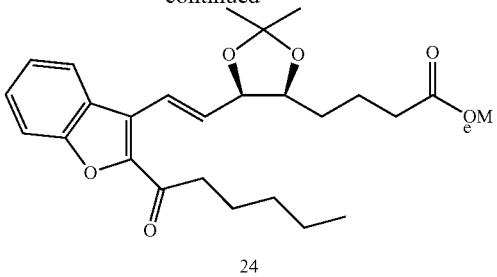

Bromide 23 (125 mg, 0.423 mmol, 1 eq) and boronic ester 61 (180 mg, 0.508 mmol, 1.2 eq) were dissolved in 1,4-dioxane (9 mL) in a Schlenk tube. PdCl$_2$(dppf).CH$_2$Cl$_2$ (41.5 mg, 0.051 mmol, 0.12 eq) was added followed by CsF (302 mg, 1.988 mmol, 4.7 eq). The mixture was heated to 85° C., sealed under nitrogen and stirred for 16 h. The reaction mixture was allowed to cool, diluted with sat. NH$_4$Cl sol. (20 mL). The aqueous layer was extracted with EtOAc (3×15 mL). Combined organic layers were washed with brine (20 mL), dried with MgSO$_4$, filtered and concentrated. The crude mixture was purified by silica gel column chromatography (8:1→4:1 cyclohexane:EtOAc) to afford 24 as pale yellow oil (120 mg, 64%). R$_f$=0.29 (6:1 pentane:EtOAc); $^1$H NMR (500 MHz, CDCl$_3$) δ 7.91 (d, J=8.0 Hz, 1H), 7.56-7.45 (m, 3H), 7.38-7.33 (m, 1H), 6.54 (dd, J=16.5, 8.0 Hz, 1H), 4.80-4.73 (m, 1H), 4.25 (ddd, J=9.5, 6.0, 4.5 Hz, 1H), 3.61 (s, 3H), 3.00 (t, J=7.5 Hz, 2H), 2.34 (t, J=7.5 Hz, 2H), 1.90-1.82 (m, 1H), 1.77-1.69 (m, 3H), 1.62-1.58 (m, 2H), 1.56 (s, 3H), 1.41 (s, 3H), 1.40-1.35 (m, 4H), 0.91 (t, J=7.0 Hz, 3H); $^{13}$C NMR (126 MHz, CDCl$_3$) δ 194.2, 173.8, 154.3, 147.8, 132.6, 128.2, 126.3, 124.4, 124.1, 123.0, 123.0, 112.6, 108.7, 80.1, 78.4, 51.6, 40.2, 33.9, 31.6, 30.2, 28.5, 25.8, 23.5, 22.6, 21.9, 14.1; IR (ATR) (v$_{max}$, cm$^{-1}$) 2932, 1736, 1676, 1249, 1160; [α]$_D$=−9.51 (c=1 in CHCl$_3$); [M+Na]$^+$ calc 465.2253 for C$_{26}$H$_{34}$O$_6$Na, found 465.2260

Methyl (5S,6R,E)-8-(2-hexanoylbenzofuran-3-yl)-5,6-dihydroxyoct-7-enoate (25)

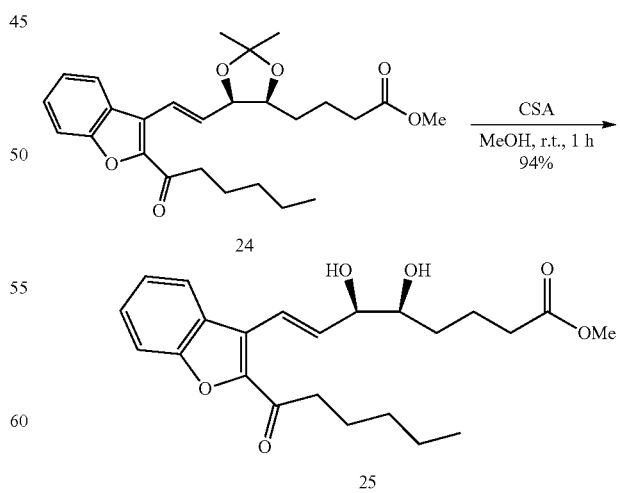

Acetonide 24 (70.0 mg, 0.158 mmol, 1 eq) was dissolved in MeOH (3 mL), camphorsulfonic acid (73.5 mg, 0.316 mmol, 2 eq) was added and the reaction mixture was stirred under nitrogen at room temperature for 1 h. The reaction mixture was concentrated and purified by silica gel column chromatography (96:4 $CH_2Cl_2$:MeOH) to give 25 as a yellow oil (60 mg, 94%). $R_f$=0.17 (2:1 pentane:EtOAc); $^1$H NMR (500 MHz, $CDCl_3$) δ 7.93 (d, J=8.0 Hz, 1H), 7.57-7.47 (m, 3H), 7.38-7.32 (m, 1H), 6.69 (dd, J=16.5, 7.0 Hz, 1H), 4.35 (dd, J=7.0, 3.5 Hz, 1H), 3.87-3.80 (m, 1H), 3.65 (s, 3H), 3.00 (t, J=7.5 Hz, 2H), 2.37 (td, J=7.5, 1.0 Hz, 2H), 1.89 (m, 1H), 1.78-1.73 (m, 2H), 1.62-1.50 (m, 3H), 1.40-1.37 (m, 4H), 0.92 (t, J=7.0 Hz, 3H); $^{13}$C NMR (126 MHz, $CDCl_3$) δ 194.4, 174.3, 154.4, 147.7, 134.4, 128.3, 126.3, 124.2, 123.9, 123.3, 123.2, 112.5, 76.4, 73.9, 51.7, 40.2, 33.9, 31.8, 31.6, 23.5, 22.7, 21.3, 14.1; IR (ATR) ($v_{max}$, $cm^{-1}$) 3450, 2932, 1734, 1673, 1215, 1053; $[α]_D$=−3.80 (c=1.5 in $CHCl_3$); HRMS (ESI) $[M+Na]^+$ calc 425.1940 for $C_{23}H_{30}O_6Na$, found 425.1922.

Methyl(5S,6R,E)-5,6-dihydroxy-8-(2-((S)-1-hydroxyhexyl)benzofuran-3-yl)oct-7-enoate ((1S)-14)

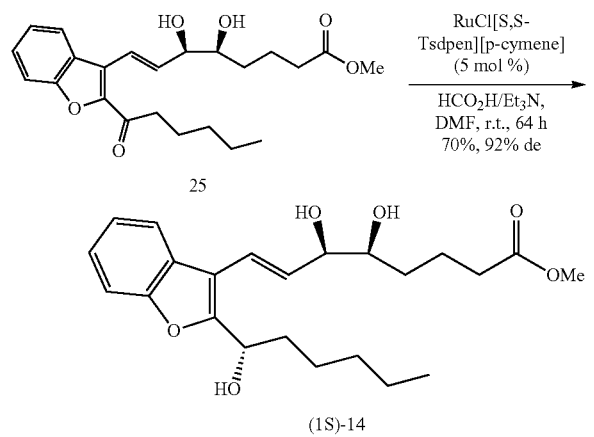

(1S)-14

Ketone 25 (70.0 mg, 0.174 mmol, 1 eq) was added to a Schlenk tube followed by RuCl[S,S-Tsdpen][p-cymene] catalyst (5.5 mg, 0.0087 mmol, 0.05 eq), $HCO_2H$ (0.028 mL, 0.748 mmol, 4.3 eq), $Et_3N$ (0.057 mL, 0.435 mmol, 2.5 eq) and DMF (0.5 mL). The reaction mixture was stirred at room temperature for 64 h, then diluted with sat. $NH_4Cl$ sol. (10 mL) and extracted with $CH_2Cl_2$ (3×10 mL). The combined organic layers were washed with $H_2O$ (15 mL), brine (15 mL), dried over $MgSO_4$, filtered and concentrated. The crude product was purified by silica gel column chromatography (96:4 $CH_2Cl_2$:MeOH) to yield (1S)-14 as a yellow oil (49 mg, 70%). $R_f$=0.21 (96:4 $CH_2Cl_2$:MeOH); $^1$H NMR (500 MHz, $CDCl_3$) δ 7.75 (d, J=7.5 Hz, 1H), 7.45 (d, J=7.5 Hz, 1H), 7.33-7.23 (m, 2H), 6.82 (d, J=16.0 Hz, 1H), 6.33 (dd, J=16.0, 7.0 Hz, 1H), 4.96 (t, J=7.0 Hz, 1H), 4.26 (dd, J=7.0, 4.0 Hz, 1H), 3.77 (dt, J=8.0, 4.0 Hz, 1H), 3.61 (s, 3H), 3.03 (br. s, 1H), 2.81 (br. s, 2H), 2.36-2.25 (m, 2H), 2.02-1.91 (m, 2H), 1.82-1.76 (m, 1H), 1.72-1.65 (m, 1H), 1.55-1.44 (m, 2H), 1.42-1.36 (m, 1H), 1.30-1.22 (m, 5H), 0.85 (t, J=7.0 Hz, 3H); $^{13}$C NMR (126 MHz, $CDCl_3$) δ 174.6, 156.2, 154.3, 128.6, 126.8, 124.8, 123.2, 122.6, 121.0, 114.2, 111.6, 76.4, 74.0, 66.6, 51.8, 35.6, 33.8, 31.8, 31.7, 25.4, 22.7, 21.1, 14.1; IR (ATR) ($v_{max}$, $cm^{-1}$) 3408, 2954, 1730, 1264, 1079); $[α]_D$=+2.05 (c=1.05 in $CHCl_3$); HRMS (ESI) [M+Na] calc 427.2097 for $C_{23}H_{32}O_6Na$, found 427.2090; de=92% as determined by SFC using a Chiralpak IC column ($CO_2$:MeCN:EtOH, gradient 75:12.5:12.5 0-1 min, then gradient to 60:20:20 until 6 min, 3 mL/min), $R_t$=1.584 min (1S)-epimer, 2.369 min (1R)-epimer.

Methyl(5S,6R,E)-5,6-dihydroxy-8-(2-((R)-1-hydroxyhexyl)benzofuran-3-yl)oct-7-enoate ((1R)-14)

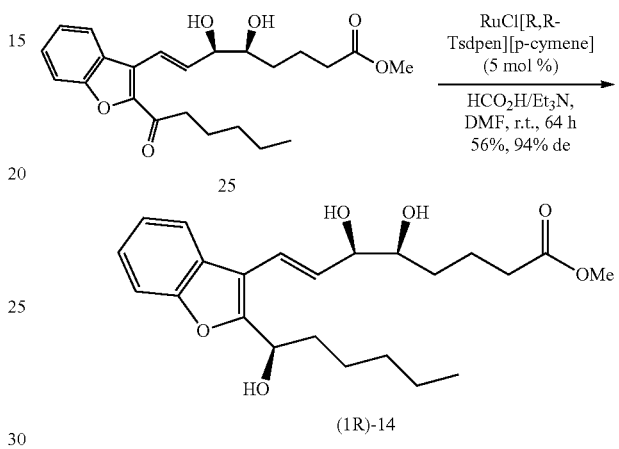

(1R)-14

Ketone 25 (50.0 mg, 0.124 mmol, 1 eq) was added to a Schlenk tube followed by RuCl[R,R-Tsdpen][p-cymene] catalyst (3.9 mg, 0.0062 mmol, 0.05 eq), $HCO_2H$ (0.020 mL, 0.533 mmol, 4.3 eq), $Et_3N$ (0.04 mL, 0.310 mmol, 2.5 eq) and DMF (0.5 mL). The reaction mixture was stirred at room temperature for 64 h, then diluted with sat. $NH_4Cl$ sol. (10 mL) and extracted with $CH_2Cl_2$ (3×10 mL). The combined organic layers were washed with $H_2O$ (15 mL), brine (15 mL), dried over $MgSO_4$, filtered and concentrated. The crude product mixture was purified by silica gel column chromatography (96:4 $CH_2Cl_2$:MeOH) to yield (1R)-14 as a yellow oil (28 mg, 56%). $R_f$=0.21 (96:4 $CH_2Cl_2$:MeOH); $^1$H NMR (500 MHz, $CDCl_3$) δ 7.75 (d, J=7.5 Hz, 1H), 7.44 (d, J=7.5 Hz, 1H), 7.31-7.22 (m, 2H), 6.79 (d, J=16.0 Hz, 1H), 6.35 (dd, J=16.0, 6.5 Hz, 1H), 4.94 (t, J=6.5 Hz, 1H), 4.29-4.20 (m, 1H), 3.81-3.72 (m, 1H), 3.63 (s, 3H), 3.20-2.66 (m, 3H), 2.31 (t, J=7.0 Hz, 2H), 1.99-1.91 (m, 2H), 1.84-1.78 (m, 1H), 1.71-1.62 (m, 1H), 1.52-1.43 (m, 2H), 1.40-1.35 (m, 1H), 1.31-1.18 (m, 5H), 0.85 (t, J=7.0 Hz, 3H); $^{13}$C NMR (126 MHz, $CDCl_3$) δ 174.5, 156.2, 154.3, 128.6, 126.8, 124.8, 123.2, 122.7, 121.1, 114.3, 111.6, 76.3, 74.0, 66.5, 51.8, 35.5, 33.8, 31.7, 31.7, 25.4, 22.7, 21.2, 14.1; IR (ATR) ($v_{max}$, $cm^{-1}$) 3408, 2954, 1730, 1264, 1079; $[α]_D$=+6.44 (c=0.9 in $CHCl_3$); HRMS (ESI) $[M+Na]^+$ calc 427.2097 for $C_{23}H_{32}O_6Na$, found 427.2115; de=93% as determined by SFC using a Chiralpak IC column ($CO_2$: MeCN:EtOH, gradient 75:12.5:12.5 0-1 min, then gradient to 60:20:20 until 6 min, 3m L/min), $R_t$=1.584 min (1S)-epimer, 2.369 min (1R)-epimer.

115

Compounds (1S)-13 and (1R)-13 of Formula (VIg2), Compounds (1R)-14 and (1S)-14 of Formula (VIq) and Compounds (1S)-34, (1R)-34, (1S)-35 and (1R)-35 of Formula (VIqq)

1-(3-Bromobenzo[b]thiophen-2-yl)hexan-1-one (16)

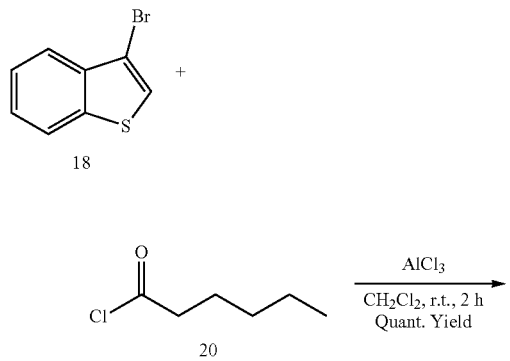

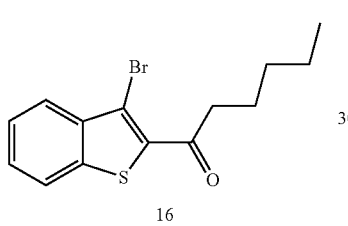

Bromobenzothiophene 18 (0.33 mL, 2.523 mmol, 1.0 eq) was dissolved in dry CH$_2$Cl$_2$ (8 mL). Hexanoyl chloride 20 (0.46 mL, 3.280 mmol, 1.3 eq) was added and the reaction mixture was cooled in an ice bath. AlCl$_3$ (505 mg, 3.784 mmol, 1.5 eq) was added slowly and the reaction mixture was stirred for 2 h while warming to room temperature. The mixture was poured onto ice water (50 mL), extracted with CH$_2$Cl$_2$ (3×30 mL), and the extracts washed with 5% NaOH solution (25 mL), H$_2$O (25 mL) and brine (30 mL). The organic layer was dried over MgSO$_4$, filtered and concentrated to give a crude mixture which was purified by silica gel column chromatography (neat pentane->50:1 pentane:EtOAc). Product 16 was isolated as a yellow solid (785 mg, 100%). R$_f$=0.29 (100:1 pentane:EtOAc); M.p.=53-57° C.; $^1$H NMR (400 MHz, CDCl$_3$) δ 7.97-7.89 (m, 1H), 7.81-7.74 (m, 1H), 7.51-7.41 (m, 2H), 3.12 (t, J=7.5 Hz, 2H), 1.81-1.73 (m, 2H), 1.43-1.32 (m, 4H), 0.91 (t, J=7.0 Hz, 3H); $^{13}$C NMR (101 MHz, CDCl$_3$) δ 194.3, 139.1, 139.1, 138.4, 128.2, 125.6, 125.6, 122.7, 111.3, 42.5, 31.4, 23.8, 22.5, 14.0; IR (CHCl$_3$) (v$_{max}$, cm$^{-1}$) 3055, 1658, 1492, 1422, 1266; HRMS (ESI) [M+H]$^+$ calc 311.0105 for C$_{14}$H$_{16}$OS$^{79}$Br, found 311.0111.

116

Methyl 4-((4S,5R)-5-((E)-2-(2-hexanoylbenzo[b]thiophen-3-yl)vinyl)-2,2-dimethyl-1,3-dioxolan-4-yl)butanoate (15)

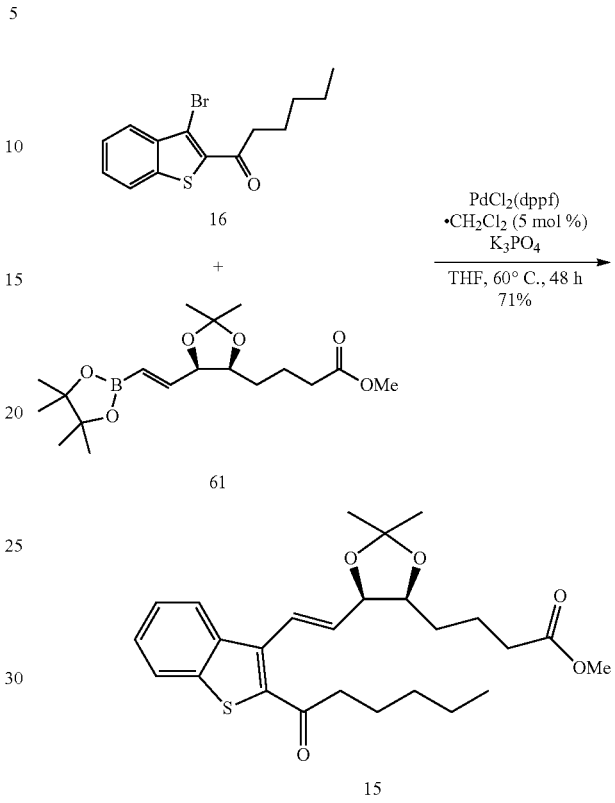

Bromide 16 (56 mg, 0.180 mmol, 1.00 eq) and boronic ester 61 (68 mg, 0.193 mmol, 1.07 eq) were dissolved in THF (3 mL) in a Schlenk tube. PdCl$_2$(dppf).CH$_2$Cl$_2$ (6.6 mg, 0.00805 mmol, 0.05 eq) was added followed by K$_3$PO$_4$ (0.32 mL of 3 M aq. sol, 0.966 mmol, 6.00 eq). The mixture was heated to 60° C., sealed under nitrogen and stirred for 30 h. The reaction mixture was allowed to cool, diluted with EtOAc (20 mL) and washed with sat. NH$_4$Cl sol. (20 mL). The aqueous layer was extracted with EtOAc (3×15 mL). Combined organic layers were washed with brine (20 mL), dried with MgSO$_4$, filtered and concentrated. The crude mixture was purified by silica gel column chromatography (20:1→6:1 pentane:EtOAc) to give 15 as pale yellow oil (59 mg, 71%). R$_f$=0.59 (6:1 pentane:EtOAc); $^1$H NMR (400 MHz, CDCl$_3$) δ=8.03 (d, J=8.0, 1H), 7.84 (d, J=8.0, 1H), 7.53-7.37 (m, 2H), 7.28 (d, J=16.5, 1H), 6.14 (ddd, J=16.5, 8.0, 1.0, 1H), 4.87-4.76 (m, 1H), 4.28 (dt, J=8.5, 5.5, 1H), 3.63 (d, J=1.0, 3H), 2.92 (t, J=7.5, 2H), 2.36 (t, J=7.5, 2H), 1.86 (ddd, J=16.5, 13.5, 7.0, 1H), 1.80-1.70 (m, 3H), 1.64-1.57 (m, 2H), 1.55 (s, 3H), 1.43 (s, 3H), 1.40-1.33 (m, 4H), 0.91 (dd, J=7.0, 6.0, 3H); $^{13}$C NMR (101 MHz, CDCl$_3$) δ 195.4, 173.7, 140.3, 138.5, 137.8, 136.4, 132.7, 127.4, 127.0, 125.3, 125.1, 122.8, 108.6, 79.7, 78.2, 51.5, 42.7, 33.8, 31.4, 30.2, 28.3, 25.7, 24.1, 22.5, 21.8, 13.9; IR (CHCl$_3$) (v$_{max}$, cm$^{-1}$) 2955, 2254, 1737, 1659, 1217; [α]$_D$=−1.77 (c=1.0 in CHCl$_3$); HRMS (ESI) [M+Na]$^+$ calc 481.2025 for C$_{26}$H$_{34}$O$_5$NaS, found 481.2013.

117

Methyl 4-((4S,5R)-5-((E)-2-(2-((S)-1-hydroxyhexyl)benzo[b]thiophen-3-yl)vinyl)-2,2-dimethyl-1,3-dioxolan-4-yl)butanoate ((1S)-23)

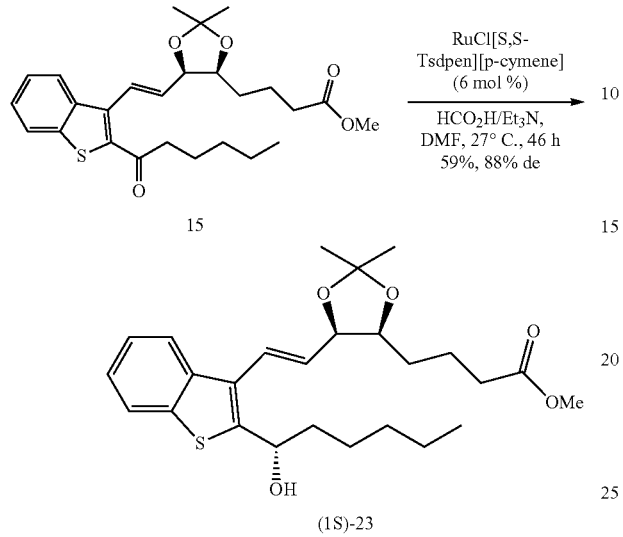

Ketone 15 (100 mg, 0.218 mmol, 1.0 eq) was added to a Schlenk tube followed by RuCl[S,S-Tsdpen][p-cymene] catalyst (9.0 mg, 0.014 mmol, 0.06 eq), $HCO_2H$ (0.035 mL, 0.937 mmol, 4.3 eq), $Et_3N$ (0.076 mL, 0.545 mmol, 2.5 eq) and DMF (0.8 mL). The reaction mixture was heated to 27° C. and stirred for 46 h. The reaction mixture was cooled to room temperature, diluted with $H_2O$ (15 mL) and extracted with EtOAc (3×20 mL). The combined organic layers were washed with sat. $NaHCO_3$ sol. (15 mL), $H_2O$ (15 mL), and brine (15 mL), dried over $MgSO_4$, filtered and concentrated. The crude mixture was purified by silica gel column chromatography (10:1→3:1 pentane:EtOAc) to afford ((1S)-23) as a yellow oil (59.0 mg, 59%). $R_f$=0.27 (6:1 pentane:EtOAc); $^1$H NMR (400 MHz, $CDCl_3$) δ=7.88-7.75 (m, 2H), 7.35 (m, 2H), 6.83-6.76 (dd, J=16.0, 1.0, 1H) 6.09 (dd, J=16.0, 8.0, 1H), 5.23-5.15 (m, 1H), 4.76-4.70 (m, 1H), 4.29-4.21 (m, 1H), 3.61 (s, 3H), 2.52 (s, 1H), 2.43-2.27 (m, 2H), 2.01-1.91 (m, 1H), 1.91-1.55 (m, 6H), 1.54 (s, 3H), 1.43 (s, 3H), 1.39-1.26 (m, 5H), 0.88 (t, J=7.0, 3H); $^{13}$C NMR (101 MHz, $CDCl_3$) δ 173.9, 146.5, 138.7, 138.4, 130.5, 128.9, 124.9, 124.5, 124.3, 122.6, 122.5, 108.5, 79.8, 78.1, 68.7, 51.6, 39.1, 33.8, 31.6, 30.1, 28.3, 25.7, 25.6, 22.5, 21.7, 14.0; IR ($CHCl_3$) ($v_{max}$, cm$^{-1}$) 2986, 1731, 1265, 1168; [α]$_D$=+6.9 (c=1.3 in $CHCl_3$); HRMS (ESI) [M+Na]$^+$ calc 483.2181 for $C_{26}H_{36}O_5NaS$, found 483.2202; de=88% as determined by SFC using a Chiralpak IC column ($CO_2$:MeCN:EtOH, gradient 75:12.5:12.5 0-1 min, then gradient to 60:20:20 until 6 min, 3 mL/min), $R_t$=2.156 min (1S)-epimer, 3.286 min (1R)-epimer.

118

Methyl 4-((4S,5R)-5-((E)-2-(2-((R)-1-hydroxyhexyl)benzo[b]thiophen-3-yl)vinyl)-2,2-dimethyl-1,3-dioxolan-4-yl)butanoate ((1R)-23)

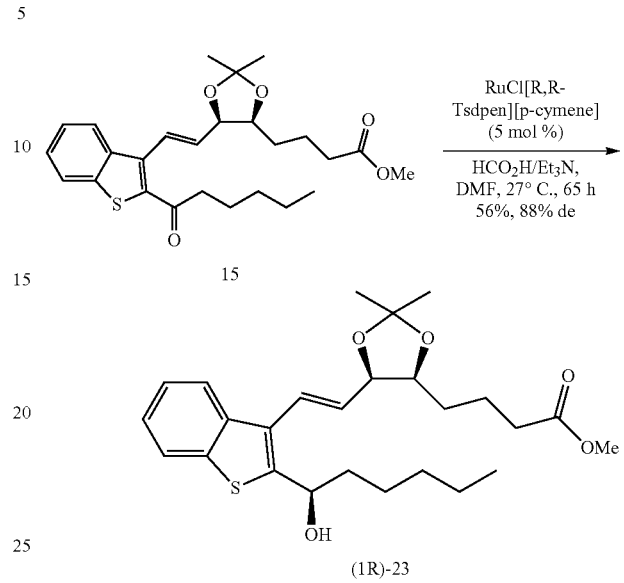

Ketone 15 (70.0 mg, 0.152 mmol, 1.0 eq) was added to a Schlenk tube followed by RuCl[R,R-Tsdpen][p-cymene] catalyst (5.0 mg, 0.0076 mmol, 0.05 eq), $HCO_2H$ (0.025 mL, 0.654 mmol, 4.3 eq), $Et_3N$ (0.05 mL, 0.380 mmol, 2.5 eq) and DMF (0.8 mL). The reaction mixture was heated to 27° C. and stirred for 65 h. The reaction mixture was cooled to room temperature, diluted with $H_2O$ (15 mL) and extracted with EtOAc (3×20 mL). The combined organic layers were washed with sat. $NaHCO_3$ sol. (15 mL), $H_2O$ (15 mL), and brine (15 mL), dried over $MgSO_4$, filtered and concentrated. The crude mixture was purified by silica gel column chromatography (10:1→3:1 pentane:EtOAc). Product ((1R)-23) was isolated as a yellow oil (39.0 mg, 56%). $R_f$=0.27 (6:1 pentane:EtOAc); $^1$H NMR (500 MHz, $CDCl_3$) δ=7.80 (d, J=9.1, 2H), 7.34 (ddd, J=16.0, 15.0, 7.0, 2H), 6.79 (dd, J=16.0, 0.5, 1H), 6.06 (dd, J=16.0, 8.0, 1H), 5.19 (dd, J=13.5, 7.0, 1H), 4.73 (t, J=7.0, 1H), 4.27-4.21 (m, 1H), 3.61 (s, 3H), 2.57 (br. s, 1H), 2.42-2.30 (m, 2H), 2.00-1.89 (m, 1H), 2.03-1.58 (m, 6H), 1.54 (s, 3H), 1.42 (s, 3H), 1.36-1.25 (m, 5H), 0.88 (t, J=7.0, 3H); $^{13}$C NMR (101 MHz, $CDCl_3$) δ 173.9, 146.5, 138.7, 138.4, 130.5, 128.9, 124.9, 124.5, 124.3, 122.6, 122.5, 108.5, 79.8, 78.1, 68.7, 51.6, 39.1, 33.8, 31.6, 30.1, 28.3, 25.7, 25.6, 22.5, 21.7, 14.0; IR ($CHCl_3$) ($v_{max}$, cm$^{-1}$) 2986, 1731, 1265, 1168; [α]$_D$=+28.8 (c=1.0 in $CHCl_3$); HRMS (ESI) [M+Na]+ calc 483.2181 for $C_6H_{36}O_5NaS$, found 483.2202; de=92% as determined by SFC using a Chiralpak IC column ($CO_2$:MeCN:EtOH, gradient 75:12.5:12.5 0-1 min, then gradient to 60:20:20 until 6 min, 3 mL/min), $R_t$=2.156 min (1S)-epimer, 3.286 min (1R)-epimer.

119

Methyl(5S,6R,E)-8-(2-hexanoylbenzo[b]thiophen-3-yl)-5,6-dihydroxyoct-7-enoate (27)

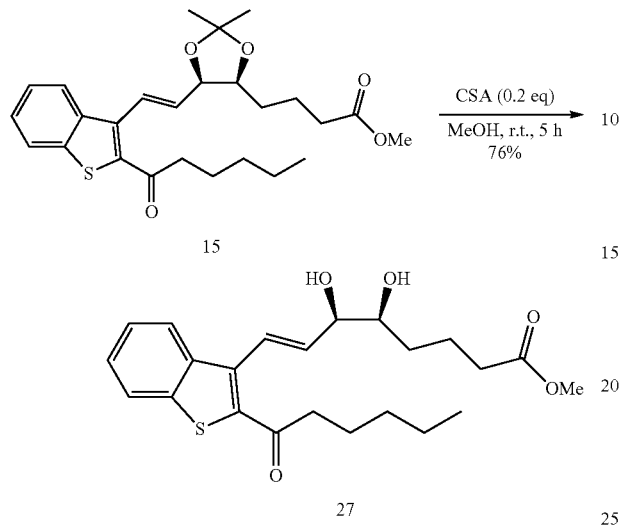

Acetonide 15 (108 mg, 0.235 mmol, 1 eq) was dissolved in MeOH (2 mL), camphorsulfonic acid (11 mg, 0.047 mmol, 0.2 eq) was added and the reaction mixture was stirred under nitrogen at room temperature for 4 h. The reaction mixture was concentrated and purified by silica gel column chromatography (98:2 4 96:4 $CH_2Cl_2$:MeOH) to afford 27 as an off-white solid (74 mg, 76%). $R_f$=0.31 (96:4 $CH_2Cl_2$:MeOH); $^1$H NMR (400 MHz, $CDCl_3$) δ 7.87-7.76 (m, 2H), 7.40-7.29 (m, 2H), 6.82 (d, J=16.0 Hz, 1H), 6.18 (dd, J=16.0, 7.0 Hz, 1H), 5.17 (t, J=7.0 Hz, 1H), 4.36-4.26 (m, 1H), 3.85-3.75 (m, 1H), 3.65 (s, 3H), 2.80-2.47 (m, 3H), 2.36 (td, J=7.0, 1.0 Hz, 2H), 2.02-1.46 (m, 8H), 1.34-1.26 (m, 5H), 0.87 (t, J=7.0 Hz, 3H); $^{13}$C NMR (101 MHz, $CDCl_3$) δ 174.2, 146.1, 138.7, 138.4, 132.0, 129.2, 124.6, 124.5, 124.4, 122.6, 122.5, 76.1, 73.9, 68.6, 51.6, 39.0, 33.6, 31.6, 31.6, 25.6, 22.5, 21.0, 14.0; IR ($CHCl_3$) ($v_{max}$, $cm^{-1}$) 3468, 2957, 1730, 1664, 1184, 1077; $[α]_D$=+2.08 (c=1.5 in $CHCl_3$); HRMS (ESI) [M+Na]$^+$ calc 441.1712 for $C_{23}H_{30}O_5SNa$, found 441.1693.

Methyl (5S,6R,E)-5,6-dihydroxy-8-(2-((S)-1-hydroxyhexyl)benzo[b]thiophen-3-yl)oct-7-enoate ((1S)-13)

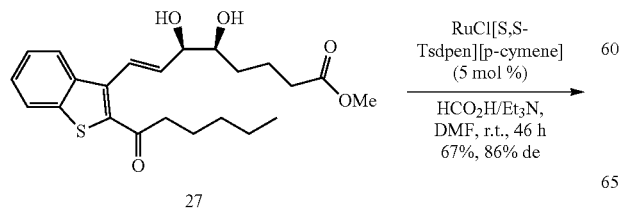

120

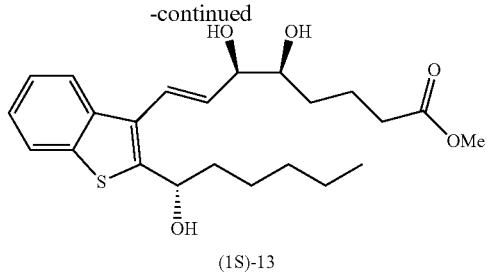

Ketone 27 (60.0 mg, 0.143 mmol, 1.0 eq) was added to Schlenk tube followed by RuCl[S,S-Tsdpen][p-cymene] catalyst (4.6 mg, 0.0072 mmol, 0.05 eq), $HCO_2H$ (0.023 mL, 0.615 mmol, 4.3 eq), $Et_3N$ (0.05 mL, 0.358 mmol, 2.5 eq) and DMF (0.75 mL). The reaction mixture was stirred at room temperature for 46 h. The reaction mixture was diluted with $H_2O$ (10 mL) and extracted with $CH_2Cl_2$ (2×20 mL). The combined organic layers were washed with $H_2O$ (4×10 mL), sat. $NH_4Cl$ sol. (10 mL), and brine (15 mL), dried over $MgSO_4$, filtered and concentrated. The crude mixture was purified by silica gel column chromatography (98:2 4 96:4 $CH_2Cl_2$:MeOH). Product ((1S)-13) was isolated as a yellow oil (40 mg, 67%). $R_f$=0.43 (98:2 $CH_2Cl_2$:MeOH); $^1$H NMR (400 MHz, $CDCl_3$) δ 7.83-7.74 (m, 2H), 7.39-7.28 (m, 2H), 6.80 (d, J=16.0 Hz, 1H), 6.16 (dd, J=16.0, 6.5 Hz, 1H), 5.15 (t, J=7.0 Hz, 1H), 4.28 (dd, J=6.5, 3.5 Hz, 1H), 3.80-3.72 (m, 1H), 3.63 (s, 3H), 3.22-2.76 (m, 3H), 2.32 (td, J=7.0, 1.5 Hz, 2H), 1.96-1.44 (m, 7H), 1.31-1.25 (m, 5H), 0.86 (t, J=6.5 Hz, 3H); $^{13}$C NMR (101 MHz, $CDCl_3$) δ 174.5, 146.1, 138.9, 138.5, 132.3, 129.5, 124.7, 124.5, 122.8, 122.7, 76.2, 74.1, 68.7, 51.8, 39.1, 33.8, 31.8, 31.8, 25.8, 22.7, 21.2, 14.2; IR ($CHCl_3$) ($v_{max}$, $cm^{-1}$) 3433, 3020, 1729, 1216, 1046; $[α]_D$=+0.80 (c=1. in $CHCl_3$); HRMS (ESI) [M+Na] calc 443.1868 for $C_{23}H_{32}O_5SNa$, found 443.1858; de=86% as determined by SFC using a Chiralpak IC column ($CO_2$: MeCN:EtOH, gradient 75:12.5:12.5 0-1 min, then gradient to 60:20:20 until 6 min, 3 mL/min), $R_t$=2.156 min (1S)-epimer, 3.286 min (1R)-epimer.

Methyl(5S,6R,E)-5,6-dihydroxy-8-(2-((R)-1-hydroxyhexyl)benzo[b]thiophen-3-yl)oct-7-enoate ((1R)-13)

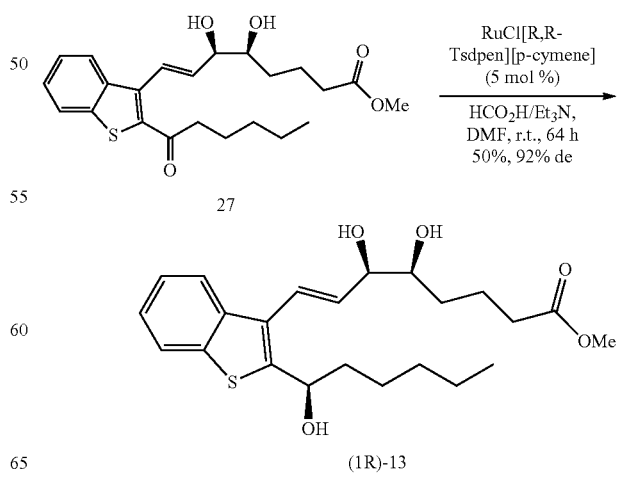

Ketone 27 (60.0 mg, 0.143 mmol, 1.0 eq) was added to Schlenk tube followed by RuCl[R,R-Tsdpen][p-cymene] catalyst (4.6 mg, 0.0072 mmol, 0.05 eq), HCO$_2$H (0.023 mL, 0.615 mmol, 4.3 eq), Et$_3$N (0.05 mL, 0.358 mmol, 2.5 eq) and DMF (0.75 mL). The reaction mixture was stirred at room temperature for 64 h, after which time it was diluted with H$_2$O (10 mL) and extracted with CH$_2$Cl$_2$ (2×20 mL). The combined organic layers were washed with H$_2$O (4×10 mL), sat. NH$_4$Cl sol. (10 mL), and brine (15 mL), dried over MgSO$_4$, filtered and concentrated. The crude mixture was purified by silica gel column chromatography (98:2-96:4 CH$_2$Cl$_2$:MeOH). Product ((1R)-13) was isolated as a yellow oil (40 mg, 67%). R$_f$=0.43 (98:2 CH$_2$Cl$_2$:MeOH); H NMR (400 MHz, CDCl$_3$) δ 7.87-7.76 (m, 2H), 7.40-7.29 (m, 2H), 6.82 (d, J=16.0 Hz, 1H), 6.18 (dd, J=16.0, 6.5 Hz, 1H), 5.17 (t, J=7.0 Hz, 1H), 4.36-4.26 (m, 1H), 3.85-3.75 (m, 1H), 3.65 (s, 3H), 2.80-2.47 (m, 3H), 2.36 (td, J=7.0, 0.8 Hz, 2H), 2.02-1.46 (m, 7H), 1.34-1.26 (m, 5H), 0.87 (t, J=7.0 Hz, 3H); $^{13}$C NMR (101 MHz, CDCl$_3$) δ 174.2, 146.1, 138.7, 138.4, 132.0, 129.2, 124.6, 124.5, 124.4, 122.6, 122.5, 76.1, 73.9, 68.6, 51.6, 39.0, 33.6, 31.6, 31.6, 25.6, 22.5, 21.0, 14.0; IR (CHCl$_3$) (v$_{max}$, cm$^{-1}$) 3433, 3020, 1729, 1216, 1046; [α]$_D$=+6.21 (c=1.5 in CHCl$_3$); HRMS (ESI) [M+Na]$^+$ calc 443.1868 for C$_{23}$H$_{32}$O$_5$SNa, found 443.1856; de=92% as determined by SFC using a Chiralpak IC column (CO$_2$: MeCN:EtOH, gradient 75:12.5:12.5 0-1 min, then gradient to 60:20:20 until 6 min, 3 mL/min), R$_t$=2.156 min (1S)-epimer, 3.286 min (1R)-epimer.

1-(3-Bromothiophen-2-yl)hexan-1-ol (29)

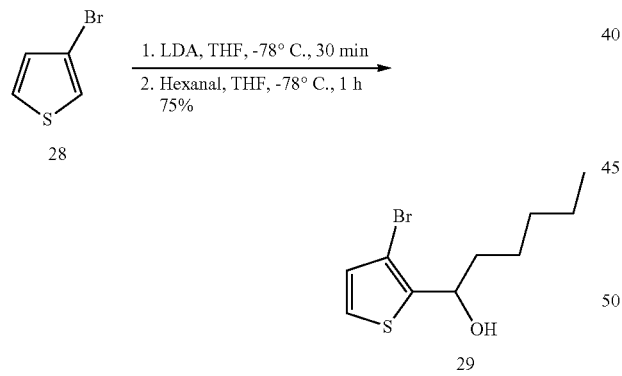

Diisopropylamine (1.54 mL, 10.9 mmol, 1.0 eq) was added to THF (30 mL) and cooled to 0$_0$° C. nBuLi (1.4 mL of 2.5 M sol., 10.96 mmol, 1.01 eq) was added dropwise and stirred for 10 min. The reaction mixture was cooled to −78° C. 3-Bromothiophene 28 (1.04 mL, 10.90 mmol, 1 eq) was added dropwise to the mixture and stirred at −78° C. for 30 min. Hexanal (1.44 mL, 12.1 mmol, 1.1 eq) was added dropwise and stirred at −78° C. for 1 h. The reaction was quenched by the addition of sat. NH$_4$Cl sol. (50 mL), extracted with Et$_2$O (3×50 mL), washed with brine (50 mL), dried over MgSO$_4$, filtered and concentrated to give a crude mixture which was purified by silica gel column chromatography (pentane:EtOAc 12:1) to afford 29 as a colourless oil (2.15 g, 75%). Spectral data were consistent with literature;$^{23}$ R$_f$=0.46 (20:1 pentane:EtOAc); $^1$H NMR (400 MHz, CDCl$_3$) δ 7.23 (d, J=5.5 Hz, 1H), 6.91 (d, J=5.5 Hz, 1H), 5.05 (m, 1H), 2.22 (s, 1H), 1.83 (m, 2H), 1.17-1.57 (m, 6H), 0.89 (m, 3H).

1-(3-Bromothiophen-2-yl)hexan-1-one (30)$^{23}$

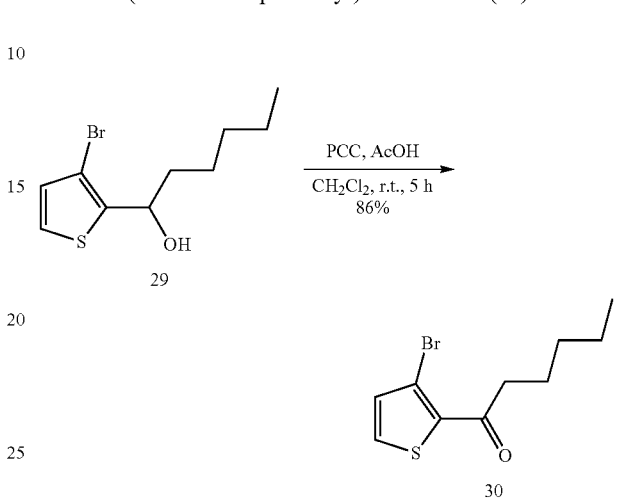

Acetic acid (0.5 mL) was added to a solution of pyridinium chlorochromate (2.23 g, 10.6 mmol, 1.5 eq) in CH$_2$Cl$_2$ (50 mL) and stirred for 5 min. Alcohol 29 (1.85 g, 7.0 mmol, 1 eq) in CH$_2$Cl$_2$ (5 mL) was added to the reaction mixture and stirred at room temperature for 5 h. The mixture was filtered through a pad of celite, eluted with Et$_2$O (100 mL) and concentrated. The crude product was purified by silica gel column chromatography (pentane:EtOAc 15:1). The product 30 was isolated as a colourless oil (1.58 g, 85%). Spectral data were consistent with literature;$^{23}$ R$_f$=0.69 (9:1 pentane:EtOAc); $^1$H NMR (400 MHz, CDCl$_3$) δ 7.49 (d, J=5.5 Hz, 1H), 7.10 (d, J=5.5 Hz, 1H), 3.02 (t, J=7.5 Hz, 2H), 1.75 (m, 2H), 1.38 (m, 4H), 0.90 (m, 3H).

Methyl 4-((4S,5R)-5-((E)-2-(2-hexanoylthiophen-3-yl)vinyl)-2,2-dimethyl-1,3-dioxolan-4-yl)butanoate (31)

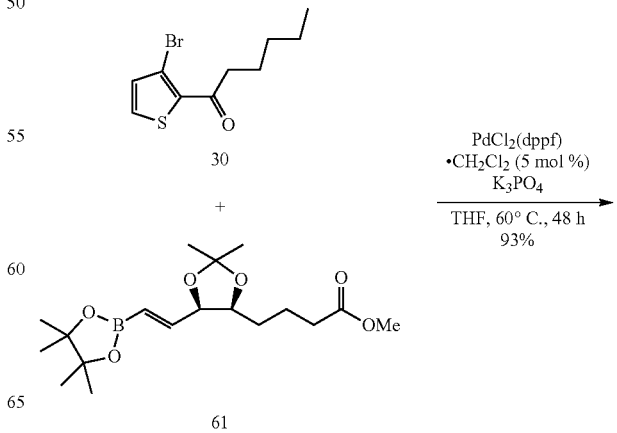

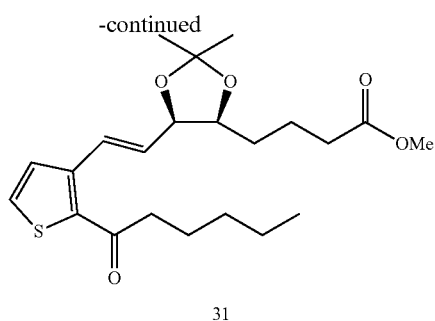

31

Bromide 30 (96.1 mg, 0.368 mmol, 1.00 eq) and boronic ester 61 (147.0 mg, 0.415 mmol, 1.13 eq) were dissolved in THF (3.8 mL) in a Schlenk tube. PdCl$_2$(dppf).CH$_2$Cl$_2$ (15.0 mg, 0.0184 mmol, 0.05 eq) was added followed by K$_3$PO$_4$ (0.77 mL of 3 M aq. sol, 2.298 mmol, 6.25 eq). The mixture was heated to 60° C., sealed under nitrogen and stirred for 50 h. The reaction mixture was allowed to cool, quenched with sat. NH$_4$Cl sol. (10 mL) and extracted with EtOAc (3×15 mL). Combined organic layers were washed with brine (20 mL), dried with MgSO$_4$, filtered and concentrated. The crude mixture was purified by silica gel column chromatography (8:1→6:1 pentane:EtOAc) to give 31 as a pale yellow oil (140 mg, 93%). R$_f$=0.56 (6:1 pentane:EtOAc); $^1$H NMR (400 MHz, CDCl$_3$) δ 7.56 (d, J=16.0 Hz, 1H), 7.41-7.35 (m, 1H), 7.33 (d, J=5.2 Hz, 1H), 6.15 (dd, J=16.0, 8.3 Hz, 1H), 4.75-4.66 (m, 1H), 4.20 (ddd, J=9.0, 6.1, 4.6 Hz, 1H), 3.63 (s, 3H), 2.82 (t, J=7.4 Hz, 2H), 2.33 (t, J=7.4 Hz, 2H), 1.85-1.66 (m, 4H), 1.51 (s, 3H), 1.51-1.42 (m, 2H), 1.38 (s, 3H), 1.37-1.30 (m, 4H), 0.90 (t, J=7.0 Hz, 3H); $^{13}$C NMR (101 MHz, CDCl$_3$) δ 194.2, 173.9, 143.3, 135.8, 130.6, 129.4, 127.8, 127.7, 108.6, 79.6, 78.5, 51.6, 42.5, 33.9, 31.5, 30.1, 28.4, 25.8, 24.5, 22.6, 21.9, 14.1; IR (CHCl$_3$) ($v_{max}$, cm$^{-1}$) 3019, 1732, 1662, 1416, 1215; [α]$_D$=−31.22 (c=0.95 in CHCl$_3$); [M+Na]$^+$ calc 431.1855 for C$_{22}$H$_{32}$O$_5$SNa, found 431.1868.

Methyl (5S,6R,E)-8-(2-hexanoylthiophen-3-yl)-5,6-dihydroxyoct-7-enoate (32)

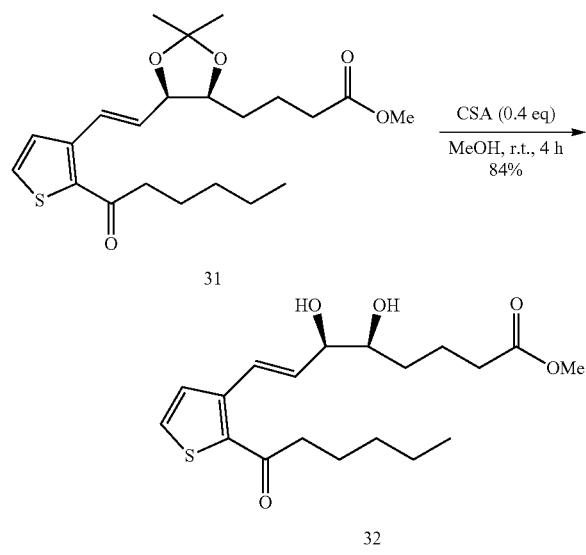

Acetonide 31 (112.0 mg, 0.274 mmol, 1 eq) was dissolved in MeOH (2 mL), camphorsulfonic acid (25.0 mg, 0.110 mmol, 0.4 eq) was added and the reaction mixture was stirred under nitrogen at room temperature for 4 h. The reaction mixture was concentrated and purified by silica gel column chromatography (98:2→96:4 CH$_2$Cl$_2$:MeOH). The product 32 was isolated as an off-white solid (85.0 mg, 84%). R$_f$=0.16 (96:4 CH$_2$Cl$_2$:MeOH); M.p.=54-57° C.; $^1$H NMR (400 MHz, CDCl$_3$) δ 7.56 (d, J=16.2 Hz, 1H), 7.38 (dd, J=5.2, 0.4 Hz, 1H), 7.33 (d, J=5.2 Hz, 1H), 6.31 (dd, J=16.2, 7.3 Hz, 1H), 4.31-4.25 (m, 1H), 3.82-3.75 (m, 1H), 3.65 (s, 3H), 2.82 (t, J=7.5 Hz, 2H), 2.50-2.38 (m, 2H), 2.35 (t, J=7.3 Hz, 2H), 1.87-1.69 (m, 4H), 1.50-1.32 (m, 6H), 0.90 (t, J=7.0 Hz, 3H); $^{13}$C NMR (101 MHz, CDCl$_3$) δ 194.5, 174.3, 143.6, 135.6, 132.3, 129.6, 127.8, 127.3, 76.0, 74.0, 51.7, 42.5, 33.9, 31.7, 31.5, 24.5, 22.6, 21.3, 14.1; IR (CHCl$_3$) ($v_{max}$, cm$^{-1}$) 3468, 1730, 1655, 1414, 1178, 1093; [α]$_D$=+1.90 (c=1.5 in CHCl$_3$); [M+Na]$^+$ calc 391.1556 for C$_{19}$H$_{28}$O$_5$SNa, found 391.1555.

Methyl(5S,6R,E)-5,6-dihydroxy-8-(2-((S)-1-hydroxyhexyl)thiophen-3-yl)oct-7-enoate (14)

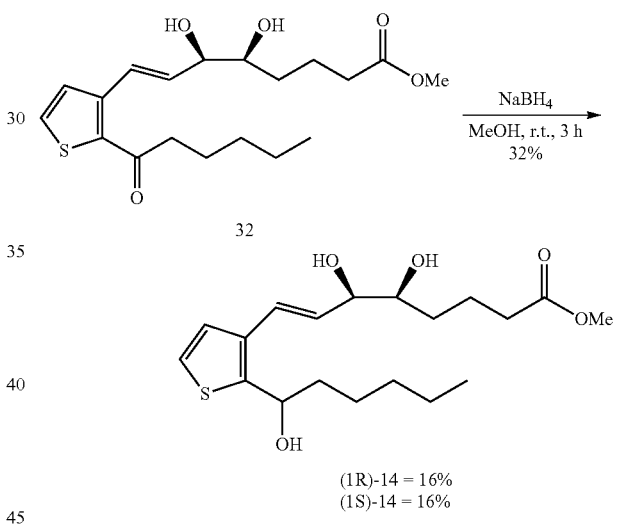

(1R)-14 = 16%
(1S)-14 = 16%

Ketone 32 (65.0 mg, 0.176 mmol, 1.0 eq) was dissolved in MeOH (2.2 mL) and NaBH$_4$ (20.0 mg, 0.529 mmol, 3.0 eq) was added and the reaction mixture was stirred at room temperature for 2 h, then diluted with sat. NH$_4$Cl sol (10 mL) and extracted with CH$_2$Cl$_2$ (3×10 mL). The combined organic layers were washed with H$_2$O (20 mL), brine (20 mL), dried over MgSO$_4$, filtered and concentrated. Crude mixture was purified by silica gel column chromatography (98:2-96:4 CH$_2$Cl$_2$:MeOH). Product (1R)-14 was isolated as a yellow oil (7.0 mg, 16%) and (1S)-14 was isolated as a yellow oil (7.0 mg, 16%). (1R)-14; R$_f$=0.36 (98:2 CH$_2$Cl$_2$:MeOH); $^1$H NMR (400 MHz, CDCl$_3$) δ 7.17 (d, J=5.3 Hz, 1H), 7.13 (d, J=5.3 Hz, 1H), 6.73 (d, J=15.8 Hz, 1H), 6.09 (dd, J=15.8, 7.0 Hz, 1H), 5.06 (t, J=6.5 Hz, 1H), 4.20 (dd, J=6.5, 3.4 Hz, 1H), 3.77-3.69 (m, 1H), 3.65 (s, 3H), 2.70-2.38 (m, 3H), 2.34 (t, J=7.0 Hz, 2H), 1.90-1.68 (m, 4H), 1.52-1.42 (m, 3H), 1.35-1.28 (m, 5H), 0.88 (t, J=6.5 Hz, 3H); $^{13}$C NMR (101 MHz, CDCl$_3$) b 174.4, 145.0, 134.9, 127.6, 125.6, 125.3, 124.1, 76.0, 74.0, 68.1, 51.8, 39.3, 33.8, 31.7, 31.7, 25.8, 22.7, 21.2, 14.2; IR (CHCl$_3$) ($v_{max}$, cm$^{-1}$) 3369, 3054, 1733, 1422, 1265, 1157; [α]$_D$=+15.23 (c=0.7 in CHCl₃); [M+Na]⁺ calc 393.1712 for $C_{19}H_{30}O_5SNa$, found 393.1710; de=97% as determined by SFC using a Chiralpak IC column (CO₂:MeCN:EtOH, gradient 75:12.5:12.5 0-1 min, then gradient to 60:20:20 until 6 min, 3 mL/min), $R_t$=1.470 min (1S)-epimer, 1.880 min (1R)-epimer. (1S)-14: $R_f$=0.40 (98:2 CH₂Cl₂: MeOH); ¹H NMR (500 MHz, CDCl₃) δ 7.16 (d, J=5.3 Hz, 1H), 7.13 (d, J=5.3 Hz, 1H), 6.73 (d, J=15.8 Hz, 1H), 6.08 (dd, J=15.8, 7.2 Hz, 1H), 5.06 (t, J=6.8 Hz, 1H), 4.27-4.17 (m, 1H), 3.75-3.69 (m, 1H), 3.63 (s, 3H), 2.69-2.45 (m, 3H), 2.39-2.27 (m, 2H), 1.92-1.67 (m, 4H), 1.56-1.40 (m, 3H), 1.35-1.26 (m, 5H), 0.87 (t, J=6.9 Hz, 3H); ¹³C NMR (101 MHz, CDCl₃) δ 174.4, 145.1, 134.8, 127.6, 125.6, 125.4, 124.1, 76.1, 73.9, 68.0, 51.8, 39.3, 33.8, 31.7, 31.7, 25.8, 22.7, 21.1, 14.2; IR (CHCl₃) ($v_{max}$, cm⁻¹) 3369, 3054, 1733, 1422, 1265, 1157; $[\alpha]_D$=−11.43 (c=0.7 in CHCl₃); [M+Na]⁺ calc 393.1712 for $C_{19}H_{30}O_5SNa$, found 393.1702; de=95% as determined by SFC using a Chiralpak IC column (CO₂:MeCN:EtOH, gradient 75:12.5:12.5 0-1 min, then gradient to 60:20:20 until 6 min, 3 mL/min), $R_t$=1.470 min (1S)-epimer, 1.880 min (1R)-epimer.

Methyl(5S,6R,E)-5,6-dihydroxy-8-(2-((R)-1-hydroxyhexyl)thiophen-3-yl)oct-7-enoate ((1R-)14)

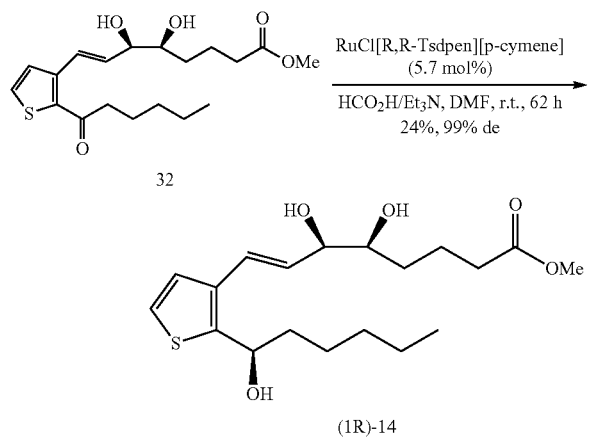

Ketone 32 (58.0 mg, 0.138 mmol, 1.0 eq) was added to Schlenk tube followed by RuCl[R,R-Tsdpen][p-cymene] catalyst (5.0 mg, 0.0079 mmol, 0.057 eq), HCO₂H (0.026 mL, 0.677 mmol, 4.9 eq), Et₃N (0.052 mL, 0.393 mmol, 2.8 eq) and DMF (0.8 mL). Reaction was stirred at room temperature for 62 h. The reaction mixture was diluted with H₂O (10 mL) and extracted with CH₂Cl₂ (2×20 mL). The combined organic layers were washed with H₂O (4×10 mL), sat. NH₄Cl sol. (10 mL), and brine (15 mL), dried over MgSO₄, filtered and concentrated. The crude mixture was purified by silica gel column chromatography (98:2-96:4 CH₂Cl₂:MeOH) to afford (1R)-14 as a yellow oil (14 mg, 24%). de=99% as determined by SFC using a Chiralpak IC column (CO₂:MeCN:EtOH, gradient 75:12.5:12.5 0-1 min, then gradient to 60:20:20 until 6 min, 3 mL/min), $R_t$=1.470 min (1S)-epimer, 1.880 min (1R)-epimer. Identical in all other physical data to the previously prepared (1R)-14.

Methyl(5S,6R,E)-5,6-dihydroxy-8-(2-((S)-1-hydroxyhexyl)thiophen-3-yl)oct-7-enoate ((1S-)14)

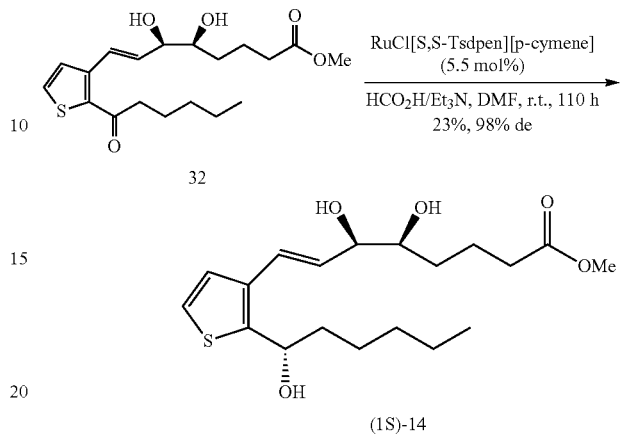

Ketone 32 (30.0 mg, 0.143 mmol, 1 eq) was added to Schlenk tube followed by RuCl[R,R-Tsdpen][p-cymene] catalyst (5.0 mg, 0.0079 mmol, 0.055 eq), HCO₂H (0.026 mL, 0.677 mmol, 4.7 eq), Et₃N (0.052 mL, 0.393 mmol, 2.7 eq) and DMF (0.8 mL). The reaction mixture was stirred at room temperature for 110 h, then diluted with H₂O (10 mL) and extracted with CH₂Cl₂ (2×20 mL). The combined organic layers were washed with H₂O (4×10 mL), sat. NH₄Cl sol. (10 mL), and brine (15 mL), dried over MgSO₄, filtered and concentrated. The crude mixture was purified by silica gel column chromatography (98:2-96:4 CH₂Cl₂:MeOH) to afford (1S)-14 as a yellow oil (14.0 mg, 23%). de=98% as determined by SFC using a Chiralpak IC column (CO₂:MeCN:EtOH, gradient 75:12.5:12.5 0-1 min, then gradient to 60:20:20 until 6 min, 3 mL/min), $R_t$=1.470 min (1S)-epimer, 1.880 min (1R)-epimer. Identical in all other physical data to the previously prepared (1S)-14.

3-Phenoxypropane-1,2-diol (45)[30]

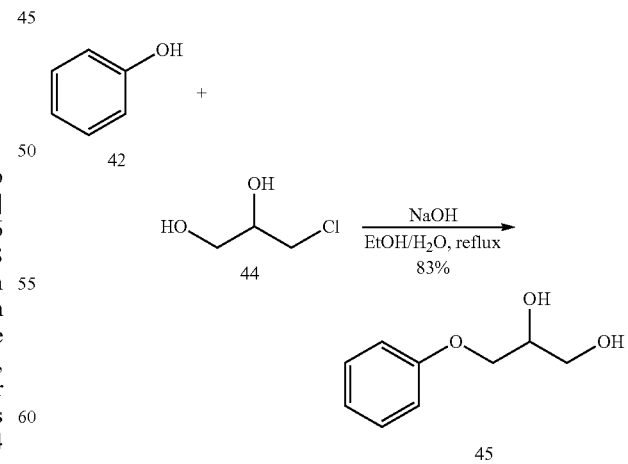

Phenol 42 (5.0 g, 53.52 mmol, 1.0 eq) was dissolved in EtOH (30 mL) and a solution of NaOH (2.68 g, 66.90 mmol, 1.25 eq) in H₂O (10 mL) was added. The reaction mixture was heated under reflux for 10 min. Then, a solution of 3-chloro-1,2-propanediol 44 (5.4 mL, 64.23 mmol, 1.25 eq) in EtOH (5 mL) was slowly added and the mixture was further heated under reflux for 16 h. EtOH was then removed and Et$_2$O (30 mL) was added, along with water (30 mL). The aqueous phase was extracted with Et$_2$O (2×30 mL) and the combined organic layers were dried over MgSO$_4$, filtered and concentrated. The crude product was purified by recrystallisation from 1:1 cyclohexane:Et$_2$O mixture and the product 45 was isolated as a white solid (7.5 g, 83%). Spectral data were consistent with literature. $^1$H NMR (500 MHz, CDCl$_3$) δ 7.30 (dd, J=8.5, 7.5 Hz, 2H), 6.98 (tt, J=7.5, 1.0 Hz, 1H), 6.92 (dd, J=8.5, 1.0 Hz, 2H), 4.15-4.10 (m, 1H), 4.05 (dd, J=5.5, 3.0 Hz, 2H), 3.85 (ddd, J=11.5, 6.5, 3.5 Hz, 1H), 3.76 (dt, J=11.5, 5.5 Hz, 1H), 2.64 (d, J=4.5 Hz, 1H).

2-Phenoxyacetaldehyde (46)

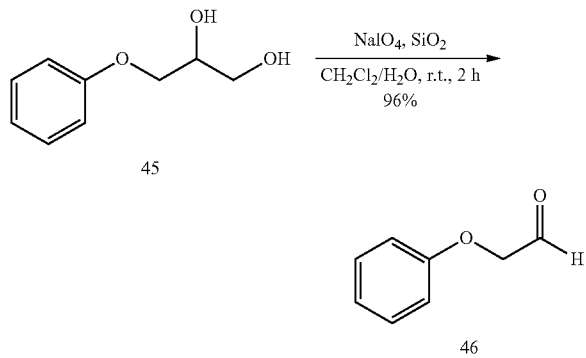

NaIO$_4$ (25.5 mL of a 0.65 M aq. solution, 16.62 mmol, 1.30 eq) was added to a vigorously stirred suspension of silica gel (25.0 g) in CH$_2$Cl$_2$ (180 mL). A solution of the diol 45 (2.15 g, 12.78 mmol, 1.0 eq) in CH$_2$Cl$_2$ (20 mL) was then added and the resulting mixture was allowed to stir at room temperature for 2 h. The reaction mixture was filtered over a small plug of silica (washing with CH$_2$Cl$_2$) and concentrated to yield the product 46 as a pale yellow oil (1.67 g, 96%). Spectral data were consistent with literature.[30] $^1$H NMR (500 MHz, CDCl$_3$) δ 9.86 (t, J=1.0 Hz, 1H), 7.35-7.29 (m, 2H), 7.05-7.01 (m, 1H), 6.93-6.89 (m, 2H), 4.57 (d, J=1.0 Hz, 2H).

1-(3-Bromobenzo[b]thiophen-2-yl)-2-phenoxyethan-1-ol (47)

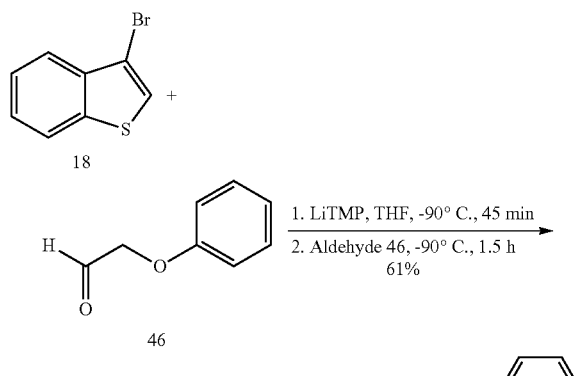

nBuLi (1.13 ml of a 2.5 M sol. in hexanes, 2.82 mmol, 1 eq) was added to THF (3 mL) and cooled to −60° C. TMP (0.52 mL, 3.05 mmol, 1.3 eq) was added and warmed to 0° C. for 30 min. The reaction mixture was cooled to −90° C. and 3-bromobenzothiophene 18 (500 mg, 2.35 mmol, 1 eq) dissolved in THF (2 mL) was added dropwise and stirred for 20 min. Phenoxyacetaldehyde 46 (415 mg, 3.05 mmol, 1.3 eq) dissolved in THF (2 mL) was added at −90° C. and stirred for 1.5 h. The reaction was quenched by addition of HCl (3 mL of 5 M aq. sol.) and warmed to room temperature. Sat. NaHCO$_3$ sol. (c. 15 mL) was added to neutralise the reaction mixture and it was extracted with EtOAc (3×10 mL), washed with brine (5 mL), dried over MgSO$_4$, filtered and concentrated. The crude mixture was purified by silica gel column chromatography (cyclohexane:EtOAc 94:6-90:10) and product 47 was isolated as a pale pink oil (500 mg, 61%). Rf=0.85 (6:1 pentane:EtOAc); $^1$H NMR (400 MHz, CDCl$_3$) δ 7.83 (dd, J=7.5, 1.5 Hz, 2H), 7.61-7.39 (m, 2H), 7.37-7.29 (m, 2H), 7.06-6.97 (m, 3H), 5.69 (dd, J=8.0, 2.5 Hz, 1H), 4.36 (dd, J=9.5, 2.5 Hz, 1H), 4.15 (dd, J=9.5, 8.0 Hz, 1H), 3.26 (s, 1H); $^{13}$C NMR (101 MHz, CDCl$_3$) δ 158.0, 138.9, 137.9, 137.6, 129.6, 125.5, 125.1, 122.9, 122.7, 121.6, 114.7, 105.4, 71.0, 69.2; IR (CHCl$_3$) (ν$_{max}$, cm$^{-1}$) 2934, 1732, 1671, 1205, 1068; HRMS (ESI) [M]$^+$ calc 347.9820 for C$_{16}$H$_{13}$O$_2$S$^{79}$Br, found 347.9834.

1-(3-Bromobenzo[b]thiophen-2-yl)-2-phenoxyethan-1-one (38)

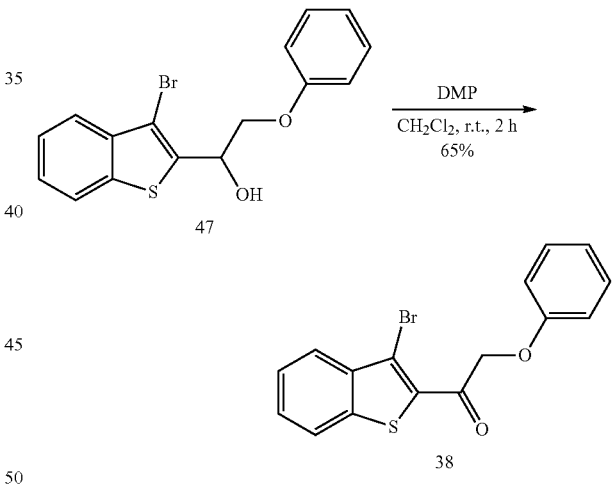

Alcohol 47 (870 mg, 2.491 mmol, 1 eq) was dissolved in CH$_2$Cl$_2$ (10 mL) and Dess-Martin periodinane (2.113 g, 4.982 mmol, 2 eq) was added and reaction mixture stirred at room temperature for 2 h. The reaction mixture was washed with 1:1 sat. NaHCO$_3$ sol.:sat. Na$_2$S$_2$O$_3$ sol. (4×10 mL), H$_2$O (10 mL), brine (10 mL), dried over MgSO$_4$, filtered and concentrated. The crude product was recrystallised from 2-propanol and product 38 was isolated as a pale pink solid (558 mg, 65%). M.p.=139-140° C.; $^1$H NMR (500 MHz, CDCl$_3$) δ 8.04-7.97 (m, 1H), 7.89-7.84 (m, 1H), 7.58-7.50 (m, 2H), 7.36-7.29 (m, 2H), 7.04-6.97 (m, 3H), 5.46 (s, 2H); $^{13}$C NMR (126 MHz, CDCl$_3$) δ 188.6, 158.0, 140.0, 138.9, 136.7, 129.8, 128.9, 126.1, 125.9, 123.0, 122.0, 115.0, 112.7, 72.9; IR (CHCl$_3$) (ν$_{max}$, cm$^{-1}$) 1670, 1586, 1490, 1090; HRMS (ESI) [M+Na]$^+$ calc 368.9561 for C$_{16}$H$_{11}$2S$^{79}$BrNa, found 368.9554.

Methyl 4-((4S,5R)-2,2-dimethyl-5-((E)-2-(2-(2-phenoxyacetyl)benzo[b]thiophen-3-yl)vinyl)-1,3-dioxolan-4-yl)butanoate (37)

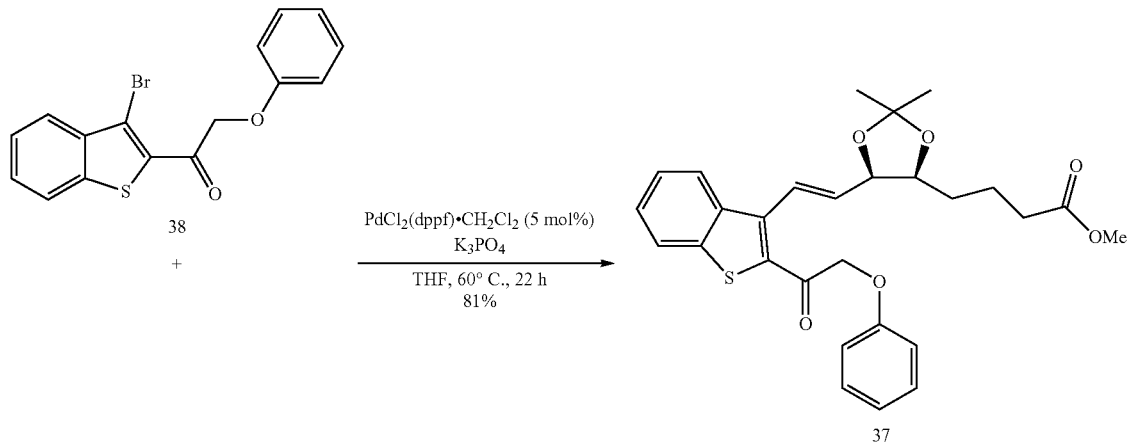

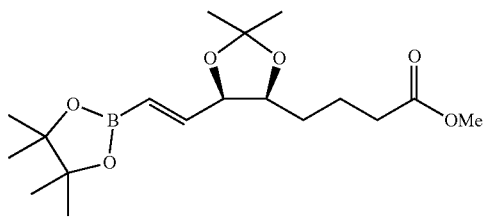

Benzothiophene bromide 38 (100.0 mg, 0.288 mmol, 1 eq) and boronic ester 61 (112 mg, 0.317 mmol, 1.1 eq) were dissolved in THF (3 mL) in a Schlenk tube. PdCl$_2$(dppf). CH$_2$Cl$_2$ (11.8 mg, 0.0144 mmol, 0.05 eq) was added followed by K$_3$PO$_4$ (0.58 mL of 3 M aq. sol, 1.728 mmol, 6 eq). The mixture was heated to 60° C., sealed under nitrogen and stirred for 22 h. The reaction was quenched by addition of sat. NH$_4$Cl sol. (20 mL) and extracted with EtOAc (3×15 mL). The combined organic layers were washed with H$_2$O (20 mL), brine (20 mL), dried with MgSO$_4$, filtered and concentrated. Crude mixture was purified by silica gel column chromatography (9:1→3:1 pentane:EtOAc) to give 37 as pale yellow oil (115 mg, 81%). R$_f$=0.29 (6:1 pentane: EtOAc); $^1$H NMR (500 MHz, CDCl$_3$) δ 8.04 (d, J=8.0 Hz, 1H), 7.88 (d, J=8.0 Hz, 1H), 7.53 (ddd, J=8.0, 7.0, 1.0 Hz, 1H), 7.46 (ddd, J=8.0, 7.0, 1.0 Hz, 1H), 7.32-7.28 (m, 2H), 7.26 (d, J=16.0 Hz, 1H), 7.02-6.95 (m, 3H), 6.19 (dd, J=16.0, 7.5 Hz, 1H), 5.13 (s, 2H), 4.82-4.77 (m, 1H), 4.28 (ddd, J=9.0, 6.0, 4.5 Hz, 1H), 3.62 (s, 3H), 2.33 (t, J=7.5 Hz, 2H), 1.89-1.82 (m, 1H), 1.78-1.72 (m, 1H), 1.63-1.56 (m, 2H), 1.55 (s, 3H), 1.43 (s, 3H). $^{13}$C NMR (126 MHz, CDCl$_3$) δ 189.8, 173.9, 158.0, 141.2, 140.1, 138.1, 134.1, 133.0, 129.7, 128.2, 126.7, 125.6, 125.5, 123.1, 121.9, 114.9, 108.8, 79.6, 78.3, 72.5, 51.6, 33.9, 30.3, 28.5, 25.8, 21.9; IR (CHCl$_3$) (v$_{max}$, cm$^{-1}$) 2934, 1732, 1671, 1205, 1068; [α]D=−9.30 (c=1.1 in CHCl$_3$); HRMS (ESI) [M+Na] calc 517.1661 for C$_{28}$H$_{30}$O$_6$NaS, found 517.1682.

Methyl (5S,6R,E)-5,6-dihydroxy-8-(2-((S)-1-hydroxy-2-phenoxyethyl)benzo[b]thiophen-3-yl)oct-7-enoate ((1S)-33)

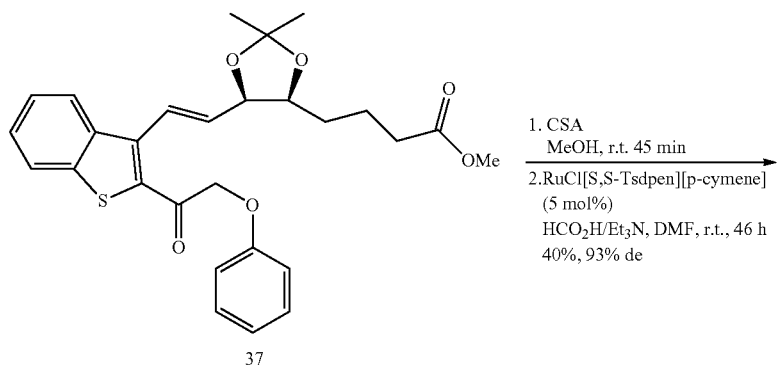

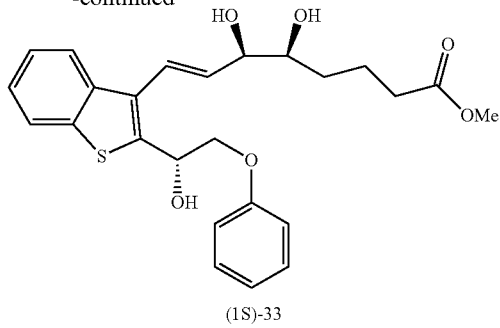

(1S)-33

Acetonide 37 (115.0 mg, 0.233 mmol, 1 eq) was dissolved in MeOH (3.5 mL), camphorsulfonic acid (108.0 mg, 0.465 mmol, 2 eq) was added and reaction mixture was stirred at room temperature for 45 min. Et$_3$N (0.06 mL, 0.465 mmol, 2 eq) was added and reaction mixture was concentrated without heat. The crude product was purified by column chromatography (4:1-1:1 cyclohexane:EtOAc) and product mixture isolated as a yellow oil (95.0 mg) which was dissolved in DMF (0.5 mL) and added to Schlenk tube followed by RuCl[S,S-Tsdpen][p-cymene] catalyst (6.7 mg, 0.0105 mmol, 0.05 eq), HCO$_2$H (0.035 mL, 0.899 mmol, 4.3 eq), Et$_3$N (0.07 mL, 0.523 mmol, 2.5 eq). The reaction mixture was stirred at room temperature for 46 h, after which time it was diluted with sat. NH$_4$Cl sol. (10 mL) and extracted with CH$_2$Cl$_2$ (2×20 mL). The combined organic layers were washed with 1:1 brine: H$_2$O (4×10 mL), dried over MgSO$_4$, filtered and concentrated. Crude mixture was purified by silica gel column chromatography (96:4 CH$_2$Cl$_2$: MeOH) to give (1S)-33 as a yellow oil (44 mg, 40%). R$_f$=0.15 (96:4 CH$_2$Cl$_2$:MeOH); $^1$H NMR (500 MHz, CDCl$_3$) δ 7.85-7.79 (m, 2H), 7.39-7.31 (m, 2H), 7.30-7.26 (m, 2H), 6.97 (t, J=7.5 Hz, 1H), 6.92 (d, J=7.5 Hz, 2H), 6.84 (d, J=16.0 Hz, 1H), 6.23 (dd, J=16.0, 6.5 Hz, 1H), 5.62 (t, J=5.5 Hz, 1H), 4.33-4.27 (m, 1H), 4.21 (d, J=5.5 Hz, 2H), 3.80-3.74 (m, 1H), 3.62 (s, 3H), 3.57 (s, 1H), 2.67 (s, 2H), 2.30 (td, J=7.0, 3.5 Hz, 2H), 1.85-1.79 (m, 1H), 1.73-1.68 (m, 1H), 1.58-1.48 (m, 2H); $^{13}$C NMR (126 MHz, CDCl$_3$) δ 174.5, 158.3, 140.4, 138.9, 138.7, 132.9, 130.7, 129.7, 124.9, 124.6, 124.3, 122.8, 122.8, 121.6, 114.8, 76.1, 74.1, 72.2, 67.7, 51.8, 33.7, 31.8, 21.2; IR (CHCl$_3$) (v$_{max}$, cm$^{-1}$) 3410, 1718, 1600, 1243, 1050; [α]$_D$=−41.94 (c=1 in CHCl$_3$); HRMS (ESI) [M+Na]$^+$ calc 479.1504 for C$_{25}$H$_{28}$O$_6$NaS, found 479.1485. de=93% as determined by SFC using a Chiralpak IC column (CO$_2$:MeCN:EtOH, gradient 75:12.5:12.5 0-1 min, then gradient to 40:30:30 until 6 min, 3 mL/min), R$_t$=2.193 min (1S)-epimer, 3.075 min (1R)-epimer.

Methyl (5S,6R,E)-5,6-dihydroxy-8-(2-((R)-1-hydroxy-2-phenoxyethyl)benzo[b]thiophen-3-yl)oct-7-enoate ((1R)-33)

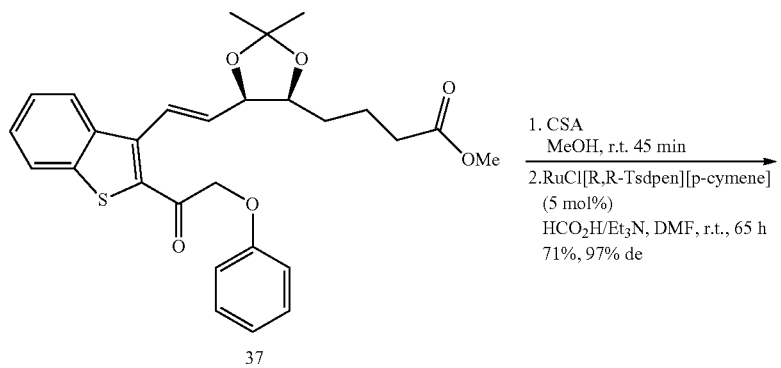

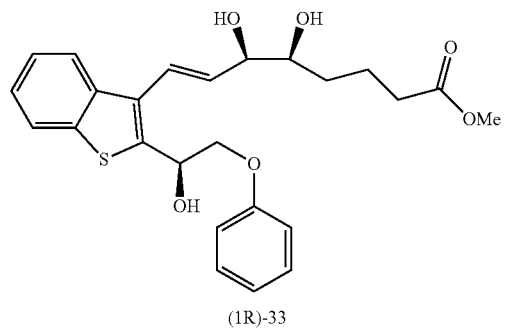

(1R)-33

Acetonide 37 (82.1 mg, 0.166 mmol, 1 eq) was dissolved in MeOH (3 mL), camphorsulfonic acid (77.1 mg, 0.332 mmol, 2 eq) was added and reaction mixture was stirred at room temperature for 45 min. Et$_3$N (0.046 mL, 0.332 mmol, 2 eq) was added and reaction mixture was concentrated without heat. The crude product was purified by column chromatography (4:1-1:1 cyclohexane:EtOAc) and product mixture isolated as a yellow oil (66.0 mg) which was dissolved in DMF (1 mL) and added to Schlenk tube followed by RuCl[R,R-Tsdpen][p-cymene] catalyst (4.6 mg, 0.0072 mmol, 0.05 eq), HCO$_2$H (0.02 mL, 0.615 mmol, 4.3 eq), Et$_3$N (0.05 mL, 0.358 mmol, 2.5 eq). The reaction mixture was stirred at room temperature for 65 h, after which time it was diluted with sat. NH$_4$Cl sol. (10 mL) and extracted with CH$_2$Cl$_2$ (2×20 mL). The combined organic layers were washed with 1:1 brine: H$_2$O (4×10 mL), dried over MgSO$_4$, filtered and concentrated. Crude mixture was purified by silica gel column chromatography (96:4 CH$_2$Cl$_2$: MeOH) to afford (1R)-33 as a yellow oil (54 mg, 71%). R$_f$=0.15 (96:4 CH$_2$Cl$_2$:MeOH); $^1$H NMR (500 MHz, CDCl$_3$) δ 7.88-7.79 (m, 2H), 7.41-7.31 (m, 2H), 7.30-7.27 (m, 2H), 6.97 (t, J=7.5 Hz, 1H), 6.92 (dd, J=8.5, 1.0 Hz, 2H), 6.85 (d, J=16.0 Hz, 1H), 6.24 (dd, J=16.0, 6.5 Hz, 1H), 5.62 (t, J=5.5 Hz, 1H), 4.31 (dd, J=6.5, 3.5 Hz, 1H), 4.21 (d, J=5.5 Hz, 2H), 3.82-3.74 (m, 1H), 3.63 (s, 3H), 3.55-3.45 (m, 1H), 2.71-2.52 (m, 2H), 2.31 (td, J=7.2, 1.5 Hz, 2H), 1.86-1.78 (m, 1H), 1.72-1.66 (m, 1H), 1.59-1.46 (m, 2H); $^{13}$C NMR (126 MHz, CDCl$_3$) δ 174.4, 158.3, 140.4, 138.9, 138.6, 133.0, 130.6, 129.7, 124.9, 124.6, 124.3, 122.8, 122.8, 121.6, 114.8, 76.0, 74.1, 72.2, 67.7, 51.8, 33.7, 31.7, 21.2; IR (CHCl$_3$) (v$_{max}$, cm$^{-1}$) 3410, 1718, 1600, 1243, 1050; [M+Na]$^+$ calc 479.1504 for C$_{25}$H$_{28}$O$_6$NaS, found 479.1486. de=97.5% as determined by SFC using a Chiralpak IC column (CO$_2$:MeCN:EtOH, gradient 75:12.5:12.5 0-1 min, then gradient to 40:30:30 until 6 min, 3 mL/min), R$_t$=2.193 min (1S)-epimer, 3.075 min (1R)-epimer.

3-(4-Fluorophenoxy)propane-1,2-diol (49)

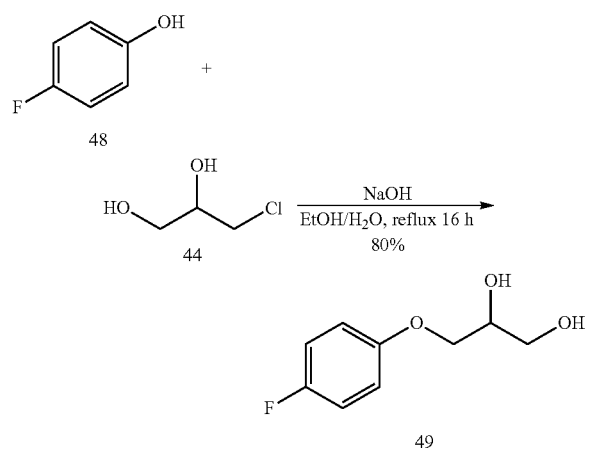

4-Fluorophenol 48 (2.0 g, 17.84 mmol, 1 eq) was dissolved in EtOH (10 mL) and a solution of NaOH (0.856 g, 21.41 mmol, 1.2 eq) in H$_2$O (3 mL) was added. The reaction mixture was heated under reflux for 10 min. Then, a solution of 3-chloro-1,2-propanediol 44 (1.8 mL, 21.41 mmol, 1.2 eq) in EtOH (2 mL) was slowly added and the mixture was further heated under reflux for 16 h. The reaction mixture was concentrated and Et$_2$O (10 mL) was added, along with water (10 mL). The aqueous phase was extracted with Et$_2$O (2×10 mL) and the combined organic layers were dried over MgSO$_4$, filtered and concentrated. The crude product was purified by recrystallisation from 1:1 cyclohexane: Et$_2$O mixture and the product was isolated as a white solid (2.66 g, 80%). Spectral data were consistent with literature.$^{31}$ R$_f$=0.30 (1:1 pentane:EtOAc); $^1$H NMR (300 MHz, CDCl$_3$) δ 7.07-6.94 (m, 2H), 6.93-6.83 (m, 2H), 4.16-4.09 (m, 1H), 4.05-4.01 (m, 2H), 3.91-3.83 (m, 1H), 3.81-3.73 (m, 1H), 2.59 (d, J=4.5 Hz, 1H), 2.00 (t, J=6.0 Hz, 1H).

2-(4-Fluorophenoxy)acetaldehyde (50)

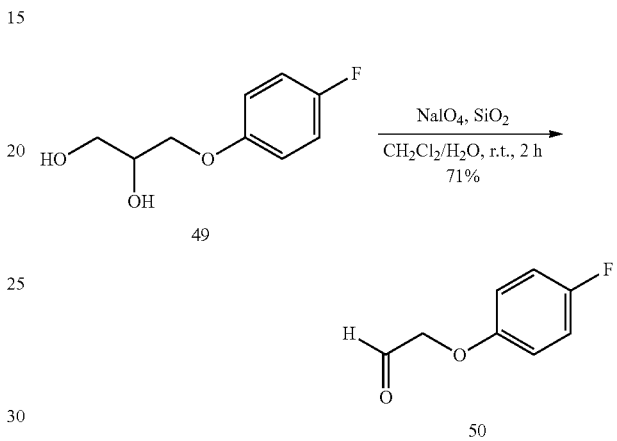

NaIO$_4$ (28.47 mL of a 0.65 M aq. solution, 18.50 mmol, 1.30 eq) was added to a vigorously stirred suspension of silica gel (25.0 g) in CH$_2$Cl$_2$ (180 mL). A solution of the diol 49 (2.65 g, 14.23 mmol, 1.0 eq) in CH$_2$Cl$_2$ (20 mL) was then added and the resulting mixture was allowed to stir at room temperature for 2 h. The reaction mixture was filtered over a small plug of silica, eluted with CH$_2$Cl$_2$ and concentrated to yield the product 50 as a pale yellow oil (1.549 g, 71%). Spectral data were consistent with literature.$^{32}$ $^1$H NMR (300 MHz, CDCl$_3$) δ 9.86 (t, J=1.0 Hz, 1H), 7.05-6.97 (m, 2H), 6.89-6.84 (m, 2H), 4.56 (d, J=1.0 Hz, 2H).

1-(3-Bromobenzo[b]thiophen-2-yl)-2-(4-fluorophenoxy)ethan-1-ol (51)

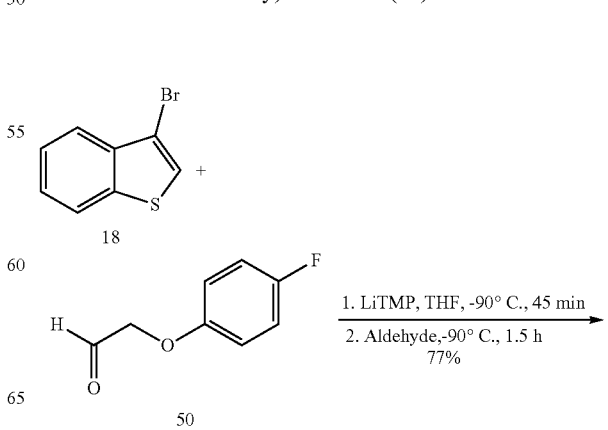

-continued

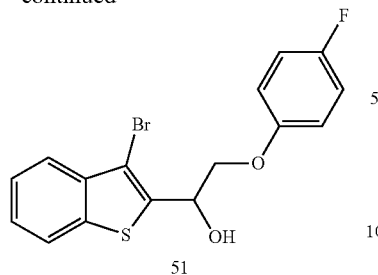

51 nBuLi (2.25 ml of a 2.5 M sol. in hexanes, 5.631 mmol, 1 eq) was added to THF (4 mL) and cooled to −60° C. TMP (1.04 mL, 6.101 mmol, 1.3 eq) was added and warmed to 0° C. for 30 min. The reaction mixture was cooled to −90° C. and 3-bromobenzothiophene 18 (1 g, 4.693 mmol, 1 eq) dissolved in THF (5 mL) was added dropwise and stirred for 20 min. Fluorophenoxyacetaldehyde 50 (1.2 g, 7.785 mmol, 1.66 eq) dissolved in THF (4 mL) was added at −90° C. and stirred for 1.5 h. Reaction was quenched by addition of 5 M HCl (3 mL) and warmed to room temperature. Sat. NaHCO$_3$ sol. (c. 20 mL) was added to neutralise the reaction mixture and it was extracted with EtOAc (3×30 mL), the extracts were washed with brine (50 mL), dried over MgSO$_4$, filtered and concentrated. The crude mixture was purified by silica gel column chromatography (cyclohexane:EtOAc 94:6-80:20) and product 51 was isolated as a pale pink oil (1.33 g, 77%). R$_f$=0.68 (6:1 pentane:EtOAc); $^1$H NMR (400 MHz, CDCl$_3$) δ 7.78 (dd, J=7.5, 1.0 Hz, 2H), 7.53-7.33 (m, 2H), 7.03-6.80 (m, 4H), 5.64 (dd, J=8.0, 3.5 Hz, 1H), 4.27 (dd, J=9.5, 3.5 Hz, 1H), 4.09 (dd, J=9.5, 8.0 Hz, 1H), 3.41 (s, 1H); $^{13}$C NMR (101 MHz, CDCl$_3$) δ 157.7 (d, J$_{F\text{-}C}$=239 Hz), 154.2 (d, J$_{F\text{-}C}$=2.0 Hz), 138.9, 137.9, 137.5, 125.6, 125.2, 122.9, 122.7, 116.0 (d, J$_{F\text{-}C}$=22.0 Hz), 115.8 (d, J$_{F\text{-}C}$=6.5 Hz), 105.4, 71.8, 69.1; IR (CHCl$_3$) (v$_{max}$, cm$^{-1}$) 3372, 1503, 1199, 1096, 1038; HRMS (ESI) [M+Na]$^+$ calc 388.9623 for C$_{16}$H$_{12}$O$_2$FS$^{79}$BrNa, found 388.9639.

1-(3-Bromobenzo[b]thiophen-2-yl)-2-(4-fluorophenoxy)ethan-1-one (52)

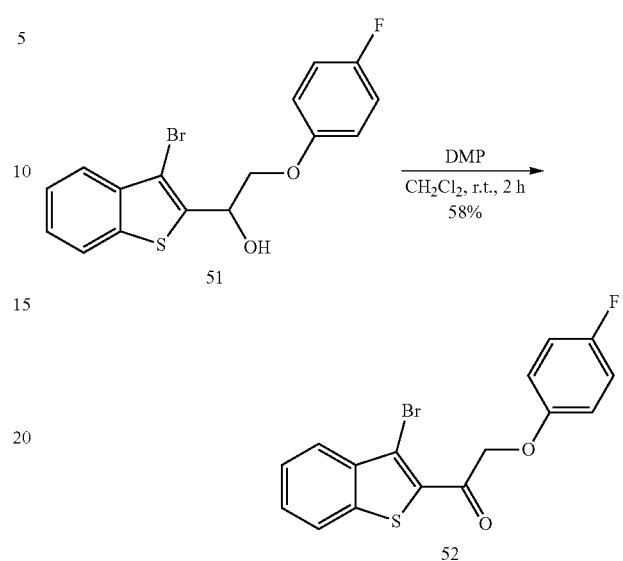

Alcohol 51 (600 mg, 1.634 mmol, 1 eq) was dissolved in CH$_2$Cl$_2$ (10 mL) and Dess-Martin periodinane (1.386 g, 3.268 mmol, 2 eq) was added and reaction mixture stirred at room temperature for 2 h. The reaction mixture was washed with 1:1 sat. NaHCO$_3$ sol.: sat. Na$_2$S$_2$O$_3$ sol. (4×10 mL), H$_2$O (10 mL), brine (10 mL), dried over MgSO$_4$, filtered and concentrated. The crude product was recrystallised from 2-propanol and product 52 isolated as a pale yellow solid (344 mg, 58%). M.p.=132-135° C.; $^1$H NMR (400 MHz, CDCl$_3$) δ 8.00 (dd, J=7.0, 2.0 Hz, 1H), 7.86 (dd, J=7.0, 2.0 Hz, 1H), 7.60-7.49 (m, 2H), 7.09-6.89 (m, 4H), 5.43 (s, 2H); $^{13}$C NMR (101 MHz, CDCl$_3$) 188.5, 158.0 (d, J$_{F\text{-}C}$=240 Hz), 154.2 (d, J$_{F\text{-}C}$=2 Hz), 140.0, 138.9, 136.6, 128.9, 126.17, 125.9, 123.0, 116.3 (d, J$_{F\text{-}C}$=8 Hz), 116.2 (d, J$_{F\text{-}C}$=23 Hz), 112.7, 73.6; IR (CHCl$_3$) (v$_{max}$, cm$^{-1}$) 1652, 1505, 1491 1199, 1085; HRMS (ESI) [M+Na]$^+$ calc 386.9467 for C$_{16}$H$_{10}$O$_2$FNaS$^{79}$Br, found 386.9454.

Methyl 4-((4S,5R)-5-((E)-2-(2-(2-(4-fluorophenoxy)acetyl)benzo[b]thiophen-3-yl)vinyl)-2,2-dimethyl-1,3-dioxolan-4-yl)butanoate (53)

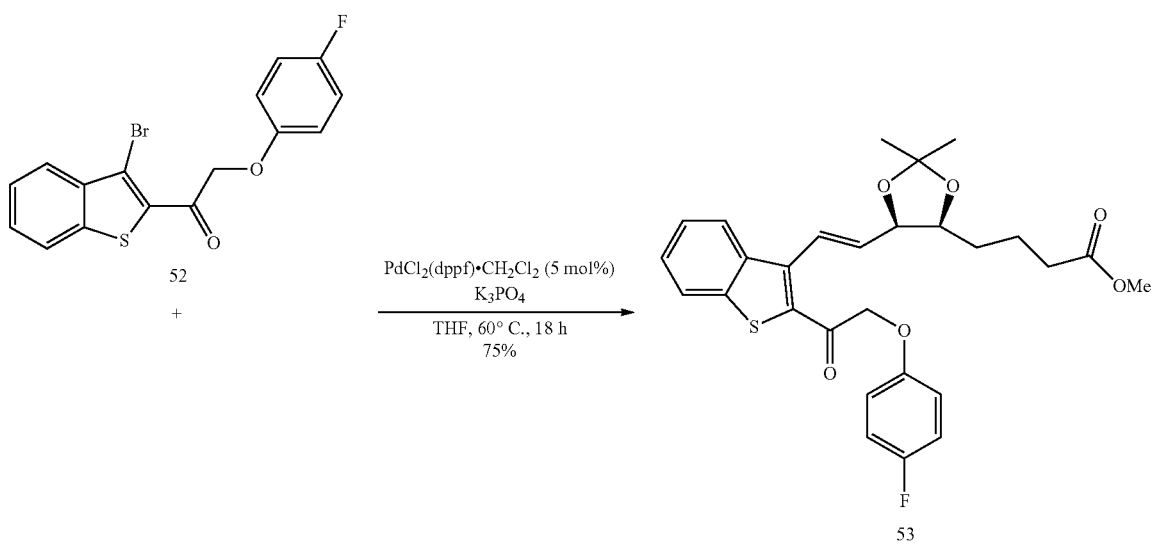

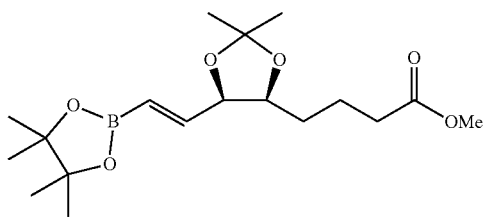

61

Benzothiophene bromide 52 (100 mg, 0.274 mmol, 1 eq) and boronic ester 61 (107 mg, 0.301 mmol, 1.1 eq) were dissolved in THF (3 mL) in a Schlenk tube. PdCl$_2$(dppf).CH$_2$Cl$_2$ (11.2 mg, 0.0137 mmol, 0.05 eq) was added followed by K$_3$PO$_4$ (0.55 mL of 3 M aq. sol, 1.644 mmol, 6 eq). The mixture was heated to 60° C., sealed under nitrogen and stirred for 48 h. The reaction mixture was quenched by addition of sat. NH$_4$Cl sol. (10 mL) and extracted with EtOAc (3×10 mL). Combined organic layers were washed with H$_2$O (20 mL), brine (20 mL), dried with MgSO$_4$, filtered and concentrated. The crude mixture was purified by silica gel column chromatography (6:1→3:1 pentane:EtOAc) to afford 53 as a yellow oil (105 mg, 75%). R$_f$=0.21 (6:1 pentane:EtOAc); $^1$H NMR (400 MHz, CDCl$_3$) δ 8.03 (d, J=8.0 Hz, 1H), 7.88 (d, J=8.0 Hz, 1H), 7.50 (m, 2H), 7.26 (dd, J=16.5, 1.0 Hz, 1H), 7.02-6.89 (m, 4H), 6.19 (dd, J=16.5, 7.7 Hz, 1H), 5.10 (s, 2H), 4.84-4.76 (m, 1H), 4.29 (ddd, J=8.5, 6.0, 5.0 Hz, 1H), 3.62 (s, 3H), 2.34 (t, J=7.5 Hz, 2H), 1.91-1.81 (m, 1H), 1.79-1.70 (m, 1H), 1.59-1.55 (m, 2H), 1.55 (s, 3H), 1.43 (s, 3H); $^{13}$C NMR (101 MHz, CDCl$_3$) δ 189.4, 173.6, 157.8 (d, J$_{F-C}$=240 Hz), 154.0 (d, J$_{F-C}$=2.0 Hz), 140.9, 140.0, 138.0, 134.1, 132.8, 128.1, 126.4, 125.5, 125.4, 122.9, 115.95 (d, J$_{F-C}$=23.5 Hz), 115.9 (d, J$_{F-C}$=8.0 Hz), 108.7, 79.4, 78.1, 72.9, 51.4, 33.7, 30.2, 28.3, 25.6, 21.8; IR (CHCl$_3$) (ν$_{max}$, cm$^{-1}$) 1732, 1671, 1504, 1199, 1163; [α]$_D$=−10.57 (c=1.1 in CHCl$_3$); HRMS (ESI) [M+Na]$^+$ calc 535.1567 for C$_{28}$H$_{29}$O$_6$FNaS, found 535.1559.

Methyl (5S,6R,E)-8-(2-((S)-2-(4-fluorophenoxy)-1-hydroxyethyl)benzo[b]thiophen-3-yl)-5,6-dihydroxyoct-7-enoate ((1S)-34)

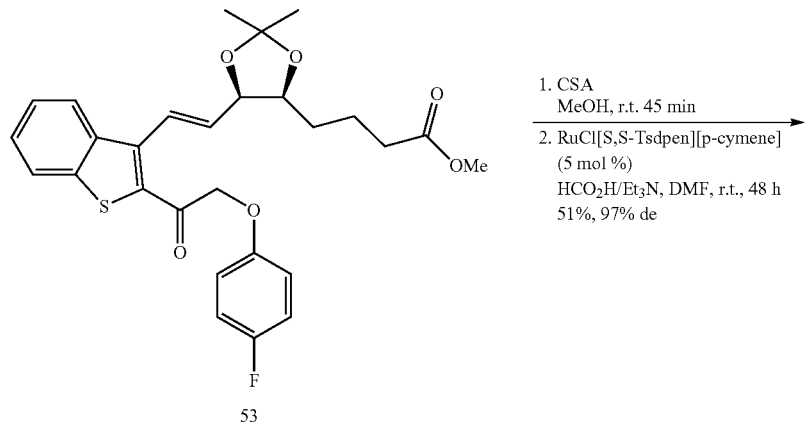

53

1. CSA
   MeOH, r.t. 45 min
2. RuCl[S,S-Tsdpen][p-cymene]
   (5 mol %)
   HCO$_2$H/Et$_3$N, DMF, r.t., 48 h
   51%, 97% de

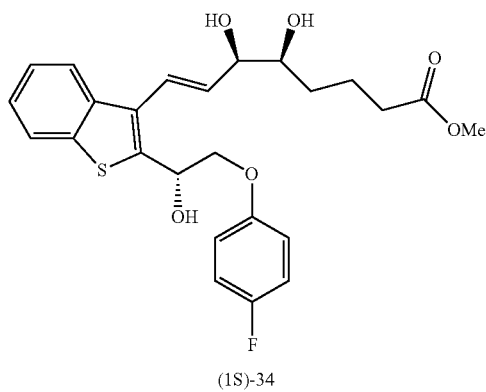

(1S)-34

Acetonide 53 (94.8 mg, 0.185 mmol, 1 eq) was dissolved in MeOH (3 mL), camphorsulfonic acid (86.2 mg, 0.371 mmol, 2 eq) was added and reaction mixture was stirred at room temperature for 45 min. Et$_3$N (0.06 mL, 0.371 mmol, 2 eq) was added and reaction mixture was concentrated without heat. The crude product was purified by silica gel column chromatography (4:1-1:1 cyclohexane:EtOAc) and product mixture isolated as a yellow oil (80 mg) which was dissolved in DMF (0.4 mL) and added to Schlenk tube followed by RuCl[S,S-Tsdpen][p-cymene] catalyst (5.4 mg, 0.0085 mmol, 0.05 eq), HCO$_2$H (0.03 mL, 0.727 mmol, 4.3 eq), Et$_3$N (0.06 mL, 0.423 mmol, 2.5 eq). The reaction mixture was stirred at room temperature for 48 h, then diluted with sat. NH$_4$Cl sol. (10 mL) and extracted with CH$_2$Cl$_2$ (2×20 mL). The combined organic layers were washed with 1:1 brine: H$_2$O (4×10 mL), dried over MgSO$_4$, filtered and concentrated. The crude mixture was purified by silica gel column chromatography (96:4 CH$_2$Cl$_2$:MeOH) to give (1S)-34 as a yellow oil (44.0 mg, 51%). R$_f$=0.16 (96:4 CH$_2$Cl$_2$:MeOH); $^1$H NMR (400 MHz, CDCl$_3$) δ 7.82-7.72 (m, 2H), 7.37-7.30 (m, 2H), 6.97-6.89 (m, 2H), 6.87-6.78 (m, 3H), 6.21 (dd, J=16.0, 6.5 Hz, 1H), 5.60 (t, J=5.5 Hz, 1H), 4.32-4.25 (m, 1H), 4.15 (d, J=5.5 Hz, 2H), 3.97 (s, 1H), 3.79-3.70 (m, 1H), 3.60 (s, 3H), 3.07 (s, 2H), 2.32-2.20 (m, 2H), 1.84-1.72 (m, 1H), 1.71-1.59 (m, 1H), 1.56-1.43 (m, 2H); $^{13}$C NMR (126 MHz, CDCl$_3$) δ 174.5, 157.7 (d, J$_{F-C}$=239.0 Hz), 154.4 (d, J$_{F-C}$=2.0 Hz), 140.3, 138.8, 138.7, 133.0, 130.8, 125.0, 124.6, 124.2, 122.7, 122.7, 116.1 (d, J$_{F-C}$=23 Hz), 115.9 (d, J$_{F-C}$=7.5 Hz), 76.0, 74.2, 73.0, 67.5, 51.8, 33.7, 31.8, 21.2; IR (CHCl$_3$) (v$_{max}$, cm$^{-1}$) 3020, 1728, 1506, 1080, 1036; [α]$_D$=−29.78 (c=1.1 in CHCl$_3$); HRMS (ESI) [M+Na] calc 497.1410 for C$_{25}$H$_{27}$O$_6$FNaS, found 497.1413. de=97% as determined by SFC using a Chiralpak IC column (CO$_2$:MeCN:EtOH, gradient 75:12.5:12.5 0-1 min, then gradient to 40:30:30 until 6 min, 3 mL/min), R$_t$=2.252 min (1S)-epimer, 3.549 min (1R)-epimer.

Methyl (5S,6R,E)-8-(2-((R)-2-(4-fluorophenoxy)-1-hydroxyethyl)benzo[b]thiophen-3-yl)-5,6-dihydroxyoct-7-enoate ((1R)-34)

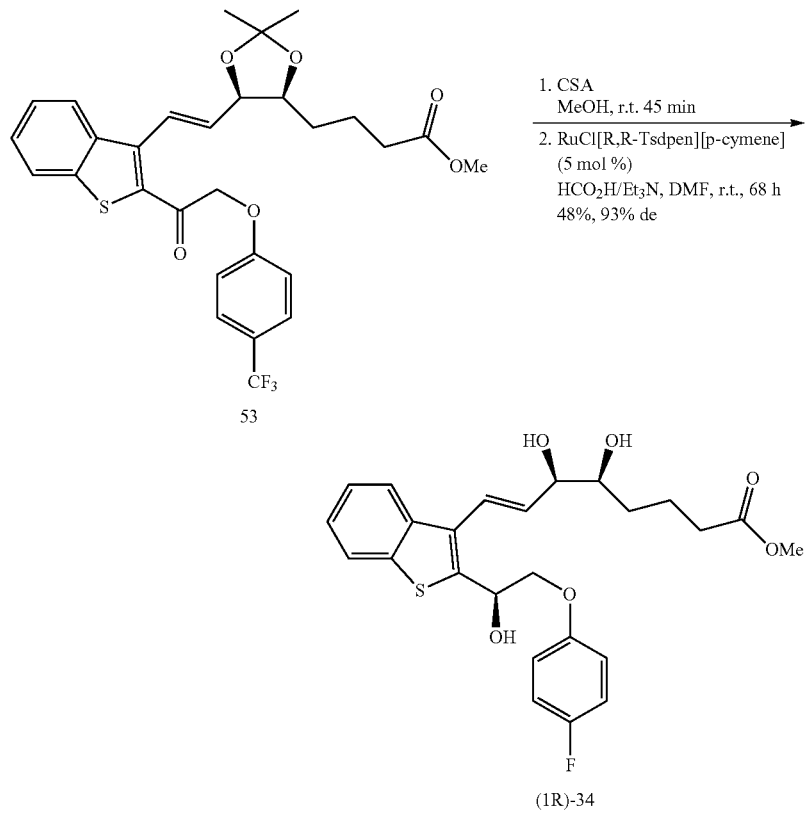

Acetonide 53 (75.9 mg, 0.148 mmol, 1 eq) was dissolved in MeOH (2.5 mL), camphorsulfonic acid (68.8 mg, 0.296 mmol, 2 eq) was added and reaction mixture was stirred at room temperature for 45 min. Et$_3$N (0.04 mL, 0.296 mmol, 2 eq) was added and reaction mixture was concentrated without heat. The crude product was purified by silica gel column chromatography (4:1-1:1 cyclohexane:EtOAc) and product mixture isolated as a yellow oil (70 mg) which was dissolved in DMF (0.4 mL) and added to Schlenk tube followed by RuCl[R,R-Tsdpen][p-cymene] catalyst (4.7 mg, 0.0074 mmol, 0.05 eq), HCO$_2$H (0.024 mL, 0.636 mmol, 4.3 eq), Et$_3$N (0.049 mL, 0.370 mmol, 2.5 eq). The reaction was stirred at room temperature for 68 h. The reaction mixture was diluted with sat. NH$_4$Cl sol. (10 mL) and extracted with CH$_2$Cl$_2$ (2×20 mL). The combined organic layers were washed with 1:1 brine: H$_2$O (4×10 mL), dried over MgSO$_4$, filtered and concentrated. The crude mixture was purified by silica gel column chromatography (96:4 CH$_2$Cl$_2$:MeOH) to give (1R)-34 as a yellow oil (36 mg, 48%). R$_f$=0.16 (96:4 CH$_2$Cl$_2$:MeOH); $^1$H NMR (400 MHz, CD$_3$CN) δ 7.95-7.86 (m, 2H), 7.45-7.35 (m, 2H), 7.08-6.97 (m, 2H), 6.98-6.89 (m, 2H), 6.82 (dd, J=16.0, 1.5 Hz, 1H), 6.23 (dd, J=16.0, 6.5 Hz, 1H), 5.56 (dd, J=7.0, 4.5 Hz, 1H), 4.30-4.04 (m, 4H), 3.58 (s, 3H), 2.29 (t, J=7.5 Hz, 2H), 2.15 (s, 2H), 1.81-1.74

(m, 1H), 1.67-1.55 (m, 2H), 1.45-1.38 (m, 1H); $^{13}$C NMR (101 MHz, CDCl$_3$) δ 174.4, 157.8 (d, J$_{F-C}$=239 Hz), 154.4 (d, J$_{F-C}$=2.0 Hz), 140.3, 138.9, 138.6, 133.1, 130.7, 125.0, 124.7, 124.3, 122.8, 122.8, 116.1 (d, J$_{F-C}$=23.0 Hz), 115.9 (d, J$_{F-C}$=8.0 Hz), 76.0, 74.1, 73.0, 67.7, 51.8, 33.7, 31.8, 21.2; IR (CHCl$_3$) (v$_{max}$, cm$^{-1}$) 3020, 1728, 1506, 1080, 1036; [α]$_D$=+45.42 (c=1 in CHCl$_3$); HRMS (ESI) [M+Na] calc 497.1410 for C$_{25}$H$_{27}$O$_6$NaSF, found 497.1418. de=93% as determined by SFC using a Chiralpak IC column (CO$_2$: MeCN:EtOH, gradient 75:12.5:12.5 0-1 min, then gradient to 40:30:30 until 6 min, 3 mL/min), R$_t$=2.252 min (1S)-epimer, 3.549 min (1R)-epimer.

Methyl 2-(4-(trifluoromethyl)phenoxy)acetate (57)[33]

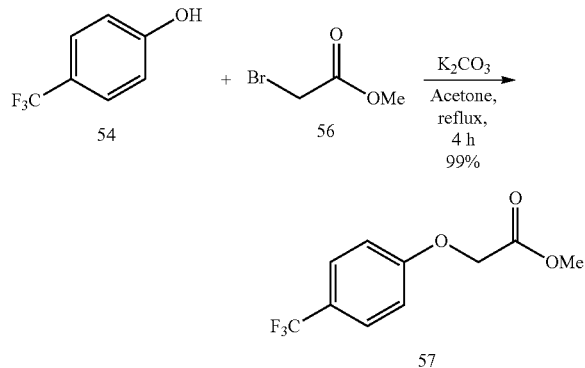

4-(Trifluoromethyl)phenol 54 (1.0 g, 6.169 mmol, 1 eq) was dissolved in acetone (25 mL). K$_2$CO$_3$ (938 mg, 6.786 mmol, 1.1 eq) and methyl bromoacetate 56 (0.58 mL, 6.169 mmol, 1 eq) were added and the reaction mixture was heated to reflux and stirred for 4 h. Reaction mixture was diluted with H$_2$O (50 mL) and extracted with CH$_2$Cl$_2$ (2×50 mL), washed with brine (50 mL), dried over MgSO$_4$, filtered and concentrated to product 57, a pale yellow oil (1.432 g, 99%). $^1$H NMR (400 MHz, CDCl$_3$) δ 7.53 (d, J=8.5 Hz, 2H), 6.94 (d, J=8.5 Hz, 2H), 4.65 (s, 2H), 3.78 (s, 3H). $^1$H NMR (400 MHz, CDCl$_3$) δ 7.53 (d, J=8.5 Hz, 2H), 6.94 (d, J=8.5 Hz, 2H), 4.65 (s, 2H), 3.78 (s, 3H); $^{13}$C NMR (101 MHz, CDCl$_3$) δ 168.7, 160.1 (q, J=2.0 Hz), 127.0 (q, J=3.5 Hz), 124.2 (q, J=271.2 Hz), 124.0 (q, J=32.8 Hz), 114.6, 65.1, 52.4; $^{19}$F NMR (376 MHz, CDCl$_3$) δ -61.76; IR (ATR) (v$_{max}$, cm$^{-1}$) 1758, 1209, 1162, 1109, 1060; [M]$^+$ calc 234.0504 for C$_{10}$H$_9$O$_3$F$_3$, found 234.0511.

2-(4-(Trifluoromethyl)phenoxy)acetaldehyde (58)

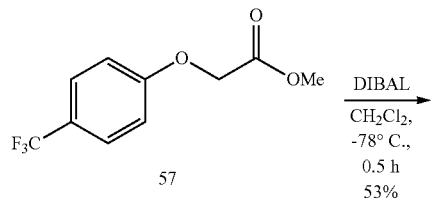

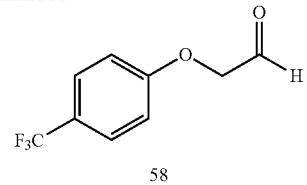

DIBAL (2.5 mL of 1 M sol. in hexanes, 2.50 mmol, 1.17 eq) was added to CH$_2$Cl$_2$ (20 mL) and cooled to -78° C. Ester 57 in CH$_2$Cl$_2$ (5 mL) was added dropwise and the reaction mixture was stirred for a further 30 min at -78° C. The reaction was quenched by the addition of MeOH (2 mL) and sat. Rochelle's salt sol. (50 mL) and stirred while warming to room temperature for 1 h. The layers were separated and the aqueous layer extracted with CH$_2$Cl$_2$ (3×20 mL). Combined organic layers were washed with brine (50 mL), dried over MgSO$_4$, filtered and concentrated. Crude mixture was purified by silica gel column chromatography (10:1→1:1 cyclohexane:EtOAc) to yield 58 as a yellow oil (230 mg, 53%). R$_f$=0.56 (1:1 cyclohexane:EtOAc); $^1$H NMR (400 MHz, CDCl$_3$) δ 9.84 (t, J=1.0 Hz, 1H), 7.56 (d, J=8.5 Hz, 2H), 6.95 (d, J=8.5 Hz, 2H), 4.62 (d, J=1.0 Hz, 2H); $^{13}$C NMR (101 MHz, CDCl$_3$) δ 197.9, 159.9 (d, J$_{F-C}$=1.0 Hz), 127.2 (q, J$_{F-C}$=3.5 Hz), 124.2 (q, J$_{F-C}$=33.0 Hz), 124.1 (q, J$_{F-C}$=271.0 Hz), 114.6, 72.5; $^{19}$F NMR (376 MHz, CDCl$_3$) δ -61.71; IR (ATR) (v$_{max}$, cm$^{-1}$) 1741, 1159, 1105, 1042, 1010; [M]$^+$ calc 204.0398 for C$_9$H$_7$O$_2$F$_3$, found 204.0405.

1-(3-Bromobenzo[b]thiophen-2-yl)-2-(4-(trifluoromethyl)phenoxy)ethan-1-ol (59)

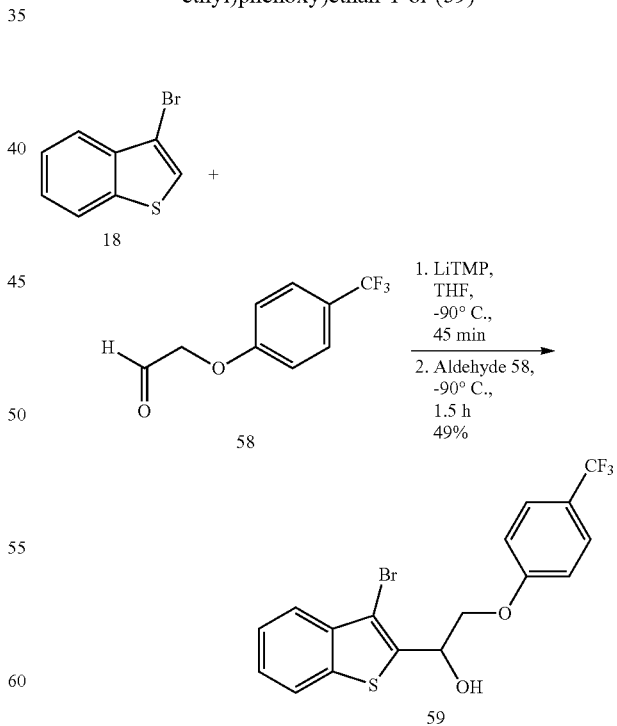

nBuLi (2.7 ml of 2.5 M sol. in hexanes, 6.783 mmol, 1 eq) was added to THF (10 mL) and cooled to -60° C. TMP (1.04 mL, 6.101 mmol, 1.3 eq) was added and warmed to 0° C. for 30 min. The reaction mixture was cooled to -78° C. and 3-bromobenzothiophene 18 (1.2 g, 5.652 mmol, 1 eq) was added dropwise and stirred for 45 min. Trifluormethylphenoxyacetaldehyde 58 (1.5 g, 7.348 mmol, 1.3 eq) dissolved in THF (5 mL) was added at −78° C. and stirred for 1.5 h. The reaction was quenched by addition of HCl (6 mL of a 5 M aq. sol.) and warmed to room temperature. Sat. NaHCO$_3$ sol. (c. 22 mL) was added to neutralise the reaction mixture and it was extracted with EtOAc (3×40 mL), the extracts were washed with brine (50 mL), dried over MgSO$_4$, filtered and concentrated. The crude mixture was purified by silica gel column chromatography (cyclohexane: EtOAc 10:1-6:1) to afford product 59 as a pale pink solid (1.166 g, 49%). R$_f$=0.35 (6:1 pentane:EtOAc); M.p.=72-76° C.; $^1$H NMR (400 MHz, CDCl$_3$) δ 7.87-7.79 (m, 2H), 7.60-7.54 (m, 2H), 7.52-7.39 (m, 2H), 7.04 (d, J=8.5 Hz, 2H), 5.70 (dt, J=8.0, 3.0 Hz, 1H), 4.38 (dd, J=9.5, 3.0 Hz, 1H), 4.20 (dd, J=9.5, 8.0 Hz, 1H), 2.95 (d, J=3.0 Hz, 1H); $^{13}$C NMR (101 MHz, CDCl$_3$) δ 160.4 (q, J$_{F-C}$=1.5 Hz), 138.3, 137.8, 137.5, 127.0 (q, J$_{F-C}$=3.5 Hz), 125.7, 125.2, 123.8 (q, J$_F$C=33.0 Hz), 122.9, 122.7, 114.7, 105.6, 71.2, 69.0 (*CF$_3$ carbon not visible); $^{19}$F NMR (376 MHz, CDCl$_3$) δ −61.66 IR (ATR) (v$_{max}$, cm$^{-1}$) 3252, 1154, 1102, 1070; HRMS (ESI) [M]$^+$ calc 415.9693 for C$_{17}$H$_{12}$O$_2$F$_3$S$^{79}$Br, found 415.9692.

1-(3-Bromobenzo[b]thiophen-2-yl)-2-(4-(trifluoromethyl)phenoxy)ethan-1-one

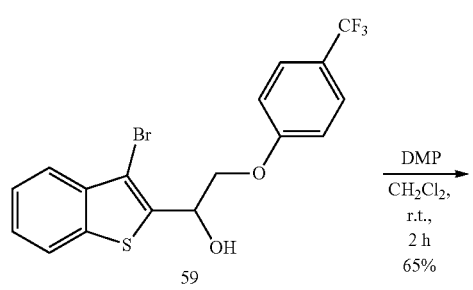

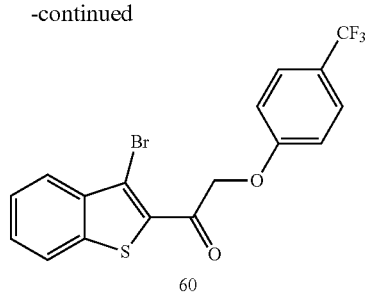

Alcohol 59 (500 mg, 1.198 mmol, 1 eq) was dissolved in CH$_2$Cl$_2$ (8 mL) and Dess-Martin periodinane (1.016 g, 2.397 mmol, 2 eq) was added and reaction mixture stirred at room temperature for 2 h. The reaction mixture was diluted with CH$_2$Cl$_2$ (10 mL), washed with 1:1 sat. NaHCO$_3$ sol.: sat. Na$_2$S$_2$O$_3$ sol. (4×10 mL), H$_2$O (10 mL), brine (10 mL), dried over MgSO$_4$, filtered and concentrated. The crude product was recrystallised from 2-propanol to yield 60 as a pale yellow solid (344 mg, 58%). R$_f$=0.50 (6:1 pentane:EtOAc); M.p.=150-154° C.; $^1$H NMR (400 MHz, CDCl$_3$) δ 8.07-7.95 (m, 1H), 7.93-7.84 (m, 1H), 7.62-7.52 (m, 4H), 7.04 (d, J=8.5 Hz, 2H), 5.53 (s, 2H); $^{13}$C NMR (101 MHz, CDCl$_3$) δ 187.6, 160.2 (q, J$_{F-C}$=1.5 Hz), 139.9, 138.7, 136.4, 128.9, 127.0 (q, J$_{F-C}$=3.5 Hz), 126.1, 125.8, 123.9 (q, J$_{F-C}$=33.0 Hz), 122.9, 114.8, 112.7, 72.4 (*CF$_3$ carbon not visible); $^{19}$F NMR (376 MHz, CDCl$_3$) δ −61.69; IR (ATR) (v$_{max}$, cm$^{-1}$) 1656, 1203, 1160; HRMS (ESI) [M+Na]$^+$ calc 436.9435 for C$_{17}$H$_{10}$O$_2$F$_3$NaS$^{79}$Br, found 436.9436.

Methyl 4-((4S,5R)-2,2-dimethyl-5-((E)-2-(2-(2-(4-trifluoromethyl)phenoxy)acetyl)benzo[b]thiophen-3-yl)vinyl)-1,3-dioxolan-4-yl)butanoate (62)

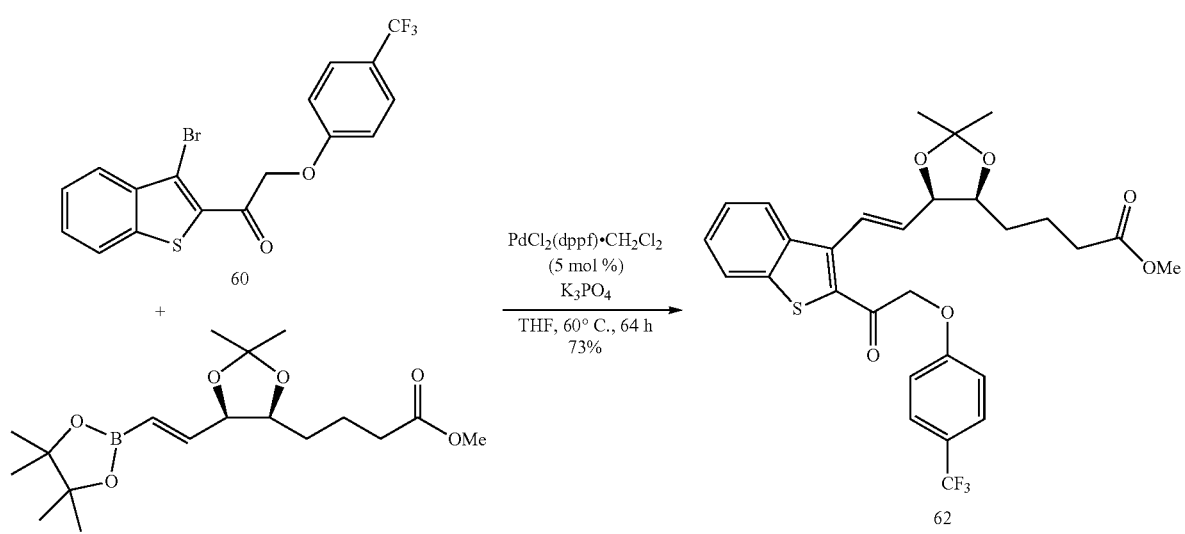

Benzothiophene bromide 60 (100 mg, 0.241 mmol, 1 eq) and boronic ester 61 (94 mg, 0.265 mmol, 1.1 eq) were dissolved in THF (3 mL) in a Schlenk tube. PdCl$_2$(dppf).CH$_2$Cl$_2$ (10 mg, 0.0121 mmol, 0.05 eq) was added followed by K$_3$PO$_4$ (0.48 mL of 3 M aq. sol, 1.446 mmol, 6 eq). The mixture was heated to 60° C., sealed under nitrogen and stirred for 64 h. The reaction mixture was quenched with sat. NH$_4$Cl sol. (10 mL) and extracted with EtOAc (3×10 mL). Combined organic layers were washed with H$_2$O (20 mL), brine (20 mL), dried with MgSO$_4$, filtered and concentrated. Crude mixture was purified by silica gel column chromatography (6:1→3:1 pentane:EtOAc) to give 62 as a yellow oil (98 mg, 73%). R$_f$=0.15 (6:1 pentane:EtOAc); $^1$H NMR (400 MHz, CDCl$_3$) δ 8.01 (d, J=8.0 Hz, 1H), 7.86 (d, J=8.0 Hz, 1H), 7.56-7.44 (m, 4H), 7.23 (dd, J=16.0, 1.0 Hz, 1H), 7.02 (d, J=8.5 Hz, 2H), 6.18 (dd, J=16.0, 7.5 Hz, 1H), 5.17 (s, 2H), 4.82-4.75 (m, 1H), 4.27 (ddd, J=8.5, 6.0, 5.0 Hz, 1H), 3.60 (s, 3H), 2.32 (td, J=7.5, 1.0 Hz, 2H), 1.89-1.80 (m, 1H), 1.77-1.56 (m, 3H), 1.53 (s, 3H), 1.41 (s, 3H); $^{13}$C NMR (101 MHz, CDCl$_3$) δ 188.8, 173.8, 160.4 (q, J$_{F-C}$=1.2 Hz), 141.1, 140.4, 138.2, 134.5, 132.8, 128.4, 127.2 (q, J$_{F-C}$=3.7 Hz), 126.4, 125.7, 125.6, 124.1 (q, J$_{F-C}$=32.9 Hz), 123.1, 114.9, 108.9, 79.5, 78.2, 72.2, 51.6, 33.8, 30.3, 28.4, 25.7, 21.90 (*CF3 carbon not visible); $^{19}$F NMR (376 MHz, CDCl$_3$) δ −61.68; IR (ATR) (v$_{max}$, cm$^{-1}$) 1733, 1671, 1326, 1210, 1159, 1110; [α]$_D$=−1.83 (c=1.26 in CHCl$_3$); [M+Na]$^+$ calc 585.1535 for C$_{29}$H$_{29}$O$_6$F$_3$NaS, found 585.1538.

Methyl(5S,6R,E)-5,6-dihydroxy-8-(2-((S)-1-hydroxy-2-(4-(trifluoromethyl)phenoxy)ethyl)benzo[b]thiophen-3-yl)oct-7-enoate ((1S)-35)

Acetonide 62 (97.8 mg, 0.174 mmol, 1 eq) was dissolved in MeOH (3 mL), camphorsulfonic acid (80.8 mg, 0.348 mmol, 2 eq) was added and reaction mixture was stirred at room temperature for 45 min. Et$_3$N (0.046 mL, 0.348 mmol, 2 eq) was added and reaction mixture was concentrated without heat. The crude product was purified by silica gel column chromatography (96:4 CH$_2$Cl$_2$:MeOH) and product mixture isolated as a yellow oil (80 mg) which was dissolved in DMF (0.6 mL) and added to Schlenk tube followed by RuCl[R,R-Tsdpen][p-cymene] catalyst (4.9 mg, 0.00765 mmol, 0.05 eq), HCO$_2$H (0.024 mL, 0.636 mmol, 4.3 eq), Et$_3$N (0.050 mL, 0.370 mmol, 2.5 eq). Reaction was stirred at room temperature for 46 h. Reaction mixture was diluted with sat. NH$_4$Cl sol. (10 mL) and extracted with CH$_2$Cl$_2$ (2×20 mL). The combined organic layers were washed with 1:1 brine:H$_2$O (4×10 mL), dried over MgSO$_4$, filtered and concentrated. The crude mixture was purified by silica gel column chromatography (92:8 CH$_2$Cl$_2$:MeOH) to give (1S)-35 as a yellow oil (35 mg, 39%). R$_f$=0.40 (92:8 CH$_2$Cl$_2$:MeOH); $^1$H NMR (500 MHz, CDCl$_3$) δ 7.81-7.74 (m, 2H), 7.49 (d, J=8.5 Hz, 2H), 7.37-7.30 (m, 2H), 6.94 (d, J=8.5 Hz, 2H), 6.82 (d, J=16.0 Hz, 1H), 6.23 (dd, J=16.0, 6.0 Hz, 1H), 5.63 (dd, J=7.0, 4.5 Hz, 1H), 4.29 (dd, J=6.0, 3.5 Hz, 1H), 4.25-4.19 (m, 2H), 3.76 (td, J=8.5, 4.5 Hz, 1H), 3.59 (s, 3H), 3.05 (br. s, 2H), 2.25 (t, J=7.0 Hz, 2H), 1.81-1.72 (m, 1H), 1.66-1.59 (m, 1H), 1.54-1.43 (m, 2H); $^{13}$C NMR (126 MHz, CDCl$_3$) δ 174.5, 160.7 (q, J$_{F-C}$=1.0 Hz), 140.1, 138.8, 138.6, 133.1, 130.9, 127.1 (q, J$_{F-C}$=3.5 Hz), 125.1, 124.7, 124.4 (q, J$_{F-C}$=271.0 Hz) 124.2, 123.7 (q, J$_{F-C}$=33.0 Hz), 122.8, 122.7, 114.8, 76.0, 74.2, 72.3, 67.3, 51.8, 33.6, 31.8, 21.1; $^{19}$F NMR (376 MHz, CDCl$_3$) δ −61.61; IR (ATR) (v$_{max}$,

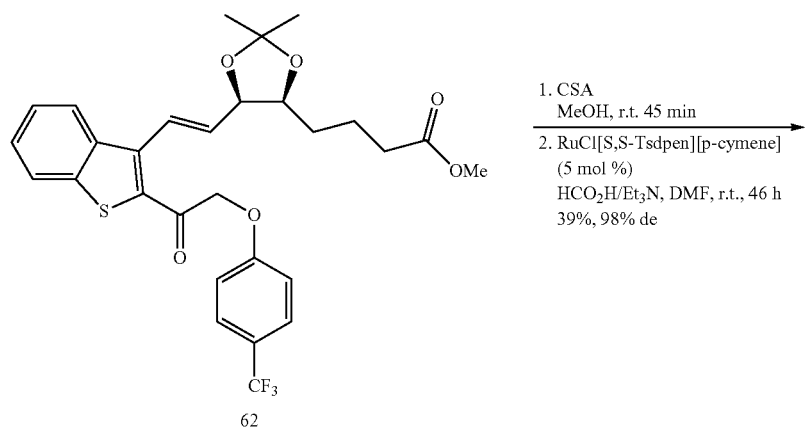

1. CSA
MeOH, r.t. 45 min

2. RuCl[S,S-Tsdpen][p-cymene]
(5 mol %)
HCO$_2$H/Et$_3$N, DMF, r.t., 46 h
39%, 98% de

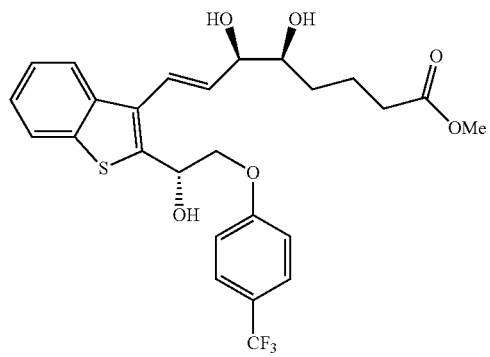

(1S)-35 cm⁻¹) 3422, 1729, 1328, 1122, 1112, 1070; [α]$_D$=−31.25 (c=1.70 in CHCl$_3$); [M+Na] calc 547.1378 for C$_{26}$H$_{27}$O$_6$FNaSF$_3$, found 547.1373; de=98% as determined by SFC using a Chiralpak IC column (CO$_2$:MeCN:EtOH, gradient 75:12.5:12.5 0-1 min, then gradient to 40:30:30 until 6 min, 3 mL/min), R$_t$=1.55 min (1S)-epimer, 2.60 min (1R)-epimer.

Methyl (5S,6R,E)-5,6-dihydroxy-8-(2-((R)-1-hydroxy-2-(4-(trifluoromethyl)phenoxy)ethyl)benzo[b]thiophen-3-yl)oct-7-enoate ((1R)-35)

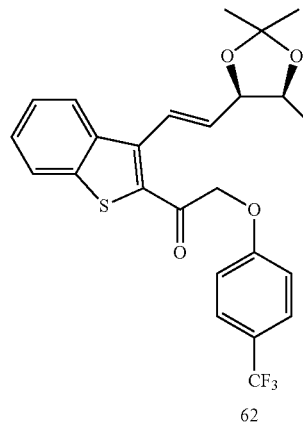

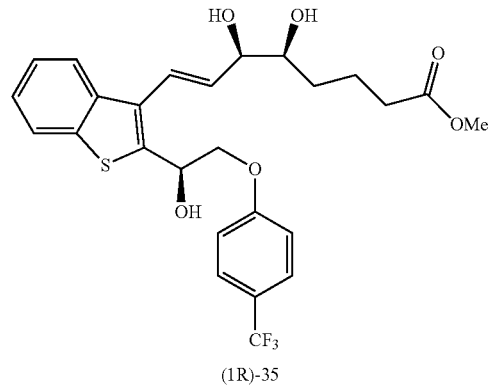

Acetonide 62 (97.8 mg, 0.174 mmol, 1 eq) was dissolved in MeOH (3 mL), camphorsulfonic acid (80.8 mg, 0.348 mmol, 2 eq) was added and reaction mixture was stirred at room temperature for 45 min. Et$_3$N (0.046 mL, 0.348 mmol, 2 eq) was added and reaction mixture was concentrated without heat. The crude product was purified by silica gel column chromatography (96:4 CH$_2$Cl$_2$:MeOH) and product mixture isolated as a yellow oil (80 mg) which was dissolved in DMF (0.6 mL) and added to Schlenk tube followed by RuCl[S,S-Tsdpen][p-cymene] catalyst (4.8 mg, 0.00765 mmol, 0.05 eq), HCO$_2$H (0.024 mL, 0.636 mmol, 4.3 eq), Et$_3$N (0.050 mL, 0.370 mmol, 2.5 eq). Reaction was stirred at room temperature for 65 h. Reaction mixture was diluted with sat. NH$_4$Cl sol. (10 mL) and extracted with CH$_2$Cl$_2$ (2×20 mL). The combined organic layers were washed with 1:1 brine:H$_2$O (4×10 mL), dried over MgSO$_4$, filtered and concentrated. The crude mixture was purified by silica gel column chromatography (92:8 CH$_2$Cl$_2$:MeOH) to yield (1R)-35 as a yellow oil (46 mg, 66%). R$_f$=0.40 (92:8 CH$_2$Cl$_2$:MeOH); $^1$H NMR (500 MHz, CDCl$_3$) δ 7.85-7.79 (m, 2H), 7.52 (d, J=8.5 Hz, 2H), 7.36 (m, 2H), 6.96 (d, J=8.5 Hz, 2H), 6.85 (d, J=16.0, 1H), 6.25 (dd, J=16.0, 6.0 Hz, 1H), 5.64 (dd, J=6.5, 5.0 Hz, 1H), 4.32 (dd, J=6.0, 3.5 Hz, 1H), 4.26-4.22 (m, 2H), 3.80-3.76 (m, 1H), 3.67 (s, 1H), 3.62 (s, 3H), 2.83 (br. s, 1H), 2.74 (br. s, 1H), 2.30 (td, J=7.0, 1.5 Hz, 2H), 1.85-1.78 (m, 1H), 1.71-1.66 (m, 1H), 1.57-1.48 (m, 2H); $^{13}$C NMR (126 MHz, CDCl$_3$) δ 174.5, 160.7 (q, J$_{F-C}$=1.5 Hz), 140.0, 138.9, 138.6, 133.2, 130.9, 127.1 (q, J$_{F-C}$=3.5 Hz), 125.1, 124.7, 124.4 (q, J$_{F-C}$=271.5 Hz), 124.2, 123.7 (q, J$_{F-C}$=32.5 Hz), 122.8, 122.8, 114.8, 75.9, 74.1, 72.3, 67.4, 51.8, 33.7, 31.8, 21.1; $^{19}$F NMR (376 MHz, CDCl$_3$) δ −61.62; IR (ATR) (ν$_{max}$, cm⁻¹) 3422, 1729, 1328, 1122, 1112, 1070; [α]$_D$=+29.81 (c=0.60 in CHCl$_3$); [M+Na] calc 547.1378 for C$_{26}$H$_{27}$O$_6$NaSF$_3$, found 547.1371; de=99% as determined by SFC using a Chiralpak IC column (CO$_2$:MeCN:EtOH, gradient 75:12.5:12.5 0-1 min, then gradient to 40:30:30 until 6 min, 3 mL/min), R$_t$=1.55 min (1S)-epimer, 2.60 min (1R)-epimer.

Compounds (1S)-2 and (1R)-2 of Formula (VIr)

1-(5-Bromopyrimidin-4-yl)hexan-1-one (26)

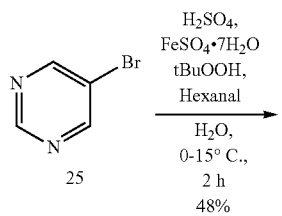

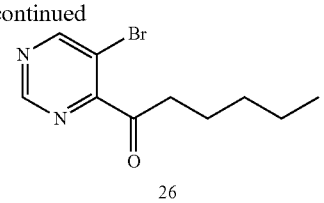

5-Bromopyrimidine 25 (800 mg, 5.032 mmol, 1 eq) was dissolved in H$_2$SO$_4$ (3.48 mL of a 4.5 N aq. sol.) and HOAc (4 mL) and reaction mixture was cooled to 0° C. A solution of FeSO$_4$.7H$_2$O (2.1 g, 7.548 mmol, 1.5 eq) in H$_2$O (3.6 mL) was added dropwise along with tBuOOH (1.2 mL of 70% aq. sol., 7.548 mmol, 1.5 eq). The reaction mixture was stirred for 2 h warming to room temperature. The pH was adjusted to 8 by addition of sat. NaHCO$_3$ sol. (c. 25 mL), the mixture was extracted with EtOAc (3×30 mL), and the extracts washed with H$_2$O (30 mL), brine (30 mL), dried over MgSO$_4$, filtered and concentrated. The crude mixture was purified by silica gel column chromatography (6:1 cyclohexane:EtOAc) to afford 26 as a yellow oil (610 mg, 48%). R$_f$=0.60 (6:1 pentane:EtOAc); $^1$H NMR (500 MHz, CDCl$_3$) δ 9.15 (s, 1H), 8.97 (s, 1H), 3.03 (t, J=7.5 Hz, 2H), 1.74-1.69 (m, 2H), 1.37-1.28 (m, 4H), 0.90 (t, J=6.0 Hz, 3H); $^{13}$C NMR (126 MHz, CDCl$_3$) δ 200.7, 161.4, 159.2, 156.4, 116.1, 39.9, 31.2, 23.0, 22.4, 13.9; IR (CHCl$_3$) (v$_{max}$, cm$^{-1}$) 2931, 1730, 1466; HRMS [M+H]$^+$ calc 257.0289 for C$_{10}$H$_{14}$N$_2$O$^{79}$Br, found 257.0300.

Methyl 4-((4S,5R)-5-((E)-2-(4-hexanoylpyrimidin-5-yl)vinyl)-2,2-dimethyl-1,3-dioxolan-4-yl)butanoate (24)

Bromide 26 (50.0 mg, 0.194 mmol, 1.0 eq) dissolved in THF (1 mL) was added to Schlenk containing PdCl$_2$(dppf).CH$_2$Cl$_2$ (8.1 mg, 0.010 mmol, 0.05 eq) and boronic ester 61 (75.8 mg, 0.214 mmol, 1.1 eq) dissolved in THF (2 mL). K$_3$PO$_4$ (0.39 mL of 3 M aq. sol., 1.17 mmol, 6.03 eq) was added and reaction mixture was heated to 60° C. and stirred for 66 h. The reaction mixture was diluted with H$_2$O (10 mL), extracted with EtOAc (3×15 mL), and the extracts washed with brine (30 mL), dried over MgSO$_4$, filtered and concentrated. The crude mixture was purified by silica gel column chromatography (6:1→3:1 cyclohexane:EtOAc) to give 24 as a yellow oil (50 mg, 67%). R$_f$=0.30 (3:1 pentane:EtOAc); $^1$H NMR (500 MHz, CDCl$_3$) δ 9.17 (s, 1H), 8.99 (s, 1H), 7.19 (d, J=16.0 Hz, 1H), 6.17 (dd, J=16.0, 7.0 Hz, 1H), 4.71 (t, J=7.0 Hz, 1H), 4.27-4.22 (m, 1H), 3.64 (s, 3H), 3.19-3.04 (m, 2H), 2.39-2.32 (m, 2H), 1.86-1.79 (m, 1H), 1.75-1.66 (m, 3H), 1.53 (s, 3H), 1.52-1.41 (m, 2H), 1.39 (s, 3H), 1.37-1.32 (m, 4H), 0.90 (t, J=6.0 Hz, 3H); $^{13}$C NMR (126 MHz, CDCl$_3$) δ 203.8, 173.8, 157.3, 156.9, 155.5, 132.2, 128.3, 126.4, 108.7, 78.9, 78.2, 51.5, 39.6, 33.7, 31.3, 29.9, 28.2, 25.6, 23.3, 22.4, 21.7, 13.9; IR (CHCl$_3$) (v$_{max}$, cm$^{-1}$) 2933, 1734, 1707, 1211, 1029; [α]$_D$=+10.62 (c=1.65 in CHCl$_3$); HRMS [M+H]$^+$ calc 405.2389 for C$_{22}$H$_{33}$N$_2$O$_5$, found 405.2399.

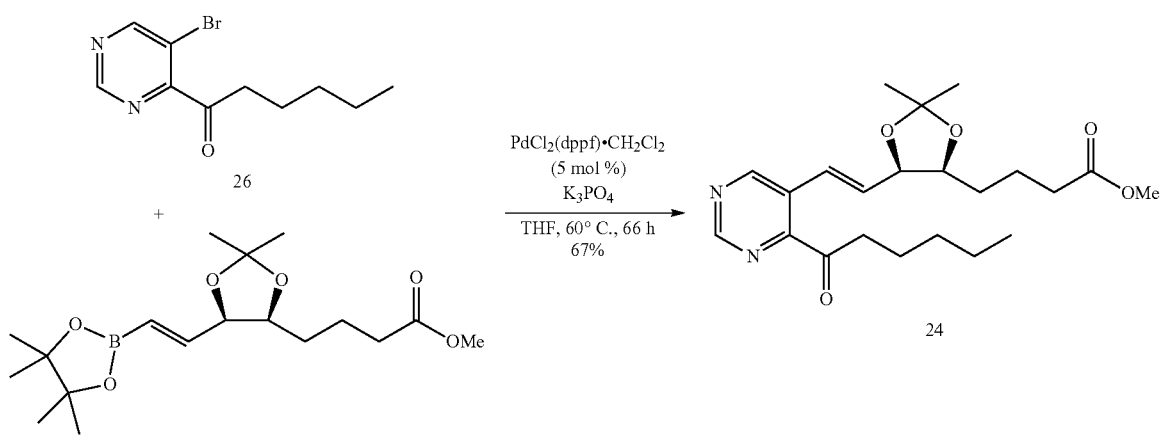

Methyl 4-((4S,5R)-5-((E)-2-(4-((S)-1-hydroxyhexyl)pyrimidin-5-yl)vinyl)-2,2-dimethyl-1,3-dioxolan-4-yl)butanoate ((1S)-23)

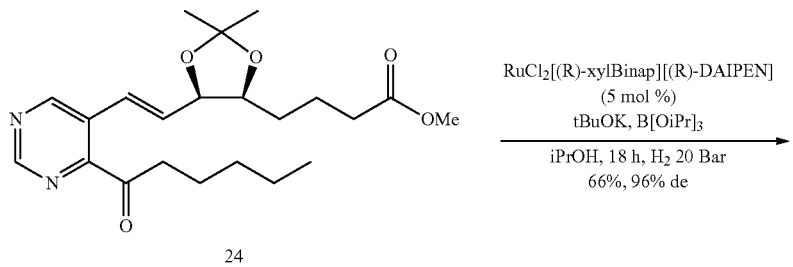

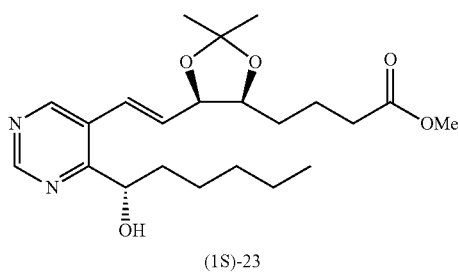

Pyrimidine ketone 24 (35.0 mg, 0.0865 mmol, 1.0 eq) was dissolved in iPrOH (1.5 mL). RuCl$_2$[(R)-xylBinap][(R)-DAIPEN] (5.3 mg, 0.0043 mmol, 0.05 eq), triisopropyl borate (0.02 mL) and KOtBu (2.4 mg, 0.0216, 0.25 eq) were added. The reaction mixture was stirred under 20 Bar of H$_2$ for 18 h, after which time it was concentrated and purified by column chromatography (95:5 CH$_2$Cl$_2$:MeOH) to yield (1S)-23 as a brown oil (23 mg, 66%). R$_f$=0.13 (3:1 pentane: EtOAc); $^1$H NMR (500 MHz, CDCl$_3$) δ 9.05 (s, 1H), 8.73 (s, 1H), 6.67 (d, J=16.0 Hz, 1H), 6.20 (dd, J=16.0, 6.5 Hz, 1H), 4.93-4.86 (m, 1H), 4.72 (t, J=6.5 Hz, 1H), 4.29-4.23 (m, 1H), 4.19 (d, J=7.5 Hz, 1H), 3.64 (s, 3H), 2.38-2.30 (m, 2H), 1.86-1.80 (m, 1H), 1.78-1.64 (m, 2H), 1.53 (s, 3H), 1.51-1.43 (m, 5H), 1.40 (s, 3H), 1.31-1.24 (m, 4H), 0.86 (t, J=7.0 Hz, 3H); $^{13}$C NMR (126 MHz, CDCl$_3$) δ 173.8, 167.0, 156.7, 154.4, 132.2, 127.2, 123.7, 108.9, 78.7, 78.3, 69.6, 51.7, 37.8, 33.7, 31.7, 30.2, 28.2, 25.6, 25.2, 22.7, 21.8, 14.1; IR (CHCl$_3$) (ν$_{max}$, cm$^{-1}$) 3449, 2949, 1735, 1024; [α]$_D$=−1.49 (c=1.15 in CHCl$_3$); HRMS [M+Na]$^+$ calc 429.2365 for C$_{22}$H$_{34}$N$_2$O$_5$Na, found 429.2376; de=96% as determined by SFC using a Chiralpak IC column (CO$_2$: MeOH, gradient 99:1 0-1 min, then gradient to 60:40 until 5 min, 3 mL/min), R$_t$=3.58 min (1S)-epimer, 3.85 min (1R)-epimer.

Methyl 4-((4S,5R)-5-((E)-2-(4-((R)-1-hydroxyhexyl)pyrimidin-5-yl)vinyl)-2,2-dimethyl-1,3-dioxolan-4-yl)butanoate ((1R)-23)

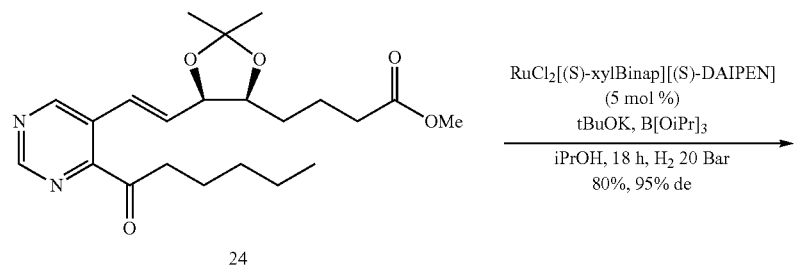

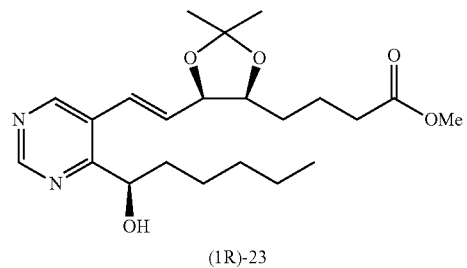

Pyrimidine Ketone 24 (63.1 mg, 0.156 mmol, 1 eq) was dissolved in iPrOH (1.5 mL). RuCl$_2$[(S)-xylBinap][(S)-DAIPEN] (9.5 mg, 0.0078 mmol, 0.05 eq), triisopropyl borate (0.02 mL) and KOtBu (4.4 mg, 0.039, 0.25 eq) were added. The reaction mixture was stirred under 20 Bar of H$_2$ for 18 h, after which time it was concentrated and purified by column chromatography (95:5 CH$_2$Cl$_2$:MeOH) to afford (1R)-23 as a yellow oil (50 mg, 80%). R$_f$=0.13 (3:1 pentane:EtOAc); $^1$H NMR (400 MHz, CDCl$_3$) δ 9.04 (s, 1H), 8.72 (s, 1H), 6.68 (d, J=16.0 Hz, 1H), 6.18 (dd, J=16.0, 7.0 Hz, 1H), 4.98-4.81 (m, 1H), 4.78-4.64 (m, 1H), 4.29-4.21 (m, 1H), 4.18 (br. s, 1H), 3.63 (s, 3H), 2.38-2.30 (m, 2H), 1.87-1.78 (m, 1H), 1.74-1.65 (m, 2H), 1.52 (s, 3H), 1.47-1.41 (m, 5H), 1.39 (s, 3H), 1.32-1.21 (m, 4H), 0.85 (t, J=7.0 Hz, 3H); $^{13}$C NMR (101 MHz, CDCl$_3$) δ 173.6, 166.9, 156.5, 154.4, 132.1, 127.1, 123.9, 108.8, 78.5, 78.1, 69.5, 51.5, 37.5, 33.5, 31.5, 30.0, 28.1, 25.5, 24.9, 22.5, 21.7, 14.0; IR (CHCl$_3$) ($v_{max}$, cm$^{-1}$) 3449, 2949, 1735, 1024; [α]$_D$=+16.02 (c=1.0 in CHCl$_3$); HRMS [M+Na]$^+$ calc 429.2365 for C$_{22}$H$_{34}$N$_2$O$_5$Na, found 429.2371; de=95% as determined by SFC using a Chiralpak IC column (CO$_2$: MeOH, gradient 99:1 0-1 min, then gradient to 60:40 until 5 min, 3 mL/min), R$_t$=3.58 min (1S)-epimer, 3.85 min (1R)-epimer.

Methyl (5S,6R,E)-5,6-dihydroxy-8-(4-((S)-1-hydroxyhexyl)pyrimidin-5-yl)oct-7-enoate ((1S)-2)

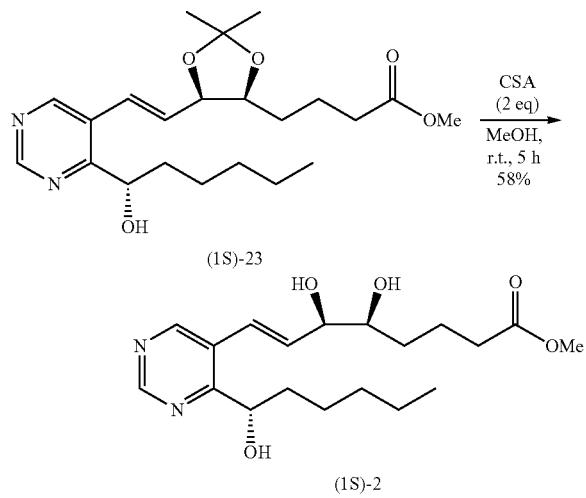

Acetonide (1S)-23 (25.0 mg, 0.0615 mmol, 1 eq) was dissolved in MeOH (1.5 mL). Camphorsulfonic acid (28.6 mg, 0.123 mmol, 2 eq) was added and the reaction mixture was stirred at room temperature for 5 h. The reaction mixture was concentrated and purified by preparative TLC (92:8 CH$_2$Cl$_2$:MeOH) to afford (1S)-2 as a yellow oil (13 mg, 58%). R$_f$=0.37 (92:8 CH$_2$Cl$_2$:MeOH); $^1$H NMR (500 MHz, CDCl$_3$) δ 9.05 (s, 1H), 8.73 (s, 1H), 6.73 (d, J=16.0 Hz, 1H), 6.32 (dd, J=16.0, 6.0 Hz, 1H), 4.97-4.87 (m, 1H), 4.38-4.31 (m, 1H), 4.24 (br. s, 1H), 3.82-3.77 (m, 1H), 3.66 (s, 3H), 2.80 (br. s, 1H), 2.72 (br. s, 1H), 2.40-2.34 (m, 2H), 1.90-1.68 (m, 4H), 1.53-1.49 (m, 2H), 1.46-1.39 (m, 2H), 1.33-1.25 (m, 4H), 0.86 (t, J=6.5 Hz, 3H); $^{13}$C NMR (126 MHz, CDCl$_3$) δ 174.2, 166.9, 156.3, 154.2, 134.0, 127.4, 123.2, 75.1, 73.8, 69.6, 51.7, 37.4, 33.5, 31.6, 31.4, 24.9, 22.5, 20.9, 14.0; IR (CHCl$_3$) ($v_{max}$, cm$^{-1}$) 3408, 2954, 1731, 1076; [α]$_D$=-7.89 (c=1.0 in CHCl$_3$); HRMS [M+Na]$^+$ calc 389.2052 for C$_{19}$H$_{30}$N$_2$O$_5$Na, found 389.2044.

Methyl (5S,6R,E)-5,6-dihydroxy-8-(4-((R)-1-hydroxyhexyl)pyrimidin-5-yl)oct-7-enoate ((1R)-2)

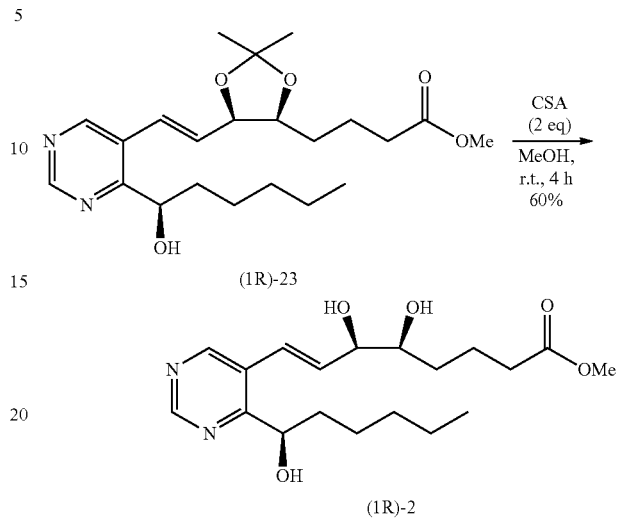

Acetonide (1R)-23 (30.0 mg, 0.0738 mmol, 1 eq) was dissolved in MeOH (1.8 mL). Camphorsulfonic acid (34.4 mg, 0.148 mmol, 2 eq) was added and the reaction mixture was stirred at room temperature for 4 h. The reaction mixture was concentrated and purified by preparative TLC (92:8 CH$_2$Cl$_2$:MeOH) to afford (1R)-2 as a yellow oil (16 mg, 60%). R$_f$=0.37 (92:8 CH$_2$Cl$_2$:MeOH); $^1$H NMR (500 MHz, CDCl$_3$) δ 9.04 (s, 1H), 8.72 (s, 1H), 6.71 (d, J=16.0 Hz, 1H), 6.32 (dd, J=16.0, 6.0 Hz, 1H), 4.90 (dd, J=7.5, 3.0 Hz, 1H), 4.36-4.30 (m, 1H), 4.23 (br. s, 1H), 3.82-3.76 (m, 1H), 3.66 (s, 3H), 2.79 (br. s, 2H), 2.41-2.33 (m, 2H), 1.91-1.82 (m, 1H), 1.77-1.67 (m, 2H), 1.58-1.47 (m, 3H), 1.45-1.37 (m, 2H), 1.31-1.22 (m, 4H), 0.86 (t, J=7.0 Hz, 3H); $^{13}$C NMR (101 MHz, CDCl$_3$) δ 174.2, 166.8, 156.4, 154.3, 133.8, 127.3, 123.4, 75.1, 73.8, 69.6, 51.7, 37.4, 33.5, 31.6, 31.5, 24.9, 22.5, 20.9, 14.0; IR (CHCl$_3$) ($v_{max}$, cm$^{-1}$) 3408, 2954, 1731, 1076; [α]$_D$=+22.25 (c=0.8 in CHCl$_3$); HRMS [M+Na] calc 389.2052 for C$_{19}$H$_3$N$_2$O$_5$Na, found 389.2046.

The forgoing embodiments are not intended to limit the scope of the protection afforded by the claims, but rather to describe examples of how the invention may be put into practice. Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention. Typically, when referring to compositions, a composition consisting essentially of a set of components will comprise less than 5% by weight, typically less than 3% by weight, more typically less than 1% by weight of non-specified components.

The term "consisting of" or "consists of" means including the components specified but excluding addition of other components.

Whenever appropriate, depending upon the context, the use of the term "comprises" or "comprising" may also be taken to encompass or include the meaning "consists essentially of" or "consisting essentially of", and may also be taken to include the meaning "consists of" or "consisting of".

Although a few preferred embodiments have been shown and described, it will be appreciated by those skilled in the art that various changes and modifications might be made without departing from the scope of the invention, as defined in the appended claims.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, and drawings), and/or all of the steps of any method or process so disclosed, may be combined in any combination, except combinations where at least some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, and drawings), or to any novel one, or any novel combination, of the steps of any method or process so disclosed.

REFERENCES (1) Serhan, C. N.; Hamberg, M.; Samuelsson, B. Trihydroxytetraenes: a novel series of compounds formed from arachidonic acid in human leukocytes. *Biochem. Biophys. Res. Comm.* 1984, 118, 943-949.

(2) Serhan, C. N.; Hamberg, M.; Samuelsson, B. Lipoxins: a novel series of biologically active compounds formed from arachidonic acid in human leukocytes. *Proc. Natl. Acac. Sci.,* 1984; pp 5335-5339.

(3) Bonnans, C.; Vachier, I.; Chavis, C.; Godard, P.; Bosquet, J.; Chanez, P. Lipoxins are potential endogenous anti-inflammatory mediators in asthma. *Am. J. Respir. Crit. Care Med.* 2002, 165, 1531-1535.

(4) Levy, B. D.; Bonnans, C.; Silverman, E. S.; Palmer, L. J.; Marigowda, G.; Israel, E. Diminished lipoxin biosynthesis in severe asthma. *Am. J. Respir. Crit. Care Med.* 2005, 172, 824-830.

(5) Kieran, N. E.; Maderna, P.; Godson, C. Lipoxins: potential anti-inflammatory, proresolution and antifibrotic mediators in renal disease. *Kidney Int.* 2004, 65, 1145-1154.

(6) McMahon, B.; Godson, C. Lipoxins: endogenous regulators of inflammation. *Am. J. Renal Physiol.* 2004, 286, F189-F201.

(7) Fiore, S.; Serhan, C. N. Lipoxin $A_4$ receptor activation is distinct from that of the formyl peptide receptor in myeloid cells: inhibition of CD11/18 expression by lipoxin $A_4$-lipoxin $A_4$ receptor interaction. *Biochemistry* 1995, 34, 16678-16686.

(8) Serhan, C. N.; Parkos, C. A.; Delp-Archer, C.; Madara, J. L. Lipoxin $A_4$ modulates transmigration of human neutrophils across intestinal epithelial monolayers. *J. Clin. Invest.* 1993, 92, 75-82.

(9) Filep, J. G.; Zouki, C.; Petasis, N. A.; Hachicha, M.; Serhan, C. N. Anti-inflammatory actions of lipoxin $A_4$ stable analogs are demonstrable in human whole blood: modulation of leukocyte adhesion molecules and inhibition of neutrophil-endothelial interactions. *Blood* 1999, 94, 4132-4142.

(10) Papayianni, A.; Serhan, C. N.; Brady, H. R. Lipoxin $A_4$ and B4 inhibit leukotriene-stimulated interactions of human neutrophils and endothelial cells. *J. Immunol.* 1996, 156, 2264-2272.

(11) Brady, H. R.; Persson, U.; Ballermann, B. J.; Brenner, B. M.; Serhan, C. N. Leukotrienes stimulate neutrophil adhesion to mesangial cells: modulation with lipoxins. *Am. J. Physiol.* 1990, 259, F809-F815.

(12) Godson, C.; Mitchell, S.; Harvey, K.; Petasis, N. A.; Hogg, N.; Brady, H. R. Cutting Edge: Lipoxins rapidly stimulate nonphlogistic phagocytosis of apoptotic neutrophils by monocyte-derived macrophages. *J. Immunol.* 2000, 164, 1663-1667.

(13) Mitchell, S.; Thomas, G.; Harvey, K.; Cottell, D. C.; Reville, K.; Berlasconi, G.; Petasis, N. A.; Erwig, L.; Rees, A. J.; Savill, J.; Brady, H. R.; Godson, C. Lipoxins, aspirin-triggered epi-lipoxins, lipoxin stable analogues, and the resolution of inflammation: stimulation of macrophage phagocytosis of apoptotic neutrophils in vivo. *J. Am. Soc. Nephrol.* 2002, 13, 2497-2507.

(13a) Brennan et al., *J Am So Nephrol.* 2013.

(13b) Borgeson et al., *Cell Metab* 2015.

(14) Serhan, C. N.; Savill, J. Resolution of inflammation: the beginning programs the end. *Nat. Immunol.* 2005, 6, 1191-1197.

(15) Levy, B. D.; Clish, C. B.; Schmidt, B.; Gronert, K.; Serhan, C. N. Lipid mediator class switching during acute inflammation: signals in resolution. *Nat. Immunol.* 2001, 2, 612-619.

(16) Clish, C. B.; Levy, B. D.; Chiang, N.; Tai, H.-H.; Serhan, C. N. A novel role for 15-oxoprostaglandin 13-reductase/leukotriene $B_4$ 12-hydroxydehydrogenase in inflammation. *J. Biol. Chem.* 2000, 275, 25372-25380.

(17) Serhan, C. N. Lipoxins and novel aspirin-triggered 15-epi-lipoxins [ATL]: a jungle of cell-cell interactions or a therapeutic opportunity? *Prostaglandins* 1997, 53, 107-137.

(18) Duffy, C. D.; Guiry, P. J., Recent advances in the chemistry and biology of stable synthetic lipoxin analogues. *Med Chem Comm* 2010, 1, 249-265.

(19) C. D. Duffy, P. Maderna, C. McCarthy, C. E. Loscher, C. Godson, P. J. Guiry, *Chem Med Chem* 2010, 5, 517-522.

The invention claimed is:

1. A compound of formula (I):

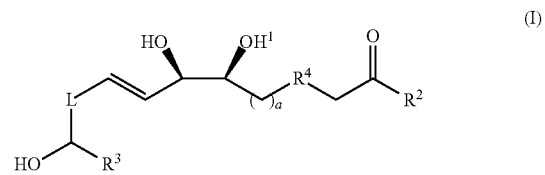

wherein L is selected from a pyrimidine, quinoline, isoquinoline, quinazoline, five-membered heterocyclic ring or benzo-fused five-membered heterocyclic ring optionally substituted with alkyl groups, aryl alkyl groups, alkoxy groups or halogens;
wherein a is 0, 1 or 2;
wherein $R^1$ is H or with $R^2$ is a bond;
wherein $R^2$ is OH or an alkoxy or aryloxy group, or with $R^1$ forms a bond;
wherein $R^3$ is an alkyl group; and
wherein $R^4$ is $CH_2$, $CMe_2$ or O.

2. The compound according to claim 1, wherein L is selected from the heterocyclic groups:

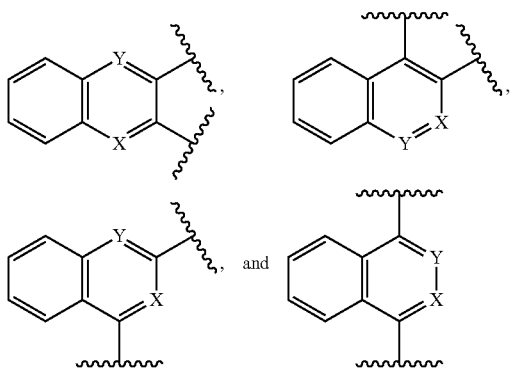

wherein X is selected from C or N,
wherein Y is selected from C or N, and
wherein at least one of X and Y is N.

3. The compound according to claim 1, wherein L is the group:

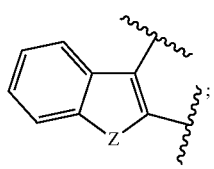

wherein Z is selected from N, O and S.

4. The compound according to claim 1, wherein L is:

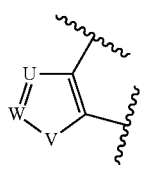

wherein V is selected from $NR^5$, O and S; wherein $R^5$ is H or an alkyl or aryl group;
wherein W is selected from $CR^6$, N, O and S; wherein $R^6$ is H or an alkyl or aryl group; and
wherein U is selected from $CR^7$ or N; wherein $R^7$ is H or an alkyl or aryl group.

5. The compound according to claim 1, wherein $R^2$ is a $C_{1-4}$ alkoxy group.

6. The compound according to claim 1 having the formula (II):

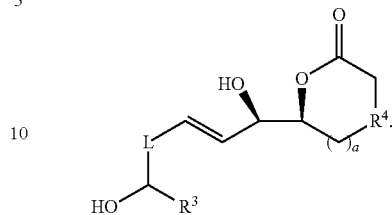

7. The compound according to claim 1, wherein $R^3$ is a $C_{1-9}$ alkyl group.

8. The compound according to claim 1, wherein $R^3$ has the formula (III):

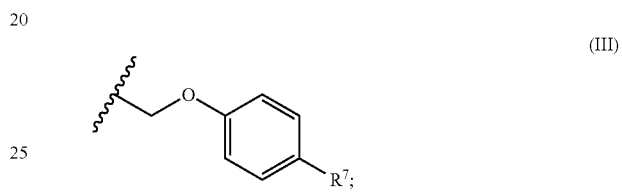

wherein $R^7$ is selected from H, F and $CF_3$.

9. The compound according to claim 1 having the formula (IV):

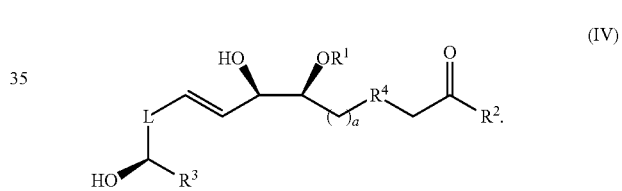

10. A pharmaceutical composition comprising a compound according to claim 1 and a pharmaceutically acceptable diluent, lubricant or carrier.

11. A medicament comprising the composition according to claim 10.

12. A method of treating a disease or condition in which inhibition of acute inflammation and/or promotion of its resolution and/or suppression of fibrosis is beneficial, the method comprising administering a therapeutically effective amount of a compound according to claim 1.

13. The method of claim 12 for use in the treatment of atherosclerosis.

14. The method of claim 12 for use in the treatment of macrovascular complications, microvascular complications, or both, associated with diabetes.

15. The method of claim 12, wherein the disease or condition is asthma.

16. The method of claim 12, wherein the disease or condition is glomerulonephritis.

* * * * *